US012790384B2

(12) United States Patent
Trager et al.

(10) Patent No.: US 12,790,384 B2
(45) Date of Patent: Nov. 10, 2026

(54) METHODS AND COMPOSITIONS FOR ENHANCED EXPANSION AND CYTOTOXICITY OF NATURAL KILLER CELLS

(71) Applicant: NKARTA, INC., South San Francisco, CA (US)

(72) Inventors: James Barnaby Trager, Albany, CA (US); Alexandra Leida Liana Lazetic, San Jose, CA (US); Ivan Chan, Millbrae, CA (US); Anmol Vohra, San Francisco, CA (US)

(73) Assignee: NKARTA, INC., South San Francisco, CA (US)

( * ) Notice: Subject to any disclaimer, the term of this patent is extended or adjusted under 35 U.S.C. 154(b) by 966 days.

(21) Appl. No.: 17/628,105

(22) PCT Filed: Jul. 29, 2020

(86) PCT No.: PCT/US2020/044033

§ 371 (c)(1),
(2) Date: Jan. 18, 2022

(87) PCT Pub. No.: WO2021/021907

PCT Pub. Date: Feb. 4, 2021

(65) Prior Publication Data

US 2022/0411754 A1 Dec. 29, 2022

Related U.S. Application Data

(60) Provisional application No. 62/932,342, filed on Nov. 7, 2019, provisional application No. 62/881,311, filed on Jul. 31, 2019.

(51) Int. Cl.

| | |
|---|---|
| ***C07K 14/705*** | (2006.01) |
| ***A61K 40/15*** | (2025.01) |
| ***A61K 40/31*** | (2025.01) |
| ***A61K 40/42*** | (2025.01) |
| ***C07K 14/54*** | (2006.01) |
| ***C12N 5/0783*** | (2010.01) |

(52) U.S. Cl.

CPC ........ *C07K 14/70575* (2013.01); *A61K 40/15* (2025.01); *A61K 40/31* (2025.01); *A61K 40/4211* (2025.01); *C07K 14/5443* (2013.01); *C12N 5/0646* (2013.01); *C07K 2319/03* (2013.01); *C12N 2501/2302* (2013.01); *C12N 2501/2312* (2013.01); *C12N 2501/2318* (2013.01); *C12N 2501/2321* (2013.01); *C12N 2502/30* (2013.01); *C12N 2502/99* (2013.01)

(58) Field of Classification Search

CPC .... A61K 40/15; A61K 40/31; A61K 40/4211; C07K 14/5443; C12N 5/0646; C12N 2501/2302; C12N 2501/2312; C12N 2501/2318

See application file for complete search history.

(56) References Cited

U.S. PATENT DOCUMENTS

| | | | |
|---|---|---|---|
| 4,650,764 | A | 3/1987 | Temin et al. |
| 4,690,915 | A | 9/1987 | Rosenberg |
| 4,844,893 | A | 7/1989 | Honsik et al. |
| 4,980,289 | A | 12/1990 | Temin et al. |
| 5,124,263 | A | 6/1992 | Temin et al. |
| 5,359,046 | A | 10/1994 | Capon et al. |
| 5,399,346 | A | 3/1995 | Anderson et al. |
| 5,653,977 | A | 8/1997 | Saleh |
| 5,674,704 | A | 10/1997 | Goodwin et al. |
| 5,686,281 | A | 11/1997 | Roberts |
| 5,712,149 | A | 1/1998 | Roberts |
| 6,103,521 | A | 8/2000 | Capon et al. |
| 6,303,121 | B1 | 10/2001 | Kwon |
| 6,319,494 | B1 | 11/2001 | Capon et al. |
| 6,355,476 | B1 | 3/2002 | Kwon et al. |
| 6,361,998 | B1 | 3/2002 | Bell et al. |
| 6,410,319 | B1 | 6/2002 | Raubitschek et al. |
| 6,797,514 | B2 | 9/2004 | Berenson et al. |
| 7,052,906 | B1 | 5/2006 | Lawson et al. |
| 7,070,995 | B2 | 7/2006 | Jensen |
| 7,435,596 | B2 | 10/2008 | Campana et al. |
| 7,446,179 | B2 | 11/2008 | Jensen et al. |
| 7,446,190 | B2 | 11/2008 | Sadelain et al. |

(Continued)

FOREIGN PATENT DOCUMENTS

| | | | |
|---|---|---|---|
| CN | 101684456 | A | 3/2010 |
| CN | 102268405 | A | 12/2011 |

(Continued)

OTHER PUBLICATIONS

Wu, Yang, Zhigang Tian, and Haiming Wei. "Developmental and functional control of natural killer cells by cytokines." Frontiers in immunology 8 (2017): 930. (Year: 2017).*

Baek, Hee-Jo, et al. "Ex vivo expansion of natural killer cells using cryopreserved irradiated feeder cells." Anticancer Research 33.5 (2013): 2011-2019. (Year: 2013).*

Romee, Rizwan, et al. "Cytokine activation induces human memory-like NK cells." Blood, The Journal of the American Society of Hematology 120.24 (2012): 4751-4760. (Year: 2012).*

AASEQ1_05172022_135256_pep_vs AASEQ2_05172022_135256_pep_align_4-1BBL (Year: 2022).

Abakushina, E.V., "Immunotherapy With Natural Killer Cells In The Treatment Of Cancer," Russian Journal of Immunology, vol. 10, No. 2, pp. 131-142 (2016) (Abstract only).

(Continued)

*Primary Examiner* — Teresa E Knight
*Assistant Examiner* — Michael Angelo Riga
(74) *Attorney, Agent, or Firm* — Knobbe Martens Olson & Bear LLP

(57) ABSTRACT

Several embodiments disclosed herein relate to methods and compositions for enhanced expansion of NK cells in culture. In several embodiments, the methods utilize one or more soluble interleukins as culture media supplements at one or more time points during expansion of the NK cell, or other immune cell, the expansion employing a feeder cell population.

5 Claims, 91 Drawing Sheets

Specification includes a Sequence Listing.

(56) References Cited

U.S. PATENT DOCUMENTS

| | | | | |
|---|---|---|---|---|
| 7,735,596 | B2 | 6/2010 | Sasaki et al. | |
| 7,763,243 | B2 | 7/2010 | Lum et al. | |
| 7,932,055 | B2 | 4/2011 | Spee et al. | |
| 7,994,298 | B2 | 8/2011 | Zhang et al. | |
| 8,026,097 | B2 | 9/2011 | Campana et al. | |
| 8,399,645 | B2 | 3/2013 | Campana et al. | |
| 8,906,682 | B2 | 12/2014 | June et al. | |
| 9,487,800 | B2 | 11/2016 | Schonfeld et al. | |
| 9,605,049 | B2 | 3/2017 | Campana et al. | |
| 9,834,590 | B2 | 12/2017 | Campana et al. | |
| 9,856,322 | B2 | 1/2018 | Campana et al. | |
| 10,428,305 | B2 | 10/2019 | Campana et al. | |
| 10,774,311 | B2 | 9/2020 | Campana et al. | |
| 11,365,236 | B2 | 6/2022 | Leong et al. | |
| 11,560,548 | B2 | 1/2023 | Campana et al. | |
| 11,673,937 | B2 | 6/2023 | Campana et al. | |
| 11,896,616 | B2 * | 2/2024 | Kamiya | A61P 35/00 |
| 12,264,335 | B2 | 4/2025 | Campana et al. | |
| 2002/0018783 | A1 | 2/2002 | Sadelain et al. | |
| 2003/0147869 | A1 | 8/2003 | Riley et al. | |
| 2003/0215427 | A1 | 11/2003 | Jensen | |
| 2004/0038886 | A1 | 2/2004 | Finney et al. | |
| 2004/0043401 | A1 | 3/2004 | Sadelain et al. | |
| 2004/0115216 | A1 | 6/2004 | Schneck et al. | |
| 2004/0126363 | A1 | 7/2004 | Jensen et al. | |
| 2005/0042208 | A1 | 2/2005 | Sagawa et al. | |
| 2005/0048549 | A1 | 3/2005 | Cao et al. | |
| 2005/0113564 | A1 | 5/2005 | Campana et al. | |
| 2005/0127473 | A1 | 6/2005 | Sakagami | |
| 2005/0233391 | A1 | 10/2005 | Spies et al. | |
| 2006/0093605 | A1 | 5/2006 | Campana et al. | |
| 2006/0247191 | A1 | 11/2006 | Finney et al. | |
| 2006/0257407 | A1 | 11/2006 | Chen et al. | |
| 2007/0160578 | A1 | 7/2007 | Waldmann et al. | |
| 2007/0166327 | A1 | 7/2007 | Cooper et al. | |
| 2008/0247990 | A1 | 10/2008 | Campbell | |
| 2009/0011498 | A1 | 1/2009 | Campana et al. | |
| 2012/0015434 | A1 | 1/2012 | Campana et al. | |
| 2012/0148552 | A1 | 6/2012 | Jensen | |
| 2012/0282256 | A1 | 11/2012 | Campana et al. | |
| 2012/0321666 | A1 | 12/2012 | Cooper et al. | |
| 2013/0266551 | A1 | 10/2013 | Campana et al. | |
| 2013/0280221 | A1 | 10/2013 | Schonfeld et al. | |
| 2013/0288368 | A1 | 10/2013 | June et al. | |
| 2013/0309258 | A1 | 11/2013 | June et al. | |
| 2014/0023626 | A1 | 1/2014 | Peled et al. | |
| 2014/0271635 | A1 | 9/2014 | Brogdon et al. | |
| 2014/0286973 | A1 | 9/2014 | Powell, Jr. | |
| 2014/0302608 | A1 | 10/2014 | Dominici et al. | |
| 2014/0322183 | A1 | 10/2014 | Milone et al. | |
| 2014/0328812 | A1 | 11/2014 | Campana et al. | |
| 2014/0341869 | A1 | 11/2014 | Campana et al. | |
| 2015/0139943 | A1 | 5/2015 | Campana et al. | |
| 2015/0190471 | A1 | 7/2015 | Copik et al. | |
| 2015/0218649 | A1 | 8/2015 | Saenger et al. | |
| 2015/0224143 | A1 | 8/2015 | Malmberg et al. | |
| 2016/0000828 | A1 | 1/2016 | Campana et al. | |
| 2016/0009784 | A1 | 1/2016 | Campana et al. | |
| 2016/0068601 | A1 | 3/2016 | Brogdon et al. | |
| 2016/0152723 | A1 | 6/2016 | Chen et al. | |
| 2016/0158285 | A1 | 6/2016 | Cooper et al. | |
| 2016/0289294 | A1 | 10/2016 | Pul et al. | |
| 2016/0326265 | A1 | 11/2016 | June et al. | |
| 2016/0377035 | A1 | 12/2016 | Osawa et al. | |
| 2017/0044227 | A1 | 2/2017 | Schnfeld et al. | |
| 2017/0073423 | A1 | 3/2017 | Juillerat et al. | |
| 2017/0073638 | A1 | 3/2017 | Campana et al. | |
| 2017/0129967 | A1 | 5/2017 | Wels et al. | |
| 2017/0283482 | A1 | 10/2017 | Campana et al. | |
| 2017/0319659 | A1 | 11/2017 | Copik et al. | |
| 2017/0355957 | A1 | 12/2017 | Biondi et al. | |
| 2018/0002397 | A1 | 1/2018 | Shah et al. | |
| 2018/0008638 | A1 | 1/2018 | Campana et al. | |
| 2018/0022828 | A1 | 1/2018 | Schonfeld et al. | |
| 2018/0044391 | A1 | 2/2018 | Gundram et al. | |
| 2018/0044404 | A1 | 2/2018 | Oda et al. | |
| 2018/0057563 | A1 | 3/2018 | Campana et al. | |
| 2018/0057795 | A1 | 3/2018 | Childs et al. | |
| 2018/0086831 | A1 | 3/2018 | Pule et al. | |
| 2018/0104278 | A1 | 4/2018 | Zhang et al. | |
| 2018/0117146 | A1 | 5/2018 | Yu et al. | |
| 2018/0118845 | A1 | 5/2018 | Campana et al. | |
| 2018/0134765 | A1 | 5/2018 | Landgraf et al. | |
| 2018/0135015 | A1 | 5/2018 | Campana et al. | |
| 2018/0353544 | A1 | 12/2018 | Rezvani et al. | |
| 2019/0000881 | A1 | 1/2019 | Sadelain et al. | |
| 2019/0038733 | A1 | 2/2019 | Campana et al. | |
| 2019/0046571 | A1 | 2/2019 | Campana et al. | |
| 2019/0290693 | A1 | 9/2019 | Qi et al. | |
| 2019/0336533 | A1 | 11/2019 | Hwang et al. | |
| 2019/0343801 | A1 | 11/2019 | Barda-Saad | |
| 2019/0376037 | A1 | 12/2019 | Campana et al. | |
| 2019/0381104 | A1 | 12/2019 | Delaney et al. | |
| 2020/0016208 | A1 * | 1/2020 | Kamiya | A61K 40/42 |
| 2020/0131244 | A1 | 4/2020 | Leong et al. | |
| 2020/0255803 | A1 | 8/2020 | Zhang et al. | |
| 2020/0390816 | A1 * | 12/2020 | Kerbauy | C07K 14/55 |
| 2020/0407686 | A1 | 12/2020 | Campana et al. | |
| 2021/0017271 | A1 | 1/2021 | Tan et al. | |
| 2021/0046115 | A1 | 2/2021 | Seow et al. | |
| 2021/0054409 | A1 | 2/2021 | Zhu et al. | |
| 2021/0077527 | A1 | 3/2021 | Lee | |
| 2021/0139914 | A1 | 5/2021 | Wucherpfennig et al. | |
| 2021/0324388 | A1 | 10/2021 | Vinanica et al. | |
| 2023/0002471 | A1 | 1/2023 | Leong et al. | |
| 2023/0220343 | A1 | 7/2023 | Campana et al. | |
| 2023/0265390 | A1 | 8/2023 | Trager et al. | |
| 2024/0092862 | A1 | 3/2024 | Campana et al. | |
| 2025/0049845 | A1 | 2/2025 | Copik et al. | |
| 2025/0320457 | A1 | 10/2025 | Campana et al. | |
| 2025/0339528 | A1 | 11/2025 | Trager et al. | |

FOREIGN PATENT DOCUMENTS

| | | | |
|---|---|---|---|
| CN | 102924596 | A | 2/2013 |
| CN | 103113470 | A | 5/2013 |
| CN | 105838677 | A | 8/2016 |
| CN | 105985931 | A | 10/2016 |
| CN | 106085958 | A | 11/2016 |
| CN | 106459914 | A | 2/2017 |
| CN | 107109363 | A | 8/2017 |
| CN | 107206100 | A | 9/2017 |
| CN | 107709548 | A | 2/2018 |
| CN | 107827990 | A | 3/2018 |
| EP | 1036327 | A2 | 9/2000 |
| EP | 1053301 | A1 | 11/2000 |
| EP | 1233058 | A1 | 8/2002 |
| EP | 1820017 | A2 | 8/2007 |
| EP | 2141997 | A1 | 1/2010 |
| EP | 2411507 | A1 | 2/2012 |
| EP | 2493485 | A1 | 9/2012 |
| EP | 2493486 | A1 | 9/2012 |
| EP | 2537416 | A1 | 12/2012 |
| EP | 2614077 | A1 | 7/2013 |
| EP | 2614151 | A1 | 7/2013 |
| EP | 2756521 | A2 | 7/2014 |
| EP | 2856876 | A1 | 4/2015 |
| EP | 2866834 | A1 | 5/2015 |
| EP | 2893003 | A1 | 7/2015 |
| EP | 2903637 | A1 | 8/2015 |
| EP | 2904106 | A2 | 8/2015 |
| EP | 2948544 | A1 | 12/2015 |
| EP | 2956175 | A1 | 12/2015 |
| EP | 2961831 | A1 | 1/2016 |
| EP | 2964753 | A1 | 1/2016 |
| EP | 2968492 | A1 | 1/2016 |
| EP | 2968601 | A1 | 1/2016 |
| EP | 2970426 | A2 | 1/2016 |
| EP | 2986636 | A1 | 2/2016 |
| EP | 2593540 | A1 | 3/2016 |
| EP | 3008173 | A2 | 4/2016 |
| EP | 3012268 | A1 | 4/2016 |
| EP | 3057986 | A1 | 8/2016 |
| EP | 3063175 | A2 | 9/2016 |

(56) References Cited

FOREIGN PATENT DOCUMENTS

| | | | |
|---|---|---|---|
| EP | 3071221 | A1 | 9/2016 |
| EP | 3071222 | A1 | 9/2016 |
| EP | 3071223 | A1 | 9/2016 |
| EP | 3083671 | A1 | 10/2016 |
| EP | 3083691 | A2 | 10/2016 |
| EP | 3094653 | A1 | 11/2016 |
| EP | 3105318 | A1 | 12/2016 |
| EP | 3105335 | A1 | 12/2016 |
| EP | 3115573 | A1 | 1/2017 |
| EP | 3119425 | A1 | 1/2017 |
| EP | 3126380 | A1 | 2/2017 |
| EP | 3134432 | A2 | 3/2017 |
| EP | 3180359 | A1 | 6/2017 |
| EP | 3189132 | A1 | 7/2017 |
| EP | 3567049 | A2 | 11/2019 |
| JP | 2017-112982 | A | 6/2017 |
| KR | 10-2017-0039307 | A | 4/2017 |
| RU | 2839702 | C2 | 5/2025 |
| WO | 95/07358 | A1 | 3/1995 |
| WO | 96/23814 | A1 | 8/1996 |
| WO | 96/24671 | A1 | 8/1996 |
| WO | 97/23613 | A2 | 7/1997 |
| WO | 98/26061 | A2 | 6/1998 |
| WO | 99/00494 | A2 | 1/1999 |
| WO | 99/28748 | A2 | 6/1999 |
| WO | 99/38954 | A1 | 8/1999 |
| WO | 99/57268 | A1 | 11/1999 |
| WO | 00/14257 | A1 | 3/2000 |
| WO | 00/23573 | A2 | 4/2000 |
| WO | 01/38494 | A1 | 5/2001 |
| WO | 02/33101 | A1 | 4/2002 |
| WO | 02/77029 | A2 | 10/2002 |
| WO | 03/89616 | A2 | 10/2003 |
| WO | 2004/027036 | A2 | 4/2004 |
| WO | 2004/039840 | A1 | 5/2004 |
| WO | 2005/000890 | A1 | 1/2005 |
| WO | 2005/044996 | A2 | 5/2005 |
| WO | 2005/118788 | A2 | 12/2005 |
| WO | 2006/036445 | A2 | 4/2006 |
| WO | 2006/052534 | A2 | 5/2006 |
| WO | 2006/061626 | A2 | 6/2006 |
| WO | 2007/046006 | A2 | 4/2007 |
| WO | 2008/121420 | A1 | 10/2008 |
| WO | 2009/117566 | A1 | 9/2009 |
| WO | 2010/071836 | A1 | 6/2010 |
| WO | 2010/110734 | A1 | 9/2010 |
| WO | 2011/020047 | A1 | 2/2011 |
| WO | 2011/053321 | A1 | 5/2011 |
| WO | 2011/053322 | A1 | 5/2011 |
| WO | 2011/069019 | A2 | 6/2011 |
| WO | 2011/080740 | A1 | 7/2011 |
| WO | 2011/150976 | A1 | 12/2011 |
| WO | 2012/009422 | A1 | 1/2012 |
| WO | 2012/031744 | A1 | 3/2012 |
| WO | 2012/040323 | A2 | 3/2012 |
| WO | 2012/071411 | A2 | 5/2012 |
| WO | 2012/079000 | A1 | 6/2012 |
| WO | 2012/136231 | A1 | 10/2012 |
| WO | 2013/040371 | A2 | 3/2013 |
| WO | 2013/040557 | A2 | 3/2013 |
| WO | 2013/043196 | A1 | 3/2013 |
| WO | 2013/123720 | A1 | 8/2013 |
| WO | 2013/123726 | A1 | 8/2013 |
| WO | 2014/005072 | A1 | 1/2014 |
| WO | 2014/011993 | A2 | 1/2014 |
| WO | 2014/037422 | A1 | 3/2014 |
| WO | 2014/055413 | A2 | 4/2014 |
| WO | 2014/055442 | A2 | 4/2014 |
| WO | 2014/055657 | A1 | 4/2014 |
| WO | 2014/055668 | A1 | 4/2014 |
| WO | 2014/099671 | A1 | 6/2014 |
| WO | 2014/117121 | A1 | 7/2014 |
| WO | 2014/127261 | A1 | 8/2014 |
| WO | 2014/134165 | A1 | 9/2014 |
| WO | 2014/138704 | A1 | 9/2014 |
| WO | 2014/145252 | A2 | 9/2014 |
| WO | 2014/164554 | A1 | 10/2014 |
| WO | 2014/172584 | A1 | 10/2014 |
| WO | 2014/186469 | A2 | 11/2014 |
| WO | 2014/201021 | A2 | 12/2014 |
| WO | 2015/058018 | A1 | 4/2015 |
| WO | 2015/066551 | A2 | 5/2015 |
| WO | 2015/075468 | A1 | 5/2015 |
| WO | 2015/075469 | A1 | 5/2015 |
| WO | 2015/075470 | A1 | 5/2015 |
| WO | 2015/092024 | A2 | 6/2015 |
| WO | 2015/095895 | A1 | 6/2015 |
| WO | 2015/105522 | A1 | 7/2015 |
| WO | 2015/120421 | A1 | 8/2015 |
| WO | 2015/123642 | A1 | 8/2015 |
| WO | 2015/142314 | A1 | 9/2015 |
| WO | 2015/142661 | A1 | 9/2015 |
| WO | 2015/150771 | A1 | 10/2015 |
| WO | 2015/154012 | A1 | 10/2015 |
| WO | 2015/164759 | A2 | 10/2015 |
| WO | 2015/174928 | A1 | 11/2015 |
| WO | 2015/188119 | A1 | 12/2015 |
| WO | 2015/193411 | A1 | 12/2015 |
| WO | 2016/011210 | A2 | 1/2016 |
| WO | 2016/025880 | A1 | 2/2016 |
| WO | 2016/030691 | A1 | 3/2016 |
| WO | 2016/033331 | A1 | 3/2016 |
| WO | 2016/033690 | A1 | 3/2016 |
| WO | 2016/040441 | A1 | 3/2016 |
| WO | 2016/042041 | A1 | 3/2016 |
| WO | 2016/042461 | A1 | 3/2016 |
| WO | 2016/061574 | A1 | 4/2016 |
| WO | 2016/069607 | A1 | 5/2016 |
| WO | 2016/073602 | A2 | 5/2016 |
| WO | 2016/073629 | A1 | 5/2016 |
| WO | 2016/073755 | A2 | 5/2016 |
| WO | 2016/075612 | A1 | 5/2016 |
| WO | 2016/100985 | A2 | 6/2016 |
| WO | 2016/109661 | A1 | 7/2016 |
| WO | 2016/109668 | A1 | 7/2016 |
| WO | 2016/115482 | A1 | 7/2016 |
| WO | 2016/118857 | A1 | 7/2016 |
| WO | 2016/123122 | A1 | 8/2016 |
| WO | 2016/123333 | A1 | 8/2016 |
| WO | 2016/124765 | A1 | 8/2016 |
| WO | 2016/124930 | A1 | 8/2016 |
| WO | 2016/126213 | A1 | 8/2016 |
| WO | 2016/126608 | A1 | 8/2016 |
| WO | 2016/139487 | A1 | 9/2016 |
| WO | 2016/141357 | A1 | 9/2016 |
| WO | 2016/142314 | A1 | 9/2016 |
| WO | 2016/149254 | A1 | 9/2016 |
| WO | 2016/151315 | A1 | 9/2016 |
| WO | 2016/154055 | A1 | 9/2016 |
| WO | 2016/154585 | A1 | 9/2016 |
| WO | 2016/172537 | A1 | 10/2016 |
| WO | 2016/172583 | A1 | 10/2016 |
| WO | 2016/174405 | A1 | 11/2016 |
| WO | 2016/174406 | A1 | 11/2016 |
| WO | 2016/174407 | A1 | 11/2016 |
| WO | 2016/174408 | A1 | 11/2016 |
| WO | 2016/174409 | A1 | 11/2016 |
| WO | 2016/174461 | A1 | 11/2016 |
| WO | 2016/174652 | A1 | 11/2016 |
| WO | 2016/179684 | A1 | 11/2016 |
| WO | 2016/191587 | A1 | 12/2016 |
| WO | 2016/191755 | A1 | 12/2016 |
| WO | 2016/196388 | A1 | 12/2016 |
| WO | 2016/197108 | A1 | 12/2016 |
| WO | 2016/201304 | A1 | 12/2016 |
| WO | 2016/210293 | A1 | 12/2016 |
| WO | 2017/004150 | A1 | 1/2017 |
| WO | 2017/011804 | A1 | 1/2017 |
| WO | 2017/021701 | A1 | 2/2017 |
| WO | 2017/023859 | A1 | 2/2017 |
| WO | 2017/024131 | A1 | 2/2017 |
| WO | 2017/027325 | A1 | 2/2017 |
| WO | 2017/029511 | A1 | 2/2017 |
| WO | 2017/032777 | A1 | 3/2017 |

(56) References Cited

FOREIGN PATENT DOCUMENTS

| | | | | |
|---|---|---|---|---|
| WO | 2017/034615 A1 | 3/2017 | | |
| WO | 2017/037083 A1 | 3/2017 | | |
| WO | 2017/058752 A1 | 4/2017 | | |
| WO | 2017/058753 A1 | 4/2017 | | |
| WO | 2017/079694 A2 | 5/2017 | | |
| WO | 2017/079705 A1 | 5/2017 | | |
| WO | 2017/079881 A1 | 5/2017 | | |
| WO | 2017/096329 A1 | 6/2017 | | |
| WO | 2017/127729 A1 | 7/2017 | | |
| WO | 2017/172981 A2 | 10/2017 | | |
| WO | WO-2017192440 A1 * | 11/2017 | ............. | A61K 35/17 |
| WO | 2018/022646 A1 | 2/2018 | | |
| WO | 2018/089476 A1 | 5/2018 | | |
| WO | 2018/103503 A1 | 6/2018 | | |
| WO | 2018/106732 A1 | 6/2018 | | |
| WO | 2018/124766 A2 | 7/2018 | | |
| WO | 2018/161017 A1 | 9/2018 | | |
| WO | 2018/182511 A1 | 10/2018 | | |
| WO | 2018/183385 A1 | 10/2018 | | |
| WO | 2019/062817 A1 | 4/2019 | | |
| WO | 2019/077037 A1 | 4/2019 | | |
| WO | 2019/081591 A1 | 5/2019 | | |
| WO | 2019/129002 A1 | 7/2019 | | |
| WO | 2019/129220 A1 | 7/2019 | | |
| WO | 2019/155286 A2 | 8/2019 | | |
| WO | 2019/155288 A1 | 8/2019 | | |
| WO | 2019/165121 A1 | 8/2019 | | |
| WO | 2019/193476 A1 | 10/2019 | | |
| WO | 2020/044239 A1 | 3/2020 | | |
| WO | 2020/083282 A1 | 4/2020 | | |
| WO | 2020/112563 A1 | 6/2020 | | |
| WO | 2020/180882 A1 | 9/2020 | | |
| WO | 2020/247392 A1 | 12/2020 | | |
| WO | 2021/009694 A1 | 1/2021 | | |
| WO | 2021/021907 A1 | 2/2021 | | |
| WO | 2021/061832 A1 | 4/2021 | | |
| WO | 2022/051749 A1 | 3/2022 | | |
| WO | 2022/226522 A1 | 10/2022 | | |

OTHER PUBLICATIONS

Abken et al., "Chimeric T-cell receptors: highly specific tools to target cytotoxic T-lymphocytes to tumour cells," Cancer Treat Rev., 23(2):97-112, Mar. 1997.
Abken, H. et al., "Antigen-specific T-cell activation independently of the MHC: chimeric antigen receptor-redirected T cells," Frontiers in Immunology, V. 4, Article 371, c. 4 (2013).
Abken, H., et al., "Tuning tumor-specific T-cell activation: a matter of costimulation?" TRENDS in Immunol. 23: 240-245 (2002).
Aguera-Gonzalez et ah, "Palmitoylation of MICA, a ligand forNKG2D, mediates its recruitment to membrane microdomains and promotes its shedding," Eur. J. Immunol. vol. 41, pp. 3667-3676 (2011).
Alderson et al., "Molecular and Biological Characterization of Human 4-1BB and its Ligand," Eur. J. Immunol., 1994, 24: 2219-2227.
Alignment I L-18 (Year: 2022).
Allison and Lanier, "Structure, function, and serology of the T-cell antigen receptor complex," Annu Rev Immunol, 1987, 5:503-40.
Alvarez-Vallina, L. and Hawkins, R.E., "Antigen-specific targeting of CD28-mediated T cell co-stimulation using chimeric single-chain antibody variable fragment-CD28 receptors," Eur. J. Immunol. 26: 2304-2309 (1996).
Amended Complaint in *Trustees of the University of Pennsylvania* v. *St. Jude Children's Research Hospital* in the U.S. District Court for the Eastern District of Pennsylvania, dated Jun. 10, 2013. (Doc. 15).
Anfosi, N. et al., "Human NK Cell Education by Inhibitory Receptors for MHC Class I" Immunity 25, 331-342, Aug. 2006.
Ang S.O. et al, "Avoiding the need for clinical-grade OKT3: ex vivo expansion of T cells using artificial antigen presenting cells genetically modified to crosslink CD3." Biology of Blood and Marrow Transplantation, Jan. 9, 2012, vol. 18, No. 2, pp. S258.
Annenkov et al. "Engineering mouse T lymphocytes specific to type II collagen by transduction with a chimeric receptor consisting of a single chain Fv and TCR zeta," Gene Therapy 7: 714-722 (2000).
Antony, G.K. et al., "Interleukin 2 in Cancer Therapy" Current Medicinal Chemistry (2010) vol. 17, pp. 3297-3302.
Aoudjit and Vuori, "Integrin Signaling in Cancer Cell Survival and Chemoresistance," Chemotherapy Research and Practice, 2012(Article ID 283181), 1-16, 2012.
Appelbaum, "Haematopoietic cell transplantation as immunotherapy," Nature, 2001, 411(6835): 385-389.
Aruffo, A., and Seed, B., "Molecular cloning of a CD28 cDNA by a high-efficiency COS cell expression system," Proc. Natl. Acad. Sci., 1987, 84:8573-8577.
ATCC (American Type Culture Collection) [online], "ATCC No. CCL-243," Designation K-562, 1975.
Azuma, M, et al., "Functional Expression of B7/BB1 on Activated T Lymphocytes," J. Exp. Med. 177: 845-850 (1993).
Baek, H. et al., "Ex Vivo Expansion of Natural Killer Cells Using Cryopreserved Irradiated Feeder Cells" Anticancer Research (2013) vol. 33, pp. 2011-2019.
Barber et al, "Treatment of Multiple Myetoma with Adoptively Transferred Chimeric NKG2D Receptor-Expressing T Cells", Gene Therapy (2011), vol. 18, pp. 509-516.
Barber et al, 2008, Immunotherapy with Chimeric NKG2D Receptors Leads to Long-Term Tumor-Free Survival and Development of Host Antitumor Immunity in Murine Ovarian Cancer, J Immunol 180: 72-78.
Barber et al. "Chimeric NKG2D Receptor-Bearing T Cells as Immunotherapy for Ovarian Cancer Research" Cancer Research, (2007) vol. 67, No. 10, pp. 5003-5008.
Barber et al. "Chimeric NKG2D Receptor-Expressing T Cells as an immunotherapy for multiple myeloma" Experimental Hematology.,(2008) vol. 36, pp. 1318:1328.
Barber et al., "Chimeric NKG2D Expressing T Cells Eliminate Immunosuppression and Activate Immunity within the Ovarian Tumor Microenvironment," J. Immunol, vol. 183, pp. 6939-6947 (2009).
Barber et al., "Chimeric NKG2D T Cells Require Both T Cell- and Host-Derived Cytokine Secretion and Perforin Expression to Increase Tumor Antigen Presentation and Systemic Immunity," J. Immunol, vol. 183, pp. 2365-2372 (2009).
Barrett, D.M., et al., "Chimeric Antigen Receptor Therapy for Cancer," Annu Rev. Med. 65: 333-347 (2014).
Bartholomew et al., "Mesenchymal stem cells suppress lymphocyte proliferation in vitro and prolong skin graft survival in vivo," Exp Hematol, Jan. 2002, 30(1): 42-48.
Batlcvi, C.L., ct al. "Novel immunothcrapics in lymphoid malignancies," Nature Rev. Clin. Oncol. 13:25-40 (2016).
Baum et al., "Side effects of retroviral gene transfer into hematopoietic stem cells," Blood, Mar. 2003, 101(6): 2099-2114.
Bejcek et al., "Development and Characterization of Three Recombinant Single Chain Antibody Fragments (scFvs) Directed against the CD19 Antigen," Cancer Res., 1995, 55:2346-2351.
Berger, C. et al., "Safety and immunologic effects of IL-15 administration in nonhuman primates," Blood, 114(12): 2417-2426 (2009).
Besser, M.J., et al., "Adoptive Transfer of Tumor-Infiltrating Lymphocytes in Patients with Metastatic Melanoma: Intent-to-Treat Analysis and Efficacy after Failure to Prior Immunotherapies," Clin. Cancer Res. 19: 4792-4800 (2013).
Better et al., "Manufacturing and Characterization of KTE-C19 in a Multicenter Trial of Subjects with Refractory Aggressive Non-Hodgkin Lymphoma (NHL) (ZUMA-1)," Poster session presented at the American Association for Cancer Research Annual Meeting, New Orleans, Louisiana (2016).
Beziat, V. et al., "NK cell responses to cytomegalovirus infection lead to stable imprints in the human KIR repertoire and involve activating KIRs", blood, Apr. 4, 2013, 121(14), 2678-2688.
Billadeau D.D. et al., "NKG2D-DAP10 triggers human NK cell-mediated killing via a Syk-independent regulatory pathway", Nature Immunology (2003), vol. 4, No. 6, pp. 557-564.

(56) References Cited

OTHER PUBLICATIONS

Bischof et al., "Autonomous induction of proliferation, JNK and NF-alphaB activation in primary resting T cells by mobilized CD28," Eur J Immunol., 30(3):876-882, Mar. 2000.

Bork et al., "The immunoglobulin fold. Structural classification, sequence patterns and common core," J Mol Biol., 242(4):309-320, Sep. 30, 1994.

Boyman, O. et al., "The role of interleukin-2 during homeostasis and activation of the immune system" Nature Reviews (2012) vol. 12, pp. 180-190.

Brand, L.J. et al., "Abstract LB-185: A PSMA-directed natural killer cell approach for prostate cancer immunotherapy," Cancer Research, 77(13 Supplement): Abstract No. LB-185, 1-4 (Jul. 2017).

Brentjens et al., "Eradication of Systemic B-Cell Tumors by Genetically Targeted Human T Lymphocytes Co-Stimulated B Cd80 and Interleukin-15," Nature Medicine, 2003, 9: 279-286.

Brentjens, R.J., et al., "CD 19-Targeted T Cells Rapidly Induce Molecular Remissions in Adults with Chemotherapy-Refractory Acute Lymphoblastic Leukemia," Sci. Trans. Med. 5: 1-9 (2013).

Brentjens, R.J., et al., "Safety and persistence of adoptively transferred autologous CD19-targeted T cells in patients with relapsed or chemotherapy refractory B-cell leukemias," Blood 119(18): 4817-4828 (2011).

Bridgeman J. S. et al., The Optimal Antigen Response of Chimeric Antigen Receptors Harboring the CD3 Transmembrane Domain Is Dependent upon incorporation of the Receptor into the Endogenous TCR/CD3 Complex. J Immunol., May 17, 2010, vol. 184, No. 12, pp. 6938-3949.

Bridgeman, J.S., et al., "Building Better Chimeric Antigen Receptors for Adoptive T Cell Therapy," Current Gene Therapy 10: 77-90 (2010).

Brocker et al., "New simplified molecular design for functional T cell receptor," Eur J Immunol., 23(7):1435-1439, Jul. 1993.

Bromley et al., "The immunological synapse and CD28-CD80 interactions," Nat Immunol., 2(12):1159-1166, Dec. 2001.

Bronte, V., and Mocellin, S., "Suppressive Influences in the Immune Response to Cancer," J. Immunother . 32: 1-11 (2009).

Budagian, V. et al., "IL-15/IL-15 receptor biology: A guided tour through an expanding universe," Cytokine & Growth Factor Reviews, 17(4): 259-280 (2006).

Bukczynski et al., "Costimulation of Human CD28-T Cells by 4-1BB Ligand," Eur. J. Immunol., 2003, 33: 446-454.

Burkett et al., "Coordinate expression and trans presentation of interleukin (IL<)-15 supports natural killer cell and memory CD8+T Cell Homeostasis," J. Exp. Med, 2004, 200:825-834.

Calabrese, et al., "IL-6 biology: implications for clinical targeting in rheumatic disease," S. Nat. Rev. Rheumatol, 10, 720-727 (2014); published online Aug. 19, 2014 (corrected online Sep. 19, 2014).

Caligiuri et al., "Immunotherapeutic approaches for hematologic malignancies," Hematology Am Soc Hematol Educ Program, 2004, 37-53.

Campana et al., "Immunophenotyping of Leukemia," Journal of Immunol Methods, 2000, 243: 59-75.

Caratelli et al., "FCy Chimeric Receptor-Engineered T Cells: Methodology, Advantages, Limitations, and Clinical Relevance," Front Immunol., vol. 8, Article 457 , 8 pages (Apr. 27, 2017).

Cardoso AA, et al. Pre-B acute lymphoblastic leukemia cells may induce T-cell anergy to alloantigen. Blood 88:41-48 (1996).

Carson et al., "A potential rold for Interleukin-15 in the regulation of human natural killer cell survival," J. Clin. Invest., 1997, 99(5):937-943.

Carter, P., et al. ., "Identification and validation of cell surface antigens for antibody targeting in oncology," Endocrine-Related Cancer 11: 659-687 (2004).

Cesano, A., et al. "Reversal of Acute Myelogenous Leukemia in Humanized SCID Mice Using a Novel Adoptive Transfer Approach," J. Clin. Invest. 94: 1076-1084 (1994).

Chambers, C.A., "The expanding world of co-stimulation: the two-signal model revisited," TRENDS in Immunol., 2001, 22(4):217-223.

Champlin R. "T-cell depletion to prevent graft-versus-host disease after bone marrow transplantation," Hematol Oncol Clin North Am. Jun. 1990;4(3):687-698.

Chang et al., "Five Different Anti-Prostate-specific Membrane Antigen (PSMA) Antibodies Confirm PSIvIA Expression in Tumor-associated Neovasculature," Cancer Res., 59: 3192-3198 (1999).

Chang et al., "A Chimeric Receptor with NKG2D Specificity Enhances Natural Killer Cell Activation and Killing of Tumor Cells", Cancer Res. (2013), vol. 73, No. 6, pp. 1777-1786.

Chao, D. T. et al., "BCL-2 Family: Regulators of Cell Death", Annu. Rev. Immunol. (1998), vol. 16, pp. 395-419.

Cheresh et al., "Disialoganghosides GD2 and GD3 Arc Involved in the Attachment of Human Melanoma and Neuroblastoma Cells to Extracellular Matrix Proteins," J Cell Biol. 1986, 102(3):688-696.

Chertova, E. et al., "Characterization and favorable in vivo properties of heterodimeric soluble IL-15.IL-15Ralpha cytokine compared to IL-15 monomer," J Biol Chem., 288(25): 18093-18103 (2013).

Cheung et al., "Anti-Idiotypic Antibody Facilitates scFv Chimeric Immune Receptor-Gene Transduction and Clonal Expansion of Human Lymphocytes for Tumor Therapy," Hybridoma and Hybridomics, 2003, 24(4): 209-218.

Chiorean and Miller, "The biology of natural killer cells and implications for therapy of human disease," J Hematother Stem Cell Res, Aug. 2001, 10(4): 451-463.

Cho, D. et al., "Expansion and activation of natural killer cells for cancer immunotherapy," The Korean Journal of Laboratory Medicine, 29(2): 89-96 (2009).

Choi, B. D. et al., Chimeric antigen receptor T-cell immunotherapy for glioblastoma: practical insights for neurosurgeons, Neurosurg Focus, 44(6):E1 3, 1-6 (2018).

Clarke et al., "Folding studies of immunoglobulin-like beta-sandwich proteins suggest that they share a common folding pathway," Structure, 7(9):1145-1153, Sep. 15, 1999.

ClinicalTrials.gov, "A Multi-Center Study Evaluating KTE-C19 in Pediatric and Adolescent Subjects With Relapsed/ Refractory B-precursor Acute Lymphoblastic Leukemia (ZUMA-4)," available at https://clinicaltrials.gov/show/NCT02625480, NCT02625480 (Retrieved from the Internet on Jun. 21, 2016).

ClinicalTrials.gov, "A Phase 1-2 Multi-Center Study Evaluating KTE-C19 in Subjects With Refractory Aggressive Non-Hodgkin Lymphoma (ZUMA-1) (ZUMA-1)," available at https://clinicaltrials.gov/show/NCT02348216, NCT02348216 (Retrieved from the Internet on Jun. 21, 2016).

ClinicalTrials.gov, "A Study Evaluating KTE-C19 in Adult Subjects With Relapsed/Refractory B-precursor Acute Lymphoblastic Leukemia (r/r ALL) (ZUMA-3) (ZUMA-3)," available at https://clinicaltrials.gov/show/NCT02614066, NCT02614066 (Retrieved from the Internet on Jun. 21, 2016).

ClinicalTrials.gov, "Administration of Anti-CD19-chimeric-antigen-receptor-transduced T Cells From the Original Transplant Donor to Patients With Recurrent or Persistent B-cell Malignancies After Allogeneic Stem Cell Transplantation," available at https://clinicaltrials.gov/show/NCTO1087294, NCTO1087294 (Retrieved from the Internet on Jun. 21, 2016).

ClinicalTrials.gov, "Anti-CD19 White Blood Cells for Children and Young Adults With B Cell Leukemia or Lymphoma," available at https://clinicaltrials.gov/show/NCT01593696, NCT01593696.

ClinicalTrials.gov, "CAR T Cell Receptor Immunotherapy for Patients With B-cell Lymphoma," available at https://clinicaltrials.gov/show/NCT00924326, NCT00924326 (Retrieved from the Internet on Jun. 21, 2016).

ClinicalTrials.gov, "CD 19 CAR T Cells for B Cell Malignancies After Allogeneic Transplant," available at https://clinicaltrials.gov/show/NCT01475058, NCT01475058 (Retrieved from the Internet on Jun. 21, 2016).

ClinicalTrials.gov, "CD 19+ CAR T Cells for Lymphoid Malignancies," available at https://clinicaltrials.gov/show/NCT02529813, NCT02529813 (Retrieved from the Internet on Jun. 21, 2016).

ClinicalTrials.gov, "CD19 Chimeric Receptor Expressing T Lymphocytes In B-Cell Non Hodgkin's Lymphoma, ALL & CLL (CRETI-NH)," available at https://clinicaltrials.gov/show/NCT00586391, NCT00586391.

(56) References Cited

OTHER PUBLICATIONS

ClinicalTrials.gov, "Consolidation Therapy With Autologous T Cells Genetically Targeted to the B Cell Specific Antigen CD19 in Patients With Chronic Lymphocytic Leukemia Following Upfront Chemotherapy With Pentostatin, Cyclophosphamide and Rituximab," available at https://clinicaltrials.Qov/show/NCT01416974, NCT01416974.
ClinicalTrials.gov, "Genetically Engineered Lymphocyte Therapy in Treating Patients With B-Cell Leukemia or Lymphoma That is Resistant or Refractory to Chemotherapy," available at https://clinicaltrials.gov/show/NCT01029366, NCT01029366.
ClinicalTrials.gov, "High Dose Therapy and Autologous Stem Cell Transplantation Followed by Infusion of Chimeric Antigen Receptor (CAR) Modified T-Cells Directed Against CD19+ B-Cells for Relapsed and Refractory Aggressive B Cell Non-Hodgkin Lymphoma," available at https://clinicaltrials.Qov/show/NCT01840566, NCT01840566.
ClinicalTrials.gov, "In Vitro Expanded Allogeneic Epstein-Barr Virus Specific C1lotoxic T-Lymphocy1es (EBV-CTLs) Genetically Targeted to the CD19 Antigen in B-cell Malignancies," available at https://clinicaltrials.gov/show/NCT01430390, NCT01430390 (Retrieved from the Internet on Jun. 21, 2016).
ClinicalTrials.gov, "Precursor B Cell Acute Lymphoblastic Leukemia (B-ALL) Treated With Autologous T Cells Genetically Targeted to the B Cell Specific Antigen CD19," available at https://clinicaltrials.gov/show/NCT01044069, NCT01044069.
ClinicalTrials.gov, "Study Evaluating the Efficacy and Safety of JCAR015 in Adult B-cell Acute Lymphoblastic Leukemia (B-ALL) (ROCKET)," available at https://clinicaltrials.gov/show/NCT02535364, NCT02535364.
ClinicalTrials.gov, "T Cells Expressing a Fully-human AntiCD19 Chimeric Antigen Receptor for Treating B-cell Malignancies," available at https://clinicaltrials.gov/show/NCT02659943, NCT02659943.
ClinicalTrials.gov, "T-Lymphocytes Genetically Targeted to the B-Cell Specific Antigen CD19 in Pediatric and Young Adult Patients With Relapsed B-Cell Acute Lymphoblastic Leukemia," available at https://clinicaltrials.gov/show/NCT01860937, NCT01860937(Retrieved from the Internet on Jun. 21, 2016).
ClinicalTrials.gov, "Treatment of Relapsed or Chemotherapy Refractory Chronic Lymphocytic Leukemia or Indolent B Cell Lymphoma Using Autologous T Cells Genetically Targeted to the B Cell Specific Antigen CD 19", Available at: https://clinicaltrials.gov/show/NCT00466531, NCT00466531(Retrieved from the Internet on Jun. 21, 2016).
Cochran et al, "Receptor clustering and transmembrane signaling in T cells," Trends Biochem Sci., 26(5):304-310, May 2001.
Collins ct al., "Donor leukocyte infusions in 140 patients with relapsed malignancy after allogeneic bone marrow transplantation," J Clin Oncol, Feb. 1997, 15(2): 433-44.
Collins et al, "Donor leukocyte infusions in acute lymphocytic leukemia," Bone Marrow Transplantation, 2000, 26: 511-516.
Complaint in *Trustees of the University of Pennsylvania* v. *St. Jude Children's Research Hospital* in the U.S. District Court for the Eastern District of Pennsylvania, dated Mar. 22, 2013.
Cooley S. et al., "Donor selection for natural killer cell receptor genes leads to superior survival after unrelated transplantation for acute myelogenous leukemia", Blood (2010), vol. 116, No. 14, pp. 2411-2419.
Cooper et al., "T-Cell Clones can be Rendered Specific for CD 19: Toward the Selective Augmentation Of the Graft-Versus-B Lineage Leukemia Effect," Blood, 2003, pp. 1637-1644, vol. 101.
Cooper et al., "In vivo evidence for a dependence on interleukin 15 for Survival of natural killer cells"; Blood 100: 3633-3638 (2002).
Cordoba, S. P. et al., "The large ectodomains of CD45 and CD148 regulate their segregation from and inhibition of ligated T-cell receptor," Blood, The Journal of the American Society of Hematology, V. 121, N. 21, p. 4295-4302, c. 4301 (2013).
Cruz et al., "Infusion of donor-derived CD 19-redirected virus-specific T cells for B-cell malignancies relapsed after allogeneic stem cell transplant: a phase 1 study," Blood 122(17):2965-2973 (2013).
Culpepper, D. J. et al., "Systematic mutation and thermodynamic analysis of central tyrosine pairs in polyspecific NKG2D receptor interactions," Molecular Immunology, V. 48, N. 4, p. 516-523, c. 521-522 (2011).
Curti, A. et al., "Successful transfer of alloreactive haploidentical KIR ligand-mismatched natural killer cells after Infusion in elderly high risk acute myeloid leukemia patients" Blood (2011) vol. 118, No. 12, pp. 3273-3279.
Dalal, A.-R. et al., Third-Generation Human Epidermal Growth Factor Receptor 2 Chimeric Antigen Receptor Expression on Human T Cells Improves with Two-Signal Activation, Human Gene Therapy, 845-852 (2018) (Abstract).
Damle et al., "Differential regulatory signals delivered by antibody binding to the CD28 (Tp44) molecule during the activation of human T lymphocytes," J Immunol., 140(6):1753-1761, Mar. 15, 1988.
Darcy, P.K., et al., "Expression in cytotoxic T lymphocytes of a single-chain anti-carcinoembryonic antigen antibody. Redirected Fas ligand-mediated lysis of colon carcinoma," Eur. J. Immunol. 28: 1663-1672 (1998).
Davila, M.L., et al., "Efficacy and Toxicity Management of 19-28z CAR T Cell Therapy in B Cell Acute Lymphoblastic Leukemia," Science Translat. Med. 6(24) (2014).
De Felipe, P., "Polycistronic Viral Vectors," Current Gene Therapy, V. 2, N. 3, p. 355-378, c. 360 (2002).
De La Chapelle, A. et al., "Truncated erythropoietin receptor causes dominantly inherited benign human erythroc)tosis," Proc Natl Acad Sci USA., vol. 90, No. 10, pp. 4495-4499 (May 1993).
Debenedette et al., "Role of 4-1BB ligand in costimulation of T lymphocyte growth and its upregulation on M12 B lymphomas by cAMP," J Exp Med, Mar. 1995, 181(3): 985-992.
DeBenedette, MA, et al.. "Costimulatin ofCD28-T Lymphocytes by 4-1 BB Ligand," J. Jmmzmol., 1997, pp. 551-559, vol. 158.
Declaration in Support of Trustees of the University of Pennsylvania's Motion for Summary Judgment for Invalidity of Patent in Suit in *Trustees of the University of Pennsylvania* v. *St. Jude Children's Research Hospital* in the US District Court for the Eastern District of Pennsylvania, dated Nov. 15, 2013. (Lit Doc. 24).
Delahaye, N. F. et al., "Alternatively spliced NKp30 isoforms affect the prognosis of gastrointestinal stromal tumors" Nature Medicine (2011) vol. 17, No. 6, pp. 700-708.
Denman et al. Membrane-Bound IL-21 Promotes Sustained Ex Vivo Proliferation of Human Natural Killer Cells. PLos One. Jan. 2012 | vol. 7 | Issue 1 | e30264 (Year: 2012).
Diefenbach et al., "Selective associations with signaling proteins determine stimulatory versus costimulatory activity of NKG2D," Nature Publishing Group, vol. 3, No. 12, pp. 1142-1149, (Dec. 2002).
Dotti ct al., "Design and Development of Therapies using Chimeric Antigen Receptor-Expressing T cells," Immunol Rev., 257(1), 35 pages, Jan. 2014.
Doubrovian, et al., "Evasion from NK Cell Immunity by MHC Class I Chain-Related Molecules Expressing Colon Adenocarcinoma," Journal ofImmunology, vol. 171, pp. 6891-6899, (2003).
Dowell, A. C. , "Studies of Human T cell Costimulation: Potential for the Immunotherapy of Cancer," A thesis submitted to The University of Birmingham for the degree of Doctor of Philosophy, Cruk Institute for Cancer Studies, 2010.
Dubois et al., "IL-15Ra recycles and presents IL-15 In trans to neighboring cells," Immunity, Nov. 2002, 17(5): 537-47.
Dubois, S. et al., "Preassociation of IL-15 with IL-15R alpha-IgG1-Fc Enhances Its Activity on Proliferation of NK and CD8+/CD44high T Cells and Its Antitumor Action" The Journal of Immunology (2008) vol. 180, pp. 2099-2106.
Dudley, M.E., et al., "Adoptive Transfer of Cloned Melanoma-Reactive T Lymphocytes for the Treatment of Patients with Metastatic Melanoma," J. Immunother. 24: 363-373 (2001).

(56) References Cited

OTHER PUBLICATIONS

Eisuke D. et al., "Synergistic effect of IL-2, IL-12 and IL-18 on the activation of ex vivo-expanded human V[gamma]9V[delta]2 T cells", J Osaka Dent Univ, Apr. 1, 2018, pp. 51-57.
Ellis et al., "Interactions of CD80 and CD86 with CD28 and CTLA4," J Immunol., 156(8):2700-2709, Apr. 15, 1996.
Eshhar et al., "Specific activation and targeting of cytotoxic lymphocytes through chimeric single chains consisting of antibody-binding domains and the y or ( subunits of the inmunoglobulin and T-cell receptors," Proc. Natl. Acad. Sci. USA, 1993, 90:720-724.
Eshhar, Z, et al , "Functional Expression of Chimeric Receptor Genes in Human T Cells," J. Immunol. Methods, 2001, 248(1-2):67-76.
Eshhar, Z., "Tumor-specific T-bodies: towards clinical application," Cancer Immunol. Immunother. 45: 131-136 (1997).
Extended European Search Report and Written Opinion dated Dec. 10, 2020 for International Application No. PCT/SG2018/050138, entitled "Stimulatory Cell Lines for Ex Vivo Expansion and Activation of Natural Killer Cells".
Eyguem et al., "Targeting a CAR to the TRAC locus with CRISPR/Cas9 enchances tumour rejction" Nature, 2017, 543(7643): 113-117.
Fagan, E.A., and Eddleston, A.L.W.F., "Immunotherapy for cancer: the use oflymphokine activated killer (LAK) cells," Gut 28: 113-116 (1987).
Fang, F., et al., "NK cell-based immunotherapy for cancer", Seminars in Immunology, vol. 31, Jun. 2017, pp. 37-54.
Farag et al., "Natural killer cell receptors: new biology and insights into the Graft-versus-leukemia effect," Blood, 2002, 100(6): 1935-1947.
Fehniger and Caligiuri, "Interleukin 15: biology and relevance to human disease," Blood, Jan. 2001, 97(1): 14-32.
Fehniger TA, et al., "Ontogeny and expansion of human natural killer cells: clinical implications", Int Rev Immunol. Jun. 2001; 20(3-4):503-534.
Femandez-Messina et al., "Human NKG2D-ligands: cell biology strategies ensure immune recognition," Frontiers in Immunology, vol. 3, Article 299, 9 Pages, (Sep. 2012).
Ferlazzo, G. et al, "Distinct roles of IL-12 and IL-15 in human natural killer cell activation by dendritic cells from secondary lymphoid organs," PNAS, 101(47): 16606- 16611 (2004).
Ferris, R. L. et al., "Tumor Antigen-Targeted, Monoclonal Antibody-Based Immunotherapy: Clinical Response, Cellular Immunity and Immunoescape" Journal of Clinical Oncology (2010) vol. 28, No. 28, pp. 4390-4399.
Finney et al., "Activation of resting human primary T cells with chimeric receptors: costimulation from CD28, inducible costimulator, CD134, and CD137 in series with signals from the TCR s chain", J Immunol. Jan. 2004 I; 172(1):104-113.
Finney et al., "Chimeric receptors providing both primary and costimulatory signaling in T cells from a single gene product," J Immunol. Sep. 15, 1998;161(6):2791-2797.
Foon et al., "Clinical and immune responses in advanced melanoma patients immunized with an anti-idiotype antibody mimicking disialoganglioside GD2," J Clin Oncol., 18(2):376-384, Jan. 2000.
Freshney, Animal Cell Culture, Cancer Research Campaign, Dept. of Oncology, University of Glasgow, 1986, 248 pages [Table of Contents Only].
Fujisaki, H. et al., "Replicative potential of human natural killer cells" British Journal of Haematology (2009) vol. 145, pp. 606-613.
Fundamental Immunology, Third Edition, Chs. 1, 13 and 32, Paul, W.E., ed., pp. 1-20, 467-504, 1143-1178, Raven Press, New York (1993).
Gacerez, A et al., "How Chimeric Antigen Receptor Design Affects Adoptive T Cell Therapy," Journal of Cellular Physiology, vol. 231, No. 12, pp. 2590-2598 (Jun. 2, 2016).
Galustian C. et al., MP84-07A tale of tails—A novel approach to immunotherapy of prostate cancer. J Ural., May 10, 2016, vol. 195, No. 4S, pp. e1092.
Gardner, R., et al., "Acquisition of a CD19 negative myeloid phenotype allows immune escape of MLL-rearranged B-ALL from CD19 CAR-T cell therapy," Blood (forthcoming 2016).
Garrity et al. "The activating NKG2D receptor assembles in the membrane with two signaling dimers into a hexameric structure", 2005, Proc. Natl. Acad. Sci. USA. 102:7641-7646.
Geiger and Jyothi, "Development and application for receptor-modified T lymphocytes for adoptive immunotherapy," Transfus Med Rev, Jan. 2001, 15(1): 21-34.
Geiger et al., "Integrated src kinase and costimulatory activity enhances signal transduction through single-chain chimeric receptors in T lymphocytes", Blood. Oct. 15, 2001; 98(8):2364-2371.
GenBank Accession No. NM 007360 GI:15221123, *Homo sapiens* killer cell lectin like receptor K1 (KLRK1), mRNA, dated May 29, 2017, 4 pages.
GenBank Accession No. NM_0 1 1612 GI: 6755830, Mus musculus tumor necrosis factor receptor superfamily, member 9 (Tnfrsf9), mRNA, dated Oct. 26, 2004, 8 pages.
GenBank Accession No. NM_000734 GI: 27886640, *Homo sapiens* CD8 antigen, alpha polypeptide (TiT3 complex) (CD3Z), transcript variant 2, mRNA, dated Oct. 27, 2004, 6 pages.
GenBank Accession No. NM_000734 GI: 37595563, *Homo sapiens* CD3Z antigen, s polypeptide (TiT3 complex) (CD3Z), transcript variant 2, mRNA, dated Oct. 27, 2004, 6 pages.
GenBank Accession No. NM_001768 GI: 27886640, *Homo sapiens* CD8 antigen, a polypeptide (p32) (CD8A), transcript variant 1, mRNA, dated Oct. 27, 2004, 5 pages.
GenBank Accession No. NM_172175.2, *Homo sapiens* interleukin 15 (IL15), transcript variant 2, mRNA, dated Feb. 12, 2011, 4 pages.
Germain et al., "T-cell signaling: the importance of receptor clustering," Curr Biol., 7(10):R640-R644, Oct. 1, 1997.
Ghobadi, et al., "Updated Phase 1 Results from ZUMA-1: A Phase 1-2 Multicenter StudyEvaluating the Safety and Efficacy of KTE-C19 (Anti-CD 19 CAR T Cells) in Subjects With Refractory Aggressive Non-Hodgkin Lymphoma," Slides accompanying oral presentation at the American Association for Cancer Research Annual Meeting, New Orleans, Louisiana 2016).
Ghorashian, S., et al., "CD 19 chimeric antigen receptor T cell therapy for haematological mali nancies," Br. J. Haematol. 169:463-478 2015).
Giebel, S. et al., "Survival advantage with KIR ligand incompatibility in hematopoietic stem cell transplantation from unrelated donors" Blood (2003) vol. 102, No. 3, pp. 814-819.
Gilfillan et al. "NKG2D recruits two distinct adapters to trigger NK cell activation and costimulation" Nature Immunnology (2002), vol. 3, No. 12, pp. 1150-1155.
Gill. S., et al., "Chimeric antigen receptor T cell therapy: 25 years in tire making," Blood Rev. (2015), 30 (3): 157-167.
Gillet et al., Selectable Markers for Gene Therapy, Chapter 26 of Gene and Cell Therapy:Therapeutic Mechanisms and Strategies, 3rd Ed. N .S. Templeton Ed, (CRC Press:Bpca Ratpm. FL), pp. 555 and 558, 2009.
Ginald, L., et al., "Levels of expression of CD19 and CD20 in chronic B cell leukaemias," J. Clin. Pathol. 51: 364-369 (1998).
Giuliani, M. et al., "Generation of a novel regulatory NK cell subset from peripheral blood CD34+ progenitors promoted by membrane-bound IL-15," PLos One, 3(5): e2241 (2008).
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neop lasia, 1999, 1(2): 123-127.
Goodier and Londei, "CD28 is not directly involved in the response of human CD3-CD56+ natural killer cells to lipopolysaccharide: a role for T cells," Immunology, Apr. 2004, 111(4): 384-90.
Goodwin et al., "Molecular cloning of a ligand for the inducible T cell gene 4-1 BB: a member of an emerging family of cytokines with homology to tumor necrosis factor", Eur J Immunol. Oct. 1993; 23( 10):263 1-2641.
Grauer et al., "Identification, Purification, and Subcellular Localization of Prostate-specific Membrane Antigen PSM' Protein in the LNCaP Prostatic Carcinoma Cell Line," Cancer Res., 58: 4787-4789 (1998).

(56) References Cited

OTHER PUBLICATIONS

Greene et al., "Covalent dimerization of CD28/CTLA-4 and oligomerization of CD80/CD86 regulate T cell costimulatory interactions," J Biol Chem., 271(43):26762-26771, Oct. 25, 1996.
Greenfield, E.A., et al., "CD28/B7 Costimulation: A Review," Crit. Rev. Immunol. 18: 389-418 (1998).
Greenwald et al., "The B7 Family Revisited," Annu. Rev. ImmunoL, 2005, 23: 515-548.
Grillo-Lopez, "Rituximab: An Insider's Historical Perspective," Seminars in Oncology 27(6 Suppl 12): 9-16 (2012).
Grillo-Lopez, A., "Rituximab: An Insider's Historical Perspective," Seminars in Oncology 27(6 Suppl 12): 9-16 (2012).
Gross and Eshhar "Endowing T cells with antibody specificity using chimeric T cell receptors," FASEB J. Dec. 1992;6(15):3370-3378.
Grupp et al., "Chimeric antigen receptor-modified T cells for acute lymphoid leukemia," N Engl J Med. Apr. 18, 2013; 368 (16):1509-1518.
Handgretinger, R., et al., "A phase I study of neuroblastoma with the anti-ganglioside GD2 antibody 14.G2a," Cancer Immunol. Immunother. 35: 199-204 (1992).
Hara et al., "NKG2D gene polymorphisms are associated with disease control of chronic myeloid leukemia by dasatinib," Int. J. Hematol., 9 pages, Aug. 9, 2017.
Harada H, et al, "Selective expansion of human natural killer cells from peripheral blood mononuclear cells by the cell line, HFWT", Jpn J Cancer Res. Mar. 2002; 93(3):313-319.
Harada, H., et al., "A Wilms Tumor Cell Line, HFWT, can Greatly Stimulate Proliferation of CD56+ Human Natural Killer Cells and their Novel Precursors in Blood Mononuclear Cells," Exp. Hematology, 2004, pp. 614-621, vol. 32.
Harding et al., "CD28-mediated signalling co-stimulates murine T cells and prevents induction of anergy in T-cell clones," Nature, 356(6370):607-609, Apr. 16, 1992.
Harmon et al., "Dexamethasone induces irreversible G1 arrest and death of a human lymphoid cell line," J Cell Physiol, Feb. 1979, 98(2): 267-278.
Hasan, A.N., "Soluble and membrane-bound interleukin (IL)-15 Ra/IL-15 complexesmediate proliferation of high-avidity central memory CD81T cells foradoptive immunotherapy of cancer and infections," Clinical and Experimental Immunology, 186: 249-265, 2016.
Haynes NM, et al., "Rejection of syngeneic colon carcinoma by CTLs expressing single-chain antibody receptors codelivering CD28 costimulation", J Immunol. Nov. 15, 2002; 169(10):5780-5786.
Haynes NM, et al., "Single-chain antigen recognition receptors that costimulate potent rejection of established experimental tumors", Blood, Nov. 2002 I; 100(9):3155-3163.
Haynes, N.M., et al., "Redirecting Mouse CTL Against Colon Carcinoma: Superior Signaling Efficacy of Single-Chain Variable Domain Chimeras Containing TCR- vs Fc£RI-y," J. Immunol. 166: 182-187 (2001).
Heuser, C., et al., "T-cell activation by recombinant immunoreceptors: Impact of the intracellular signalling domain on the stability of receptor expression and antigen-specific activation of grafted T cells," Gene Therapy 10: 1408-1419 (2003).
Hoffmann, S.C. et al. "2B4 Engagement Mediates Rapid LFA-1 and Actin-Dependent NK Cell Adhesion to Tumor Cells as Measured by Single Cell Force Spectroscopy," J. Immunol, 186(5): 2757-2764 (Jan. 2011).
Hollyman, D , et al., "Manufacturing Validation of Biologically Functional T Cells Targeted to CD19 Antigen for Autologous Adoptive T cell Therapy," J. Immunother. 32: 169-180 (2009).
Hombach , et al., "Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule", J Immunol., Dec. 1, 2001; 167(11 ):6123-6131.
Hombach et al., "T-Cell Activation by Recombinant Receptors: CD28 Costimulation Is Required for Interleukin 2 Secretion and Receptor-mediated T-Cell Proliferation but Does Not Affect Receptor-mediated Target Cell Lysis," Cancer Res., Mar. 1, 2001, 61:1976-1982.
Hombach et al., "Costimulation by chimeric antigen receptors revisited the T cell antitumor response benefits from combined CD28-OX40 signalling," Int. J. Canc. 129:2935-2944 (2011).
Hombach et al., "The recombinant T cell receptor strategy: insights into structure and function of recombinant immunoreceptors on the \vay towards an optimal receptor design for cellular immunotherapy," Curr Gene Ther. 2002 2 (2):211-226.
Hombach, A., et al., "Adoptive immunotherapy with genetically engineered T cells: modification of the IgG1 Fe 'spacer' domain in the extracellular moiety of chimeric antigen receptors avoids 'offtarget' activation and unintended initiation of an innate immune response," Gene Therapy 17: 1206-1213 (2010).
Hombach, A., et al., "T cell activation by recombinant Fc£RI y-chain immune receptors: an extracellular spacer domain impairs antigendependent T cell activation but not antigen recognition," Gene Therapy 7: 1067-1075 (2000).
Horng et al., "NKG2D signaling is coupled to the interleukin 15 receptor signaling pathway," Nature Immunology, vol. 8, No. 12, pp. 1345-1352, Dec. 2007.
Hsu, C. er al., "Cytokine-independent growth and clonal expansion of a primary human CD8+ T-cell Clone following retroviral transduction with the IL-15 gene," Blood, 109(12): 5168-5177 (2007).
Hsu, K. C. et al., "Improved outcome in HLA-identical sibling hematopoietic stem-cell transplantation for acute myelogenous leukemia predicted by KIR and HLA genotypes" Blood (2005) vol. 105, No. 12, pp. 4878-4884.
https ://www.proteinatlas.org/ENSG00000177455-CD19/ pathology, accessed Jun. 27, 2019.
Huang Q. S. et al., Expansion of human natural killer cells ex vivo. Chine J Cell Mol Immunol, Dec. 31, 2008, vol. 24, No. 12, pp. 1167-1170.
Hurtado et al., "Potential role of 4-IBB in T cell activation. Comparison with the costimulatory molecule CD28," J Immunol, Oct. 1995, 155(7): 3360-3367.
Hurtado et al., "Signals through 4-1 BB are costimulatory to previously activated splenic T cells and inhibit activation-induced cell death", J Immunol., Mar. 1997, 158(6):2600-2609.
Hurton et al., "Tethered IL-15 augments antitumor activity and promotes a stem-cell memory subset in tumor-specific T cells," Proc. Natl. Acad. Sci, USA, 113(48):E7788-E7797 (Nov. 2016).
Ignacio et al, "Monoclonal antibodies against the 4-1BB T-cell activation molecule eradicate established tumors," Nature Med., 1997, 3:682-685.
Imai C et al. "Genetic modification of primary natural killer cells overcomes inhibitory signals and induces specific killing of leukemic cells," Blood. 2005;106:376-383.
Imai C, et al., "Chimeric receptors with 4-1BB signaling capacity provoke potent cytotoxicity against acute lymphoblastic leukemia", Leukemia. Feb. 12, 2004; 18(4):676-684.
Imai C, et al., "T-cell immunotherapy for B-lineage acute lymphoblastic leukemia using chimeric antigen receptors that deliver 4-1 BB-mediated costimulatory signals", Blood. Nov. 16, 2003; 102(11):66a-67a.
Imai et al. "Genetic modification of T cells for cancer therapy", Journal of Biological Regulators and Homeostatic Agents, 18 (1): p. 62-71; Jan. 2004; (abstract only).
Imai, C., et al., "A novel method for propagating primary natural killer (NK) cells allows highly efficient expression of anti-CD19 chimeric receptors and generation of powerful cytotoxicity against NK-resistant acute lymphoblastic leukemia cells", Abtract #306, Blood 104 (Nov. 16, 2004).
Imamura M et al. Autonomous growth and increased cytotoxicity of natural killer cells expressing membrane-bound interleukin-15. Blood (2014) 124 (7): 1081-1088) (Year: 2014).
Inaguma et al., "Expression of neural cell adhesion molecule L1 (CD171) in neuroectodermal and other tumors. An immunohistochemical study of 5155 tumors and critical evaluation of CD171 prognostic value in gastrointestinal stromal tumors," Oncotarge., 7(34):55276-55289, Jul. 11, 2016.

(56) References Cited

OTHER PUBLICATIONS

International Preliminary Report on Patentability, re PCT Application No. PCT/SG2018/050138, dated Oct. 10, 2019.
International Preliminary Report on Patentability, re PCT Application No. PCT/US2020/044033, dated Feb. 10, 2022.
International Preliminary Report on Patentability, re PCT Application No. PCT/US2021/071330, dated Mar. 16, 2023.
International Preliminary Report on Patentability, re PCT Application No. PCT/US2022/074164, dated Feb. 8, 2024.
International Search Report and Written Opinion for International Application No. PCT/US21/71330, mailed Feb. 15, 2022, in 20 pages.
International Search Report and Written Opinion, re PCT Application No. PCT/US2024/013779, dated May 10, 2024.
International Search Report and Written Opinion, re PCT Application No. PCT/SG2018/050138, dated Jul. 4, 2018.
International Search Report and Written Opinion, re PCT Application No. PCT/US2020/044033, dated Dec. 18, 2020.
International Search Report and Written Opinion, re PCT Application No. PCT/US2022/074164, dated Oct. 18, 2022.
International Search Report and Written Opinion, re PCT Application No. PCT/US2023/077336, dated Apr. 12, 2024.
Ishii, H. et al., "Monocytes enhance cell proliferation and LMP1 expression of nasal natural killer/T-cell lymphoma cells by cell contact-dependent interaction through membrane-bound IL-15," International Journal of Cancer, 130: 48-58 (2012).
Ishiwata I, et al., "Carcinoembryonic proteins produced by Wilms' tumor cells in vitro and in vivo", Exp Pathol. 1991; 41(1):1-9.
Israeli, R.S., et al., "Expression of the Prostate-specific Membrane Antigen," Cancer Res., 1994, 54:1807-1811.
Ito et al., "Hyperdiploid acute lymphoblastic leukemia with 51 to 65 chromosomes: a distinct biological entity with a marked propensity to undergo apoptosis," Blood, Jan. 1999, 93(1): 315-20.
Jena et al., "Redirecting T-cell specificity by introducing a tumor-specific chimeric antigen receptor," Blood, 2010, 116 (7):1035-1044.
Jenkins et al., "Inhibition of antigen-specific proliferation of type 1 murine T cell clones after stimulation with immobilized anti-CD3 monoclonal antibody," J Immunol., 144(1):16-22, Jan. 1, 1990.
Jensen, M., et al., "CD20 is a molecular target for scFvFc: receptor redirected T cells: implications for cellular immunotherapy of CD20+ malignancy," Biol. Blood and Marrow Transplantation 4: 75-83 (1998).
Jensen, M.C. et al., "Anti-transgene Rejection Responses Contribute to Attenuated Persistence of Adoptively Transferred CD20/CD19—Specific Chimeric Antigen Receptor Redirected T Cells in Humans," Biol. Blood Marrow Transplant 16: 1245-1256 (2010).
Jiang et al., "Functional characterization of interleukin-15 gene transduction into the human natural killer cell line NKL," Cytother. 10(3):265-274, 2008.
Jiang, W. et al., "hIL-15 gene-modified human natural killer cells (NKL-IL15) augments the anti-human hepatocellular carcinoma effect in vivo," Immunobiology, 219: 547-553 (Mar. 12, 2014).
Johnson and Jenkins, "The role of anergy in peripheral T cell unresponsiveness," Life Sci, 1994, 55(23): 1767-1780.
June et al., "The B7 and CD28 receptor families," Immunol Today, Jul. 1994, 15(7): 321- 331.
Juno Therapeutics, Inc.'s Answer to Amended Complaint in *Trustees of the University of Pennsylvania* v. *St. Jude Children's Research Hospital* in the U.S. District Court for the Eastern District of Pennsylvania, dated Dec. 20, 2013. (Lit Doc. 50).
Kabalak et al., "Association of an NKG2D gene variant with systemic lupus erythematosus in two populations," Human Immunology, vol. 71, pp. 74-78, 2010.
Kaiser, B.K. et al., "Structural basis for NKG2A/CD94 Recognition of HLA-E," Proc Nat'l Acad Sci USA, 105(18):6696-6701 (Apr. 2008).
Kalos et al, "T Cells vvith Chimeric Antigen Receptors Have Potent Antitumor Effects and Can Establish Memory in Patients with Advanced Leukemia," Sci Transl Med. Aug. 10, 2011;3(95):95ra73.
Kariv, I., ct al., "Analysis of the Site of Interaction of CD28 with Its Counter-Receptors CD80 and CD86 and Correlation with Function," J. of Immunol. 157: 29-38 (1996).
Kershaw, M.H., et al., "A Phase I Study on Adoptive Immunotherapy Using Gene-Modified T Cells for Ovarian Cancer," Clin. Cancer Res. 12: 6106-6115 (2006).
Khammari, A., et al., "Long-term follow-up of patients treated by adoptive transfer of melanoma tumor-infiltrating lymphocytes as adjuvant therapy for stage III melanoma," Cancer Immunol. Immunother. 56: 1853-1860 (2007).
Kim Y J, et al., "Human 4-1 BB regulates CD28 co-stimulation to promote Th1 cell responses. Eur J Immunol", Mar. 1998; 28(3):881-890.
Kim Y J, et al., "Novel T cell antigen 4-1 BB associates with the protein tyrosine kinase p56 I ckl", J Immunol. Aug. 1993 I; 151(3): 1255-1262.
Kitaya, K. et al., "IL-15 expression at human endometrium and decidua," Biology of Reproduction, 63(3): 683-687 (2000).
Kitaya, K. et al., "Regulatory role of membrane-bound form interleukin-15 on human uterine microvascular endothelial cells in circulating CD16(-) natural killer cell extravasation into human endometrium," Bioloav of Reproduction, 89(3): 70 (2013).
Kite Pharma Inc.'s Reply to Patent Owner'S Response to the Petition re: 1PR2015-01719, 35 pages, Aug. 4, 2016.
Klein E, et al., "Properties of the K562 cell line, derived from a patient with chronic myeloid leukemia", Int J Cancer. Oct. 15, 1976; 18(4 ):421-431.
Klingemann HG, et al., "Ex vivo expansion of natural killer cells for clinical applications", Cy1otherapy. 2004; 6(1 ):15-22.
Kobayashi et al., "Role of trans-cellular IL-15 presentation in the activation ofNK cell-mediated killing, which leads to enhanced tumor immunosurveillance," Blood, Jan. 2005, 105(2): 721-727.
Kober, J., et al. "The capacity of the TNF family members 4-1BBL, OX40L, CD70, GITRL, CD30L and LIGHT to costimulate human T cells," Eur J Immuno, vol. 38, No. 10, pp. 2678-2688 (Oct. 28, 2008).
Kochenderfer, J .N., et al., "B-cell depletion and remissions of malignancy along With cytokine-associated toxicity in a clinical trial of anti-CD19 chimeric-antigen-receptor-transduced T cells," Blood 119(12):2709-2720 (2012).
Kochenderfer, J.N. et al. "Construction and Preclinical Evaluation of an Anti-CD19 Chimeric Antigen Receptor," J. Immunother. 32(7):689-702 (2009).
Kochenderfer, J.N., "Eradication of B-lineage and regression of lymphoma in a patient treated with autologous T cells genetically engineered to recognize CD19," Blood, 2010, 116(20), 4099-4102.
Kochenderfer, J.N., et al. "Chemotherapy-Refractory Diffuse Large B-Cell Lymphoma and Indolent B-Cell Malignancies Can be Effectively Treated With Autologous T Cells Expressing an Anti-CD19 Chimeric Antigen Receptor," J. Clin. Oneal. (2014).
Kochenderfer, J.N., et al. "Donor-derived CD19-targeted T cells cause regression of malignancy persisting after allogeneic hematopoietic stem cell transplantation," Blood 122(25): 4129-4139 (2013).
Koeffler and Golde, "Acute myelogenous leukemia: a human cell line responsive to colony-stimulating activity," Science, Jun. 1978, 200(4337): 1153-1154.
Koehler et al. "Engineered T Cells for the Adoptive Therapy of B-Cell Chronic Lymphocytic Leukaemia," Advances in Hematology, vol. 2012, Article ID 595060, 13 pages; doi:10.1155/2012/595060.
Kohn et al. "CARs on track in the clinic," Mar. 2011, Molecular Therapy: The Journal of the American Society of Gene Therapy, 19:432-438.
Koka, R. et al., "Cutting edge: murine dendritic cells require IL-15R a to prime NK cells," J Immunol., 173(6): 3594-3598 (2004).
Kolb HJ, et al., "Graft-versus-leukemia effect of donor lymphocyte transfusions in marrow grafted patients," Blood, 1995, 6:2041-2050.
Kowalik, C.M., "CD28 Costimulation Provided through a CD19-Specific Chimeric Antigen Receptor Enhances In vivo Persistence and Antitumor Efficacy of Adoptively Transferred T Cells," Cancer Research 66: 10995-11004 (2006).

(56) References Cited

OTHER PUBLICATIONS

Krampera et al., "Bone marrow mesenchymal stem cells inhibit the respnose of nai:Ve and memory antigen-specific T cells to their cognate peptide," Blood, May 2003, 101(9): 3722-9.
Krause et al., "Antigen-dependent CD28 Signaling Selectively Enhances Survival and Proliferation in Genetically Modified Activated Human Primary T Lymphocytes," J. Exp. Med., 1998, 188(4): 619-626.
Krug, C., et al., "Stability and activity of MCSP-specific chimeric antigen receptors (CARs) depend on the scFv antigen-binding domain and the protein backbone," Cancer Immunol. Immunother. 64:1623-1635 (2015).
Kumar B. B. et al., "Natural Killer Cells Expanded and Preactivated Exhibit Enhanced Antitumor Activity against Different Tumor Cells in Vitro", Asian Pacific Journal of Cancer Prevention, vol. 21, No. 6, Jun. 6, 2020, pp. 1595-1605.
Kuo et al., "Efficient gene transfer into primary murine lymphocytes obviating the need for drug selection," Blood, Aug. 1993, 82(3): 845-52.
Kurokawa, M. and S. Kombluth, "Caspascs and kinascs in a death grip," Cell, 138(5): 838-854 (2009).
Kwon B, et al., "cDNA sequences of two inducible T-cell genes", Proc Natl Acad Sci U SA., Mar. 1986; 86(6):1963-1967.
LaBonte, M.L. et al., "Molecular Determinants Regulating the Pairing of NKG2 Molecules with CD94 for Cell Surface Heterodimer Expression," J Immunol, 172(11): 6902-6912 (May 2004).
Lafreniere, R., et al.., "Successful Immunotherapy of Murine Experimental Hepatic Metastases with Lymphokine-activated Killer Cells and Recombinant Interleukin 2," Cancer Res. 45: 3735-3741 (1985).
Lamers, C.H.J., et al., "Treatment of Metastatic Renal Cell Carcinoma With Autologous T-Lymphocytes Genetically Retargeted Against Carbonic Anhydrase IX: First Clinical Experience," J. Clin. Oncol. 24: e20-e22 (2006).
Lang et al., "Absence of B7.1-CD28/CTLA-4-mediated co-stimulation in human NK cells," Eur. J. Immunol, Mar. 1998, 28: 780-786.
Langer et al., "Comparative Evaluation of Peripheral Blood T Cells and Resultant Engineered Anti-CD19 CAR T-Cell Products From Patients With Relapsed/Refractory Non-Hodgkin Lymphoma (NHL)," Poster session presented at the American Association for Cancer Research Annual Meeting, New Orleans, Louisiana.
Lanier, Lewis L., "NK Cell Recognition," Annual Review of Immunology, vol. 23, No. 1, pp. 225-274 (2005).
Lanzavecchia et al., "Antigen decoding by T lymphocytes: from synapses to fate determination," Nat Immunol., 2(6):487-492, Jun. 2001.
Lapteva, N. et al., "Large-scale ex vivo expansion and characterization of natural killer cells for clinical applications," Cytotherapy, 14(9): 1131-1143 (2012).
Lauwerys, et al., "Synergistic Proliferation And Activation Of Natural Killer Cells By Interleukin 12 And Interleukin 18", Cytokine, vol. 11, No. 11, Nov. 1, 1999, pp. 822-830.
Le Blanc et al., "Mesenchymal stem cells inhibit and stimulate mixed lymphocyte cultures and mitogenic responses independently of the major histocompatability complex," Scand J Immunol, Jan. 2003, 57(1): 11-20.
Lee et al., "T cells expressing CD19 chimeric antigen receptors for acute lymphoblastic leukaemia in children and young adults: a phase 1 dose-escalation trial," Lancet 385:517-528 (2015).
Lehner at al. "Redirecting T Cells to Ewing's Sarcoma family of Tumors by a Chimeric NKG2D Receptor Expressed by Lentiviral Transduction or Mrna Transfection", 2012, PloS. One 7:e31210.
Leitner et al., "T cell stimulator cells, an efficient and versatile cellular system to assess the role of costimulatory ligands in the activation of human T cells," Journal of Immunological Methods, 362, 131-141, 2010.
Leung et al., "Determinants of antileukemia effects of allogneic NK cells," J Immunol, Jan. 2004, 172(1): 644-50.
Li et al., "Costimulation by CD48 and B7-1 induces immunity against poorly immunogenic tumors," J Exp Med, Feb. 1996, 183(2): 639-644.
Li et al., "Polarization Effects of 4-1BB during CD28 Costimulation in Generating Tumor-reactive T Cells for Cancer Immunotherapy," Cancer Research, vol. 63, pp. 2546-2552, May 15, 2003.
Li Q. et al., Bifacial effects of engineering tumour cell-derived exosomes on human natural killer cells. Experimental Cell Research, Dec. 19, 2017, vol. 363, No. 2, pp. 141-150.
Liao, W. et al. ., "Interleukin-2 at the crossroads of effector responses, tolerance, and immunotherapy." Immunity, 38(1): 13-25 (2013).
Liebowitz et al., "Costimulatory approaches to adoptive immunotherapy," Curr Opin Oncol, Nov. 1998, 10(6): 533-41.
Lima, et al., "Interleukin-6 Neutralization by Antibodies Immobilized at the Surface of Polymeric Nanoparticles as a Therapeutic Strategy for Arthritic Diseases," ACS Appl. Mater. Interfaces 2018, 10, 13839-13850.
Linsley and Ledbetter, "The role of CD28 receptor during T cell responses to antigen," Annu Rev Immunol, 1993, 191-212.
Liu, E. et al., "GMP-Compliant Universal Antigen Presenting Cells (Uapc) Promote the Metabolic Fitness and Antitumor Activity of Armored Cord Blood CAR-NK Cells", frontiers in Immunology, Feb. 26, 2021, vol. 12, Article 626098, 14 pages.
Liu, E. et al., "Use of CAR-Transduced Natural Killer Cells in CD19-Positive Lymphoid Tumors", N. Engl .J. Med., vol. 382, No. 6, Feb. 6, 2020, pp. 545-553.
Liu, H., et al., "Monoclonal Antibodies to the Extracellular Domain of Prostate-specific Membrane Antigen Also React with Tumor Vascular Endothelium," Cancer Res. 57: 3629-3634 (1997).
Liu, L, et al. "Novel CD4-Based Bispecific Chimeric Antigen Receptor Designed for Enhanced Anti-HIV Potency and Absence of HIV Entry Receptor Activity," J. Viral. 89(13):6685-6694 (2015).
Lode et al., "Targeted cytokines for cancer immunotherapy," Immunol Res., 21(2-3):279-288, (2000).
Lopez-Requena et al., "Gangliosides, Ab1 and Ab2 antibodies III. The idiotype of anti-ganglioside mAb P3 is immtmogenic in a T cell-dependent manner," Mol Immunol, 2007, 44(11):2915-2922.
Lopez-Requena et al., "Gangliosides, Ab1 and Ab2 antibodies IV, Dominance of VH domain in the induction of anti-idiotypic antibodies by Jene gun immunization," Mol Immunol. Apr. 2007;44(11):3070-3075. Epub Mar. 2, 2007.
Lozzio C.B. and Lozzio, B.B.; "Human chronic myelogeneous leukemia cell-line with positive Philadelphia chromosome"; Blood 45:321-334 (1975).
Lozzio et al., "Properties and Usefulness of the Original K-562 Human Myelogenous Leukemia Cell Line," Leukemia Research, vol. 3, No. 6, pp. 363-370, 1979.
Lugli, E. et al., "Transient and presistent effects of IL-15 on lymphocyte homeostasis in nonhuman primates" Blood vol. 116, No. 17, pp. 3238-3248.
Ma et al., "Chapter 15: Genetically engineered T cells as adoptive immunotherapy of cancer," Cancer Chemotherapy and Biological Response Modifiers Annual 20, Ch. 15, 315-341, Giaccone.
Maher J, et al., "Human T-lymphocyte cytotoxicity and proliferation directed by a single chimeric TCRzeta/CD28 receptor", Nat Biotechnol. Jan. 2002; 20(1):70-75.
Maloney, D.G., "Newer Treatments for Non-Hodgkin's Lymphoma: Monoclonal Antibodies," Oncology 12(10): 63-76 (1998).
Manabe et al., "Interleukin-4 induces programmed cell death (apoptosis) in cases of high-risk acute lymphoblastic leukemia," Blood, Apr. 1994, 83(7): 1731-1737.
Mann et al., "Construction of a retrovirus packaging mutant and its use to produce helper-free defective retrovirus," Cell, May 1983, 33(1): 153-159.
Manzke et al., "Immunotherapeutic strategies in neuroblastoma: antitumoral activity of deglycosylated Ricin A conjugated anti-GD2 antibodies and anti-CD3xanti-GD2 bispecific antibodies," Med Pediatr Oncol., 36(1):185-189, Jan. 2001.
Manzke et al., "Locoregional treatment of low-grade B-cell lymphoma with CD3xCD19 bispecific antibodies and CD28 costimulation. I. Clinical phase I evaluation," Int J Cancer., 91(4):508-515, Feb. 15, 2001.

(56) References Cited

OTHER PUBLICATIONS

Manzke et al., "Locoregional treatment of low-grade B-cell lymphoma with CD3xCD19 bispecific antibodies and CD28 costimulation. II. Assessment of cellular immune responses," Int J Cancer., 91(4):516-522, Feb. 15, 2001.
Marincola, F.M., et al., "Escape of Human Solid Tumors from T-Cell Recognition: Molecular Mechanisms and Functional Significance," Adv. Immunol. 74: 181-273 (2000).
Markowitz et al., "A safe packaging line for gene transfer: separating viral genes on two different plasmids," J Virol, Apr. 1988, 62(4): 1120-1124.
Marktel et al., "Immunologic potential of donor lymphocytes expressing a suicide gene for early immune reconstitution after hematopoietic T-cell-depleted stem cell transplantation," Blood, Feb. 2003, 101(4): 1290-1298.
Martinet O., et al., "T cell activation with systemic agonistic antibody versus local 4-1 BB ligand gene delivery combined with interleukin-12 eradicate liver metastases of breast cancer," Gene Ther. Jun. 2002; 9(12):786-792.
Martinez et al. "Cutting Edge: NKG2D-Dependent Cytotoxicity Is Controlled by Ligand Distribution in the Target Cell Membrane", 2011, J. Immunol. 186:5538-5542.
Maude et al., "Chimeric antigen receptor T cells for sustained remissions in leukemia," N Engl J Med., 371(16):1507-1517, Oct. 16, 2014.
Maus MV, et al., "Ex vivo expansion of polyclonal and antigen-specific cytotoxic T lymphocytes by artificial APCs expressing ligands for the T-cell receptor, CD28 and 4-1BB", Nat BiotechnoL Feb. 2002; 20(2): 143-148.
May KF, Jr et al., "Anti-4-1 BB monoclonal antibody enhances rejection oflarge tumor burden by promoting survival but not clonal expansion of tumor-specific CDs+ T cells," Cancer Res. 2002, 62(12):3459-3465.
McLaughlin et al., "Adoptive T-cell therapies for refractory/relapsed leukemia and lymphoma: current strategies and recent advances," Ther Adv Hematol., 6(6):295-307, Dec. 2015.
Melero et al., "Monoclonal antibodies against the 4-IBB T-cell activation molecule eradicate established tumors," Nat. Med., 1997, 3(6): 682-685.
Melero I, et al., "Amplification of tumor immunity by gene transfer of the co-stimulatory 4-1 BB ligand: synergy with the CD28 co-stimulatory pathway," Eur J Immunol., 1998, 28(3):1116-1121.
Melero I, et al., "NK1 .1 cells express 4-1BB(CDw137) costimulatory molecule and are required for tumor immunity elicited by anti-4-1 BB monoclonal antibodies," Cell Immunol., 1998, 190(2): 167-172.
Memorandum Consolidating the Actions in *Trustees of the University of Pennsylvania* v. *St. Jude Children's Research Hospital* in the US District Court for the Eastern District of Pennsylvania, dated Nov. 13, 2013. (Lit. Doc. 20).
Mihara et al., "Development and functional characterization of human bone marrow mesenchymal cells immortalized by enforced expression of telomerase," Br J Haematol, Mar. 2003, 120(5): 846-849.
Miller et al. Successful adoptive transfer and in vivo expansion of human haploidentical NK cells in patients with cancer. Blood. (2005) vol. 105, No. 8, pp. 3051-3057. doi: 10.1182/blood-2004-07-2974.
Miller et al., "Role of monocyles in the expansion of human activated natural killer cells," Blood, Nov. 1992, 80(9): 2221-2229.
Miller, J. S. et al., "Therapeutic applications: natural killer cells in the clinic" Hematology (2013) pp. 247-253.
Milone MC, et al., "Chimeric receptors containing CD137 signal transduction domains mediate enhanced survival of T cells and increased anti leukemic efficacy in vivo", Mol Ther. Apr. 21, 2009; 17(8):1453-1464.
Minamoto, S. et al., "Acquired Erythopoietin Responsiveness of Interleukin-2-dependent T lymphocytes Retrovirally Transduced with Genes Encoding Chimeric Erythropoietin/Interleukin-2 Receptors," Blood, vol. 86, No. 6, pp. 2281-2287 (1995).
Mishra, A. et al., "Aberrant Overexpression of IL-15 Initiates Large Granular Lymphocyte Leukemia through Chromosomal Instability and DNA Hypermethylalion" Cancer Cell (2012) vol. 22, pp. 645-655.
Mogi et al., "Tumour rejection by gene transfer of 4-IBB ligand and into a CD80(+) murine squamous cell carcinoma and the requirements of co-stimulatory molecules on tumour and host cells," Immunology, Dec. 2000, 101(4): 541-7.
Mohammed, S. et al., "Improving Chimeric Antigen Receptor-Modified T Cell Function by Reversing the Immunosuppressive Tumor Microenvironment of Pancreatic Cancer," Mol. Ther. 4, vol. 25, No. 1, pp. 249-258 (2017).
Mondino and Jenkins, "Surface proteins involved in T cell costimulation," J Leukoc Biol, Jun. 1994, 55(6): 805-15.
Mora, "Dinutuximab for the treatment of pediatric patients with high-risk neuroblastoma," Expert Rev Clin Pharmacol., 9(5):647-653, Epub Mar. 21, 2016.
Morandi, B. et al., "NK cells provide helper signal for CD8+ T cells by inducing the expression of membrane-bound IL-15 on DCs" Int. Immunology (2009) vol. 21, No. 5, pp. 599-606.
Moretta L, et a., "Unravelling natural killer cell function: triggering and inhibitory human NK receptors," EMBO J., 2004, 23(2):255-259.
Morgan, R.A. et al., Recognition of Glioma Stem Cells by Genetically Modified T Cells Targeting EGFRvIII and Development of Adoptive Cell Therapy for Glioma, Human Gene Therapy, 23(10), 1043-1053 (2012).
Moritz and Groner "A spacer region between the single chain antibody—and the CD3 chain domain of chimeric T cell receptor components is required for efficient ligand binding and signaling activity," Gene Tuer. Oct. 1995; 2(8):539-546.
Moritz, D., et al., "Cylotoxic T lymphocytes with a grafted recognition specificity for ERBB2-expressing tumor cells," Proc. Natl. Acad. Sci. USA 91:4318-4322 (1994).
Mortier, E. et al., "IL-15Ralpha chaperones IL-15 to stable dendrilic cell membrane complexes that activate NK cells trans presentation" JEM (2008), pp. 1213-1225.
Motion to Intervene filed by *Juno Therapeutics, Inc. in Trustees of the University of Pennsylvania* v. *St. Jude Children's Research Hospital* in the U.S. District Court for the Eastern District of Pennsylvania, dated Dec. 13, 2013. (Doc. 24).
Musso, T et al., "Human monocytes constitutively express membrane-bound, biologically active, and interferon-gamma-upregulated interleukin-15," Blood, 93(10): 3531-3539 (1999).
Nadler et al., "B4, a human B lymphocyte-associated antigen expressed on normal, mitogen-activated, and malignant B lymphocytes," J Immunol, Jul. 1983, 131(1): 244-250.
Nagashima et al., "Stable transduction of the interleukin-2 gene into human natural killer cell lines and their phenotypic and functional characterization in vitro and in vivo," Blood, May 1998, 91(10): 3850-3861.
Nakamura et al., "Chimeric anti-ganglioside GM2 antibody with antitumor activity," Cancer Res. Mar. 15, 1994; 54(6): 1511-6.
Naume et al., "A comparative study of IL-12 (cytotoxic lymphocyte maturation factor)-, IL-2-, and IL-7-induced effects on immunomagnetically purified CD56+ NK cells," J Immunol, Apr. 1992, 148(8): 2429- 36.
Nayyar G. et al., "Overcoming Resistance to Natural Killer Cell Based Immunotherapies for Solid Tumors", Frontiers in Oncology, vol. 9, Feb. 11, 2019, XP055700879.
NCI Thesaurus, Bicistronic chimeric antigen receptor vector, Retrieved online from: <URL:https://ncit.nci.nih.gov/ncitbrowser/pages/home.jsf;jsessionid= 12B0F7AF7I E9A4035C38B5E4F6C055B0>, Retrieved on: Jan. 21, 2021, 2021.
Neeplapu et al., "Phase 1 Biomarker Analysis of the ZUMA-1 Study: A Phase 1-2 Multi-Center Study Evaluating the Safety and Efficacy of Anti-CD19 CAR T Cells (KTE-C19) in Subjects with Refractory Aggressive Non-Hodgkin Lymphoma," Poster session presented at the American Society of Hematology Annual Meeting, Orlando, Florida (Dec. 5-8, 2015).
Negrini, S. et al., "Membrane-bound IL-15 stimulation of peripheral blood natural killer progenitors leads to the generation of an

(56) References Cited

OTHER PUBLICATIONS adherent subset co-expressing dendritic cells and natural killer functional markers," Haematologica, 96(5): 762-766 (2011).
Nicholson et al., "Construction and characterisation of a functional CD19 specific single chain Fv fragment for immunotherapy of B lineage leukaemia and lymphoma," Mol Immunol., 34(16-17):1157-1165, Nov.-Dec. 1997.
Nishigaki et al., "Prevalence and growth characteristics of malignant stem cells in B-lineage acute lymphoblastic leukemia," Blood, May 1997, 89(10): 3735-3744.
Novartis Pharmaceuticals Corp.'s Motion to Intervene in *Trustees of the University of Pennsylvania* v. *St. Jude Children's Research Hospital* in the U.S. District Court for the Eastern District of Pennsylvania, dated Jan. 22, 2014. (Doc. 57).
Nunes et al., "The role of p21ras in CD28 signal transduction: triggering of CD28 With antibodies, but not the ligand B7-1, activates p21ras," J Exp Med, 180(3): 1067-1076, Sep. 1, 1994.
Oelke M, et al., "Ex vivo induction and expansion of antigen-specific cytotoxic T cells by HLA-1g-coated artificial antigen-presenting cells," Nat Med., 2003, 9(5):619-624.
Office Action in U.S. Appl. No. 10/981,352, dated Nov. 29, 2006.
Office Action in U.S. Appl. No. 13/548,148, dated Aug. 9, 2012.
Office Action in U.S. Appl. No. 13/548,148, dated Oct. 11, 2012.
Office Action in U.S. Appl. No. 11/074,525, dated Jan. 3, 2008.
Office Action of U.S. Appl. No. 10/981,352, dated Jan. 4, 2007.
Office Action of U.S. Appl. No. 10/981,352, dated Jan. 4, 2008.
Office Action of U.S. Appl. No. 10/981,352, dated Jun. 7, 2007.
Office Action of U.S. Appl. No. 10/981,352, dated Mar. 14, 2007.
Office Action of U.S. Appl. No. 11/074,525, dated Mar. 23, 2007.
Office Action of U.S. Appl. No. 11/074,525, dated Sep. 18, 2007.
Olsen, S. et al., "Crystal Structure of the Inteleukin-15-Interleukin-15 Receptor alpha complex" The Journal for Biological Chemistry (2007) vol. 282, No. 51, pp. 37191-37204.
Order in *Trustees of the University of Pennsylvania* v. *St. Jude Children's Research Hospital* in the U.S. District Court for the Eastern District of Pennsylvania, dated Nov. 13, 2013. (Doc. 39).
Order in *Trustees of the University of Pennsylvania* v. *St. Jude Children's Research Hospital* in the U.S. District Court for the Eastern District of Pennsylvania, dated Nov. 18, 2013. (Doc. 21).
Order in *Trustees of the University of Pennsylvania* v. *St. Jude Children's Research Hospital* in the U.S. District Court for the Eastern District of Pennsylvania, dated Nov. 18, 2013. (Doc. 26).
Order in *Trustees of the University of Pennsylvania* v. *St. Jude Children's Research Hospital* in the U.S. District Court for the Eastern District of Pennsylvania, dated Nov. 22, 2013. (Doc. 27).
Oyer et al., "Natural killer cells stimulated with PM21 particles expand and biodistribute in vivo: Clinical implications for cancer treatment," Cytotherapy, 18: 653-663, 2016.
Ozkaynak, M.F. et al., "Phase I Study of Chimeric Human/Murine Anti-Ganglioside GD2 Monoclonal Antibody (chl4.18) With Granulocyte-Macrophage Colony-Stimulating Factor in Children With Nueroblastoma Immediately After Hematopoietic Stem-Cell Transplantation: A Children's Cancer Group Study," J. Clinical Oncol. 18: 4077-4085 (2000).
Pakula, A. A. et al., "Genetic analysis of protein stability and function," Annual Review of Genetics, V. 23, N. 1, p. 289-310, c. 305-306 (1989).
Pan et al., "Regulation of dendritic cell function by NK cells: mechanisms underlying the synergism in the combination therapy of IL-12 and 4-1BB activation," J Immunol, Apr. 2004, 172(8): 4779-89.
Park et al. "Complex regulation of human NKG2D-DAP10 cell surface expression: opposing roles of the Ye cytokines and TGF-B1", 2011, Blood 118:3019-3027.
Park et al., "CD19-Targeted 19-28z CAR Modified Autologous T Cells Induce High Rates of Complete Remission and Durable Responses in Adult Patients with Relapsed, Refractory B-Cell ALL," Abstract presented at the American Society of Hematology Annual Meeting, San Francisco, California, available at https://ash.confex.com/ash/2014/webprogram/Paper76573.html.
Park, J.H., and Brentjens, R J., "Are All Chimeric Antigen Receptors Created Equal?" J. Clin. Oncol. 33:651-653 (2015).
Park, J.H., et al., Abstract, "682 Implications of Minimal Residual Disease Negative Complete Remission (MRD-CR) and Allogeneic Stem Cell Transplant on Safety and Clinical Outcome of CD19-Targeted 19-28z CAR Modified T cells in Adult Patients with Relapsed, Refractory B-Cell ALL," Am. Soc'v Hematol., available at httos://ash.confex.com/ash/2015/weboroaram/Paoer86688.html.
Parkhurst, M. R., et al., "Adoptive Transfer of Autologous Natural Killer Cells Leads to High Levels of Circulating Natural Killer Cells but Does Not Mediate Tumor Regression", Clinical Cancer Research (2011), vol. 17, No. 19, pp. 6287-6297.
Patel, S.D., et al., "Impact of chimeric immune receptor extracellular protein domains on T cell function," Gene Therapy 6: 412-419 (1999).
Paul, W.E., Fundamental Immunology, Third Edition, Chs. 1, 13 and 32 (pp. 1-20, 467- 504, and 1143-1178), Raven Press, New York (1993).
Peach, R.J. et al., "Complementarity Determining Region 1 (CDR1)- and CDR3-analogous Regions in CTLA-4 and CD28 Determine the Binding to B7-1," J. Exp. Med. 180: 2049-2058 (1994).
Perussia et al., "Preferential proliferation of natural killer cells among peripheral blood mononuclear cells cocultured with B lymphoblastoid cell lines," Nat Immun Cell Growth Regul, 1987, 6(4): 171-88.
Petition for Inter Partes Review of U.S. Pat. No. 7,446,190 Under 35 U.S.C. ?? 311-319 and 37 C.F.R, ?? 42.1-.80,42.100-.123, 64 pages, Aug. 13, 2015.
Pollok et al., "Regulation of 4-1BB expression by cell-cell interactions and the cytokines, interleukin-2 and interleukin-4," Eur J Imnunol, Feb. 1995, 25(2): 488-494.
Pollok KE, et al., "Inducible T cell antigen 4-1 BB Analysis of expression and function," J Immunol., 1993, 150(3):771-781.
Porter and Antin, "The graft-versus-leukemia of allogeneic cell therapy," Annu Rev Med, 1999, 50: 369-86.
Porter DL et al., "Chimeric Antigen Receptor-Modified T Cells in Chronic Lymphoid Leukemia", N. Eng. J. Med. Aug. 25, 2011; 365(8):725-733.
Porter et al., "Induction of graft-versus-host disease as immunotherapy for relapsed chronic myeloid leukemia," N Engl J Med, Jan. 1994, 330(2): 100-6.
Proposed Order in *Trustees of the University of Pennsylvania* v. *St. Jude Children's Research Hospital* in the U.S. District Court for the Eastern District of Pennsylvania, dated Nov. 15, 2013. (Doc. 25).
Pui et al., "Childhood acute lymphoblastic leukaemia—current status and future perspectives," Lancet Oncol, Oct. 2001, 2(10): 597-607.
Pule et al. "Virus-specific T cells engineered to coexpress tumor-specific receptors: persistence and antitumor activity in individuals with neuroblastoma," Nature Med., 2008, 14(1 1):1264-1270.
Qi L. et al, "Multiple effects of IL-21 on the ex vivo expansion of human primary NK cells," Immunology, Nov. 28, 2014, vol. 143, No. S2, p. 62-176, Poster Abstract 708.
Qian, L. et al., "Construction of a plasmid for co-expression of mouse membrane-bound form of IL-15 and RAE-1 (e) and its biological activity" Plasmid (2011) vol. 65, pp. 239-245.
Rajagopalan et al., Found: a cellular activating ligand for N Kp44, Blood, 122( 17):2921-2922, Oct. 2013.
Ramos and Dotti, "Chimeric antigen receptor (CAR)-engineered lymphocytes for cancer therapy," Expert Opin Biol Ther., 2011, 11(7):855-873.
Ramos, C.A., et al., "CD19-CAR Trials," The Cancer J. 20: 112-118 (2014).
Ren, P.-P. et al., Anti-EGFRvIII Chimeric Antigen Receptor-Modified T Cells for Adoptive Cell Therapy of Glioblastoma, Current Pharmaceutical Design, 23(14), 2113-2116 (2017).
Riddell, S.P., et al., "T-Cell Therapy of Leukemia," Cancer Control 9: 114-122 (2002).
Riley et al., "The CD28 family: a T-cell rheostat for therapeutic control of T-cell activation," Blood, 2005, 105:13-21.
Roberts et al., "Antigen-specific cytolysis by neutrophils and NK cells expressing chimeric immune receptors bearing zeta or gamma signaling domains," J Immunol, Jul. 1998, 161(1): 375-84.

(56) References Cited

OTHER PUBLICATIONS

Robertson MJ, et al., "Costimulation of human natural killer cell proliferation: role of accessory cytokines and cell contact-dependent signals", Nat Immun. 1996-1997; 15(5):213-226.
Romee R, Rosario M, Berrien-Elliott MM, et al. Cytokine-induced memory-like natural killer cells exhibit enhanced responses against myeloid leukemia. Sci Transl Med. 2016;8(357):357ra123. doi:10.1126/scitranslmed.aaf2341.
Romee R. et al., "Cytokine activation induces human memory-like NK cells", Blood, Jan. 1, 2012, pp. 4751-4760.
Rooney et al., "Use of gene-modified virus-specific T lymphocytes to control Epstein-Barr-virus-related lymphoproliferation," Lancet, Jan. 1995, 345(8941): 9-13.
Rosenberg et al., "Special Report: Use of tumor-infiltrating lymphocytes and interleukin-2 in the immunotherapy of patients with metastatic melanoma," N. Engl. J. Med., 1988, 319:1676-1680.
Rosenberg, S.A., and Dudley, M.E., "Adoptive cell therapy for the treatment of patients with metastatic melanoma," Curr. Opin. Immunol. 21: 233-240 (2009).
Rosenfeld et al., "Phenotypic characterization of a unique non-T, non-B acute lymphoblastic leukaemia cell line," Nature, Jun. 1977, 267(5614): 841-843.
Rosenstein, M. et al., "Extravasation Of Intravascular Fluid Mediated By The Systemic Administration Of Recombinant Interleukin 2" The Journal of Immunology (1986) vol. 137, No. 5, pp. 1735-1742.
Ross et al., "Classification of pediatric acute lymphoblastic leukemia by gene expression profiling," Blood, Oct. 2003, 102(8): 2951-2959.
Rossi, J.M., et al., "Phase 1 Biomarker Analysis of ZUMA-1 (KTEC19-101) Study: A Phase 1-2 Multi-Center Study Evaluating the Safety and Efficacy of Anti-CD19 CART cells (KTE-C19) in Subjects with Refractory Aggressive Non-Hodgkin Lymphoma (NHL)," Abstract presented at the American Society of Hematology Annual Meeting, Orlando, Florida, available at https://ash.confex.com/ash/2015/webprogramscheduler/Paper80339.html.
Rossig C, et al., "Epstein-Barr virus-specific human T lymphocytes expressing antitumor chimeric T-cell receptors: potential for improved immunotherapy," Blood, 2002, 99:2009-2016.
Rossig et al., "Targeting of G(D2)-positive tumor cells by human T lymphocytes engineered to express chimeric T-cell receptor genes," Int J Cancer, Oct. 2001, 94(2): 228-236.
Rowley, J. et al., "Expression of IL-15RA or an IL-15/IL-15RA fusion on CD8+ T cells modifies adoptively transferred T-cell function in cis," European Journal of Immunology, 39: 491-506 (2009).
Rubnitz et al., 2010, NKAML: A Pilot Study to Determine the Safety and Feasibility of Haploidentical Natural Killer Cell Transplantation in Childhood Acute Myeloid Leukemia, J Clin Oncol. 28:955-959.
Ruggeri L, et al, "Effectiveness of donor natural killer cell alloreactivity in mismatched hematopoietic transplants," Science, 2002, 295 :2097-2100.
Sadelain et al., "Targeting tumours with genetically enhanced T lymphocytes," Nat Rev Cancer. Jan. 2003;3(1):35-45.
Sadelain et al., "The promise and potential pitfalls of chimeric antigen receptors," Curr Opin Immunol., 2009, 21(2):215-223.
Sadelain, M. et al., "The Basic Principles of Chimeric Antigen Receptor Design," Cancer Discovery, vol. 3, No. 4, pp. 388-398 (Apr. 1, 2013).
Sadelain, M., "CAR Therapy: the CD19 Paradigm," J. Clin. Investigation 125: 3392-3400 (2015).
Sahm et al., "Expression of IL-15 in N K cells results in rapid enrichment and selective cytotoxicity of gene-modified effectors that carry a tumor-specific antigen receptor," Cancer hunol. Immunother., 61 (9): 1451-1461, Feb. 2012.
Salih et al., "Cutting Edge: Down-Regulation of MICA on Human Tumors by Proteolytic Shedding", J. Immunol. (2002), vol. 169, pp. 4098-4102.
Salomon and Bluestone, "Complexities of CD28/B7: CTLA-4 costimulatory pathways in autoimmunity and transplantation," Annu Rev Immunol, 2001, 19: 225-252.
Sambrook et al., "Molecular Cloning: A Laboratory Manual," (1989) [Table of Contents and Preface Only].
Sankhla, S.K. et al., "Adoptive immunotherapy using lymphokineactivated killer (LAK) cells and interleukin-2 for recurrent malignant primary brain tumors," J Neurooncol. 27: 133-140 (1995).
Santegoets S. J. et al., IL-21 promotes the expansion of CD27+ CD28+tumor infiltrating lymphocytes with high cytotoxic potential and low collateral expansion of regulatory T cells. Journal of Translational Medicine, Feb. 12, 2013, vol. 11, No. 37, pp. e1-e10.
Savoldo, B., et al., "CD28 costimulation improves expansion and persistence of chimeric antigen receptor modified T cells in lymphoma patients," J. Clin. Invest. 121(5):1822-1826 (2011).
Schlums, H. et al., "Cytomegalovirus Infection Drives Adaptive Epigenetic Diversification of NK Cells with Altered Signaling and Effector Function", Immunity Author manuscript, Mar. 17, 2015, 42(3), 443-456, in 28 pages.
Schmaltz et al., "T cells require TRAIL for optimal graft-versus-tumor activity," Nat Med, Dec. 2002, 8(12): 1433-7.
Schneider et al., "Characterization of EBV-genome negative "null" and "T" cell lines derived from children with acute lymphoblastic leukemia and leukemic transformed non-Hodgkin lymphoma," Int J Cancer, May 1977, 19(5): 621-626.
Schroers et al., "Gene transfer into human T lymphocytes and natural killer cells by Ad5/F35 chimeric adenoviral vectors," Exp Hematol, Jun. 2004, 32(6): 536-46.
Schulz, G., et al., "Detection of Ganglioside GD2 in Tumor Tissues and Sera of Neuroblastoma Patients," Cancer Research 44: 5914-5920 (1984).
Schumacher, "T-cell-receptor gene therapy," Nat Rev Immunol, Jul. 2002, 2(7): 512-519.
Schwartz et al., "Structural basis for co-stimulation by the human CTLA-4/B7-2 complex," Nature, 410(6828):604-608, Mar. 29, 2001.
Schwarz et al., "ILA, the human 4-1BB homologue, is inducible in lymphoid and other cell lineages," Blood, Feb. 1995, 85(4): 1043-1052.
Scott, A. M. et al., "Antibody therapy of cancer" Nature Reviews (2012) vol. 12, pp. 278-287.
Search Report and Written Opinion for Singapore Application No. 11201908337V, titled, "Stimulatory cell lines for ex vivo expansion and activation of natural killer cells," Date Completed: Nov. 25, 2020.
Seif et al., "The role of JAK-STAT signaling pathway and its regulators in the fate of T helper cells" Cell Communication and Signaling (2017) 15:23.
Sentman, C. L. et al., "NK Cell Receptors as Tools in Cancer Immunotherapy" Advances in Cancer Research (2006) pp. 249-292.
Sentman, C. L., et al., "NKG2D CARs as Cell Therapy for Cancer", The Cancer Journal (2014), vol. 20, No. 2, pp. 156-159.
Sheard, M. A. et al., "Membrane-bound TRAIL Supplements Natural Killer Cell Cytotoxicity Against Neuroblastoma Cells" J. Immunother. (2013) vol. 36, No. 5, pp. 319-329.
Shimasaki et al., "A Clinically Adaptable Method to Enhance the Cytotoxicity of Natural Killer Cells Against B-cell Malignancies", Cytotherapy (2012), vol. 14, pp. 830-840.
Shook et al., "Natural Killer Cell Engineering for Cellular Therapy of Cancer," National Institutes of Health, Tissue Antigens, vol. 78, No. 6, pp. 409-415, Dec. 2011.
Shuford WW, et al., "4-1 BB costimulatory signals preferentially induce CDS+ T cell proliferation and lead to the amplification in vivo of cytotoxic T cell responses", J Exp Med. Jul. 7, 1997; 186(1):47-55.
Shum et al., "Conservation and Variation in Human and Common Chimpanzee CD($ and NKG2 Genes," The American Association of Immunologists, The Journal of Immunology, pp. 240-252, Downloaded on Jun. 18, 2017.
Sica G, Chen L. Modulation of the immune response through 4-1 BB. In: Habib N, ed. Cancer gene therapy: past achievements and future challenges. New York: Kluwer Academic/Plenum Publishers; 355-362 (2000) [Book].

(56) References Cited

OTHER PUBLICATIONS

Slavik et al., "CD28/CTLA-4 and CD80/CD86 families: signaling and function," Immunol Res., 19(1):1-24, 1999.
Slavin et al., "Allogeneic cell therapy with donor peripheral blood cells and recombinant human interleukin-2 to treat leukemia relapse after allogeneic bone marrow transplantation," Blood, Mar. 1996, 87(6): 2195-204.
Sloan Kettering Institute for Cancer Research'a Patent Owner Response re: IPR2015-01719, 86 pages, May 5, 2016.
Sloan Kettering Institute for Cancer Research's Patent Owner Preliminary Response re: IPR2015-01719, 68 pages, dated Nov. 25, 2015.
Sneller, M.C. et al., "IL-15 administered by continuous infusion to rhesus macaques induces massive expansion of CD8+ T effector memory population in peripheral blood," Blood, 118(26): 6845-6848 (2011).
Sokolic et al, "A Selectable Bicistronic Retroviral Vector Corrects the Molecular Defect in a Cell Line Derived from a Patient with Leukocyte Adhesion Deficiency," Biol. Blood Marrow Transpl. 12(2) Suppl 1: Feb. 20-21, 2006.
Somanchi, S.S. et al., "Expansion, purification, and functional assessment of human peripheral blood NK cells," Journal of Visualized Experiments, 48A: 2540 (2011).
Song et al., "Chimeric NKG2D CAR-Expressing T Cell-Mediated Attack of Human Ovarian Cancer is Enhanced by Histone Deacetylase Inhibition," Human Gene Therapy, vol. 24, pp. 295-305, Mar. 2013.
Spear al., "Collaboration of Chimeric Antigen Receptor (CAR)-expressing T Cells for Optimal Elimination of Established Ovarian Tumors", OncoImmunology (2013), vol. 2, No. 4, pp. e23564-1-e23564-12.
Spear et al., 2013, NKG2D CAR T-Cell Therapy Inhibits the Growth of NKG2D Ligand Heterogeneous Tumors, Immunology and Cell Biology 91: 435-440.
Spear et al., "Chimeric Antigen Receptor T Cells Shape Myeloid Cell Function within the Tumor Microenvironment through IFN-y and GM-CSF," The Journal of Immunology, pp. 6389-6399, 2014.
Srinivasan et al., "A retro-inverso peptide mimic of CD28 encompassing the MYPPPY motif adopts a polyproline type II helix and inhibits encephalitogenic T cells in vitro," J Immunol., 167(1):578-585, Jul. 1, 2001.
Srivannaboon et al., "Interleukin-4 variant (BAY 36-1677) selectively induces apoptosis in acute lymphoblastic leukemia cells," Blood, Feb. 2001, 97(3): 752-758.
St. Jude Children's Research Hospital's Answer and Counterclaims in *Trustees of the University of Pennsylvania* v. *St. Jude Children's Research Hospital* in the U.S. District Court for the Eastern District of Pennsylvania, dated Jun. 27, 2013. (Doc 17).
St. Jude Children's Research Hospital's Motion in *Trustees of the University of Pennsylvania* v. *St. Jude Children's Research Hospital* in the U.S. District Court for the Eastern District of Pennsylvania, dated Dec. 3, 2013. (Doc. 31).
St. Jude Children's Research Hospital's Opposition to Trustees of the University of Pennsylvania's Motion to Dismiss Willful Infringement Allegations of Counterclaim in *Trustees of the University of Pennsylvania* v. *St. Jude Children's Research Hospital* in the U.S. District Court for the Eastern District of Pennsylvania, dated Aug. 8, 2013. (Doc. 19).
Stamper et al., "Crystal structure of the B7-1/CTLA-4 complex that inhibits human immune responses," Nature, 410(6828):608-611, Mar. 29, 2001.
Steel et al., "Interleukin-15 biology and its therapeutic implications in cancer," Trends Pharmacol. Sci. 33(1) :35-41, Jan. 2012.
Stein, P.H., et al., "The Cytoplasmic Domain of CD28 is both Necessary and Sufficient for Costimulation of Interleukin-2 Secretion and Association with Phosphatidylinositol 3'-Kinase," Mol. Cell. Biol. 14: 3392-3402 (1994).
Stong RC, et al., "Human acute leukemia cell line with the t(4;11) chromosomal rearrangement exhibits B lineage and monocytic characteristics," Blood, 1985,65:21-31.
Suerth et al., "Efficient Generation of Gene-Modified Human Natural Killer Cells via Alpharetroviral Vectors," J. Mol. Med. 94:83-93, 2016, published online Aug. 25, 2015.
Sullivan, L.C. et al., "The Heterodimenc Assembly of the CD94-NKG2 Receptor Family and Implications for Human Leukocyte Antigen-E Recognition," Immunity, 27(6): 900-911 (Dec. 2007).
Sun, J ., et al., "Early transduction produces highly functional chimeric antigen receptor-modified virus-specific T-cells with central memory markers: a Production Assistant for Cell Therapy (PACT) translational application," J. Immunother. Cancer (2015).
Sundstrom and Nilsson, "Establishment and characterization of a human histiocy1ic lymphoma cell line (U-937)," Int J Cancer, May 1976, 17(5): 565-577.
Sussman et al., "Protein Data Bank (PDB): database of three-dimensional structural information of biological macromolecules," Acta Crystallogr D Biol Crystallogr., 54(Pt 6 Pt 1):1078-1084, Nov. 1, 1998.
Tacke et al., "CD28-mediated induction of proliferation in resting T cells in vitro and in vivo without engagement of the T cell receptor: evidence for functionally distinct forms of CD28," Eur J Immunol., 27(1):239-247, Jan. 1997.
Tagaya, Y. et al., "IL-15: A Pleiotropic Cytokine with Diverse Receptor/Signaling Pathways Whose Expression Is Controlled at Multiple Levels" Immunity (1996) vol. 4, pp. 329-336.
Takahashi C, et al., "Cutting edge: 4-1 BB is a bona fide CDS T cell survival signal", J Immunol. May 1, 1999; 162(9):5037-5040.
The human protein atlas, [retrieved from: https://www.proteinatlas.org/ENSG00000177455-CD19/pathology], accessed Jun. 27, 2019, 3 pages.
Themeli et al., "Generation of tumor-targeted human T lympocytes from Induced pluripotent stem cells for cancer therapy", Nat Biotechnol., Oct. 2013; 31(10): 928-933.
Thomas et al., "Monoclonal antibody therapy with rituximab for acute lymphoblastic leukemia," Hematol Oncol Clin North Am., 23(5):949-971, Oct. 2009.
Topp, M.S., et al, "Universal chimeric immunoreceptors for targeting B-cell malignancies with engineered CTL: combining CD 19-specific TCR zeta signaling with engineered CD28-mediated co-stimulation," Mol. Ther. 3(5)(part 2 of 2): S21 (2001).
Trinchieri et al., "Response of resting human peripheral blood natural killer cells to interleukin 2," J Exp Med, Oct. 1984, 160(4): 1147-1169.
Trompeter et al., "Rapid and highly efficient gene transfer into natural killer cells by nucelofection," J Immunol Methods, Mar. 2003, 274(1-2): 245-256.
Trustees of the University of Pennsylvania's Answer to Defendant's Counterclaims in *Trustees of the University of Pennsylvania* v. *St. Jude Children's Research Hospital* in the U.S. District Court for the Eastern District of Pennsylvania, dated Nov. 29, 2013. (Doc. 28).
Trustees of the University of Pennsylvania's Answer to Juno Therapeutics, Inc.'s Counterclaim in *Trustees of the University of Pennsylvania* v. *St. Jude Children's Research Hospital* in the U.S. District Court for the Eastern District of Pennsylvania, dated Jan. 13, 2014. (Doc. 56).
Trustees of the University of Pennsylvania's Brief in Support of Motion for Summary Judgment for Invalidity of Patent in Suit in *Trustees of the University of Pennsylvania* v. *St. Jude Children's Research Hospital* in the U.S. District Court for the Eastern District of Pennsylvania, dated Nov. 15, 2013. (Doc. 23).
Trustees of the University of Pennsylvania's Motion for Summary Judgment for Invalidity of Patent in Suit in *Trustees of the University of Pennsylvania* v. *St. Jude Children's Research Hospital* in the U.S. District Court for the Eastern District of Pennsylvania, dated Nov. 15, 2013.
Trustees of the University of Pennsylvania's Motion to Dismiss in *Trustees of the University of Pennsylvania* v. *St. Jude Children's Research Hospital* in the U.S. District Court for the Eastern District of Pennsylvania, dated Jul. 22, 2013. (Doc. 18).
Tsukamoto, K. er al., "Juxtacrine function of interleukin-15/interleukin-15 receptor system in tumour derived human B-cell lines," Clinical and Experimental Immunology, 146(3): 559-566 (2006).

(56) References Cited

OTHER PUBLICATIONS

Turtle, "Therapy of B Cell Malignancies with CD19-Specific Chimeric Antigen Receptor Modified T Cells of Defined Subset Composition," Blood 124(21): 384, 6 pages, 2014.
Turtle, C.J., et al., Abstract, "A Phase I/II Clinical Trial of Immunotherapy for CD19+ B Cell Malignancies With Defined Composition of CD4+ and CD8+ Central Memory T Cells Lentivirally Engineered to Express a CD19-Specific Chimeric Antigen Receptor" Mol. Ther., 2014, 22(Supp. 1):296.
U.S. Appl. No. 11/074,525, filed Mar. 8, 2005, U.S. Pat. No. 7,435,596, Oct. 14, 2008, Campana et al.
U.S. Appl. No. 12/206,204, filed Sep. 8, 2008, U.S. Pat. No. 8,026,097, Sep. 27, 2011, Campana et al.
U.S. Appl. No. 13/548,148, filed Jul. 12, 2012, U.S. Pat. No. 8,399,645, Mar. 19, 2013, Campana et al.
U.S. Appl. No. 14/301,122, filed Jun. 10, 2014, U.S. Pat. No. 9,605,049, Mar. 28, 2017, Campana et al.
U.S. Appl. No. 14/303,331, filed Jun. 12, 2014, U.S. Pat. No. 9,856,322, Jan. 2, 2018, Campana et al.
U.S. Appl. No. 14/872,947, filed Oct. 1, 2015, U.S. Pat. No. 9,834,590, Dec. 5, 2017, Campana et al.
U.S. Appl. No. 15/470,678, filed Mar. 27, 2017, 2017-0283482, Oct. 5, 2017, Campana et al.
U.S. Appl. No. 15/837,715, filed Dec. 11, 2017, Campana et al.
U.S. Appl. No. 60/383,872, filed May 28, 2002, Sadelain et al.
Upshaw et al., "NKG2D-Mediated Signaling Requires a DAP10-Bound Grb2-Vav1 Intermediate and Phosphatidylinositol-3-kinase in Human Natural Killer Cells", Nat. Immunol. (2006), vol. 7, pp. 524-532.
Venna and Stock, "Management of adult acute lymphoblastic leukemia: moving tmvard a risk-adapted approach," Curr Opin Oncol, Jan. 2001, 13(1): 14-20.
Verdonck et al., "Donor leukocyte infusions for recurrent hematologic malignancies after allogeneic bone marrow transplantation: impact of infused and residual donor T cells," Bone Marrmv Transplant, Dec. 1998, 22(11): 1057-1063.
Vinanica, N., et al., "Specific stimulation of T lymphocytes with erythropoietin for adoptive immunotherapy", Blood, 135(9): 668-679 (Feb. 27, 2020).
Vinay OS, et al., "Role of 4-1 BB in immune responses", Semin Immunol. Dec. 1998; 10(6):481-489.
Viola, "The amplification of TCR signaling by dynamic membrane microdomains," Trends Immunol., 22(6):322-327, Jun. 2001.
Vivier, E. et al., "Innate or Adaptive Immunity? The Example of Natural Killer Cells" Science (2011) vol. 331, pp. 44-49.
Vohra et al., Use of Stimulatory Cells in Conjunction with IL-12 and IL-18 augments NK cell expansion and transduction, drives a memory phenotype, and improve in vitro and in vivo CAR NK Activity, Journal for ImmunoTherapy of Cancer, vol. 7, Supplement 1: p. 194, 2019.
Vohra, et al., Stimulatory cells plus IL-12 and IL-18 augments KN cell expansion, transduction, memory phenotype, and in vitro and in vivo CAR NK cytotoxicity & persistence, SITC, Nov. 2019.
Voss et al., "Targeting p53, hdm2, and CD19: vaccination and immunologic strategies," Bone Marrow Transplant., 25 Suppl 2:S43-S45, May 2000.
Vujanovic, L. et al, "Virally infected and matured human dendritic cells activate natural killer cells via cooperative activity of plasma membrane-bound TNF and IL-15" Blood (2010) vol. 116, No. 4, pp. 575-583.
Waldmann, T.A. et al., "Safety (toxicity), pharmacokinetics, immunogenicity, and impact on elements of the normal immune system of recombinant human IL-15 in rhesus macaques," Blood, 117(18): 4787-4795 (2011).
Walter et al., "Reconstitution of cellular immunity against cytomegalovirus in recipients of allogeneic bone marrow by transfer of T-cell clones from the donor," N Engl J Med, Oct. 1995, 333(16): 1038-1044.
Wang et al., "Human NK cells maintain licensing status and are subject to killer immunoglobulin-like receptor (KIR) and KIR-ligand inhibition following ex vivo expansion," Cancer Immunol Immunother, 65:1047-1059, 2016.
Wang, et al., "Phase I Studies of central-memory-derived CD19 CAR T cell therapy following autologous HSCT in patients with B-Cell NHL," Blood (forthcoming 2016).
Warrens AN, et al., "Splicing by overlap extension by PCR using asymmetric amplification: an improved technique for the generation of hybrid proteins of immunological interest," Gene 20;186: 29-35 (1997).
Watowich et al., "The Erythropoietin Receptor: Molecular Structure and Hematopoietic Signaling Pathways," J. Investig Med. 2011, 59(7): 1067-1072.
Watzl, C. et al., "Signal Transduction During Activation and Inhibition of Natural Killer Cells" Curr. Protec. Immunol (2010), doi:10.1002/0471142735.im1109bs90, 19 pages total.
Weijtens, M.E.M., et al., "Functional balance between T cell chimeric receptor density and tumor associated antigen density: CTL mediated cytolysis and lymphokine production," Gene Ther. 7: 35-42 (2000).
Weissman et al., "Molecular cloning and chromosomal localization of the human T-cell receptor—chain: Distinction from the molecular CD3 complex," PNAS USA, 1988, 85:9709-9713.
Westwood, J.A., et al., "Adoptive transfer of T cells modified with a humanized chimeric receptor gene inhibits growth of Lewis-Y expressing tumors in mice," PNAS 102(52): 19051-19056 (2005).
WHO, "WHO Classification of Tumours of Haematopoietic and Lymphoid Tissues," International Agency for Research on Cancer (IARC), 4th Edition, 40 pages, 2008.
Wilcox et al., "Signaling through NK cell-associated CD137 promotes both helper function for CD8+ cytolytic T cells and responsiveness to IL-2 but not cytolytic activity," J. Immunol., Oct. 2002, 169(8):4230-6.
Wilkie, S. et al., "Selective Expansion of Chimeric Antigen Receptor-targeted T-cells with Potent Effector Function Using Interleukin-4," J Biol Chem., vol. 285, No. 33, pp. 25538-25544 (2010).
Willimsky, G. and Blankenstein, T., "Sporadic immunogenic tumours avoid destruction by inducing T-cell tolerance," Nature 437: 141-146 (2005).
Wittnebel, S. et al., "Membrane-Bound Interleukin (IL)-15 on Renal Tumor Cells Rescues Natural Killer Cells from IL-2 Starvation-Induced Apoptosis" Cancer Research (2007) vol. 67, No. 12, pp. 5594-5599.
Wu and Lanier, "Natural killer cells and cancer," Adv Cancer Res, 2003, 90: 127-156.
Wu, J. et al., "An Activating Immunoreceptor Complex Formed by NKG2D and DAP10" Science (1999) vol. 285, pp. 730-732.
Wyss-Coray, T., et al., "The B7 adhesion molecule is expressed on activated human T cells: functional involvement in T-T cell interactions," Eur. J. ImmunoL., 23: 2175-2180 (1993).
Xu, Y., et al., "Closely related T-memory stem cells correlate with in vivo expansion of CAR.CD19-T cells and are preserved by IL-7 and IL-15," Blood 123(24):3750-3759 (2014).
Yan et al., "Murine CD8 lymphocyte expansion in vitro by artificial antigen-presenting cells expressing CD137L (4-1 BBL) is superior to CD28, and CD137L expressed on neuroblastoma expands CD8 tumour-reactive effector cells in vivo," Immunology, 2004, 112(1):105-116.
Ye et al. "Effects of target cell overexpression of IL-15, 4-1 BBL and IL-18 1-102 combine with IL-2 on NK cell activation and cytotoxicity during ex vivo expansion" Chin J Cancer Biother, Oct. 31, 2014, vol. 21, No. 5, pp. 537-542.
Ye et al., "Gene therapy for cancer using single-chain Fv fragments specific for 4-IBB," Nat Med, Apr. 2002, 8(4): 343-348.
Yeoh et al., "Classification, subtype discovery, and prediction of outcome in pediatric acute lymphoblastic leukemia by gene expression profiling," Cancer Cell, Mar. 2002, 1(2): 133-143.
Yoshida et al., "A novel adenovims expressing human 4-1BB ligand enhances antitumor immunity," Cancer Immunol Immunother, Feb. 2003, 52(2): 97-106.
Zah E. et al., T Cells Expressing CD19/CD20 Bispecific Chimeric Antigen Receptors Prevent Antigen Escape by Malignant B Cells. Cancer Immunol Res., Apr. 8, 2016, vol. 4, No. 6, pp. 498-508.

(56) References Cited

OTHER PUBLICATIONS

Zanoni, I. et al., "IL-15 cis presentation is required for optimal NK cell activation in lipopolysaccharide-mediated inflammatory conditions," Cell Reports, 4: 1235-1249 (2013).
Zeis et al., "Allogeneic MHC-Mismatched Activated Natural Killer Cells Administered After Bone Marrow Transplantation Provide a Strong Graft-Versus-Leukemia Effect in Mice," BrJ Haematol, 1997, 96:757-761.
Zhang at al., Chimeric NKG2D-Modified T Cells Inhibit Systemic T-Cell Lymphoma Growth in a Manner Involving Multiple Cytokines and Cytotoxic Pathways, Cancer Res (2007), vol. 67, pp. 11029-11036.
Zhang et al, "Generation of Antitumor Responses by Genetic Modification of Primary Human T Cells with a chimeric NKG2D Receptor", Cancer Res (2006), vol. 66, No. 11, pp. 5927-5933.
Zhang et al, "Mouse Tumor Vasculature Expresses NKG2D Ligands and Can Be Targeted by Chimeric NKG2D-Modified T Cells", J Immunol (2013), vol. 190, pp. 2455-2463.
Zhang et al. Chimeric NK-receptor-bearing T cells mediate antitumor immunotherapy, Sep. 1, 2005, Blood Journal 106(5): 1544-1551.
Zhang et al., "Improving Adoptive T Cell Therapy by Targeting and Controlling IL-12 Expression to the Tumor Environment," The American Society of Gene & Cell Therapy Molecular Therapy, vol. 19, No. 4, 751-759, 2011.
Zhang et al., Characterization of interleukin-15 gene-modified human natural killer cells: implications for adoptive cellular immunotherapy, Haematologica, 89: 338-347, Jan. 2004. (Year: 2004).
Zhao, et al., "A Herceptin-Based Chimeric Antigen Receptor with Modified Signaling Domains Leads to Enhanced Survival of Transduced T Lymphocytes and Antitumor Activity", The Journal of Immunology, 2009; 183:5563-5574.
European Examination, re EP 20848600.1, dated Dec. 12, 2024.
International Preliminary Report on Patentability, re PCT Application No. PCT/US2023/077336, dated May 1, 2025.
Lemar H et al: "KIR haplotype can inform donor selection production of allogeneic memory-like CAR NK cells for clinical application", Journal For Immunotherapy Of Cancer, vol. 9, No. Suppl. 2, Nov. 10, 2021, p. A137.
Porrata, L. et al., "Infusion of NKp30/KIR2DL2 Natural Killer Cell Ratio and Survival Post-Autologous Stem Cell Transplantation in Lymphomas", Blood, vol. 132, No. Suppl. 1, Nov. 29, 2018, 3 pages.
Denman, Cecele J. et al., "Membrane-Bound IL-21 Promotes Sustained Ex Vivo Proliferation of Human Natural Killer Cells" PLoS ONE, Jan. 2012, pp. 1-13, vol. 7, Issue 1, e30264.
Rex, D.A.B et al., "A comprehensive pathway map of IL-18-mediated signaling" Journal of Cell Communication and Signalling, 2020, pp. 257-266, vol. 14.
Spolski, Rosanne et al., "The Yc family of cytokines: fine-tuning signals from IL-2 and IL-21 in the regulation of the immune response [version 1; referees: 3 approved]" F1000Research, 2017, pp. 1-12, vol. 6, No. 1872.
Cheng et al., "Allogeneic CAR-T Therapy Enabled by Base Editing of Lck to Resist Dasatinib Used to Prevent Rejection Mediated through Both T and NK in Host", Blood, Nov. 2022, vol. 140, 7 pages.
Granzin et al., "Shaping of Natural Killer Cell Antitumor Activity by Ex Vivo Cultivation", Front. Immunol., vol. 8, Article 458, Apr. 2017, pp. 1-18.
Hu et al., "Chimeric antigen receptor (CAR)-transduced natural killer cells in tumor immunotherapy", Acta Pharmacologica Sinica, vol. 39, 2018, pp. 167-176.
International Preliminary Report on Patentability, re PCT Application No. PCT/US2024/013779, dated Aug. 14, 2025.
Lusty et al., "IL-18/IL-15/IL-12 synergy induces elevated and prolonged IFN-? production by ex vivo expanded NK cells which is not due to enhanced STAT4 activation", Molecular Immunology, vol. 88, Aug. 2017, pp. 138-147.
Michen et al., "Artificial feeder cells expressing ligands for killer cell immunoglobulin-like receptors and CD94/NKG2A for expansion of functional primary natural killer cells with tolerance to self", Cytotherapy, vol. 22, No. 7, Jul. 2020, pp. 354-368.
Rückert et al., "Clonal expansion and epigenetic inheritance of long-lasting NK cell memory", nature immunology, vol. 23, Oct. 26, 2022, pp. 1551-1563.
Streltsova et al., "Recurrent Stimulation of Natural Killer Cell Clones with K562 Expressing Membrane-Bound Interleukin-21 Affects Their Phenotype, Interferon-? Production, and Lifespan", Int. J. Mol. Sci., vol. 20, No. 443, 2019, 18 pages.
Uchiyama et al., "Direct effect of dasatinib on proliferation and cytotoxicity of natural killer cells in in vitro study", Hematological Oncology, 2013, vol. 13, pp. 156-163.
Whang et al., "Large-Scale Expansion and Engineering of Human NK Cells Sourced from Peripheral Blood Versus Umbilical Cord Blood", nkarta, 2022, 1 page.
Whang et al., "Potentiating the Large-Scale Expansion and Engineering of Peripheral Blood-Derived CAR NK Cells for Off-the-Shelf Application", nkarta, 2021, 1 page.
Xiaomei et al, Expansion of NK cells from PBMCs using immobilized 4-1 BBL and interleukin-21, International Journal Of Oncology, 2015, vol. 47, No. 1, pp. 335-342.

* cited by examiner

Donor 224

Figure 7A

| | IL-12 conc. (ng/ml) | IL-18 conc. (ng/ml) |
|---|---|---|
| Over saturated | 200 * | 400 * |
| Saturated 12&18 | 20 | 25 |
| Saturated 12, Sub-sat 18 | 20 | 0.05 |
| Sub-sat 12&18 | 0.02 | 0.05 |

* 18 and 12 over-saturated off-scale

A

B

15 feeder v/s sat 12& 18

| | |
|---|---|
| P value | 0.0255 |
| P value summary | * |
| Significantly different (P < 0.05)? | Yes |

15 feeder v/s sat 12 & sub-sat 18

| | |
|---|---|
| P value | 0.0122 |
| P value summary | * |
| Significantly different (P < 0.05)? | Yes |

15 feeder v/s mb12-18 feeder

| | |
|---|---|
| P value | 0.0123 |
| P value summary | * |
| Significantly different (P < 0.05)? | Yes |

C

D

E

F

G

H

A

B 15 feeder v/s sat 12 & 18

| | |
|---|---|
| P value | 0.7461 |
| P value summary | ns |
| Significantly different (P < 0.05)? | No |

15 feeder v/s sat 12 & sub-sat 18

| | |
|---|---|
| P value | 0.1111 |
| P value summary | ns |
| Significantly different (P < 0.05)? | No |

15 feeder v/s mb-12-18 feeder

| | |
|---|---|
| P value | 0.4750 |
| P value summary | ns |
| Significantly different (P < 0.05)? | No |

Donor 224 15 Feeder Alone

| | Sample Name | Geometric Mean : Comp-PE-A |
|---|---|---|
| (back-hatched) | Plt1 - 10000 Events C01 | 4335 |
| (hatched) | Plt1 - 10000 Events A01 | 752 |
| (dotted) | Plt1 - 10000 Events B01 | 710 |

Donor 224 Feeder + 12-18

| | Sample Name | Geometric Mean : Comp-PE-A |
|---|---|---|
| (back-hatched) | Plt1 - 10000 Events C02 | 10945 |
| (hatched) | Plt1 - 10000 Events A02 | 537 |
| (dotted) | Plt1 - 10000 Events B02 | 213 |

Donor 543 Feeder Alone

| | Sample Name | Geometric Mean : Comp-PE-A |
|---|---|---|
| | Plt1 - 10000 Events C03 | 6894 |
| | Plt1 - 10000 Events A03 | 454 |
| | Plt1 - 10000 Events B03 | 503 |

Donor 543 Feeder + 12-18

| | Sample Name | Geometric Mean : Comp-PE-A |
|---|---|---|
| | Plt1 - 10000 Events C04 | 17465 |
| | Plt1 - 10000 Events A04 | 402 |
| | Plt1 - 10000 Events B04 | 236 |

B

GFP transduced feeder v/s 12-18:

| | |
|---|---|
| P value | 0.7423 |
| P value summary | ns |
| Significantly different (P < 0.05)? | No |

45_4 transduced feeder v/s 12-18:

| | |
|---|---|
| P value | 0.3798 |
| P value summary | ns |
| Significantly different (P < 0.05)? | No |

Figure 19

| Expansion day 6 cell counts: | #e6 live cells/ml | % viable | Total live e6 (60 ml) | Fold Expansion |
|---|---|---|---|---|
| 1062 (NKstim only) | 0.56 | 84.7 | 33.6 | 56 |
| 1196 (NKstim only) | 0.36 | 82.3 | 21.6 | 36 |
| 1200 (NKstim only) | 0.35 | 80.7 | 21.0 | 35 |
| 1062 +IL-12/18 | 0.86 | 87.3 | 51.6 | 86 |
| 1196 +IL-12/18 | 0.63 | 84.1 | 37.8 | 63 |
| 1200 +IL-12/18 | 0.58 | 87 | 34.8 | 58 |

IL-12 & IL-18 Increases Cytotoxic Potency

NK persistence in vivo with or without IL-12 and IL-18

NK persistence in vivo with or without IL-12 and IL-18

UN transduced NK cells (fresh)

PBS

Day 1

Day 6

Day 30

UN transduced NK cells (fresh)

PBS

Day 30

Day 56

Day 1

Day 6

Longitudinal Imaging Results for NK19 IL12/18 Fresh vs Frozen Days 1-56

Day 4 in vivo stain

Day 4 in vivo stain

C

Day 4 in vivo stain

Day 12 in vivo stain

A

Day 18

B

Day 18

C

Day 18

D

Day 18

E

Day 18

Single dose, naive

METHODS AND COMPOSITIONS FOR ENHANCED EXPANSION AND CYTOTOXICITY OF NATURAL KILLER CELLS

CROSS-REFERENCE TO RELATED APPLICATIONS

This application is the United States National Phase application, pursuant to 35 U.S.C. 371, of International Patent Application No. PCT/US2020/044033, filed Jul. 29, 2020, which claims priority to U.S. Provisional Patent Application No. 62/881,311, filed Jul. 31, 2019 and U.S. Provisional Patent Application No. 62/932,342, filed Nov. 7, 2019, the entire contents of each of which is incorporated by reference herein.

FIELD

Some embodiments of the methods and compositions disclosed herein relate to enhanced expansion and/or enhanced cytotoxicity of engineered immune cells, such as Natural Killer (NK) cells and/or T cells.

BACKGROUND

The use of engineered cells for cellular immunotherapy allows for treatment of cancers or other diseases by leveraging various aspects of the immune system to target and destroy diseased or damaged cells. Such therapies require engineered cells in numbers sufficient for therapeutically relevant doses.

INCORPORATION BY REFERENCE OF MATERIAL IN ASCII TEXT FILE

This application incorporates by reference the Sequence Listing contained in the following ASCII text file being submitted concurrently herewith: File name: NKT034WO_ST25.txt; created Jul. 20, 2020, 123 KB in size.

SUMMARY

In several embodiments, there are provided various methods for enhancing the expansion of immune cells for use in cellular immunotherapy. For example, in several embodiments, there is provided a method in which immune cells are co-cultured with a feeder cell line in a media supplemented with one or more soluble cytokines, the cytokines being added to the media at least once during the co-culture. In several embodiments, the immune cells are NK cells. In several embodiments, the expanded NK cells are unexpectedly amenable to cellular engineering, such as engineering the cells to express a chimeric receptor (for example, for use in cancer immunotherapy). In several embodiments, the NK cells (or other immune cells) co-cultured with a soluble interleukin-supplemented media express such chimeric receptors more robustly than NK cells not subject to the co-cultured in a soluble interleukin-supplemented media. Further, in several embodiments, the engineered NK cells exhibit an unexpectedly enhanced cytotoxicity.

In several embodiments, there is provided a method for enhancing the expansion of natural killer cells for use in immunotherapy, comprising co-culturing, in a culture media, a population of natural killer (NK) cells with a feeder cell population, supplementing the culture media with interleukin 2 (IL2) and supplementing the culture media with at least one soluble stimulatory agent selected from interleukin 12 (IL12), interleukin 18 (IL18), interleukin 21 (IL21), and combinations thereof. In several embodiments, the feeder cell population comprises cells engineered to express 4-1BBL and membrane-bound interleukin-15 (mbIL15).

In several embodiments, there are provided methods for enhancing cytotoxicity of natural killer (NK) cells, comprising contacting NK cells with a nucleic acid encoding a chimeric antigen receptor (CAR) to cause the NK cells to express the CAR, co-culturing in a culture media, the population of NK cells with a feeder cell population, supplementing the culture media with interleukin 2, supplementing the culture media with at least one soluble stimulatory agent, wherein the soluble stimulatory agent is selected from interleukin 12, interleukin 18, interleukin 21, and combinations thereof, wherein the supplementation of the media with the at least one soluble stimulatory agent results in enhanced cytotoxicity by the CAR-expressing NK cells as compared to NK cells co-cultured with the feeder cells in the absence of the at least one soluble stimulatory agent.

In several embodiments, the supplementation of the media with the at least one soluble stimulatory agent results in enhanced NK cell expansion as compared to co-culturing NK cells with the feeder cells in the absence of the at least one soluble stimulatory agent.

In several embodiments, the supplementation of the media with the at least one soluble stimulatory agent results in enhanced NK cell expansion as compared to co-culturing NK cells with the feeder cells in the absence of the at least one soluble stimulatory agent. In several embodiments, one or more additional characteristics of the NK cells is enhanced, such as, for example, activity (e.g., cytotoxicity against a target cell or cells), lifespan (either in culture or in vivo), activity (e.g., enhanced activity or longevity of activity), etc. For example, in several embodiments, the culturing methods enhances one or more of the persistence and/or cytotoxicity of the NK cells compared to the resulting persistence and/or cytotoxicity of NK cells co-cultured with the feeder cells in the absence of the at least one soluble stimulatory agent. In several embodiments, the resulting NK cells exhibit a memory-like phenotype characterized by (i) increased NKG2C expression by the NK cells and/or (ii) decreased or equivalent CD62 ligand expression by the NK cells, the expression in (i) and (ii) both as compared to NK cells cultured in the same conditions but without the one or more soluble stimulatory molecule. Advantageously, in several embodiments, the resulting NK cells exhibit reduced signs of cytokine withdrawal upon administration to a subject as compared to NK cells cultured in media comprising at least one soluble stimulatory agent but not feeder cells. This is in contrast to other methods of expanding NK cells which result in the NK cells exhibiting a dependence on the high concentrations of cytokines used. In such methods the NK cells exhibit reduced viability when removed from the culture conditions, such as when administered to a patient, which can limit the utility and/or efficacy of such cells in eradicating tumor cells.

In several embodiments, the soluble stimulatory agent used to supplement the medial is a combination of IL12 and IL18. In several embodiments, when IL12 and IL18 are used in combination, IL21 is not used. In several embodiments, IL21 is not used. In several embodiments, the concentration of the at least one soluble stimulatory agent is between about 0.01 ng/mL and about 50 ng/mL at a time point within 1, 2, 4, 6, 8, 10, 12, 16, 18, 20, or 24 hours of the start of the co-culturing. In several embodiments, the concentration of the at least one soluble stimulatory agent is between about 0.01 ng/mL and about 30 ng/mL at a time point within 1, 2, 4, 6, 8, 10, 12, 16, 18, 20, or 24 hours of the start of the co-culturing. In several embodiments, the concentration of the at least one soluble stimulatory agent is between about 0.01 ng/mL and about 50 ng/mL at a time point within 120 hours of the start of the co-culturing. In several embodiments, the at least one stimulatory agent comprises soluble IL12 at a concentration of less than about 10 ng/mL at a time point within 1, 2, 4, 6, 8, 10, 12, 16, 18, 20, or 24 hours of the start of the co-culturing. In several embodiments, the at least one stimulatory agent comprises soluble IL18 at a concentration of less than about 50 ng/mL at a time point within 24 hours of the start of the co-culturing. In several embodiments, the concentration of the at least one soluble stimulatory agent is between about 0.01 ng/mL and about 30 ng/mL at a time point within 120 hours of the start of the co-culturing. In several embodiments, the at least one stimulatory agent comprises soluble IL12 at a concentration of less than about 10 ng/mL at a time point within 120 hours of the start of the co-culturing. In several embodiments, the at least one stimulatory agent comprises soluble IL18 at a concentration of less than about 50 ng/mL at a time point within 120 hours of the start of the co-culturing. In several embodiments, the at least one stimulatory agent comprises (i) soluble IL12 at a concentration between about 0.01 ng/mL and about 8 ng/mL and (ii) soluble IL18 at a concentration between about 0.01 ng/mL and about 30 ng/mL, and wherein the culture media is supplemented for a second time with interleukin 2 at a concentration that is greater than the first supplementation of the culture media with IL2, wherein said concentrations are present at a time point within 1, 2, 4, 6, 8, 10, 12, 16, 18, 20, or 24 hours of the start of the co-culturing. In several embodiments, the at least one stimulatory agent comprises (i) soluble IL12 at a concentration between about 0.01 ng/mL and about 8 ng/mL and (ii) soluble IL18 at a concentration between about 0.01 ng/mL and about 30 ng/mL, and wherein the culture media is supplemented for a second time with IL2 at a concentration that is greater than the first supplementation of the culture media with IL2, wherein said concentrations are present at a time point within 120 hours of the start of the co-culturing.

In several embodiments, the feeder cell population comprises K562 cells. In several embodiments, the feeder cell population is not a 721.221 cell line. In several embodiments, the feeder cells (e.g., K562 cells) are irradiated prior to co-culture. In several embodiments, the feeder cells (e.g., the K562) cells express both 4-1BBL and mbIL15. In several embodiments, the feeder cells (e.g., the K562) cells express both 4-1BBL and mbIL15 and are irradiated prior to the inception of co-culturing.

According to several embodiments, the at least one stimulatory agent comprises (i) soluble IL12 at a concentration between about 0.01 ng/mL and about 8 ng/mL and (ii) soluble IL18 at a concentration between about 0.01 ng/mL and about 30 ng/mL. In several embodiments, the In several embodiments, in which IL12 is used, the IL12 is added to the cell culture media at a concentration of less than about 7 ng/mL. In several embodiments, in which IL18 is used, the IL18 is added to the cell culture media at a concentration of less than about 40 ng/mL. In several embodiments using multiple stimulatory cytokines, the concentration of IL12 is less than about 7 ng/mL, the concentration of IL18 is less than about 40 ng/mL. In some such embodiments IL2 is present at an initial concentration and later additional IL2 is added. In some such embodiments the initial concentration of IL2 is between about 50 IU/mL and about 500 IU/mL. In several embodiments, the media is supplemented with IL2 to concentration less than about 500 IU/mL. In additional embodiments, the media is supplemented with IL2 to concentration less than about 50 IU/mL. In several embodiments, the initial concentration of IL2 is less than about 50 IU/mL. In several embodiments the media is supplemented later with additional IL2, to a concentration of less than about 500 IU/mL.

In several embodiments, the concentration of the at least one soluble stimulatory agent is between about 0.01 ng/mL and about 50 ng/mL at a time point within 120 hours of said co-culturing. In several embodiments, the feeder cell population comprising cells engineered to express 4-1BBL and membrane-bound IL-15 (mbIL15). In several embodiments, the at least one soluble stimulatory agent comprises a combination of said interleukin 12 and said interleukin 18. In several embodiments, the concentration of the at least one soluble stimulatory agent is between about 0.01 ng/mL and about 30 ng/mL at a time point within 120 hours of the co-culturing. In several embodiments, the at least one stimulatory agent comprises soluble IL12 at a concentration of less than about 10 ng/mL at a time point within 120 hours of the co-culturing. In several embodiments, the at least one stimulatory agent comprises soluble IL18 at a concentration of less than about 50 ng/mL at a time point within 120 hours of the co-culturing. In several embodiments, the at least one stimulatory agent comprises (i) soluble IL12 at a concentration between about 0.01 ng/mL and about 8 ng/mL and (ii) soluble IL18 at a concentration between about 0.01 ng/mL and about 30 ng/mL, and wherein the culture media is supplemented for a second time with interleukin 2 at a concentration that is greater than the first supplementation of the culture media with IL2, wherein each concentration is at a time point within 120 hours of the co-culturing. In several embodiments, the methods described herein further comprise supplementing the media with an additional amount of at least one of the soluble stimulatory agents. In several embodiments, the second supplementation of the media is between 12 hours and 120 hours from the first supplementation. In additional embodiments, further supplementation of the media is made at later time points. In several embodiments, the concentrations of the soluble agents, e.g., IL12 and/or IL18, are the same at a first time point as at a respective second time point. In some embodiments, they subsequent concentrations are different (e.g., greater).

In several embodiments, there is provided a population of engineered natural killer cells comprising an engineered chimeric receptor configured to bind a marker on a target cancer cell and upon binding, induce the NK cell to exert a cytotoxic effect against the target cancer cell, wherein the NK cell was expanded in culture in the presence of at least one soluble stimulatory agent, wherein the soluble stimulatory agent is selected from interleukin 12, interleukin 18, interleukin 21, and combinations thereof, and wherein the population of engineered NK cells, at least in part, have a memory-like phenotype characterized by (i) increased NKG2C expression by the NK cells and/or (ii) decreased or equivalent CD62 ligand expression by the NK cells, the expression in (i) and (ii) both as compared to NK cells cultured in the same conditions but without the soluble stimulatory agent.

In several embodiments, the engineered chimeric receptor is encoded by a sequence at least 85%, 90%, 95%, 86%, 97%, 98%, or 99% identical in sequence to SEQ ID NO: 1, 3, 5, 7, 9, 11, 13, 15, 17, 19, 21, 23, 25, or 27. In several embodiments, the engineered chimeric receptor has an amino acid sequence at least 85%, 90%, 95%, 86%, 97%, 98%, or 99% identical in sequence to SEQ ID NO: 2, 4, 6, 8, 10, 12, 14, 16, 18, 20, 22, 24, 26, or 28.

In several embodiments, the methods further comprise contacting the NK cells with a vector encoding a chimeric antigen receptor (CAR). In some embodiments, the CAR is configured to target one or more of CD19, CD123, CD70, BCMA, or a ligand of the natural killer receptor group D (NKG2D). In several embodiments, the CAR does not include a DAP10 or DAP12 subdomain.

In several embodiments, the NK cells produced by the methods disclosed herein are used in the preparation of a medicament for the treatment of cancer. In several embodiments, the NK cells produced by the methods disclosed herein are for the treatment of cancer. Also provided are methods of treating cancer in a subject in need thereof, comprising administering to the subject a therapeutically effective amount of the engineered NK cells expanded using any of the methods disclosed herein.

In several embodiments, there is also provided a culture media for expanding cells, the culture media comprising IL2 provided at a concentration of less than about 500 IU/mL; IL12 provided at a concentration of less than about 10 ng/mL; and IL18 provided at a concentration of about 30 ng/mL.

In several embodiments, there is also provided a combination culture media for expanding cells, the combination comprising IL2 provided at a concentration of less than about 500 IU/mL, IL12 provided at a concentration of less than about 10 ng/mL, IL18 provided at a concentration of about 30 ng/mL, and IL15 that is bound to a cell membrane surface (mbIL15). In several embodiments, the mbIL15 is bound to the cell membrane surface of a feeder cell. In several embodiments, the culture media and/or the combination culture media further comprise at least one amino acid, at least one inorganic salt, and at least one vitamin.

In several embodiments, there is provided a method for enhancing the expansion of natural killer cells for use in immunotherapy, comprising co-culturing, in a culture media, a population of natural killer (NK) cells with a feeder cell population, supplementing, at a first time point, the culture media with at least one soluble stimulatory agent, wherein the soluble stimulatory agent is selected from interleukin 12, interleukin 18, interleukin 21, and combinations thereof, and supplementing, at a second time point, the culture media with and additional amount of at least one of the soluble stimulatory agents. In several embodiments, the NK are co-cultured with the feeder cells for a second period of time. In several embodiments, the supplementation of the media with the at least one soluble stimulatory agent results in enhanced NK cell expansion as compared to co-culturing NK cells with the feeder cells in the absence of the at least one soluble stimulatory agent.

In several embodiments, the concentration of the at least one soluble stimulatory agent is between about 0.01 ng/mL and about 100 ng/mL. In several embodiments, the feeder cell population comprising cells engineered to express one or more of 4-1BBL and membrane-bound IL-15. In several embodiments, the method also involves supplementing the culture media with interleukin 2. In several embodiments, the first and second time point are greater than 12 hours apart and less than 120 hours apart. In several embodiments, the concentrations provided herein are the final concentrations of the molecule or agent in question in a culture media. In several embodiments, the concentrations provided herein are the concentrations of the molecule or agent as reconstituted (if applicable) prior to addition to a given volume of media.

In some embodiments, the concentration is present at a time point within 12, 24, 72 or 120 hours. In some embodiments, when more than one agent is use, the concentration of each agent is between about 0.01 ng/mL and about 100 ng/mL or about 1 IU/mL to about 1000 IU/mL (and e.g., is present at a time point within 12, 24, 72 or 120 hours). In other embodiments, when more than one agent is use, the concentration of all agents is between about 0.01 ng/mL and about 100 ng/mL or about 1 IU/mL to about 1000 IU/mL (and e.g., is present at a time point within 12, 24, 72 or 120 hours).

In several embodiments, the at least one soluble stimulatory agent comprises a combination of IL12 and IL18. In several embodiments, the first time point is at the inception of the co-culturing of the NK cells with the feeder cell and/or the second time point is at the inception of the second period of time. In several embodiments, the first time point and second time point are between about 24 and 120 hours apart, and the concentration of the stimulatory agent is between about 0.01 ng/mL and about 30 ng/mL.

In several embodiments, the at least one stimulatory agent comprises (i) soluble IL12 at a concentration between about 10 ng/mL and about 30 ng/mL and (ii) soluble IL18 at a concentration between about 0.01 ng/mL and about 30 ng/mL. In several embodiments, the at least one stimulatory agent comprises (i) soluble IL12 at a concentration between about 0.01 ng/mL and about 10 ng/mL and (ii) soluble IL18 at a concentration between about 0.01 ng/mL and about 30 ng/mL. In several embodiments, the concentration of the soluble IL12 and soluble IL18 is each the same at the first time point as at the respective second time point. In several embodiments, the concentration of the soluble IL12 and soluble IL18 is each different at the first time point as at the respective second time point. In several embodiments, the concentration of the soluble IL12 and soluble IL18 are equivalent to one another.

In several embodiments, the method also comprises transducing the expanded NK cells with a nucleic acid construct encoding a chimeric receptor, wherein expression of the chimeric receptor is enhanced as compared to expression of the chimeric receptor on NK cells co-cultured with the feeder cells in the absence of the at least one soluble stimulatory agent. In several embodiments, the cytotoxic activity of the chimeric receptor is unexpectedly enhanced as compared to cytotoxic activity of the chimeric receptor on NK cells co-cultured with the feeder cells in the absence of the at least one soluble stimulatory agent.

There is also provided for herein use of the NK cells expanded by the method disclosed herein for the treatment of cancer and/or for preparation of a medicament for the treatment of cancer.

BRIEF DESCRIPTION OF THE DRAWINGS

The descriptions of the figures below are related to experiments and results that represent non-limiting embodiments of the inventions disclosed herein.

FIG. 3A shows flow cytometry data measuring expression of NKG2D on the surface of NK cells when expanded with feeder cells alone (top row) or using cytokine supplementation (bottom row). FIG. 3B measures the mean fluorescence intensity of (representing transduction with an NKG2D bearing chimeric receptor construct (NKX101) under the various conditions.

FIGS. 7A-7B relate to NK cell expansion under various conditions. FIG. 7A shows the various concentrations determined to be over-saturated, saturated, or sub-saturated for IL12/18. FIG. 7B shows NK cell proliferation data under various culture conditions.

FIG. 9A shows summary data for each of the culture groups. FIG. 9B provides statistical comparisons of the groups. FIG. 9C shows fold expansion data (at Day 7) for a specific titration data set involving various concentrations of IL12 with IL18 at 4 ng/ml.

FIG. 9D shows similar data with IL18 at 20 ng/ml. FIG. 9E shows viability of engineered NK cells at day 7 of culture with 20 ng/mL IL18, 40 IU/mL IL-2 and the indicated concentrations of IL12. FIG. 9F shows viability of engineered NK cells at day 8 of culture with 20 ng/mL IL18, 400 IU/mL IL-2 and the indicated concentrations of IL12. FIG. 9G shows viability of engineered NK cells at day 7 of culture with 4 ng/mL IL18, 40 IU/mL IL-2 and the indicated concentrations of IL12. FIG. 9H shows viability of engineered NK cells at day 8 of culture with 4 ng/mL IL18, 400 IU/mL IL-2 and the indicated concentrations of IL12.

FIG. 10A shows summary data for the cytotoxicity of NK cells in each of the culture groups after 8 days of culture. FIG. 10B provides statistical comparisons of the cytotoxicity.

FIG. 11A shows summary data for the cytotoxicity of NK cells in each of the culture groups after 15 days of culture. FIG. 11B provides statistical comparisons of the cytotoxicity.

FIG. 14A shows summary data related to the cytotoxicity of NK cells transduced with a chimeric receptor targeting NKG2D ligands and cultured in the indicated conditions. FIG. 14B shows statistical comparisons of the groups.

FIGS. 15A and 15B show data regarding cytotoxicity of NK cells from two different donors 13 days-post transduction with either a GFP-encoding vector or a vector encoding a chimeric receptor targeting NKG2D ligands. FIGS. 15C and 15D show corresponding cytotoxicity data from the same two donors at day 21 post-transduction.

FIG. 16A shows data related to the expression of markers associated with a memory-like phenotype by NK cells over time in the indicated culture conditions. FIG. 16B shows flow cytometry data showing the progression of marker expression over time in culture.

FIG. 17A shows expression data related to CD62 ligand, FIG. 17B shows expression of NKG2C, FIG. 17C shows expression of CD57, and FIG. 17D shows expression of both CD62L and NKG2C.

FIG. 19 shows cell viability and expansion data for NK cells grown under varied culture conditions.

FIG. 22B shows summary cytotoxicity data. FIG. 22C shows cytotoxicity data as a function of effector to target ratio.

FIG. 26A shows data related to the cytotoxicity of NK cells expanded under the indicated conditions against Nalm6 cells in a xenograft model. FIG. 26B shows a survival curve for mice receiving the indicated treatments. FIG. 26C shows data related to the detection of human NK cells in the murine blood 18 days post-injection, separated based on the expansion culture conditions. FIG. 26D shows data related to the detection of CAR-positive NK cells in the murine blood 18 days post-injection, separated based on the expansion culture conditions. FIG. 26E shows expression data related to the percentage of NK cells (either fresh or cryopreserved) expressing a non-limiting embodiment of an anti-CD19 CAR at day 15 of expansion and in the presence or absence of additional stimulatory molecules. FIG. 26F shows expression data related to the percentage of NK cells (either fresh or cryopreserved) expressing a non-limiting embodiment of an anti-CD19 CAR at day 22 of expansion and in the presence or absence of additional stimulatory molecules.

FIG. 27A shows a schematic depiction of an experimental protocol for assessing the effectiveness of humanized, NK cells expressing various CD19-directed CAR constructs in vivo. The various experimental groups tested are as indicated. For cells with an "IL12/IL18" designation, the cells were expanded in the presence of soluble IL12 and/or IL18, according to embodiments disclosed herein. FIGS. 27B and 27C show bioluminescence data from animals dosed with Nalm6 tumor cells and treated with the indicated construct.

FIG. 28A shows bioluminescence (as photon/second flux) from animals receiving untransduced NK cells. FIG. 28B shows flux measured in animals receiving PBS as a vehicle. FIG. 28C shows flux measured in animals receiving previously frozen NK cells expressing the NK19 NF2 CAR (as a non-limiting example of a CAR). FIG. 28D shows flux measured in animals receiving previously frozen NK cells expressing the NK19 NF2 CAR (as a non-limiting example of a CAR) expanded using IL12 and/or IL18. FIG. 28E and FIG. 28F show flux measured in animals receiving fresh NK cells expressing the NK19 NF2 CAR (as a non-limiting example of a CAR). FIG. 28G and FIG. 28H show flux measured in animals receiving previously fresh NK cells expressing the NK19 NF2 CAR (as a non-limiting example of a CAR) expanded using IL12 and/or IL18. FIG. 28I shows a line graph depicting the bioluminescence measured in the various groups over the first 30 days post-tumor inoculation. FIG. 28J shows a line graph depicting the bioluminescence measured in the various groups over the first 56 days post-tumor inoculation.

FIG. 30A shows data related to the percentage of NK cells expressing CARs in the blood of animals over time. FIG. 30B shows data related to the percentage of NK cells expressing CARs in the blood of animals over a period of 50 days. FIG. 30C shows data related to the percentage of NK cells expressing CARs over time and based on the number of live cells tested.

FIG. 33A shows the percentage of $CD3^{-}CD56^{+}$ NK cells from in whole blood samples for the indicated experimental groups. FIG. 33B shows the percentage of NK cells expressing a specific anti-CD19 CAR for each experimental group. FIG. 33C shows data relating to the number of GFP positive tumor cells detected for each experimental group.

FIG. 34A shows the percentage of $CD3^{-}CD56^{+}$ NK cells from in whole blood samples for the indicated experimental groups. FIG. 34B shows the percentage of NK cells expressing a specific anti-CD19 CAR for each experimental group. FIG. 34C shows data relating to the number of GFP positive tumor cells detected for each experimental group.

FIG. 35A shows the percentage of $CD3^{-}CD56^{+}$ NK cells from whole blood samples for the indicated experimental groups. FIG. 35B shows the percentage of CD19-positive tumor cells for each experimental group as measured using a phycoerythrin (PE)-conjugated antibody. FIG. 35C shows data relating to the number of GFP positive tumor cells detected for each experimental group. FIG. 35D shows the percentage of NK cells expressing a specific anti-CD19 CAR for each experimental group as measured using an anti CD19 FC antibody. FIG. 35E shows the percentage of NK cells in each treatment group expressing the CD19 CAR.

DETAILED DESCRIPTION

Figure 1A:
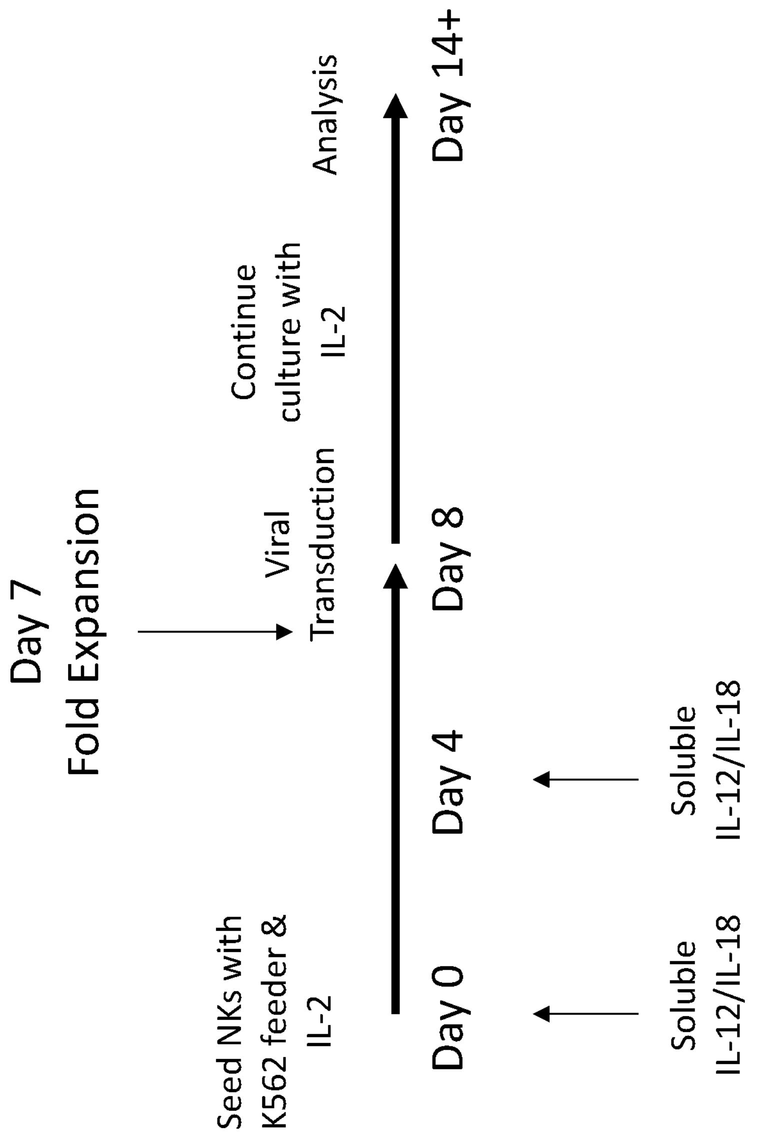
FIGS. 1A and 1B depict a non-limiting examples of expansion protocol used to enhance the expansion of NK cells according to embodiments disclosed herein.

While cancer immunotherapy, or cellular therapy for other diseases, has advanced greatly in terms of the ability to engineer cells to express constructs of interest, there is still a need for clinically relevant number of those cells for patient administration. This is particularly important when the underlying native immune cell to be engineered and later administered is less prevalent than other immune cell types. This requires either starting with a larger amount of starting material, which may not be practical, or developing more efficient methods and compositions to expand (in some cases preferentially) the immune cell of interest, such as an NK cell. There are therefore provided herein, in several embodiments, methods and compositions that advantageously allow for the enhanced expansion of NK cells (or other immune cells) but also allow for enhanced cytotoxicity of those cells.

In several embodiments, there are provided populations of expanded and activated NK cells derived from co-culturing a modified "feeder" cell disclosed herein with a starting population of immune cells and supplementing the co-culture with various cytokines at certain time points during the expansion.

Cells for Use in Immune Cell Expansion

In several embodiments, cell lines are used in a co-culture with a population of immune cells that are to be expanded. Such cell lines are referred to herein as "stimulatory cells," which can also be referred to as "feeder cells". In several embodiments, the entire population of immune cells is to be expanded, while in several embodiments, a selected immune cell subpopulation is to expanded. For example, in several embodiments, NK cells are expanded relative to other immune cell subpopulations (such as T cells). In other embodiments, both NK cells and T cells are expanded. In several embodiments, the feeder cells are themselves genetically modified. In some embodiments, the feeder cells do not express MHC I molecules, which have an inhibitory effect on NK cells. In some embodiments, the feeder cells need not entirely lack MHC I expression, however they may express MHC I molecules at a lower level than a wild type cell. For example, in several embodiments, if a wild type cell expresses an MHC at a level of X, the cell lines used may express MHC at a level less than 95% of X, less than 90% of X, less than 85% of X, less than 80% of X, less than 70% of X, less than 50% of X, less than 25% of X, and any expression level between (and including) those listed. In several embodiments, the stimulatory cells are immortalized, e.g., a cancer cell line. However, in several embodiments, the stimulatory cells are primary cells.

Various cell types can be used as feeder cells, depending on the embodiment. These include, but are not limited to, K562 cells, certain Wilm's Tumor cell lines (for example Wilms tumor cell line HFWT), endometrial tumor cells (for example, HHUA), melanoma cells (e.g., HMV-II), hepatoblastoma cells (e.g., HuH-6), lung small cell carcinoma cells (e.g., Lu-130 and Lu-134-A), neuroblastoma cells (e.g., NB19 and NB69), embryonal carcinoma testis cells (e.g., NEC14), cervical carcinoma cells (TCO-2), neuroblastoma cells (e.g., TNB1), 721.221 EBV transformed B cell line, among others.

In additional embodiments, the feeder cells also have reduced (or lack) MHC II expression, as well as having reduced (or lacking) MHC I expression. In some embodiments, other cell lines that may initially express MHC class I molecules can be used, in conjunction with genetic modification of those cells to reduce or knock out MHC I expression. Genetic modification can be accomplished through the use of gene editing techniques (e.g. a crispr/cas system; RNA editing with an Adenosine deaminases acting on RNA (ADAR), zinc fingers, TALENS, etc.), inhibitory RNA (e.g., siRNA), or other molecular methods to disrupt and/or reduce the expression of MHC I molecules on the surface of the cells.

As discussed in more detail below, in several embodiments, the feeder cells are engineered to express certain stimulatory molecules (e.g. interleukins, CD3, 4-1BBL, etc.) to promote immune cell expansion and activation. Engineered feeder cells are disclosed in, for example, International Patent Application PCT/SG2018/050138, which is incorporated in its entirety by reference herein. In several embodiments, the stimulatory molecules, such as interleukin 12, 18, and/or 21 are separately added to the co-culture media, for example at defined times and in particular amounts, to effect an enhanced expansion of a desired sub-population(s) of immune cells.

Stimulatory Molecules

As discussed briefly above, certain molecules promote the expansion of immune cells, such as NK cells or T cells, including engineered NK or T cells. Depending on the embodiment, the stimulatory molecule, or molecules, can be expressed on the surface of the feeder cells used to expand the immune population. For example, in several embodiments a K562 feeder cell population is engineered to express 4-1BBL and/or membrane bound interleukin 15 (mbIL15). Additional embodiments relate to further membrane bound interleukins or stimulatory agents. Examples of such additional membrane bound stimulatory molecules can be found in International Patent Application PCT/SG2018/050138, which is incorporated in its entirety by reference herein.

In several embodiments, the methods disclosed herein relate to addition of one or more stimulatory molecules to the culture media in which engineered feeder cells and engineered NK cells are co-cultured. In several embodiments, one or more interleukins is added. For example, in several embodiments, IL2 is added to the media. In several embodiments, IL12 is added to the media. In several embodiments, IL18 is added to the media. In several embodiments, IL21 is added to the media. In several embodiments, combinations of two or more of IL2, IL12, IL18, and/or IL21 is added to the media. In some embodiments, rather than using a feeder cell with mbIL15, soluble IL15 is added to the media (alone or in combination with any of IL2, IL12, IL18, and IL21).

In several embodiments, the media comprises one or more vitamin, inorganic salt and/or amino acids. In several embodiments, the media comprises 1, 2, 3, 4, 5, 6, 7, 8, 9, 10 or all of Glycine, L-Arginine, L-Asparagine, L-Aspartic acid, L-Cystine (e.g., L-Cystine 2HCl), L-Glutamic Acid, L-Glutamine, L-Histidine, L-Hydroxyproline, L-Isoleucine, L-Leucine, L-Lysine hydrochloride, L-Methionine, L-Phenylalanine, L-Proline, L-Serine, L-Threonine L-Tryptophan, L-Tyrosine (e.g., L-Tyrosine disodium salt dehydrate), and L-Valine. In several embodiments, the media comprises 1, 2, 3, 4, or more of Biotin, Choline chloride, D-Calcium pantothenate, Folic Acid, i-Inositol, Niacinamide, Para-Aminobenzoic Acid, Pyridoxine hydrochloride, Riboflavin, Thiamine hydrochloride, and Vitamin B12. In several embodiments, the media comprises 1, 2, 3, 4, or more of Calcium nitrate ($Ca(NO_3)2\ 4H_2O$), Magnesium Sulfate ($MgSO_4$) (e.g., Magnesium Sulfate ($MgSO_4$) (anhyd.)), Potassium Chloride (KCl), Sodium Bicarbonate ($NaHCO_3$), Sodium Chloride (NaCl), and Sodium Phosphate dibasic ($Na_2HPO_4$) (e.g., Sodium Phosphate dibasic ($Na_2HPO_4$) anhydrous).

In several embodiments, the media further comprises D-Glucose and/or glutathione (optionally reduced glutathione). In several embodiments, the media further comprises serum (e.g., fetal bovine serum) in an amount ranging from about 1% to about 20%. In several embodiments, the serum is heat-inactivated. In several embodiments, the media is serum-free. In several embodiments, the media is xenofree.

Depending on the embodiment, IL2 is used to supplement the culture media and enhance expansion, or other characteristics, of NK cells. In several embodiments, the concentration of IL2 used ranges from about 1 IU/mL to about 1000 IU/mL, including for example, about 1 IU/mL to about 5 IU/mL (e.g., 1, 2, 3, 4, and 5, about 5 IU/mL to about 10 IU/mL (e.g., 5, 6, 7, 8, 9, and 10), about 10 IU/mL to about 20 IU/mL (e.g., about 10, 12, 14, 16, 18, and 20), about 20 IU/mL to about 30 IU/mL (e.g., about 20, 22, 24, 26, 28, and 30), about 30 IU/mL to about 40 IU/mL (e.g., 30, 32, 34, 36, 38, and 40), about 40 to about 50 IU/mL (e.g., 40, 42, 44, 46, 48, 50), about 50 IU/mL to about 75 IU/mL (e.g., 50, 55, 60, 65, 70, and 75), about 75 IU/mL to about 100 IU/mL (e.g., 75, 80, 85, 90, 95, and 100), about 100 IU/mL to about 200 IU/mL (e.g., 100, 125, 150, 275, and 200), about 200 IU/mL to about 300 IU/mL (e.g., 200, 225, 250, 275, and 300), about 300 IU/mL to about 400 IU/mL (e.g., 300, 325, 350, 375, and 400), about 400 IU/mL to about 500 IU/mL (e.g., 400, 425, 450, 475, and 500), about 500 IU/mL to about 750 IU/mL (e.g., 500, 550, 600, 650, 700, and 750), or about 750 IU/mL to about 1000 IU/mL (e.g., 750, 800, 850, 900, 950, and 1000), and any concentration therebetween, including endpoints. In several embodiments, IL2 may be added at multiple time points during culture. In some such embodiments the concentration of IL2 used differs between selected time points.

Depending on the embodiment, IL12A and/or IL12B is used to supplement the culture media and enhance expansion, or other characteristics, of NK cells. In several embodiments, the concentration of IL12 (either IL12A or IL12B)

used ranges from about 0.01 ng/ml to about 100 ng/mL, including, for example, about 0.01 ng/mL to about 0.05 ng/mL (e.g., 0.01, 0.02, 0.03, 0.04, and 0.05), about 0.05 ng/mL to about 0.1 ng/mL (e.g., 0.05, 0.06, 0.07, 0.08, 0.09 and 0.1), about 0.1 ng/mL to about 0.5 ng/mL (e.g., 0.1, 0.2, 0.3, 0.4, and 0.5), about 0.5 ng/mL to about 1.0 ng/mL (e.g., 0.5, 0.6, 0.7, 0.8, 0.9, and 1.0), about 1.0 ng/mL to about 2.0 ng/mL (e.g., 1.1, 1.2, 1.3, 1.4, 1.5, 1.6, 1.7, 1.8, 1.9, and 2.0), about 2.0 ng/mL to about 5.0 ng/mL (e.g., 2.0, 3.0, 4.0, and 5.0), about 5.0 ng/mL to about 10.0 ng/mL (e.g., 5.0, 6.0, 7.0, 8.0, 9.0 and 10.0), about 10.0 ng/mL to about 15.0 ng/mL (e.g., 10.0, 11.0, 12.0, 13.0, 14.0, and 15.0), about 15.0 ng/mL to about 20.0 ng/mL (e.g., 15.0, 16.0, 17.0, 18.0, 19.0, and 20.0), about 20.0 ng/mL to about 25.0 ng/mL (e.g., 20.0, 21.0, 22.0, 23.0, 24.0, and 25.0), about 25.0 ng/mL to about 30.0 ng/mL (e.g., 25.0, 26.0, 27.0, 28.0, 29.0, and 30.0), about 30.0 ng/mL to about 50.0 ng/mL (e.g., 30.0, 35.0, 40.0, 45.0, and 50.0), about 50.0 ng/mL to about 75.0 ng/mL (e.g., 50.0, 55.0, 60.0, 65.0, 70.0, and 75.0), about 75.0 ng/mL to about 100.0 ng/mL (e.g., 75.0, 80.0, 85.0, 90.0, 95.0, and 100.0), and any concentration therebetween, including endpoints. In several embodiments, the concentration of IL12 is between about 0.01 ng/mL and about 8 ng/mL, including any concentration therebetween, including endpoints.

In some embodiments, a mixture of IL12A and IL12B is used. In several embodiments, a particular ratio of IL12A:IL12B is used, for example, 1:10, 1:50, 1:100, 1:150, 1:200, 1:250, 1:500, 1:1000, 1:10,000, 10,000:1, 1000:1, 500:1, 250:1, 150:1, 100:1, 10:1 and any ratio there between, including endpoint.

In some embodiments, interleukin 18 (IL18) is used to enhance expansion, or other characteristics, of NK cells. In several embodiments, the concentration of IL18 used ranges from about 0.01 ng/ml to about 100 ng/mL, including, for example, about 0.01 ng/mL to about 0.05 ng/mL (e.g., 0.01, 0.02, 0.03, 0.04, and 0.05), about 0.05 ng/mL to about 0.1 ng/mL (e.g., 0.05, 0.06, 0.07, 0.08, 0.09 and 0.1), about 0.1 ng/mL to about 0.5 ng/mL (e.g., 0.1, 0.2, 0.3, 0.4, and 0.5), about 0.5 ng/mL to about 1.0 ng/mL (e.g., 0.5, 0.6, 0.7, 0.8, 0.9, and 1.0), about 1.0 ng/mL to about 2.0 ng/mL (e.g., 1.1, 1.2, 1.3, 1.4, 1.5, 1.6, 1.7, 1.8, 1.9, and 2.0), about 2.0 ng/mL to about 5.0 ng/mL (e.g., 2.0, 3.0, 4.0, and 5.0), about 5.0 ng/mL to about 10.0 ng/mL (e.g., 5.0, 6.0, 7.0, 8.0, 9.0 and 10.0), about 10.0 ng/mL to about 15.0 ng/mL (e.g., 10.0, 11.0, 12.0, 13.0, 14.0, and 15.0), about 15.0 ng/mL to about 20.0 ng/mL (e.g., 15.0, 16.0, 17.0, 18.0, 19.0, and 20.0), about 20.0 ng/mL to about 25.0 ng/mL (e.g., 20.0, 21.0, 22.0, 23.0, 24.0, and 25.0), about 25.0 ng/mL to about 30.0 ng/mL (e.g., 25.0, 26.0, 27.0, 28.0, 29.0, and 30.0), about 30.0 ng/mL to about 50.0 ng/mL (e.g., 30.0, 35.0, 40.0, 45.0, and 50.0), about 50.0 ng/mL to about 75.0 ng/mL (e.g., 50.0, 55.0, 60.0, 65.0, 70.0, and 75.0), about 75.0 ng/mL to about 100.0 ng/mL (e.g., 75.0, 80.0, 85.0, 90.0, 95.0, and 100.0), and any concentration therebetween, including endpoints.

In some embodiments interleukin 21 (IL21) is used to enhance expansion, or other characteristics, of NK cells. In several embodiments, the concentration of IL21 used ranges from about 0.01 ng/ml to about 100 ng/mL, including, for example, about 0.01 ng/mL to about 0.05 ng/mL (e.g., 0.01, 0.02, 0.03, 0.04, and 0.05), about 0.05 ng/mL to about 0.1 ng/mL (e.g., 0.05, 0.06, 0.07, 0.08, 0.09 and 0.1), about 0.1 ng/mL to about 0.5 ng/mL (e.g., 0.1, 0.2, 0.3, 0.4, and 0.5), about 0.5 ng/mL to about 1.0 ng/mL (e.g., 0.5, 0.6, 0.7, 0.8, 0.9, and 1.0), about 1.0 ng/mL to about 2.0 ng/mL (e.g., 1.1, 1.2, 1.3, 1.4, 1.5, 1.6, 1.7, 1.8, 1.9, and 2.0), about 2.0 ng/mL to about 5.0 ng/mL (e.g., 2.0, 3.0, 4.0, and 5.0), about 5.0 ng/mL to about 10.0 ng/mL (e.g., 5.0, 6.0, 7.0, 8.0, 9.0 and 10.0), about 10.0 ng/mL to about 15.0 ng/mL (e.g., 10.0, 11.0, 12.0, 13.0, 14.0, and 15.0), about 15.0 ng/mL to about 20.0 ng/mL (e.g., 15.0, 16.0, 17.0, 18.0, 19.0, and 20.0), about 20.0 ng/mL to about 25.0 ng/mL (e.g., 20.0, 21.0, 22.0, 23.0, 24.0, and 25.0), about 25.0 ng/mL to about 30.0 ng/mL (e.g., 25.0, 26.0, 27.0, 28.0, 29.0, and 30.0), about 30.0 ng/mL to about 50.0 ng/mL (e.g., 30.0, 35.0, 40.0, 45.0, and 50.0), about 50.0 ng/mL to about 75.0 ng/mL (e.g., 50.0, 55.0, 60.0, 65.0, 70.0, and 75.0), about 75.0 ng/mL to about 100.0 ng/mL (e.g., 75.0, 80.0, 85.0, 90.0, 95.0, and 100.0), and any concentration therebetween, including endpoints.

In some embodiments interleukin 15 (IL15) is used in a soluble format (either in place of, or in addition to mbIL15 on the feeder cells) to enhance expansion, or other characteristics, of NK cells. In several embodiments, the concentration of IL15 used ranges from about 0.01 ng/ml to about 100 ng/mL, including, for example, about 0.01 ng/mL to about 0.05 ng/mL (e.g., 0.01, 0.02, 0.03, 0.04, and 0.05), about 0.05 ng/mL to about 0.1 ng/mL (e.g., 0.05, 0.06, 0.07, 0.08, 0.09 and 0.1), about 0.1 ng/mL to about 0.5 ng/mL (e.g., 0.1, 0.2, 0.3, 0.4, and 0.5), about 0.5 ng/mL to about 1.0 ng/mL (e.g., 0.5, 0.6, 0.7, 0.8, 0.9, and 1.0), about 1.0 ng/mL to about 2.0 ng/mL (e.g., 1.1, 1.2, 1.3, 1.4, 1.5, 1.6, 1.7, 1.8, 1.9, and 2.0), about 2.0 ng/mL to about 5.0 ng/mL (e.g., 2.0, 3.0, 4.0, and 5.0), about 5.0 ng/mL to about 10.0 ng/mL (e.g., 5.0, 6.0, 7.0, 8.0, 9.0 and 10.0), about 10.0 ng/mL to about 15.0 ng/mL (e.g., 10.0, 11.0, 12.0, 13.0, 14.0, and 15.0), about 15.0 ng/mL to about 20.0 ng/mL (e.g., 15.0, 16.0, 17.0, 18.0, 19.0, and 20.0), about 20.0 ng/mL to about 25.0 ng/mL (e.g., 20.0, 21.0, 22.0, 23.0, 24.0, and 25.0), about 25.0 ng/mL to about 30.0 ng/mL (e.g., 25.0, 26.0, 27.0, 28.0, 29.0, and 30.0), about 30.0 ng/mL to about 50.0 ng/mL (e.g., 30.0, 35.0, 40.0, 45.0, and 50.0), about 50.0 ng/mL to about 75.0 ng/mL (e.g., 50.0, 55.0, 60.0, 65.0, 70.0, and 75.0), about 75.0 ng/mL to about 100.0 ng/mL (e.g., 75.0, 80.0, 85.0, 90.0, 95.0, and 100.0), and any concentration therebetween, including endpoints.

In some embodiments interleukin 22 (IL22) is used to facilitate expansion of NK cells. In several embodiments, the concentration of IL22 used ranges from about 0.01 ng/ml to about 100 ng/mL, including, for example, about 0.01 ng/mL to about 0.05 ng/mL (e.g., 0.01, 0.02, 0.03, 0.04, and 0.05), about 0.05 ng/mL to about 0.1 ng/mL (e.g., 0.05, 0.06, 0.07, 0.08, 0.09 and 0.1), about 0.1 ng/mL to about 0.5 ng/mL (e.g., 0.1, 0.2, 0.3, 0.4, and 0.5), about 0.5 ng/mL to about 1.0 ng/mL (e.g., 0.5, 0.6, 0.7, 0.8, 0.9, and 1.0), about 1.0 ng/mL to about 2.0 ng/mL (e.g., 1.1, 1.2, 1.3, 1.4, 1.5, 1.6, 1.7, 1.8, 1.9, and 2.0), about 2.0 ng/mL to about 5.0 ng/mL (e.g., 2.0, 3.0, 4.0, and 5.0), about 5.0 ng/mL to about 10.0 ng/mL (e.g., 5.0, 6.0, 7.0, 8.0, 9.0 and 10.0), about 10.0 ng/mL to about 15.0 ng/mL (e.g., 10.0, 11.0, 12.0, 13.0, 14.0, and 15.0), about 15.0 ng/mL to about 20.0 ng/mL (e.g., 15.0, 16.0, 17.0, 18.0, 19.0, and 20.0), about 20.0 ng/mL to about 25.0 ng/mL (e.g., 20.0, 21.0, 22.0, 23.0, 24.0, and 25.0), about 25.0 ng/mL to about 30.0 ng/mL (e.g., 25.0, 26.0, 27.0, 28.0, 29.0, and 30.0), about 30.0 ng/mL to about 50.0 ng/mL (e.g., 30.0, 35.0, 40.0, 45.0, and 50.0), about 50.0 ng/mL to about 75.0 ng/mL (e.g., 50.0, 55.0, 60.0, 65.0, 70.0, and 75.0), about 75.0 ng/mL to about 100.0 ng/mL (e.g., 75.0, 80.0, 85.0, 90.0, 95.0, and 100.0), and any concentration therebetween, including endpoints.

If two stimulatory agents are used, the relative ratio between the two can range from a ratio of 1:10, 1:20, 1:50, 1:100, 1:150, 1:200, 1:250, 1:500, 1:750, 1:1,000, 1:10,000, 1:50,000, 1:100,000, 100,000:1, 50,000:1, 10,000:1, 1,000:1, 750:1, 500:1, 250:1, 200:1, 150:1, 100:1, 50:1, 20:1, 10:1, and any ratio in between those listed, including endpoints. Likewise, if three, or more, agents are used, the ratio between those additional agents and the other agents can employ any of the aforementioned ratios.

As discussed in more detail below, depending on the embodiment, the stimulatory molecules may be added at a specific point (or points) during the expansion process, or can be added such that they are present as a component of the culture medium through the co-culture process.

Methods of Co-Culture and Immune Cell Expansion

In some embodiments, NK cells isolated from a peripheral blood donor sample are co-cultured with K562 cells modified to express 4-1BBL and mbIL15. While other approaches involve the expression of other membrane-bound cytokines, the generation of a feeder cell with multiple stimulatory molecules can be difficult to generate (e.g., to achieve desired levels of expression of the various stimulatory molecule, expression at the right time during expansion, etc.). Thus, several embodiments disclosed herein relate to the supplementation of the culture media with particular concentrations of various stimulatory agents at particular times. In several embodiments, feeder cells are seeded into culture vessels and allowed to reach near confluence. Immune cells can then be added to the culture at a desired concentration, ranging, in several embodiments from about $0.5\times10^6$ cells/cm$^2$ to about $5\times10^6$ cells/cm$^2$, including any density between those listed, including endpoints.

In several embodiments, immune cells are separated from a peripheral blood sample. Thereafter, in several embodiments, the immune cells can be expanded together, or an isolated subpopulation of cells, such as NK cells, is used.

Thereafter, the NK cells are seeded with the feeder cells, an optionally one or more cytokines (either in the culture media or as an exogenous supplement) and cultured for a first period of time, for example about 6 hours, about 12 hours, about 18 hours, about 24 hours, about 2 days, about 3 days, about 4 days, about 5 days, about 6 days, about 7 days, about 8 days, about 9 days, about 10 days, about 11 days, about 12 days, about 13 days, about 14 days, or for any time between those listed, including endpoints.

In several embodiments, after the first period of expansion, the expanded cells (e.g., NK cells) are transduced with an engineered construct, such as a chimeric antigen receptor. Any variety of chimeric antigen receptor can be expressed in the engineered cells, such as NK cells, including those described in International PCT Application PCT/US2018/024650, PCT/IB2019/000141, PCT/IB2019/000181, and/or PCT/US2020/020824, PCT/US2020, 035752, U.S. Provisional Application No. 62/924,967, 62/960,285, and/or 623/038,645, each of which is incorporated in its entirety by reference herein.

After viral transduction, the engineered cells are cultured for a second period of time, for example about 6 hours, about 12 hours, about 18 hours, about 24 hours, about 2 days, about 3 days, about 4 days, about 5 days, about 6 days, about 7 days, about 8 days, about 9 days, about 10 days, about 11 days, about 12 days, about 13 days, about 14 days, or for any time between those listed, including endpoints. It shall be noted that certain data presented herein relates to viral expression of a chimeric receptor complex expressing an NKG2D ligand binding domain (e.g., NKX101) or CD19 (e.g., NK19-1 or NKX101). However, any suitable chimeric receptor or chimeric antigen receptor can be used.

Supplementation of the media with one or more stimulatory agents, such as IL12 and/or IL18 can occur at any time during the culturing process. For example, one or more stimulatory agents can be added at the inception of culturing, for example at time point zero (e.g., inception of culture). The agent, or agents, can be added a second, third, fourth, fifth, or more times. Subsequent additions may, or may not, be at the same concentration as a prior addition. The interval between multiple additions can vary, for example a time interval of about 12 hours, about 24 hours, about 36 hours, about 48 hours, about 72 hours, or longer, and any time therebetween, including endpoints.

If multiple additions of a stimulatory agent are used, the concentrations of a first supplemental addition can be at the same or a different concentration than the second (and/or any supplemental addition). For example, in several embodiments, the addition of a stimulatory agent over multiple time points can ramp up, ramp down, stay constant, or vary across multiple, non-equivalent concentrations.

In several embodiments, certain ratios of feeder cells to cells to be expanded are used. For example, in several embodiments a feeder cell: "target" cell ratio of about 5:1 is used. In several embodiments, 1:1 ratios are used, while in additional embodiments, can range from about: 1:10, 1:20, 1:50, 1:100, 1:1,000, 1:10,000, 1:50,000, 1:100,000, 100,000:1, 50,000:1, 10,000:1, 1,000:1, 100:1, 50:1, 20:1, 10:1, and any ratio in between those listed, including endpoints.

EXAMPLES

The materials and methods disclosed in the Examples are non-limiting examples of materials and methods (including reagents and conditions) applicable to various embodiments provided in the present application.

Example 1—Initial Assessment of Expansion Conditions

Figure 1B:
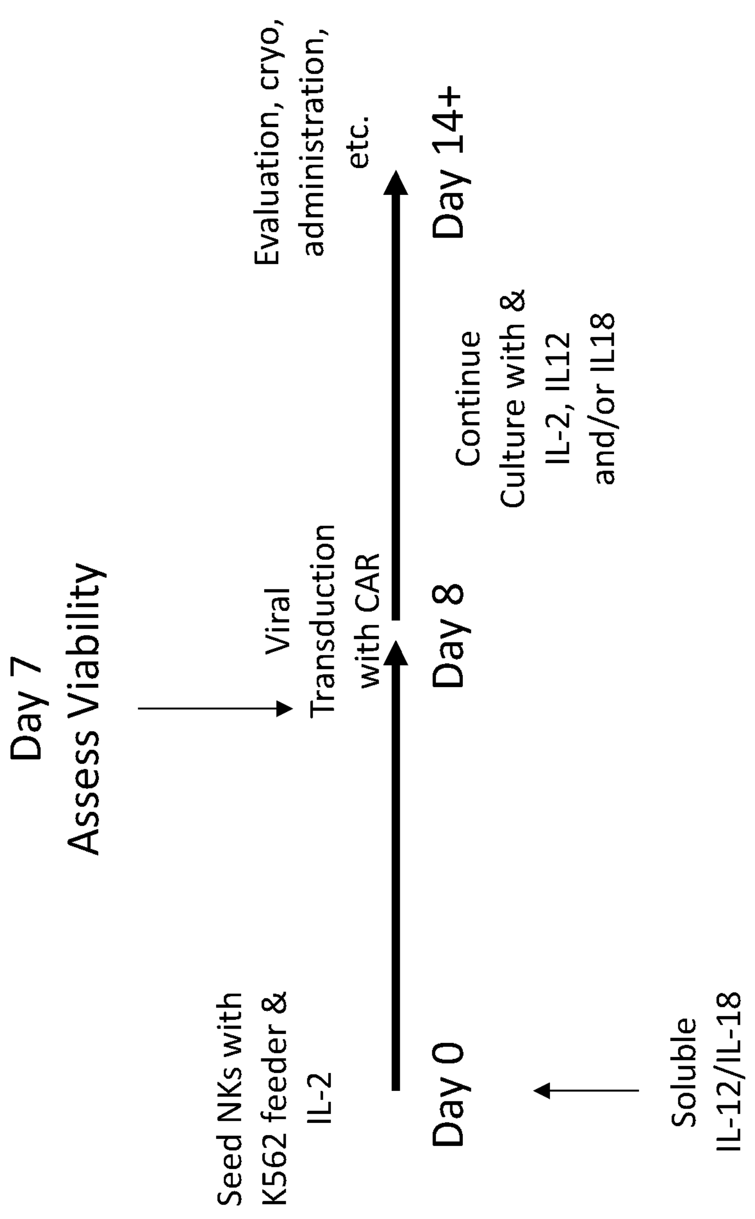

FIG. 1A shows a non-limiting example of an expansion process. In this example, stimulatory cytokines are added on day 0 and the same dose is added again at day 4, which was used for certain embodiments discussed herein. FIG. 1B represents a non-limiting embodiment of a single dose process, which was used for certain embodiments discussed herein.

Figure 2:
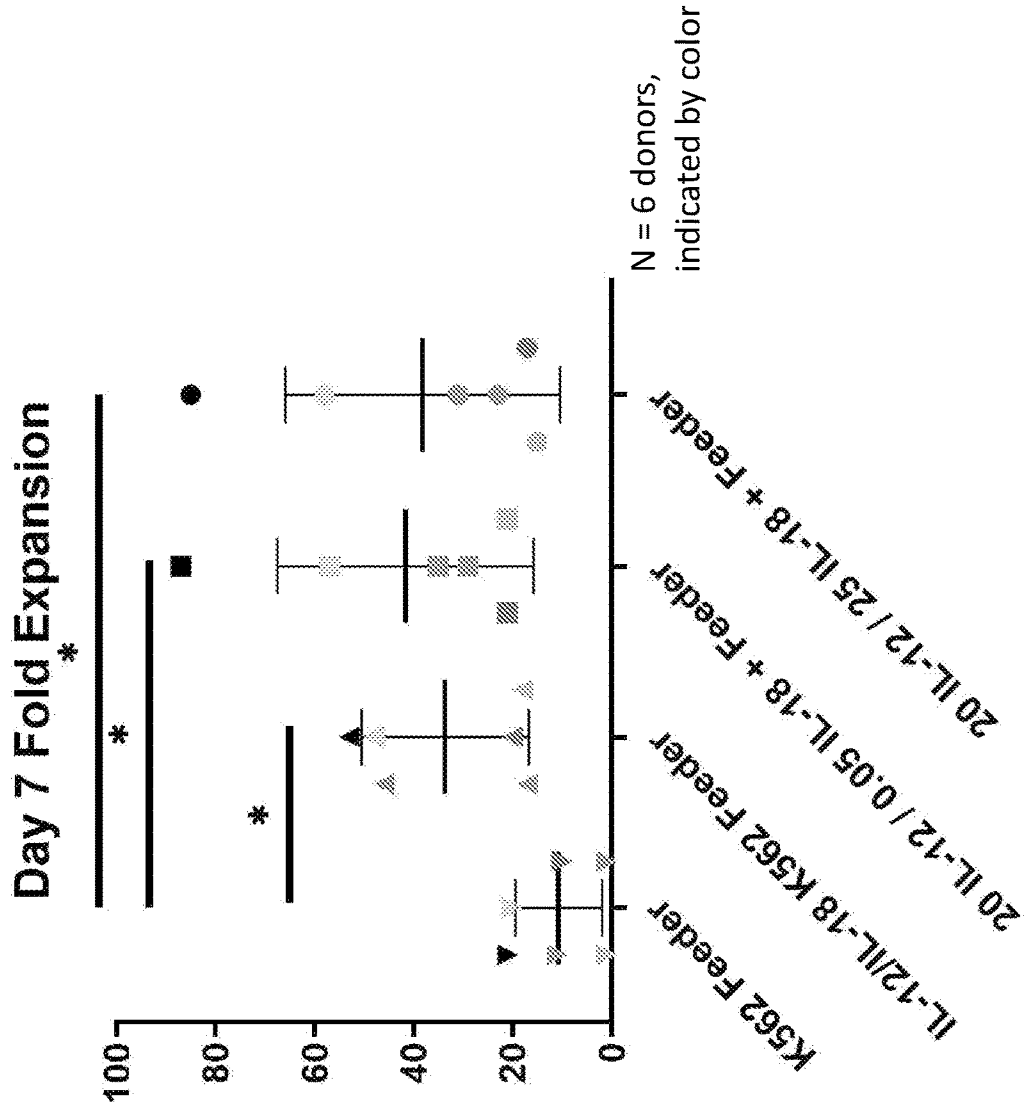
FIG. 2 depicts data comparing fold expansion of NK cells using various expansion methodologies, including non-limiting embodiments of those disclosed herein.

FIG. 2 shows data related to the fold expansion of the NK cells using various methods. The left-most data set shows expansion of NK cells using K562 (expressing mbIL15 and 4-1BBL) feeder cells alone, while each of the three data sets to the right show the increased fold expansion when supplementing the media with IL12 and IL18 at various concentrations. The presence of supplemental IL12 and IL18 at any amount resulted in a significant increase in expansion of NK cells, thereby demonstrating that additional stimulatory agents can enhance NK cell expansion.

Figure 3A:
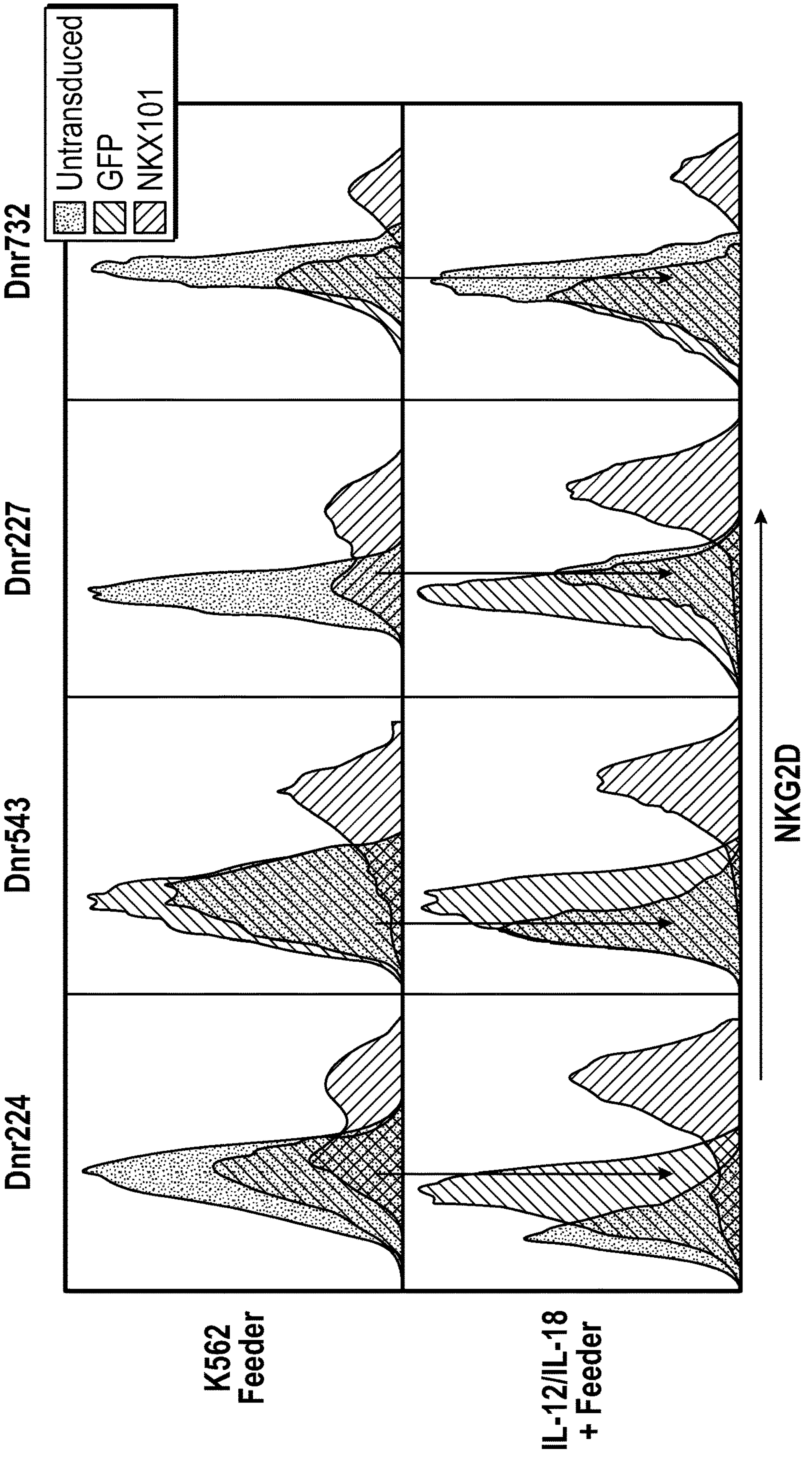
FIGS. 3A-3B depict data related to the expansion of NK cells under various conditions from four different donors.
Figure 3B:
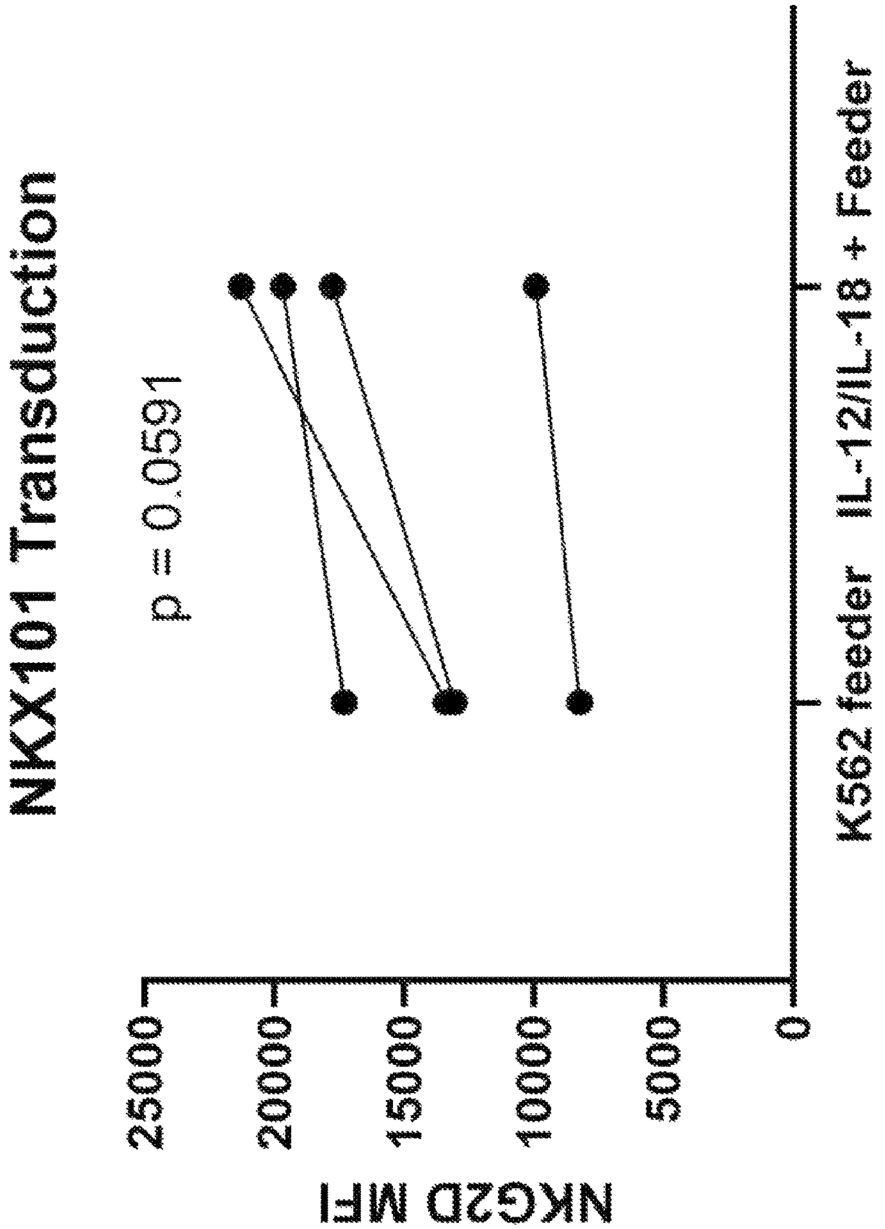

FIG. 3A shows flow cytometry data related to the expression of NKG2D in NK cells from four different donors, expanded either with K562 cells alone (top row) or with IL12/18 supplementation. As can be seen from the increased height of the right-shifted curve (which relates to cells transduced with NKX101), there is greater expression of NKG2D. The designation of NKX101 refers to an engineered NK cell that expresses a truncated NKG2D extracellular domain capable of binding ligands of the NKG2D receptor. In several embodiments the truncated NKG2D domain is coupled to a CD8alpha hinge and CD8alpha TM domain. In several embodiments, the truncated NKG2D domain is coupled to an OX40 co-stimulatory domain and a CD3zeta signaling domain. In several embodiments, the construct further comprises membrane bound IL15. In several embodiments, the NKX101 has the nucleotide sequence of SEQ ID NO: 1 or the amino acid sequence set forth in SEQ ID NO: 2. Further supporting the enhanced expression of NKG2D is FIG. 3A, in which the greater mean fluorescence intensity (MFI) when using supplemental soluble IL12/18 demonstrates greater presence of NKG2D on a given cell. Thus, not only does supplementing a feeder cell with soluble IL12/18 enhance expansion of NK cells, it also improves the expression of chimeric receptors by those NK cells. This is an unexpected benefit, as the greater NK cell number now expresses greater amounts of a receptor that will target an undesired cell, such as a tumor.

Other receptors can be used to target NK cells to tumors. For example, in several embodiments the receptor is a chimeric antigen receptor targeting CD19 on tumor cells. In several embodiments, the anti-CD19 CAR comprises an scFv that binds to CD19 (for example an FMC63 scFv or variant thereof) coupled to an OX40 costimulatory domain and a CD3zeta signaling domain. In several embodiments, a nucleic acid sequence encoding the CAR further encodes IL15. In several embodiments, the IL15 is configured to be expressed by a host cell (e.g., an NK cell or a T cell) in a membrane-bound form. In several embodiments, the CAR is encoded by a nucleotide sequence having at least 95%, 97%, 98%, 99% or more sequence identity to the sequence of SEQ ID NO: 3, 5, 7, 9, 11, 13, 15, 17, 19, 21, 23, 25, or 27. In several embodiments, the CAR is has an amino acid sequence having at least 95%, 97%, 98%, 99% or more sequence identity to the sequence of SEQ ID NO: 4, 6, 8, 10, 12, 14, 16, 18, 20, 22, 24, 26, or 28. In several embodiments, the CAR employs a humanized anti-CD19 binder.

Figure 4:
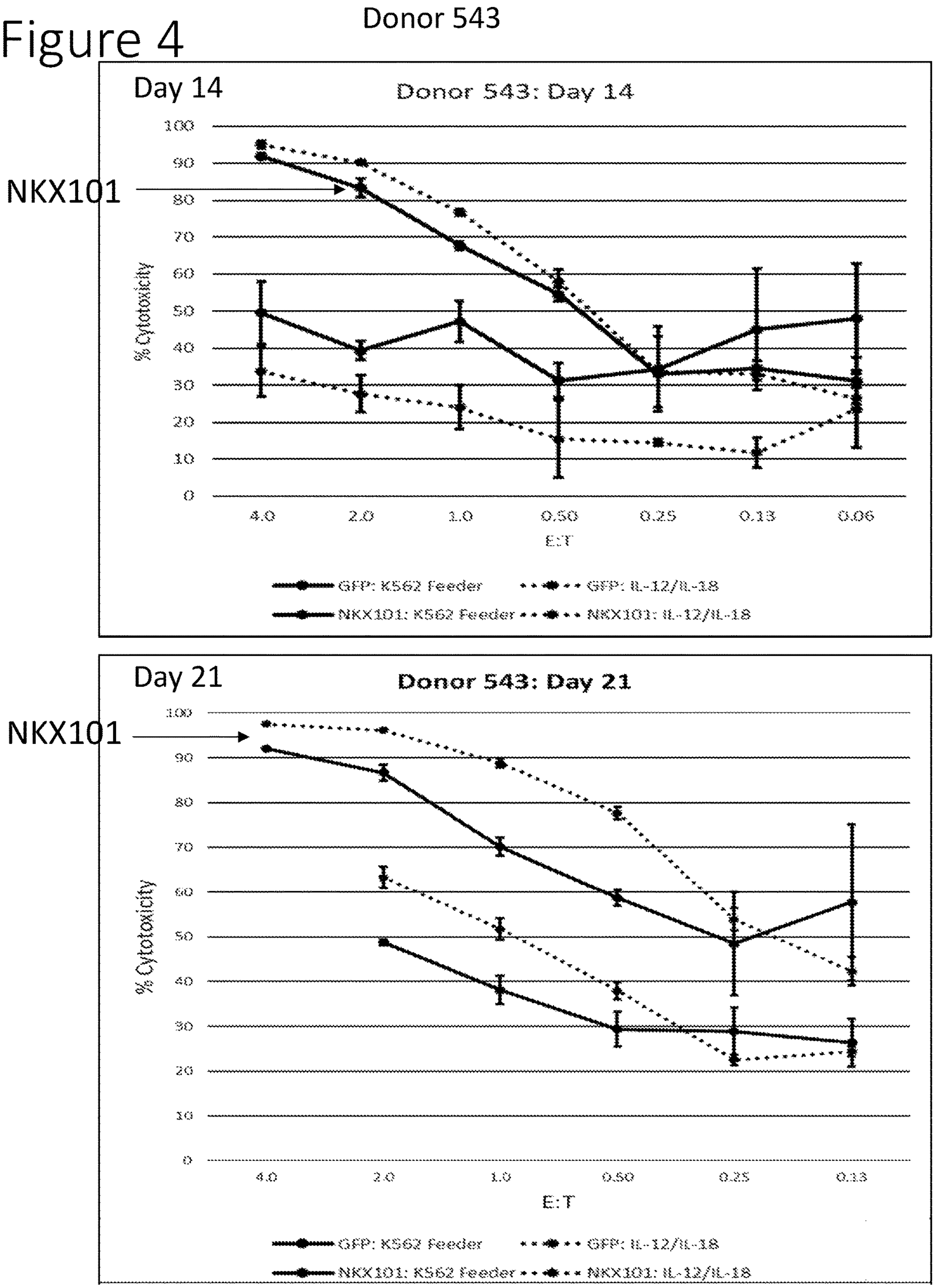
FIG. 4 shows data by related to NK cell cytotoxicity at various time points after expansion under conditions using feeder cells alone, or with cytokine supplementation.
Figure 4:
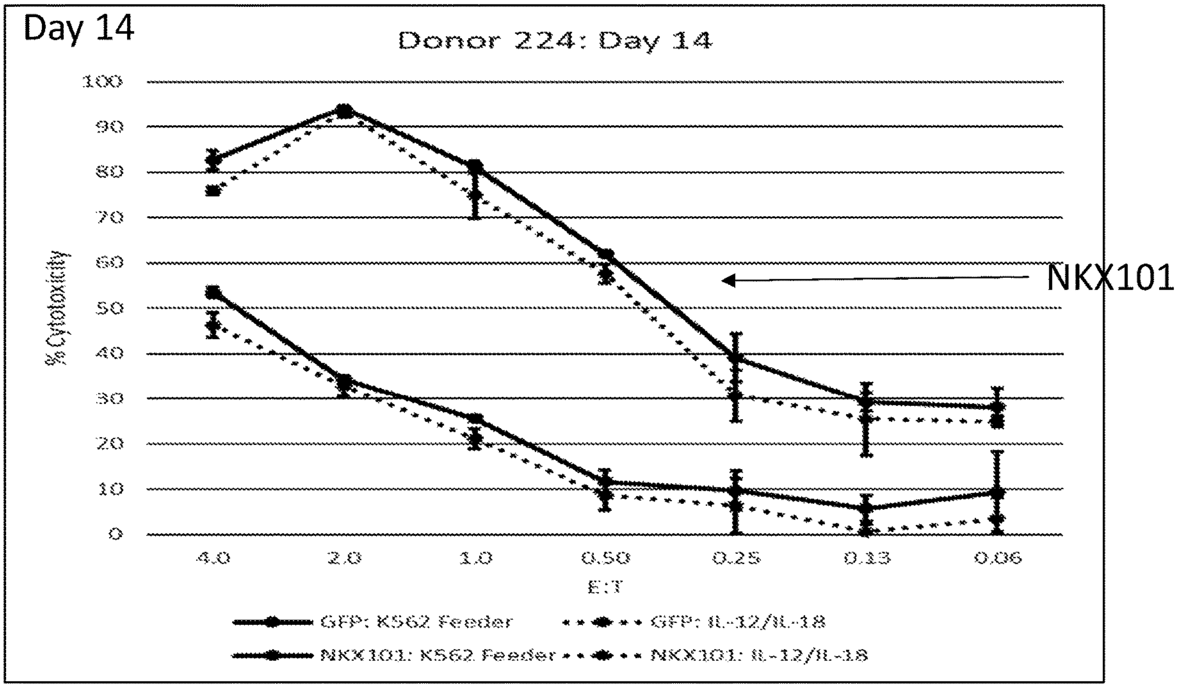
Figure 4:
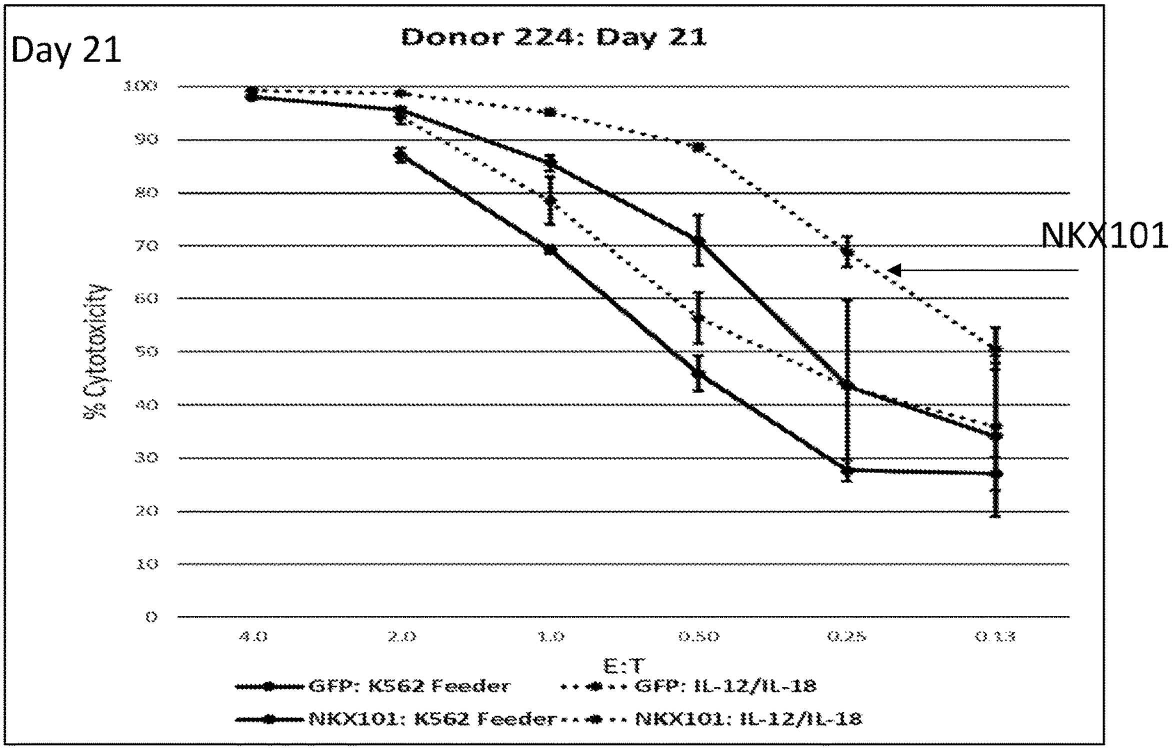

FIG. 4 depicts data in which the use of supplemental soluble IL12/18 when expanding NK cells actually leads to enhanced cytotoxicity of those expanded NK cells. FIG. 4 shows data from two different donors, at two time points, 14 days, and 21 days post viral transduction. Culture conditions used to expand the NK cells were either with the use of soluble IL12/18 (dashed lines) or K562 (expressing 4-1BBL and mbIL15) alone (solid lines). GFP transduced cells were used as controls—NKX101 curves are indicated by arrows on FIG. 4. As the data indicate, relative to expansion on K562 cells alone, the use of IL12/18 enhances NK cell cytotoxicity at 21 days post-transduction (lower panels). While the effect at 14 days was limited in this specific experiment, in several embodiments, perhaps depending on donor and/or specific IL concentrations, in several embodiments, enhanced cytotoxicity is achieved at earlier time points, such as 14, 15, 16, 17, 18, 19 20, 21, 22, or 23 days post viral transduction. Regardless of the time, it is unexpected that the use of soluble interleukins during the expansion process can significantly enhance the cytotoxicity of the expanded cells.

Figures 5A, 5B:
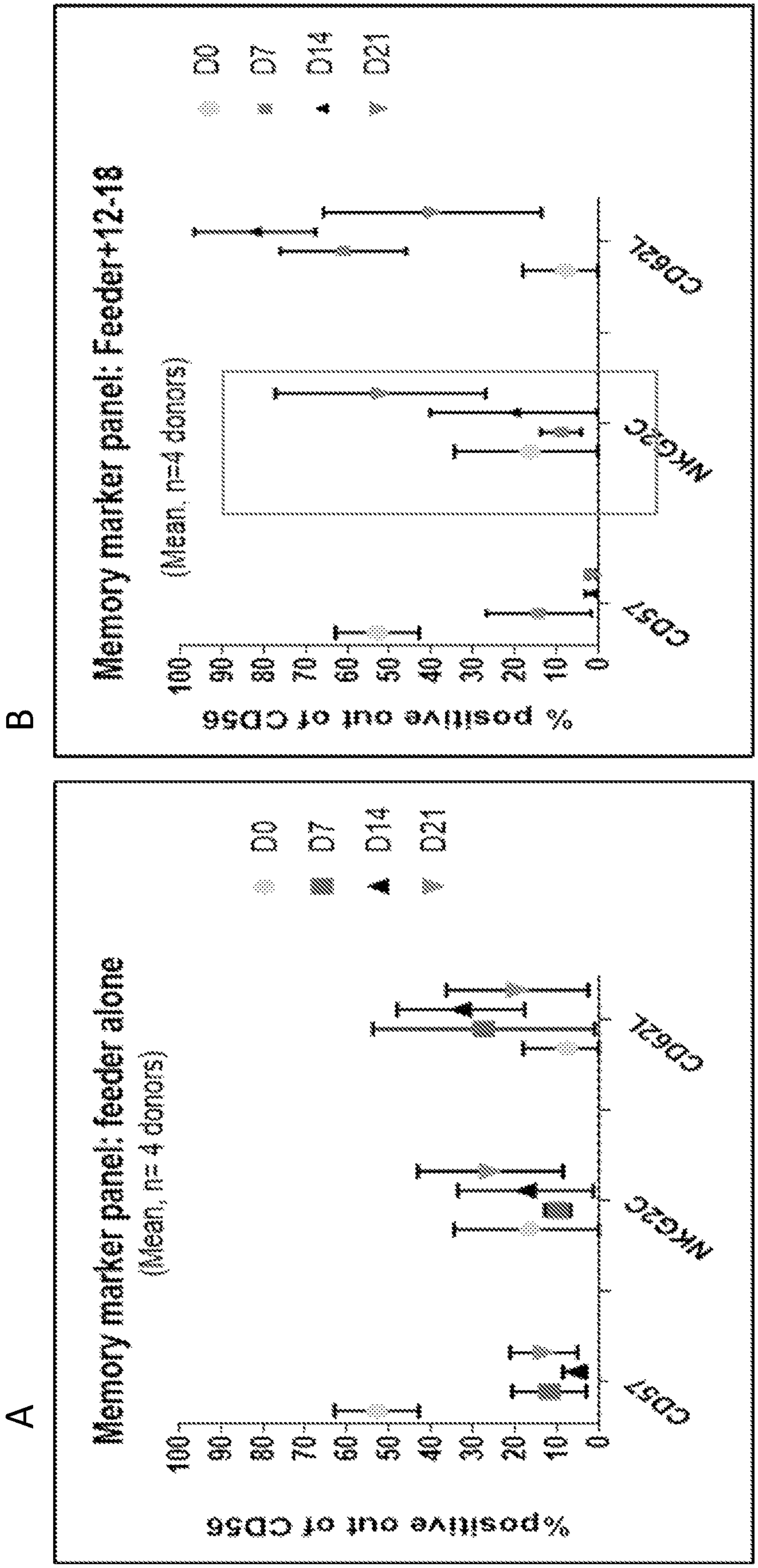
FIGS. 5A-5B depict data related to expression of certain markers indicative of a memory phenotype by NK cells.

In several embodiments, the increased cytotoxicity of the engineered NK cells is, at least in part, due to the cells moving towards a specific phenotype. FIGS. 5A and 5B depict data related to certain markers related to NK cell memory over time. FIG. 5A shows the expression of CD57, NKG2C and CD62L in NK cells expanded on feeder cells alone, while FIG. 5B shows the use of feeder cells plus soluble IL12/18. NKG2C expression was elevated at Day 21 in those NK cells expanded with IL12/18. NKG2C is a marker of cytokine-induced NK cell memory. Increased CD67L was also observed in the later time points with NK cells expanded using soluble IL12/18. CD67L is associated with increased lymphocyte extravasation (evidence of increased cell activity). Taken together, these data suggest that the use of soluble interleukins during NK cell expansion have the capacity to set in motion different signaling pathways that are associated with NK cell memory for antigens and enhanced cytotoxicity against cells bearing those antigens.

Figure 6:
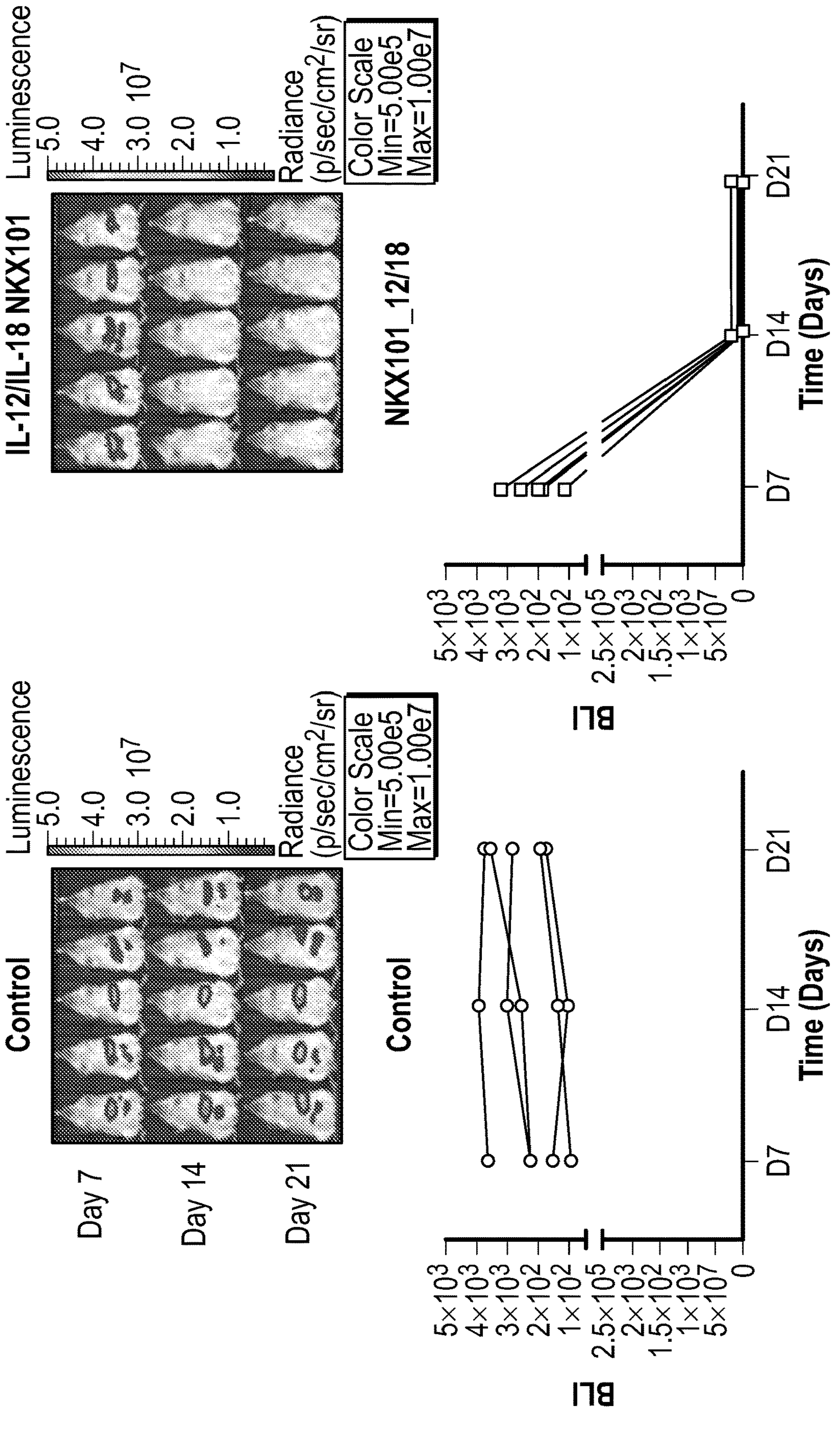
FIG. 6 shows in vivo data related to the anti-tumor activity of NK cells expanded with or without the indicated cytokine stimulation during expansion.
Figure 6:
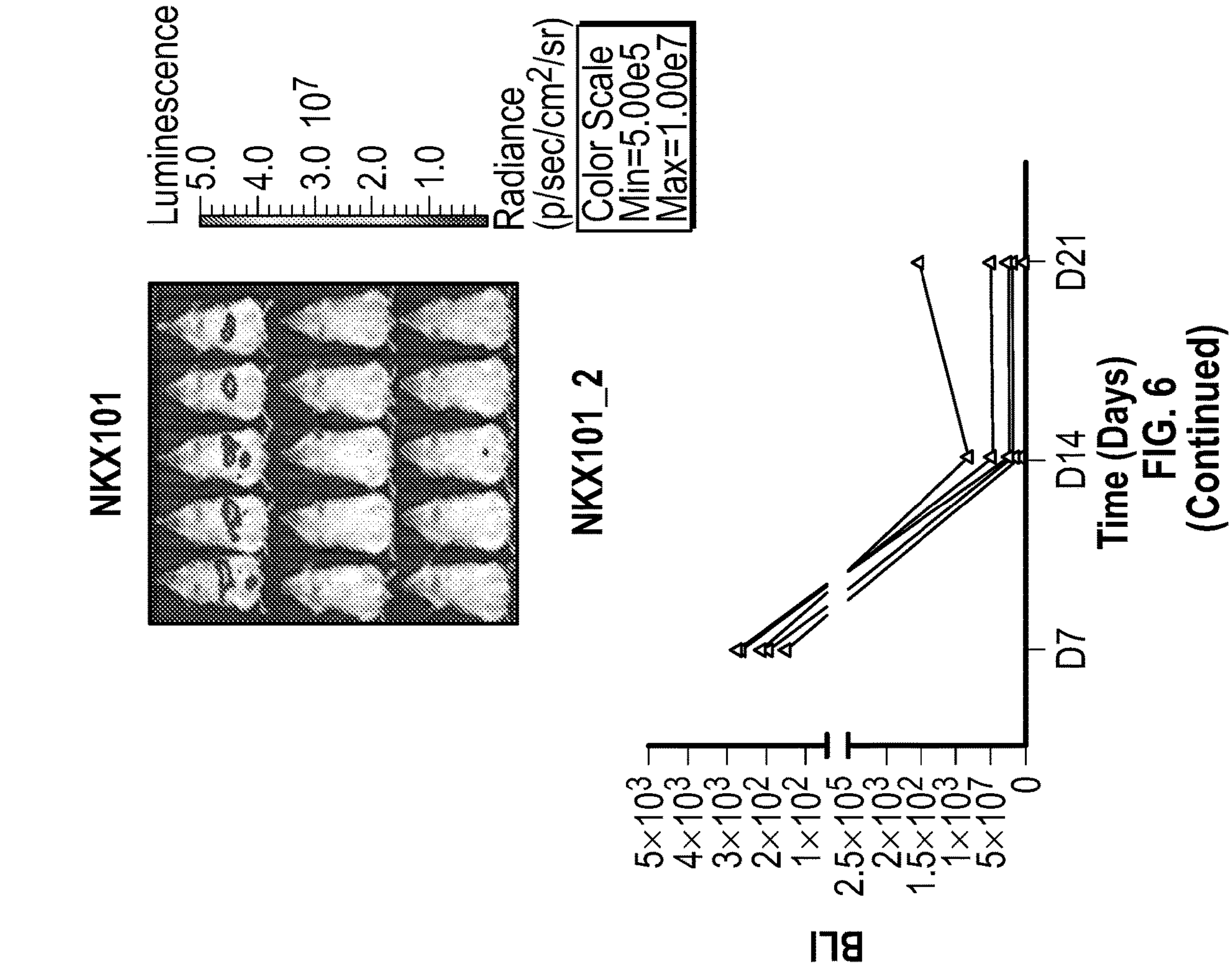

FIG. 6 depicts in vivo data related to the anti-tumor effect of NK cells expressing NKX101 when the underlying NK cells were expanded using K562 cells alone, vs. supplanting the expansion media with soluble IL12/18. The animal model involves dosing mice with $4\times10^6$ SNU499 hepatocellular carcinoma cells (intraperitoneally) at Day 0, followed by $3\times10^6$ NK cells expressing NKX101, having been expanded with, or without IL12/18 supplementing the expansion media (or control). As shown in the left panels, control mice have significant tumor burden as early as day 7, with tumor signal being present, and modestly increased in some mice, on days 14 and 21. In vivo bioluminescent imaging (BLI) is shown below the images. The right panel shows the experiment done with NK cells expressing NKX101. As shown in the images, tumor burden was present at day 7, but largely non-detectable by day 14, and maintained as such by day 21. In the center panel, the experimental images are shown for NK cells expressing NKX101, the NK cells having been expanded using soluble IL12/18. The effect on tumor burden was at least as effective as with NKX101 cells ("standard" expansion), although the significant degree of NKX101 efficacy can make the improved effect with IL12/18 difficult to detect. Nevertheless, according to several embodiments disclosed herein, the use of soluble IL12/18 to supplement NK cell expansion media results not only in enhanced expansion, but also enhanced chimeric receptor expression and enhanced cytotoxicity.

Example 2—Further Assessments of Expansion and Efficacy

As discussed above, in several embodiments disclosed herein, one or more soluble stimulating factors are used to enhance the expansion and/or cytotoxicity of engineered immune cells, such as NK cells, T cells, or combinations thereof. The experiments conducted for the present example were performed in order to assess the efficacy of various concentrations of selected stimulators molecules as compared to an established expansion system. While other stimulating agents can be used, depending on the embodiment, this example employed soluble interleukin 12 and soluble interleukin 18. These cytokines were added (in the various concentrations described below) and the resultant expanded cells were compared to cells expanded using K562 cells modified to express membrane-bound interleukin 15 and 4-1BBL (described more fully in U.S. Pat. Nos. 7,435,596 and 8,026,097 the entire contents of each of which is incorporated in its entirety by reference herein). Expanded cells were assessed with respect to proliferation, cytokine secretion, cytotoxicity and phenotype.

Experiments were set up using NK cells from multiple donors which were expanded using various conditions. One group of NK cells was expanded on mbIL15-expressing feeder cells (K562/4-1BBL/mbIL15). Another group of NK cells was expanded on mbIL15-expressing cells that were further modified to express IL12 and IL18 on the cell surface. Various culture conditions were used across the other groups, and a proliferation assays were performed to determine the effects of various concentrations of stimulatory cytokines. For example, one group of cells was exposed to a fixed concentration of IL12 (5 ng/mL) and varied concentrations of IL18. An additional group was exposed to another fixed concentration of IL12 (2.5 ng/mL) and varied concentrations of IL18. Note that those cultures that are exposed to IL12 and IL18 in soluble form were exposed to the dose of IL12/18 at day zero of culture (and again at day 4). As discussed above, the addition of soluble cytokines at day 0 and day 4 was used in the experiments generating the data shown in FIGS. 2-18 and FIGS. 23-24. The other experiments utilized exposure to the soluble cytokines at day 0 only.

Figure 7B:
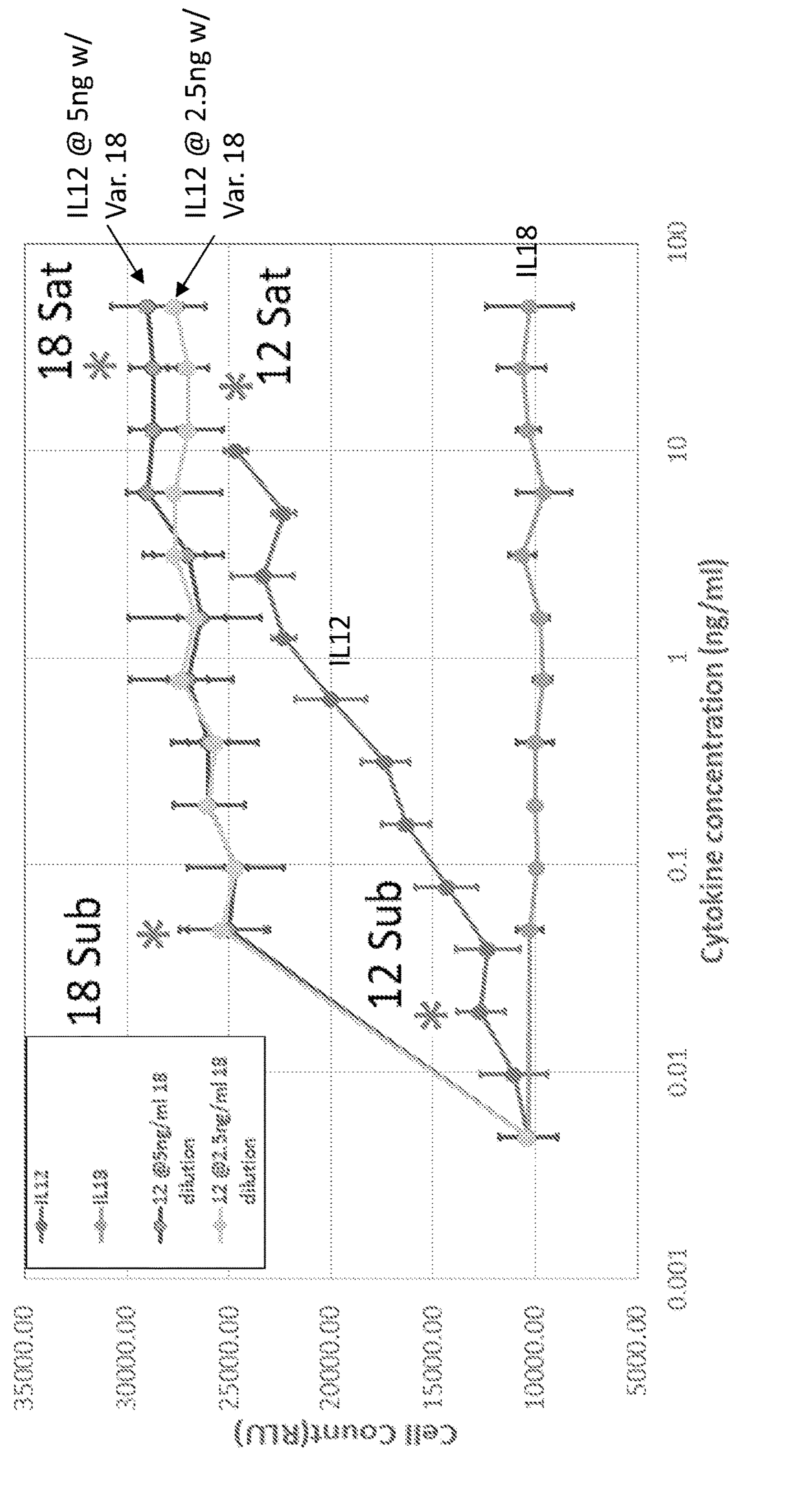

FIG. 7A a schematic table of various culture conditions used for expansion of NK cells. FIG. 7B shows data related to the cell count after 72 hours of exposure to the various conditions. As seen from the lower trace, the addition of IL18 alone, at any concentration, had limited impact on NK cell proliferation. In contrast, addition of IL12 alone increased NK cell proliferation in a dose-dependent manner. The combination of IL12 (either at 2.5 ng/mL or 5 ng/mL) with varied concentrations had further enhanced NK cell proliferation, suggesting a synergistic interaction between these two interleukins. The data for IL12 at 2.5 ng/mL and 5 ng/mL both demonstrate robust NK cell expansion, with near maximal levels achieved when IL18 was present at a concentration between about 0.1 and about 1 ng/mL. Addition of IL18 at higher concentrations was still able to positively enhance NK cell expansion, with the highest concentration of IL18 at 50 ng/mL in combination with IL12 at 5 ng/mL resulting in slightly enhanced expansion as compared to IL12 at 2.5 ng/mL. The data for expansion with oversaturated concentrations of IL12 or IL18 were off the scale and are not shown.

Figure 8:
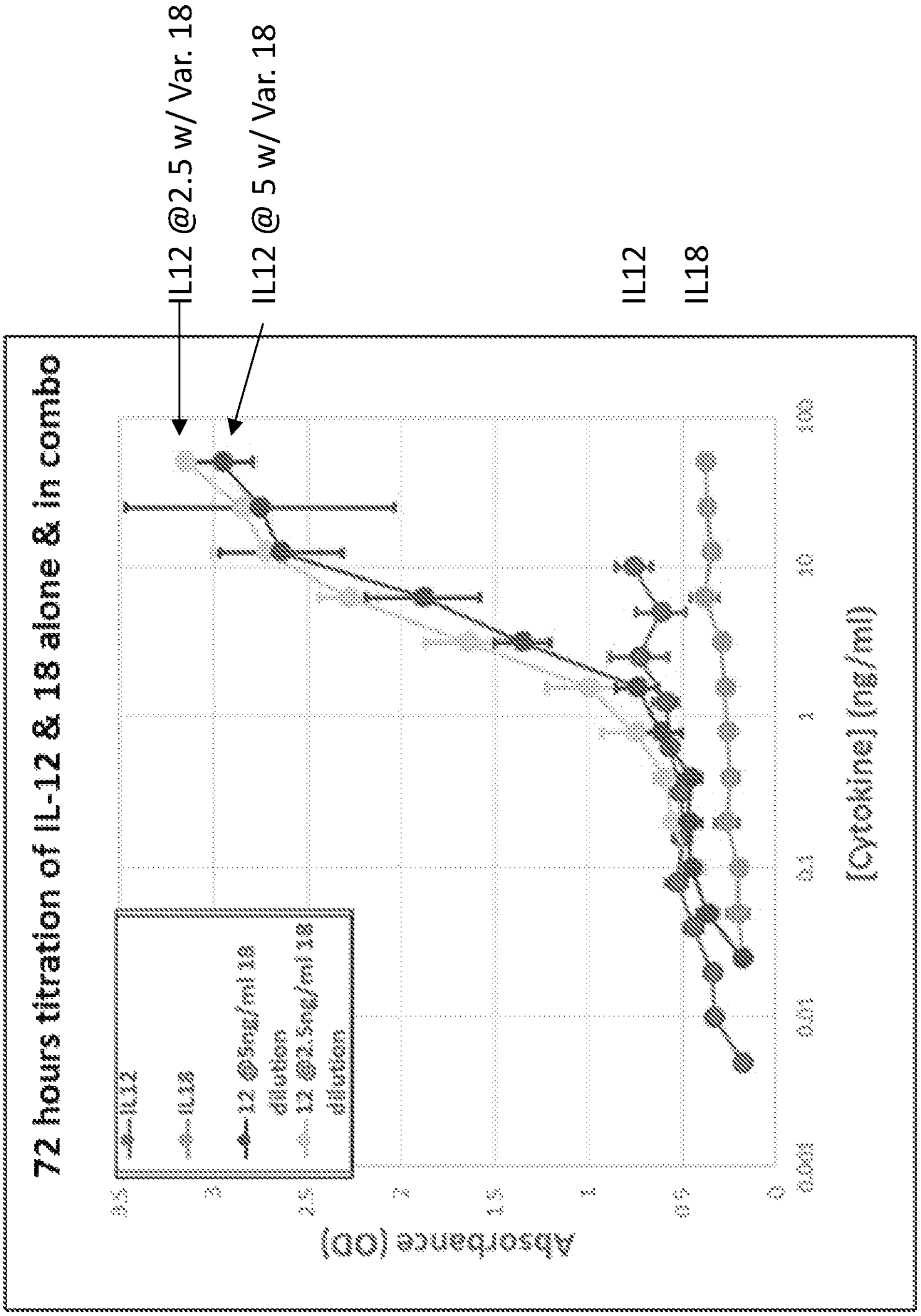
FIG. 8 shows data related to the release of interferon gamma by NK cells cultured in with varying concentrations of IL12 and/or IL18 in the culture media.

FIG. 8 shows data related to IFNg concentrations after 72 hours of culture with varied concentrations of either IL12 or IL18. The data plot represents the concentration of IFNg (as measured by absorbance during an ELISA assay) in relation to increasing concentrations of the selected interleukin. Similar to the proliferation data, addition of IL12 resulted in greater production of IFNg as compared to addition of IL18. That said, the addition of increasing concentrations of IL18 did result in increased IFNg production. IL12, on the other hand, resulted in greater IFNg production by the NK cells at nearly every concentration tested. As with proliferation, the combination of either concentration of IL12 with concentrations of IL18 of about 1 ng/mL (or greater) yielded enhanced IFNg production. The combination of IL12 (at either concentration) with IL18 at concentrations below about 0.5 ng/mL resulted in IFNg production similar to that achieved with IL12 alone. On the other hand, inclusion of IL18 at about 1 ng/mL or greater led to significantly enhanced IFNg production, again indicating a synergistic stimulation of the NK cells.

Figures 9A, 9B:
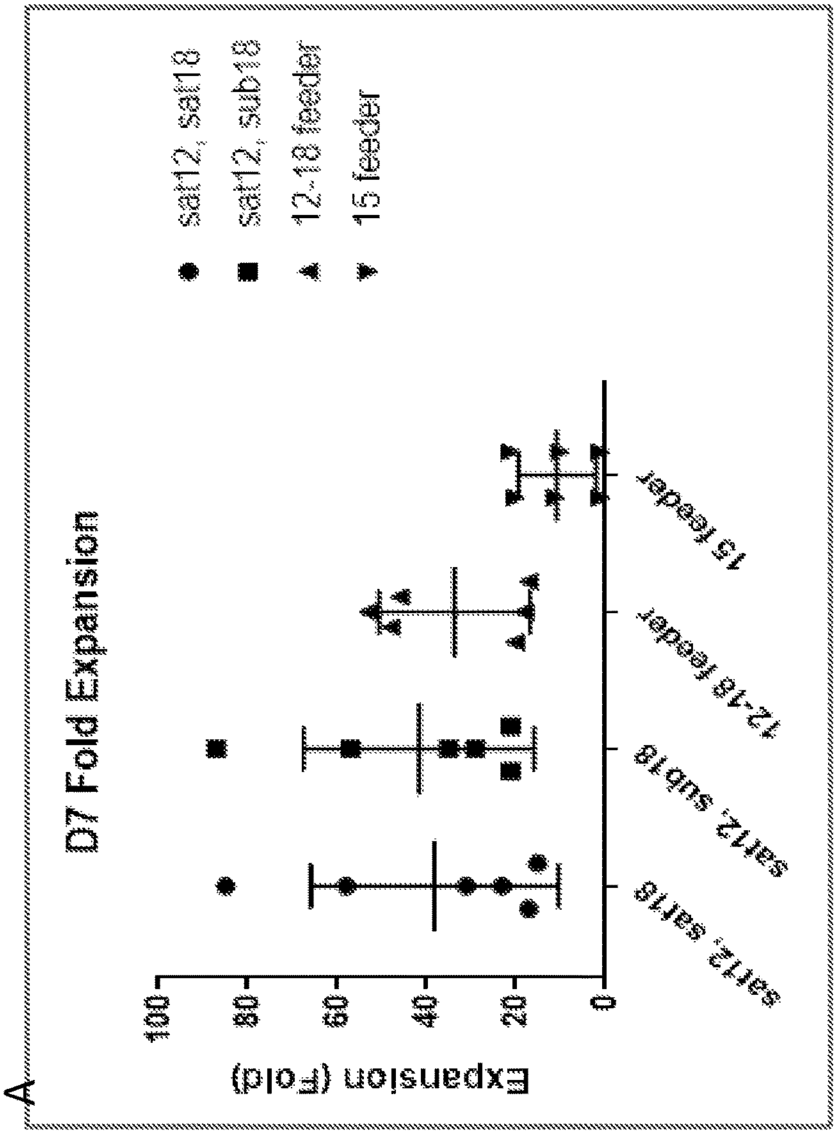
FIGS. 9A-9H relate to assessment of NK cell expansion after seven days of culture in the indicated conditions.
Figure 9C:
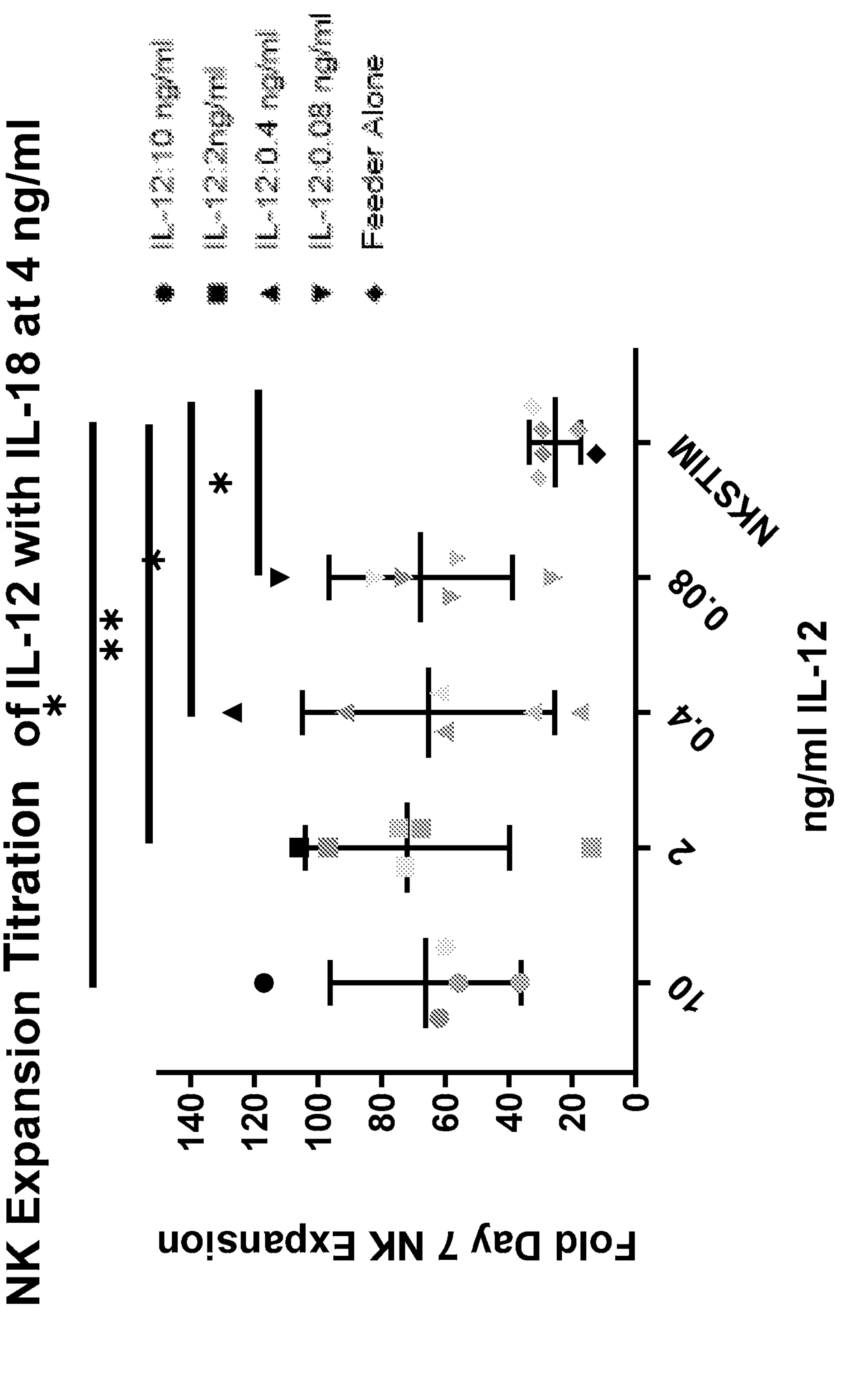
Figure 9D:
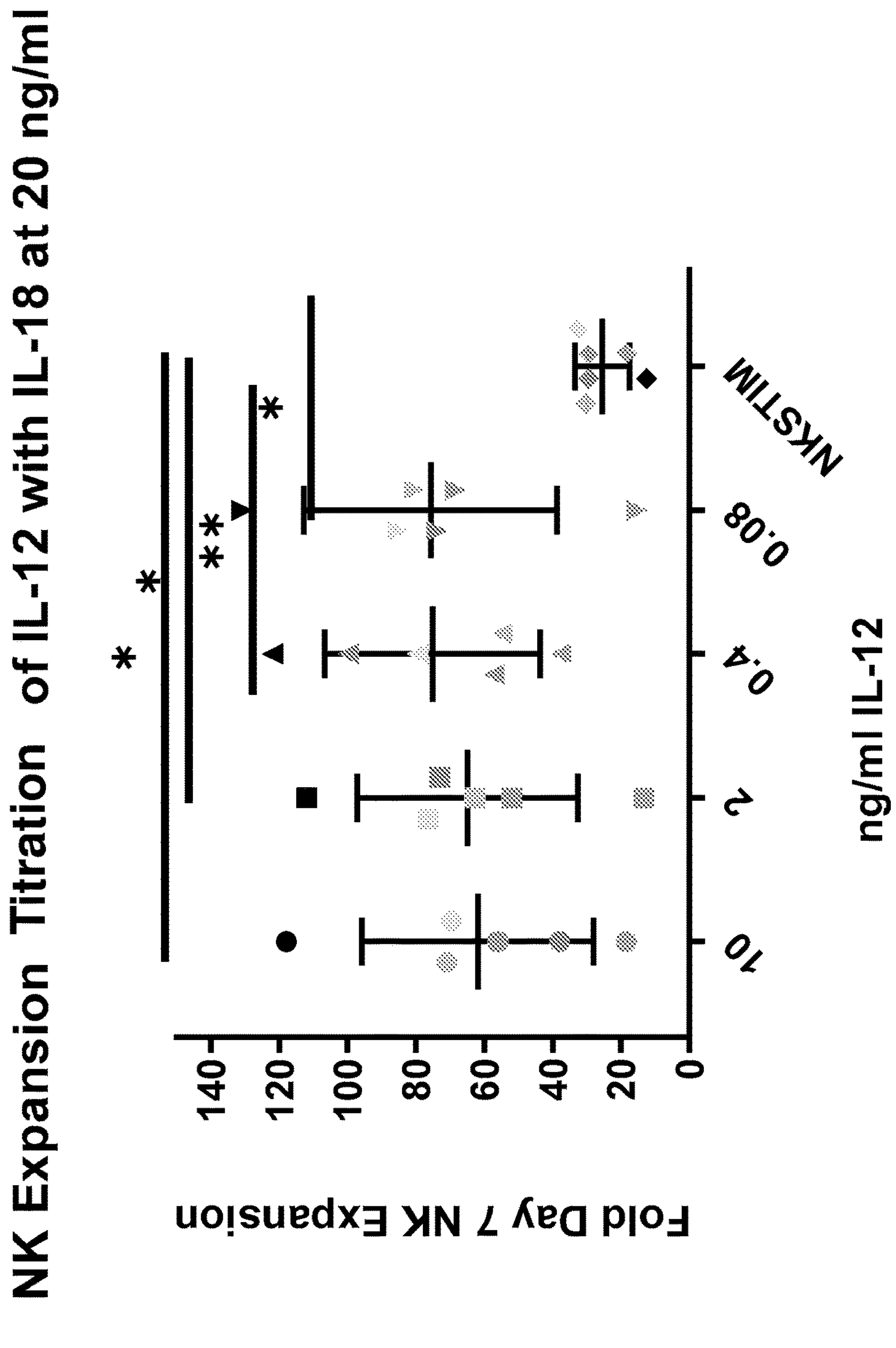
Figure 9E:
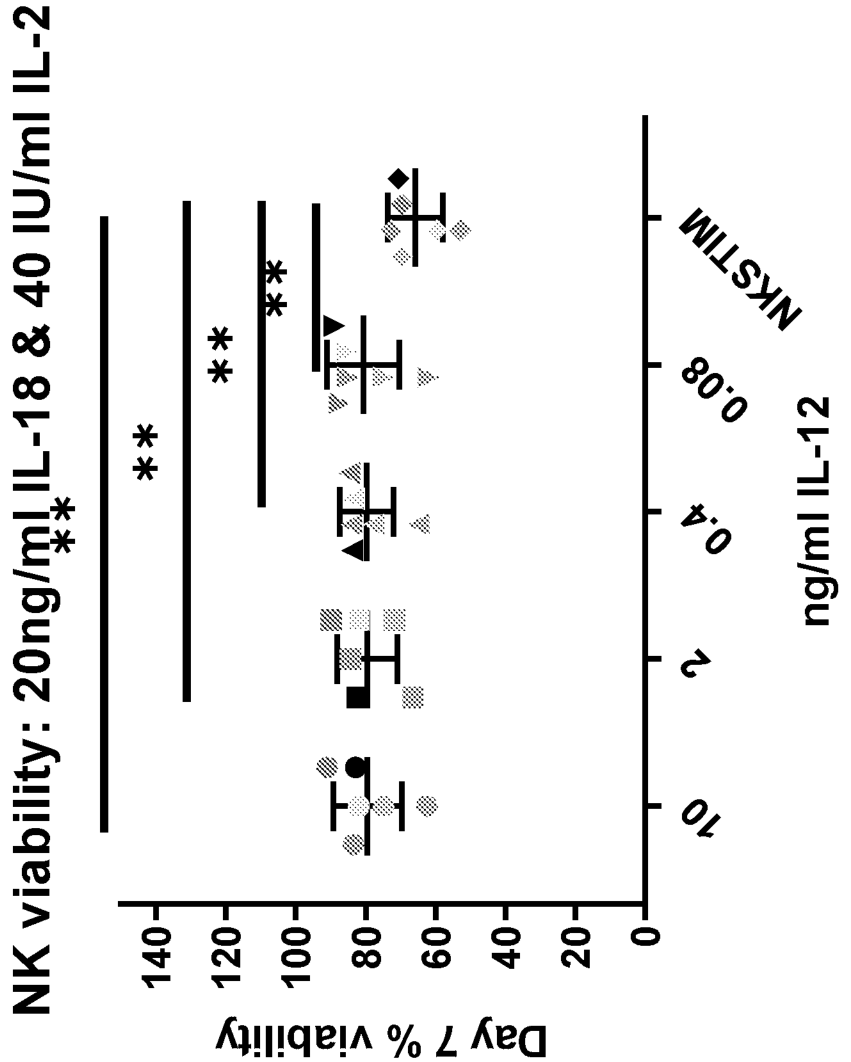
Figure 9F:
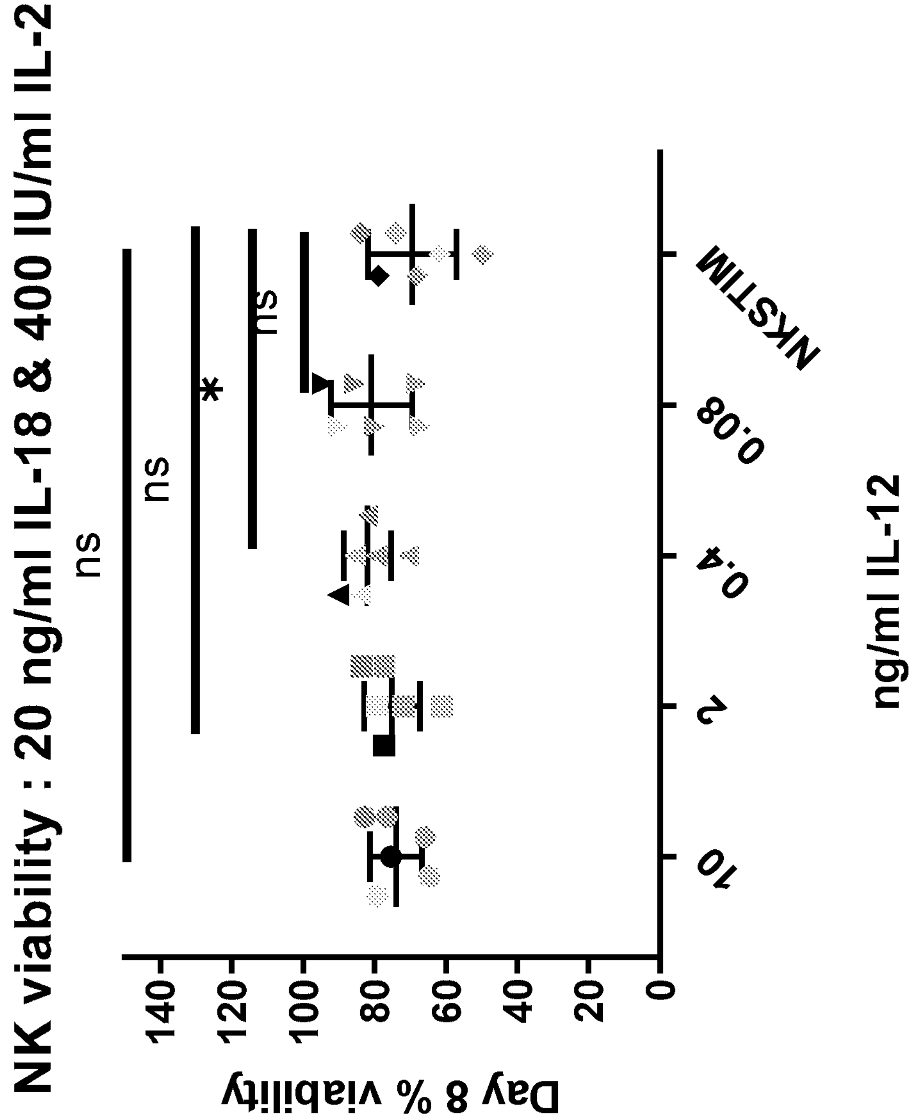
Figure 9G:
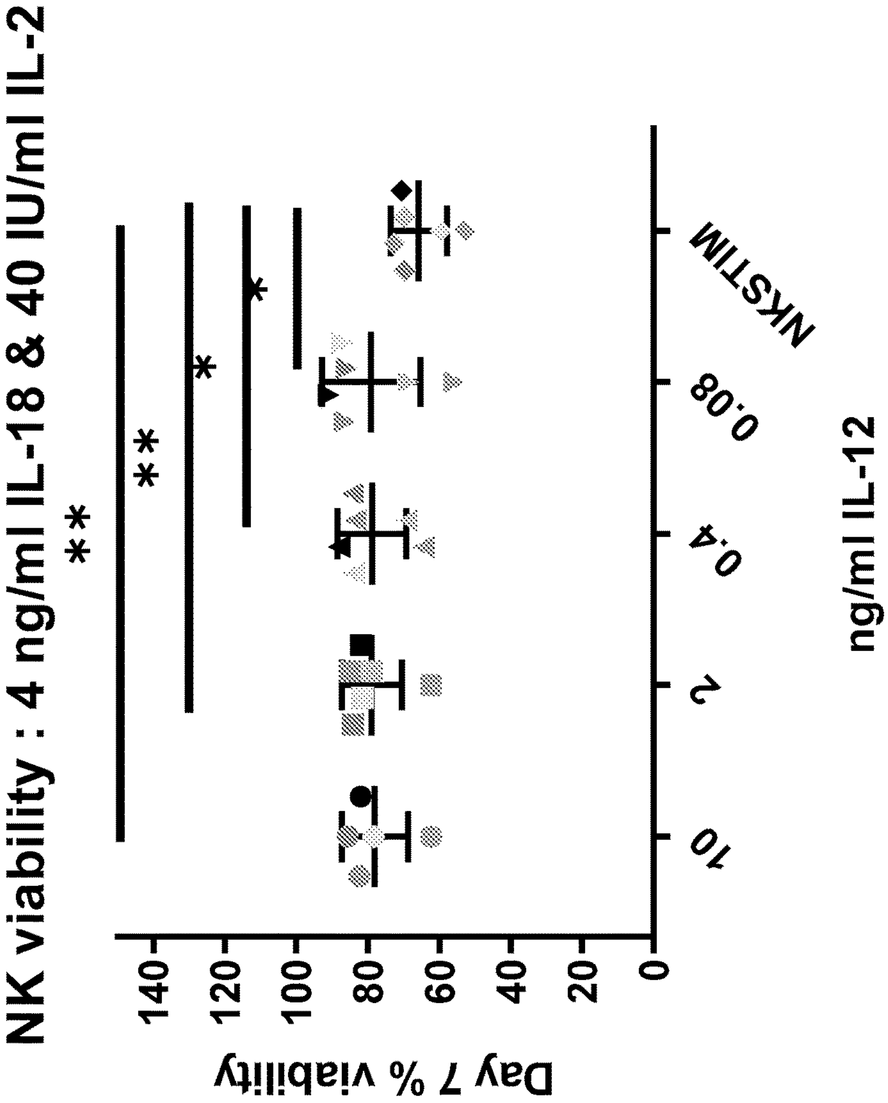
Figure 9H:
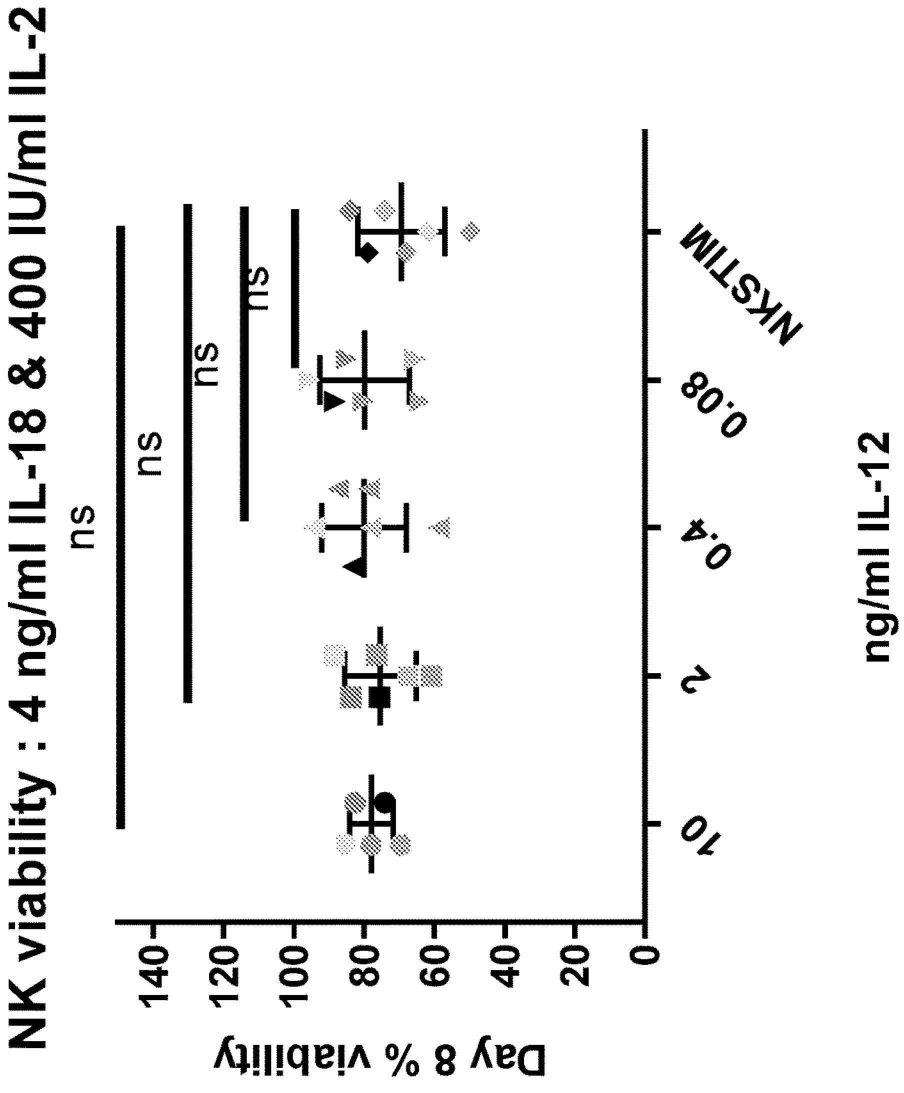

FIGS. 9A-9B shows data related the expansion of NK cells (untransduced) after 7 days of expansion in the indicated culture conditions. A first group was expanded using saturated concentrations of both IL12 (20 ng/mL) and IL18 (25 ng/mL). A second group was expanded using saturated concentrations of IL12 (20 ng/mL) and sub-saturated concentrations of IL18 (0.05 ng/mL). A third group was expanded using feeder cells engineered to express membrane-bound forms of each of IL15, IL12 and IL18 (further details on this feeder cell line can be found in International Patent Application No. PCT/SG2018/0501387, which is incorporated by reference herein in its entirety). A fourth group, as a control, was expanded on an established feeder cell line (K562 cells expressing mbIL15 and 4-1BBL). FIG. 9A shows the calculated expansion data and FIG. 9B shows the statistical analysis. FIGS. 9C and 9D display data to specific titration curves and NK cell expansion. FIG. 9C shows data for various concentrations of IL12 with IL18 held constant at 4 ng/mL. FIG. 9D shows similar data with IL12 varied and IL18 at 20 ng/mL. Taken together, these data indicate that addition of IL12 and IL18, whether in soluble format or membrane bound on the feeder cells (such as K562 cells expressing mbIL15) yields significantly enhanced NK cell expansion. Interestingly, IL12 appears to be a primary driver of expansion, with its activity enhanced by inclusion of IL18, even at low concentrations (see, e.g., the similar expansion numbers for saturated and sub-saturated concentrations of IL18. These data indicated that combinations of IL12 and IL18 robustly enhance NK cell expansion.

Figures 10A, 10B:
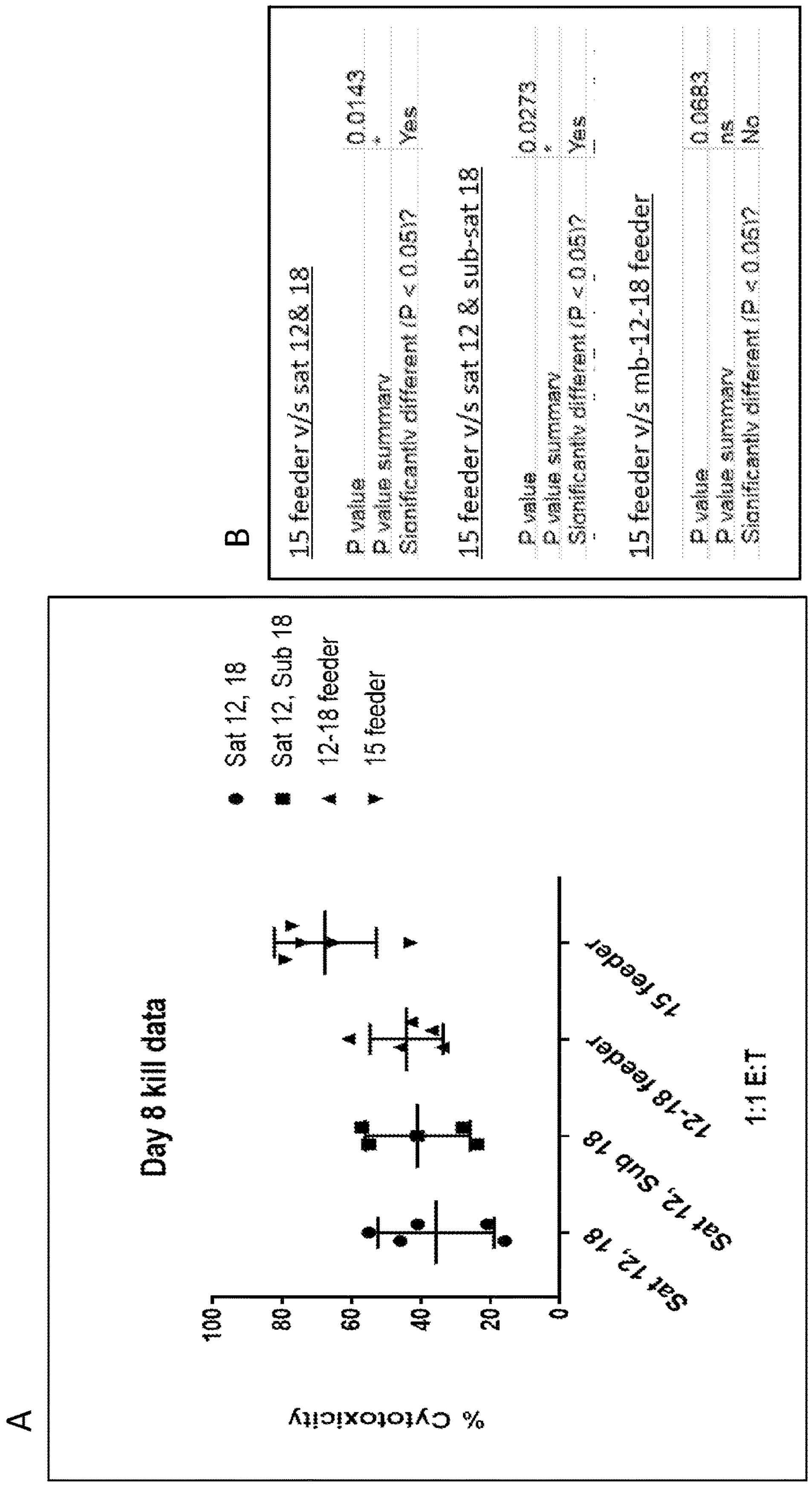
FIGS. 10A-10B related to assessment of NK cell cytotoxicity.

FIGS. 10A-10B show cytotoxicity data for the untransduced NK cells after 8 days of expansion in the indicated conditions (and IL-2 media supplementation at 40 IU/mL). Target cells were Reh acute lymphocytic leukemia (non-T; non-B) cells at a 1:1 effector target ratio. Regardless of culture conditions, all cells exhibited between about 40% and about 65% cytotoxicity. Cells expanded on mbIL15-expressing feeder cells without any IL12 or IL18 exhibited the highest degree of cytotoxicity, significantly more than either of the groups cultured in soluble IL12/IL18. Use of feeder cells with membrane-bound IL12 and IL18 exhibited greater degrees of cytotoxicity than those with soluble cytokines.

Figures 11A, 11B:
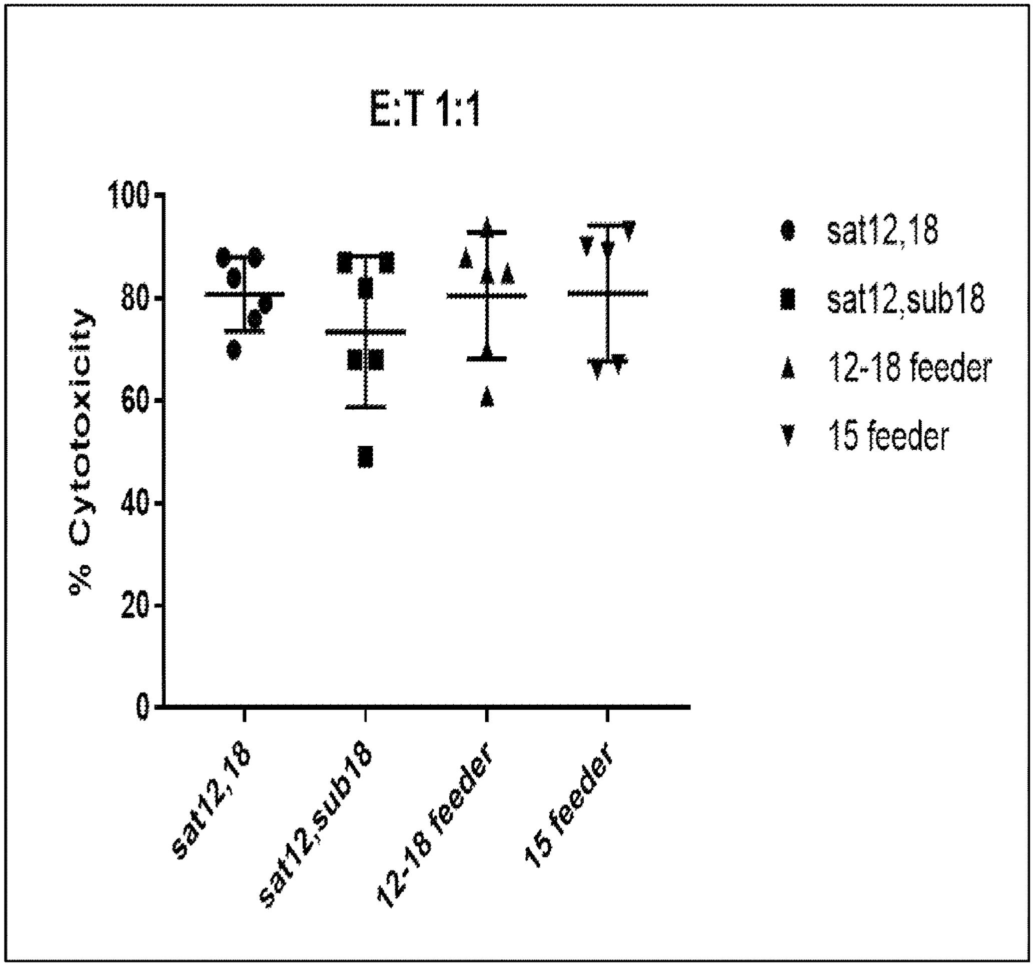
FIGS. 11A-11B related to assessment of NK cell cytotoxicity.

FIGS. 11A-11B show cytotoxicity data for untransduced NK cells at day 15 of culture (IL2 concentrations of 400 IU/mL) against Reh cells at 1:1 effector target ratio. These data exhibit not only greater degrees of cytotoxicity across the groups tested, but limited differences between the groups. In other words, all groups show increased cytotoxicity to the degree that there is not a significant difference between the culture conditions. According to some embodiments, the use of IL12 and IL18 induces a pathway or signaling cascade that impacts expansion in the early portion of culture. In several embodiments, that pathway or cascade (or pathways/cascades) has a delayed impact on enhanced cytotoxicity. In several embodiments, the use of certain stimulating factors induce a phenotypic change in the NK cells, such as a memory-like phenotype, that primes the NK cells to exert cytotoxic effects against a target cell. In several embodiments, the induction of that phenotypic change can take 1-2, 3-4, 5-6, 7-8 or more days to be recognized, depending on the characteristic of the NK cell being evaluated.

Figure 12:
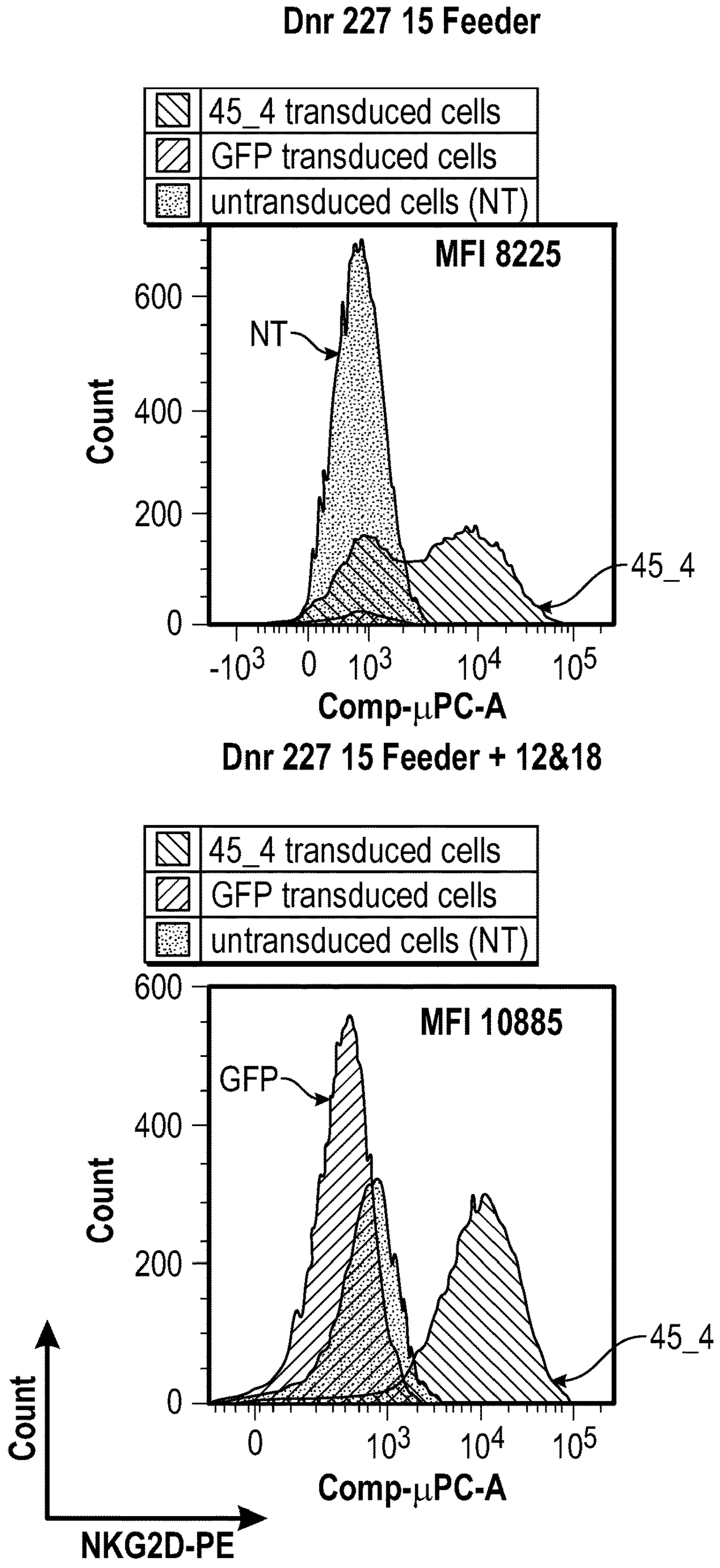
FIG. 12 shows expression data for NK cells transduced with a chimeric receptor construct and cultured in various conditions from two donors.
Figure 12:
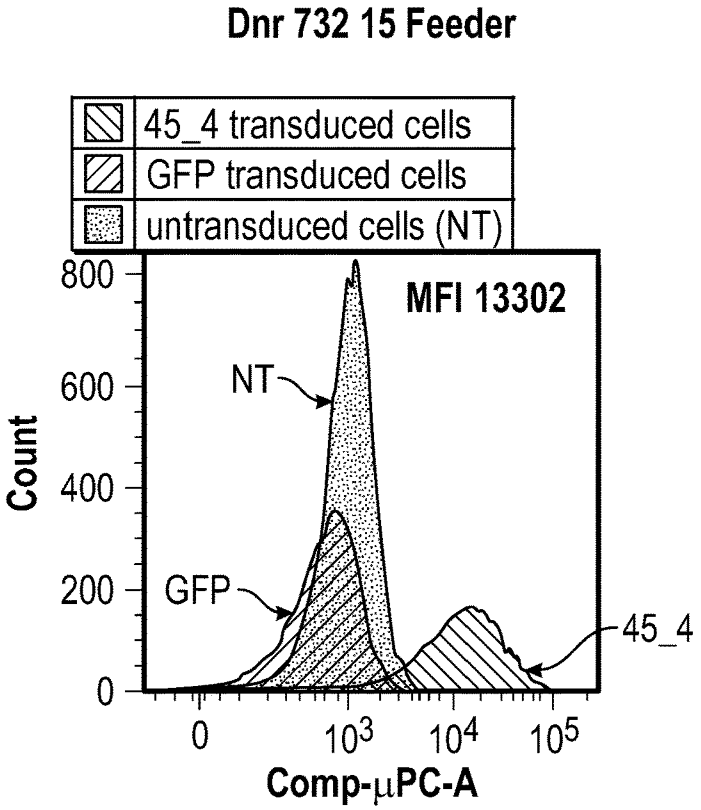
Figure 12:
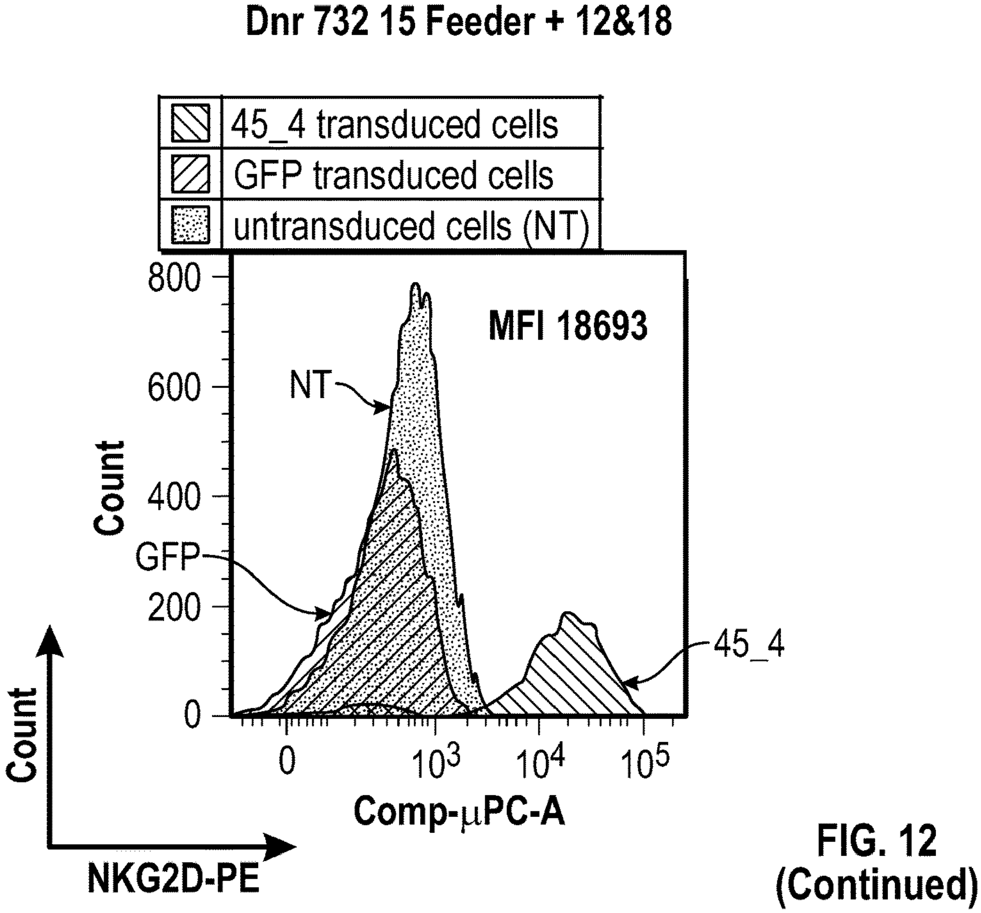
Figure 13:
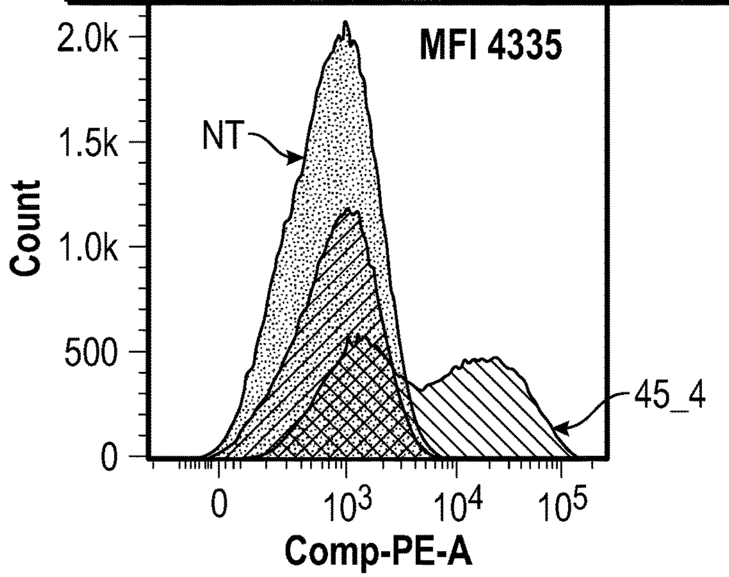
FIG. 13 shows expression data for NK cells transduced with a chimeric receptor construct and cultured in various conditions from two additional donors.
Figure 13:
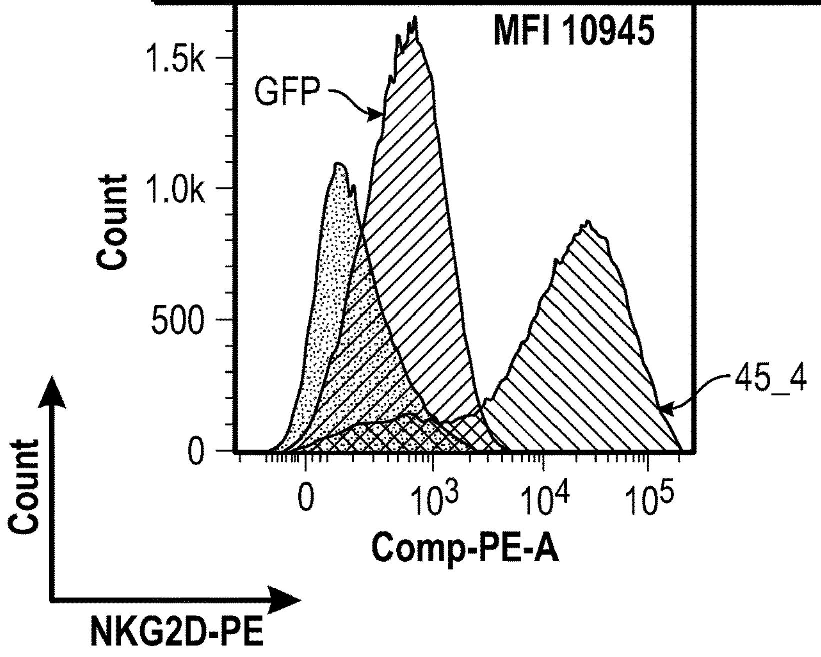
Figure 13:
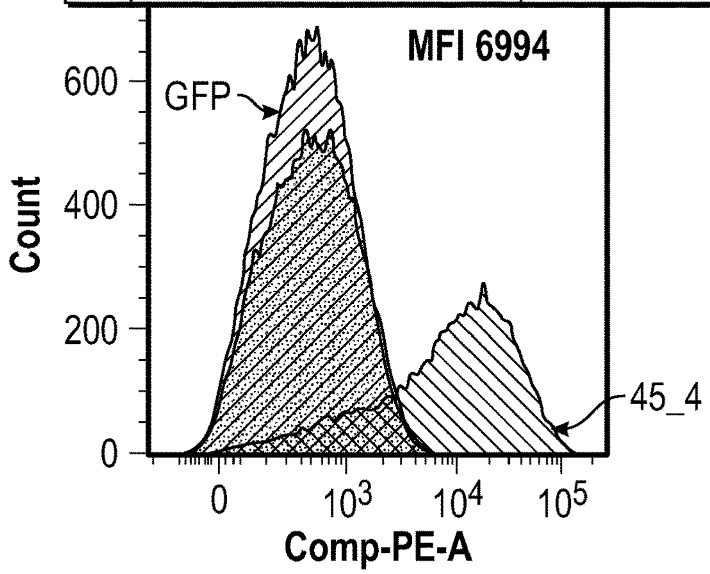
Figure 13:
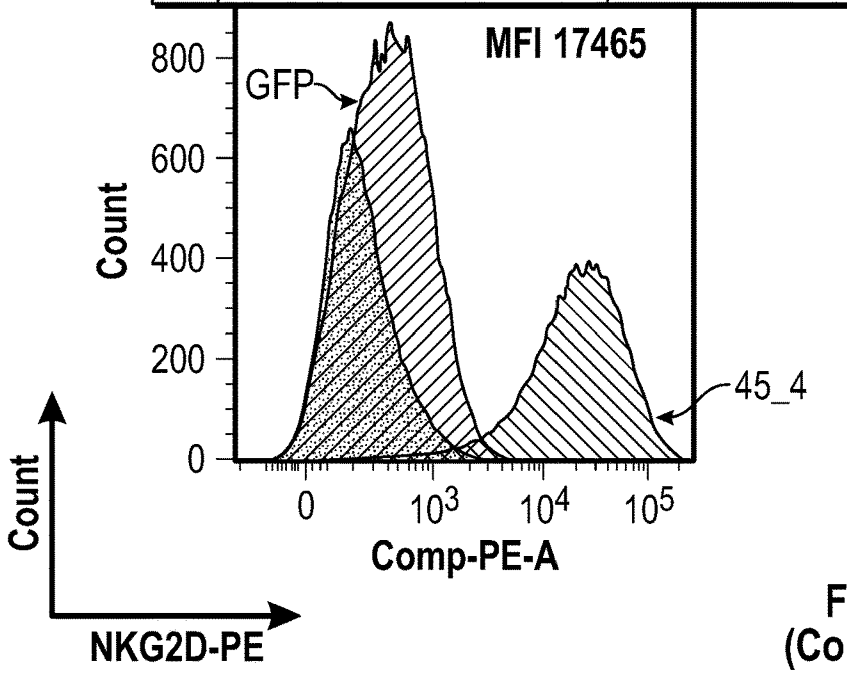

While the experiments above were performed with untransduced NK cells, they demonstrate that inclusion of IL12 and IL18, at various concentrations can enhance expansion and cytotoxicity of the NK cells. Further experiments were undertaken with NK cells transduced with a chimeric receptor (as compared to GFP-transduced cells or untransduced (NT) NK cells). As a non-limiting example the chimeric receptor employed comprises a truncated NKG2D domain is coupled to a CD8alpha hinge and CD8alpha TM domain an OX40 co-stimulatory domain, a CD3zeta signaling domain, and membrane bound IL15. FIG. 12 shows flow cytometry data evaluating the expression of the chimeric receptor (indicated as 45_4) on NK cells from various donors that were cultured under various conditions. In the left column of FIG. 12, data is shown for NK cells cultured on mbIL15 expressing feeder cells for two donors (227 on top, 732 on bottom). The curve identified as "45_4" shows greater expression of NKG2D (as expected for those cells being transduced with the NKG2D-containing chimeric receptor). The right column shows the expression results for NK cells cultured on mbIL15-expressing feeder cells with soluble IL12 and soluble IL18 added to the media at day 0 at 20 ng/mL and 25 ng/mL, respectively. FIG. 13 shows corresponding data for two additional donors. As can be seen from the MFI data in both FIG. 12 and FIG. 13, use of IL12 and IL18 resulted in enhanced NKG2D expression, further supporting the prior data that certain stimulating factors can robustly drive NK cell expansion. These data also confirm that use of stimulatory molecules, such as IL12 and IL18 are compatible with transduced NK cells.

Figures 14A, 14B:
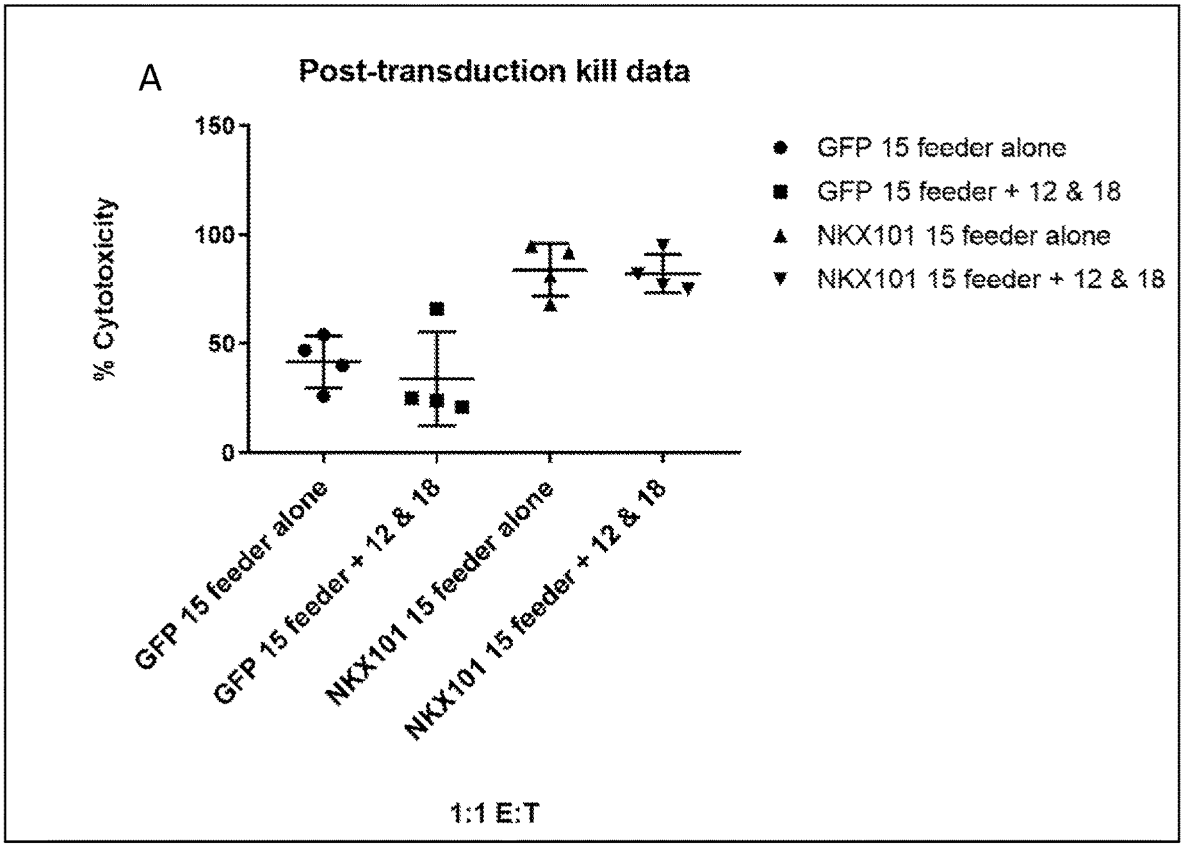
FIGS. 14A-14B show cytotoxicity data.

Having confirmed that stimulatory cytokines enhance the expansion of transduced NK cells, cytotoxicity was evaluated. FIGS. 14A and 14B show data related to cytotoxicity of NK cells transduced with the indicated constructs and expanded using the indicated culture conditions. Groups were: GFP-transduced NK cells grown on mblL-15-expressing feeder cells; GFP-transduced NK cells grown on mblL-15-expressing feeder cells and exposed to IL12 and IL18, NKX101-transduced NK cells grown on mblL-15-expressing feeder cells and NKX101-transduced NK cells grown on mblL-15-expressing feeder cells and exposed to IL12 and IL18. Target cells were Reh cells at 1:1 E:T ratio. The cytotoxicity was evaluated at Day 13 post-expansion using cells from four different donors. As shown, both GFP-transduced and NKX101-transduced NK cells exhibited cytotoxicity, with NKX101-expressing cells showing greater effects against the target cells. No significant differences were detected based on the expansion culture conditions used (see 14B).

Figures 15A, 15B:
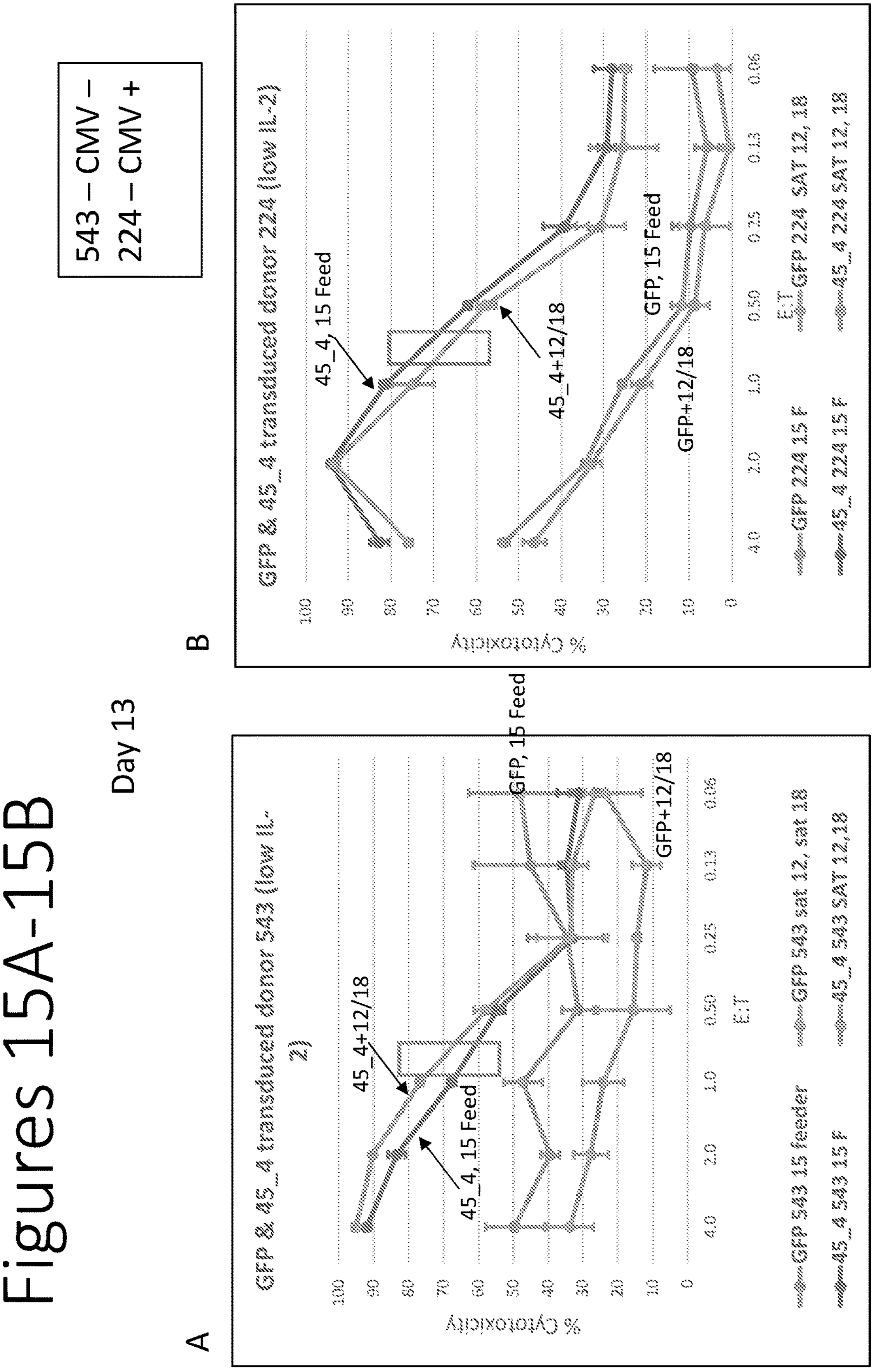
FIGS. 15A-15D relate to cytotoxic effects of NK cells transduced with an NKG2D targeting chimeric receptor after being cultured under the indicated conditions.
Figures 15C, 15D:
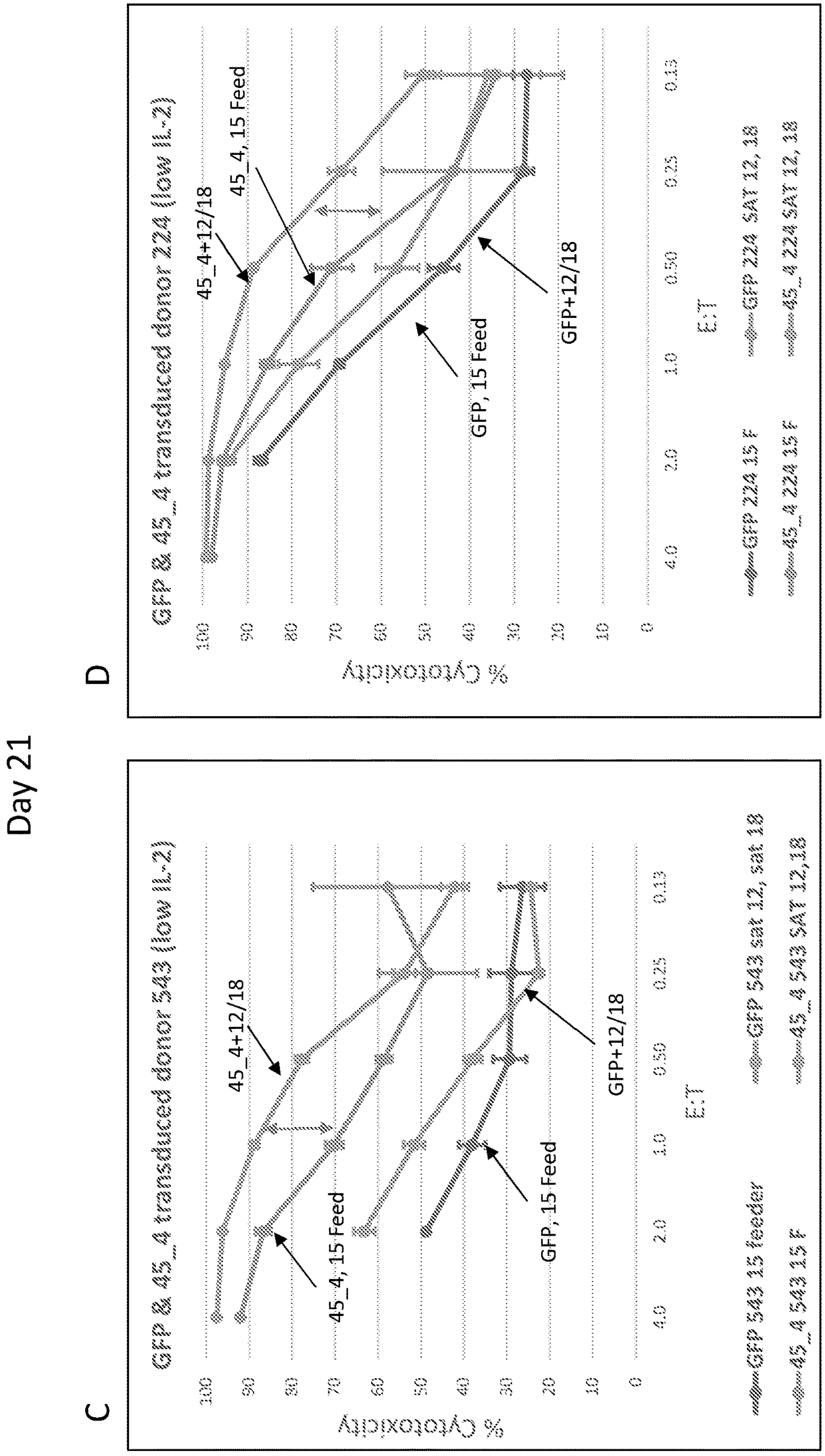

FIGS. 15A-15B show additional cytotoxicity data from two donors where different E:T ratios were tested. These data show a pattern consistent with that shown in FIG. 14. FIG. 15A shows data for the four culture conditions for a first donor, and 15B shows the corresponding data for a second donor. Note that donor 543 (FIG. 15A) was negative for cytomegalovirus and donor 224 (15B) was positive for CMV. CMV positive individuals have a subpopulation of NK cells that have a memory-like phenotype, meaning that they are characterized by a more rapid response to target cells. The data in 15A-15B was collected at day 13 post-expansion. These curves are similar to the data above and at this relatively early time point, the presence or absence of IL12/IL18 has a limited effect on the cytotoxicity induced by NK cells. FIGS. 15C and 15D show data from the same donors/conditions, but at 21 day post-expansion. Notably, the use of IL12/IL18 results in enhanced cytotoxicity against the target cells at most E:T ratios tested. These data are consistent with those discussed above for the untransduced NK cells, in that there is a delay in the induction of enhanced cytotoxicity, but it is detectable at later time points. As discussed above, this effect may be due to the time required to induce a phenotypic change in the NK cells.

Figure 16A:
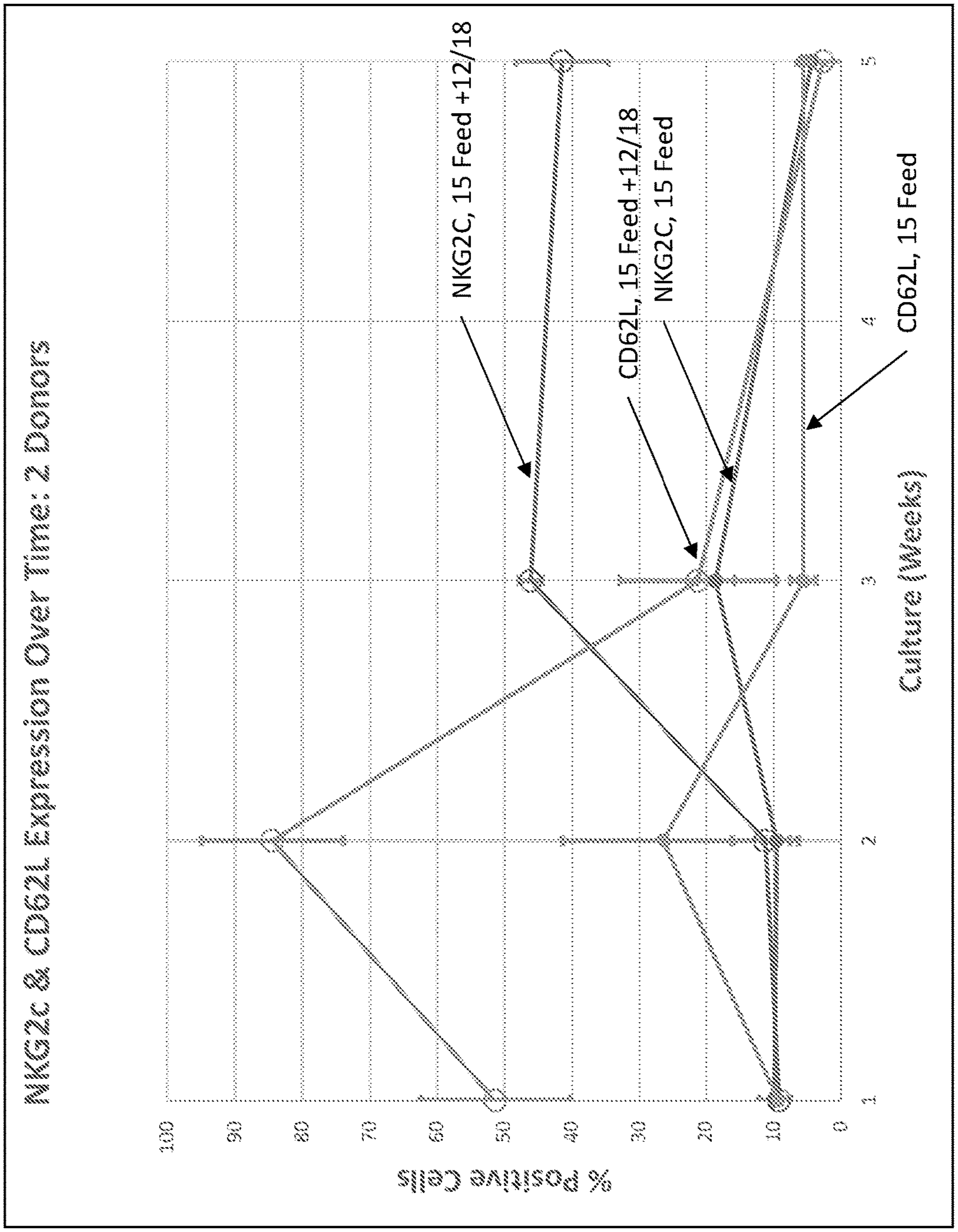
FIGS. 16A-16B show data related to the phenotype of NK cells.
Figure 16B:
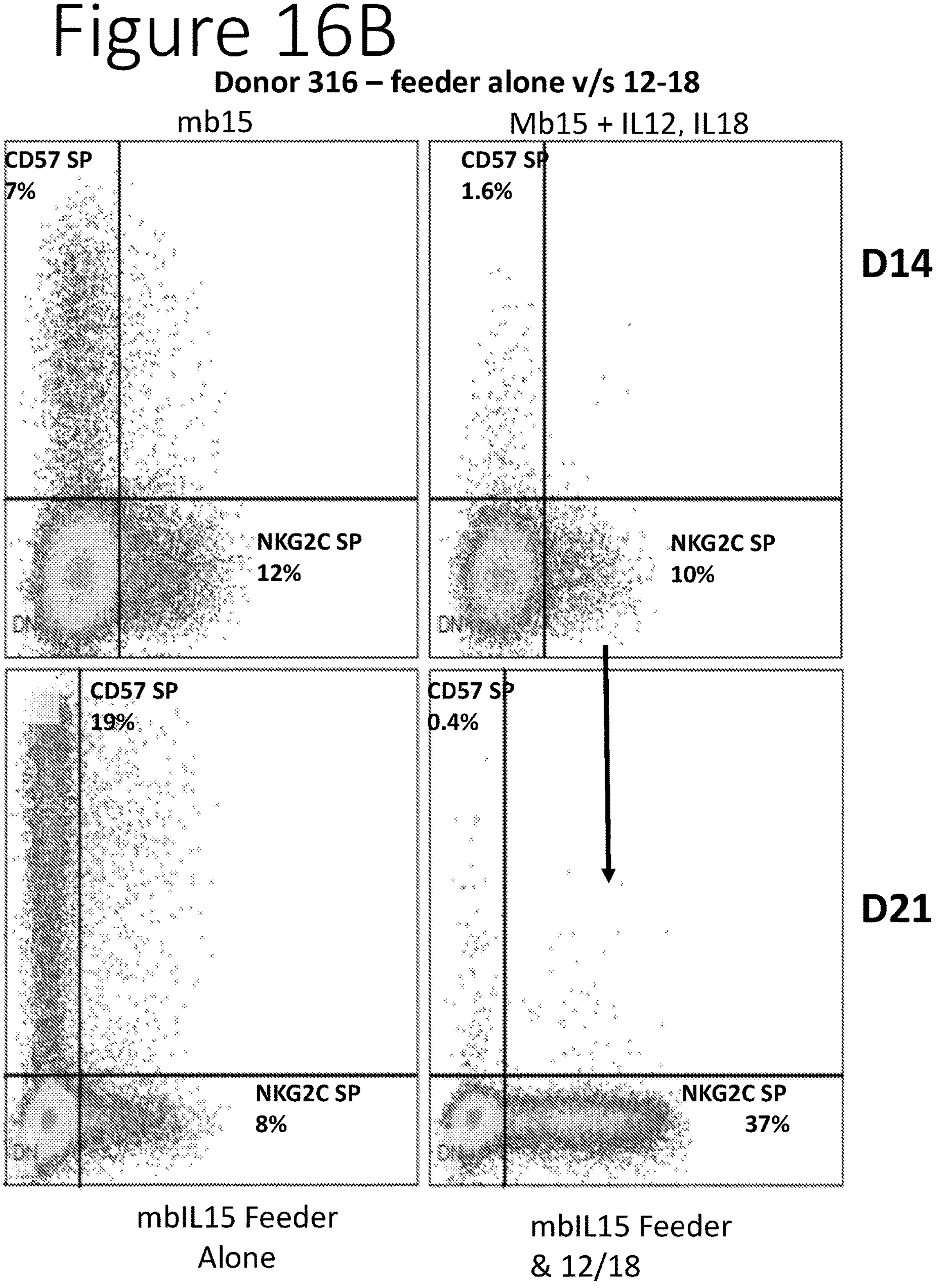

FIGS. 16A-16B relate to the evaluation of the phenotype of NK cells cultured in different conditions over time. FIG. 16A shows the expression levels of NKG2C and CD62L (L-selectin) over 5 weeks of culture under the indicated conditions. Neither CD62L or NKG2C expression levels varied significantly over the 5 weeks of culture when using mbIL15-expressing feeder cells. In contrast however, use of those feeder cells and supplementing the media with IL12 and IL18 at day 0 had significant impact on the expression of both NKG2C and CD62L. CD62L was initially present on about 50% of the NK cells after week 1 of culture. While this increased after a week, there was then a significant decline in CD62L expression, with limited detection possible at 4 weeks of culture. In contrast, NKG2C expression increased slightly after a week in culture, expression of NKG2C increased on the NK cells, with over 40% of the cells expressing NKG2C after 5 weeks. Thus, the culture, at 5 weeks, could be characterized as having elevated NKG2C as compared to NK cells grown without the stimulatory cytokine and having reduced or equivalent CD62L expression as compared to NK cells grown without the stimulatory cytokine. FIG. 16B shows further data supporting the development of an altered, memory-like phenotype by the NK cells. FIG. 16B shows expression data by FACS analysis of donor NK cells at day 14 (top row) and day 21 (bottom row) cultured with mbIL15-expressing cells (left column) or mbIL15-expressing cells plus IL12 and IL18 addition at day 0 (right column). CD57 expression is also shown, with the relatively low percentage of cells positive for expression confirming a trend to loss of expression of that marker when NK cells are cultured (fresh NK cells would have a higher CD57 expression). As can be seen in the mbIL15 column, NKG2C expression (X-axis) is not significantly change. In contrast (as indicated by the arrow) the percentage of cells expressing NKG2C is increased by 40% after an additional week in culture after an initial exposure to soluble IL12 and soluble IL18.

Figures 17A, 17B:
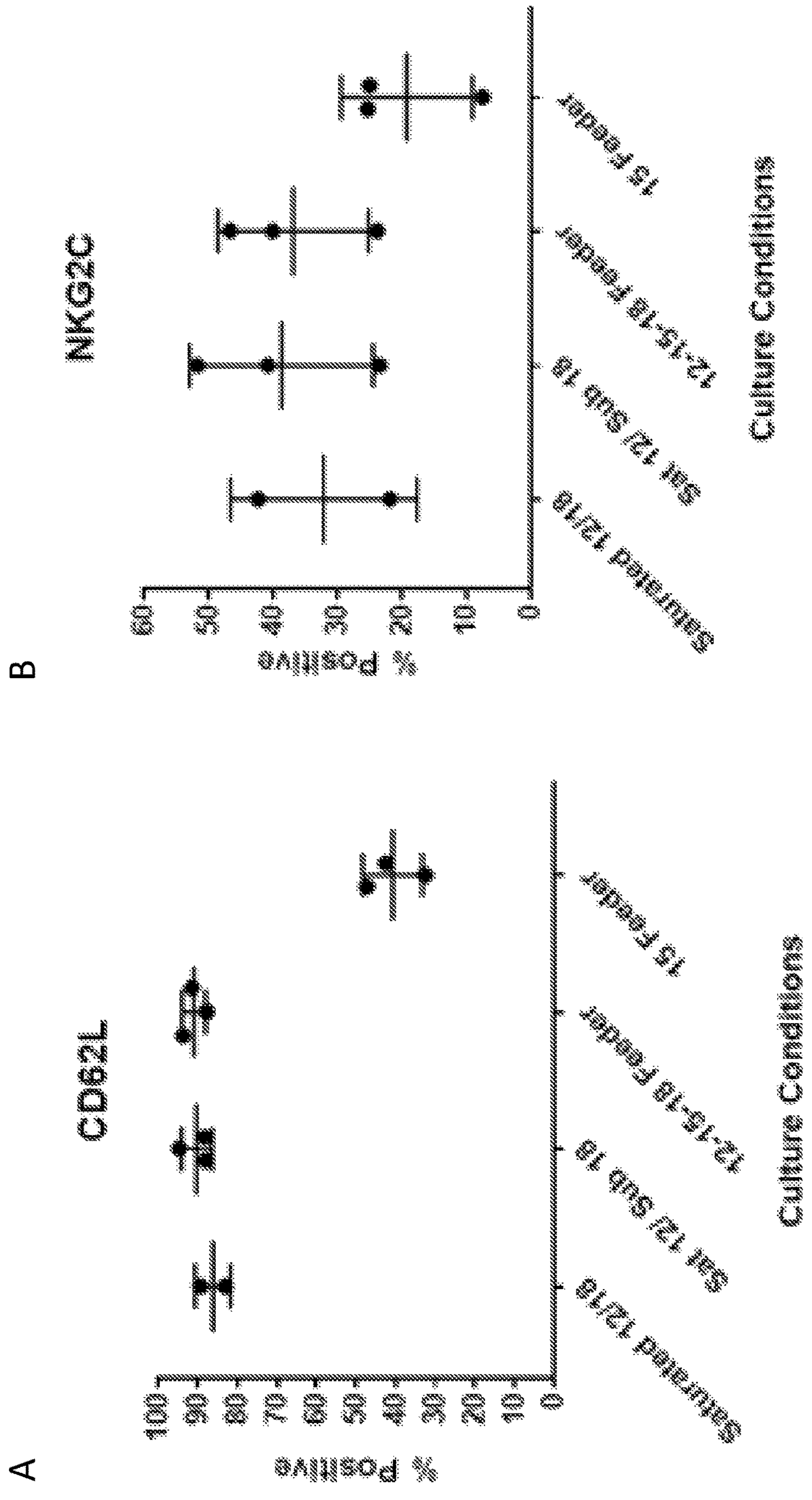
FIGS. 17A-17D shows summary expression data related to selected markers by NK cells in various culture conditions.
Figures 17C, 17D:
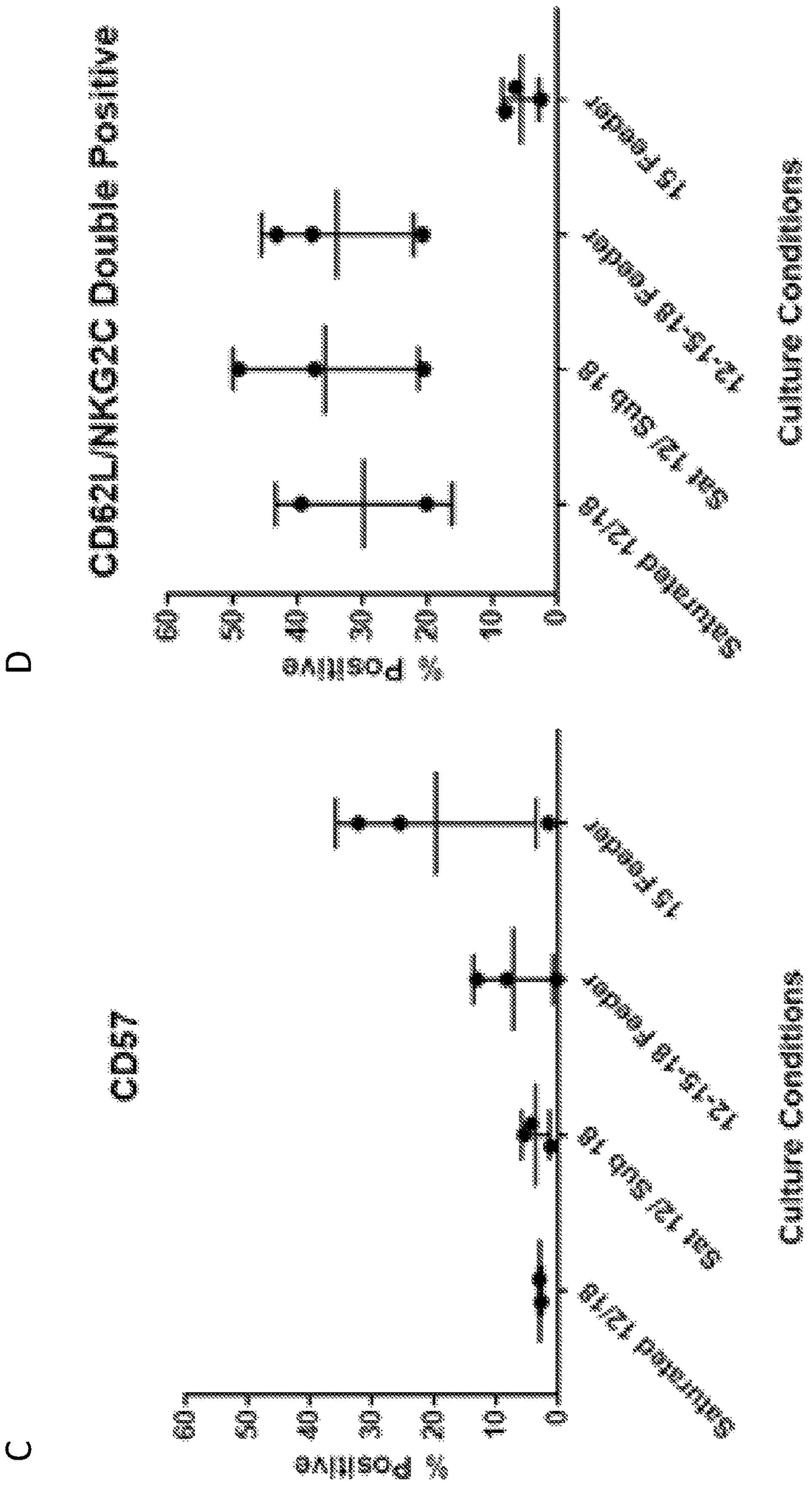

FIGS. 17A-17D show summary data related to marker expression on NK cells after 14 days in culture, under the indicated conditions. As shown in 17A, at this time point, CD62L is enhanced by the use of IL12 and IL18, whether in soluble or membrane-bound formats. As discussed above, this expression drops over additional time in culture. FIG. 17B shows enhanced NKG2D expression when IL12 and IL18 are introduced into the media at Day 1. As with other data, it is noted that the effects on the NK cell phenotype (like expansion and cytotoxicity) are roughly equivalent when the IL18 concentration is varied (e.g., effect is seen with saturated or sub-saturated concentrations of IL18). CD57 expression levels were relatively low under all conditions, reflective of the cells as cultured (rather than freshly isolated), as shown in 17D. FIG. 17D shows double positive marker expression for CD62L and NKG2C, again expression levels were enhanced with the presence of IL12 and IL18 in the culture. These data reflect the shifting phenotype of NK cells cultured with IL12 and IL18 (whether soluble or membrane-bound) towards a more potent memory-like phenotype. In several embodiments, this phenotype endows the NK cells, particularly those engineered to express a chimeric receptor, with enhanced expansion ability and/or enhanced cytotoxicity, making for a more potent cancer immunotherapy product.

Figure 18:
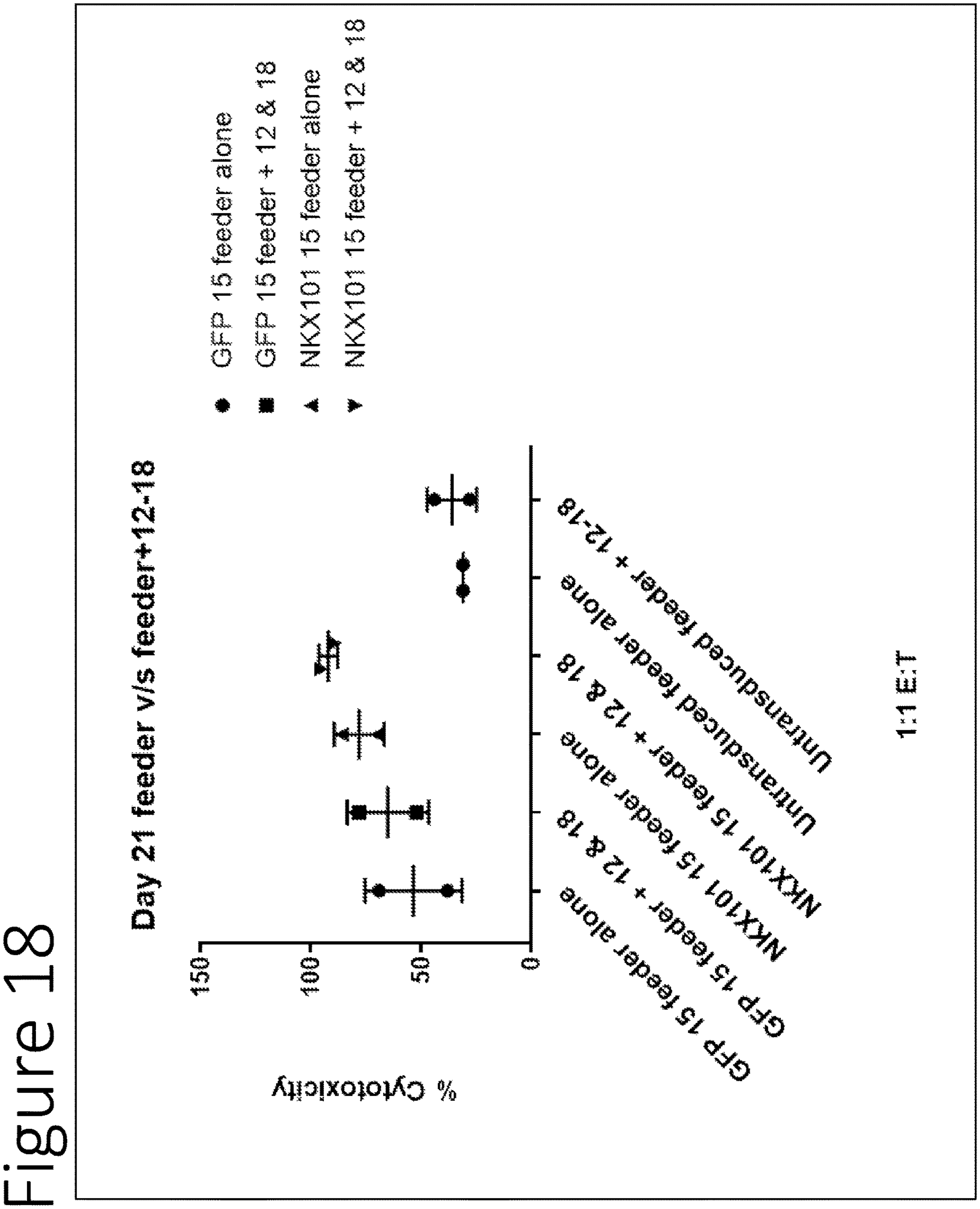
FIG. 18 shows cytotoxicity data for NK cells expressing either GFP and or an NKG2D-ligand directed chimeric receptor at day 21 post-transduction.

FIG. 18 shows that the use of IL12 and IL18 enhance the cytotoxicity of engineered NK cells, even at later time points (shown is cytotoxicity at 21 days post-expansion). Notably the two central points on the figure represent NKX101-transduced NK cells, which exhibit the greatest cytotoxic effect of any of the groups. Importantly, the NKX101-transduced NK cells cultured with soluble IL12 and 18 on mbIL15-expressing feeder cells show the highest degree of cytotoxicity towards target cells (by way of non-limiting example, the target here was Reh leukemia cells). Thus, according to several embodiments, the use of soluble stimulatory factors, such as IL12, IL18, IL21 and the like, in culture of NK cells, provides for an unexpectedly improved expansion of the cells (which is highly relevant for producing clinically meaningful cell numbers) as well as unexpectedly enhanced cytotoxicity against target cells.

Example 3—Evaluation of Expansion, Cryopreservation and Cytotoxicity

As disclosed herein, in several embodiments, the engineered NK cells that are expanded are for use in an autologous scenario. In several embodiments, an allogeneic approach is used. In several embodiments, the NK cells are designed to be "off the shelf", referring to a pre-existing population of NK cells that has been expanded and engineered, and then is preserved for dosing to a patient at a later time. In several embodiments, the preservation is through cryopreservation. As with any freeze-thaw cycle, viability and activity of cells can be an issue. FIG. 19 shows data related to the characteristics of NK cells from three different donors cultured with mbIL15-expressing feeder cells or mbIL15-expressing feeder cells supplemented with soluble IL12/18 at the inception of culture. The bottom three rows of the table evidence the positive impacts of soluble IL12 and 18 on NK cells in culture. After day 6 of expansion, viability of NK cells in IL12/18 media was slightly higher, while the total cell number and thus, fold expansion, was notably higher when using IL12/18.

Figure 20:
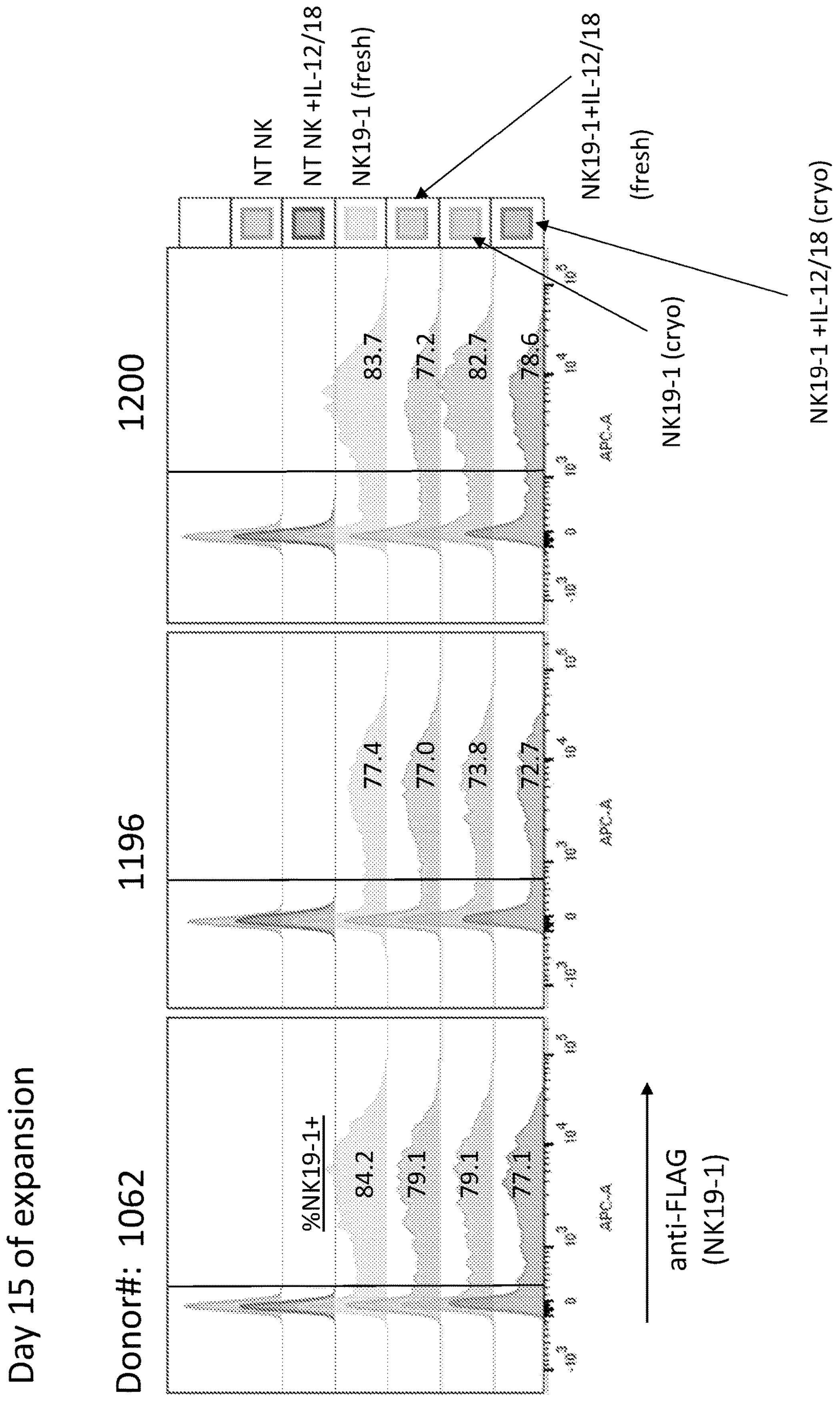
FIG. 20 shows expression data (based on a Flag tag) for NK cells transduced with an anti-CD19 CAR and cultured using the indicated conditions. This data was collected at day 15 of expansion.
Figure 21:
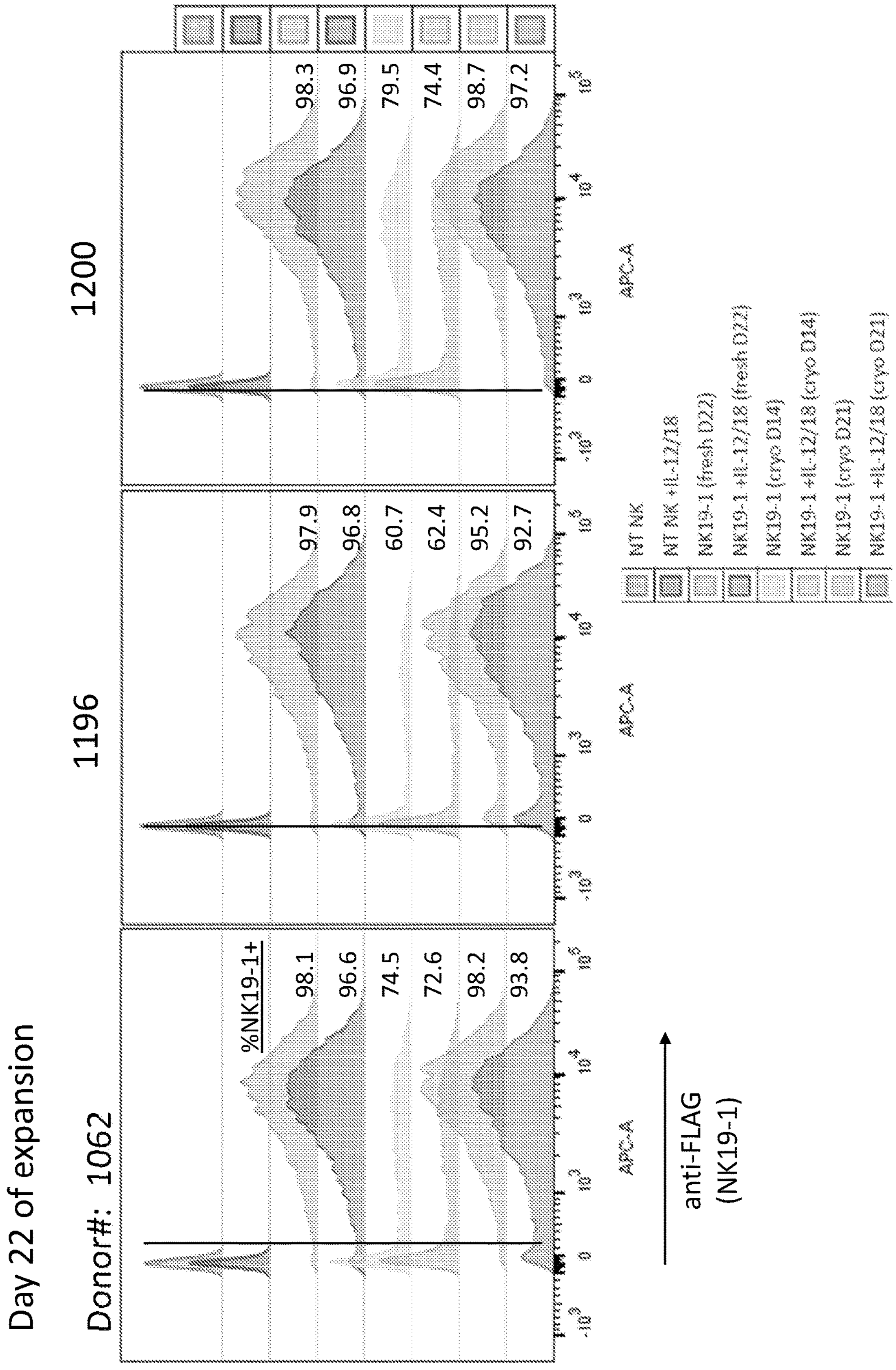
FIG. 21 shows expression data (based on a Flag tag) for NK cells transduced with an anti-CD19 CAR and cultured using the indicated conditions. This data was collected at day 22 of expansion.

Building on this data, cells were transduced with an anti-CD19 chimeric antigen receptor and cultured with or without soluble IL12 and 18 (using mbIL15-expressing feeder cells). A portion of cells were cryopreserved and then compared with corresponding fresh cells. Using FACS, the NK cells were evaluated for expression of FLAG (the tag within the NK19-1 construct, though it shall be appreciated that corresponding non-tagged constructs are provided for herein). As shown in FIG. 20, NK cells from 3 donors both fresh and cryopreserved cells maintain expression of the CD19 CAR. The presence of IL12/18 appears to have limited impact on CAR expression. FIG. 21 shows the cells from the same donors at day 22 of expansion. Interestingly, the percentage of cells expressing the anti-CD19 CAR was reduced at day 14 as compared to day 21. The expression of the construct at Day 21, was approximately the same as in fresh NK cells (e.g., not frozen) (compare rows 3-4 with rows 7-8). These data indicate that the NK cells cultured according to methods disclosed herein are robust cell populations and able to survive cryopreservation and still maintain viability and maintain significant expression levels of cytotoxicity inducing constructs.

Figure 22A:
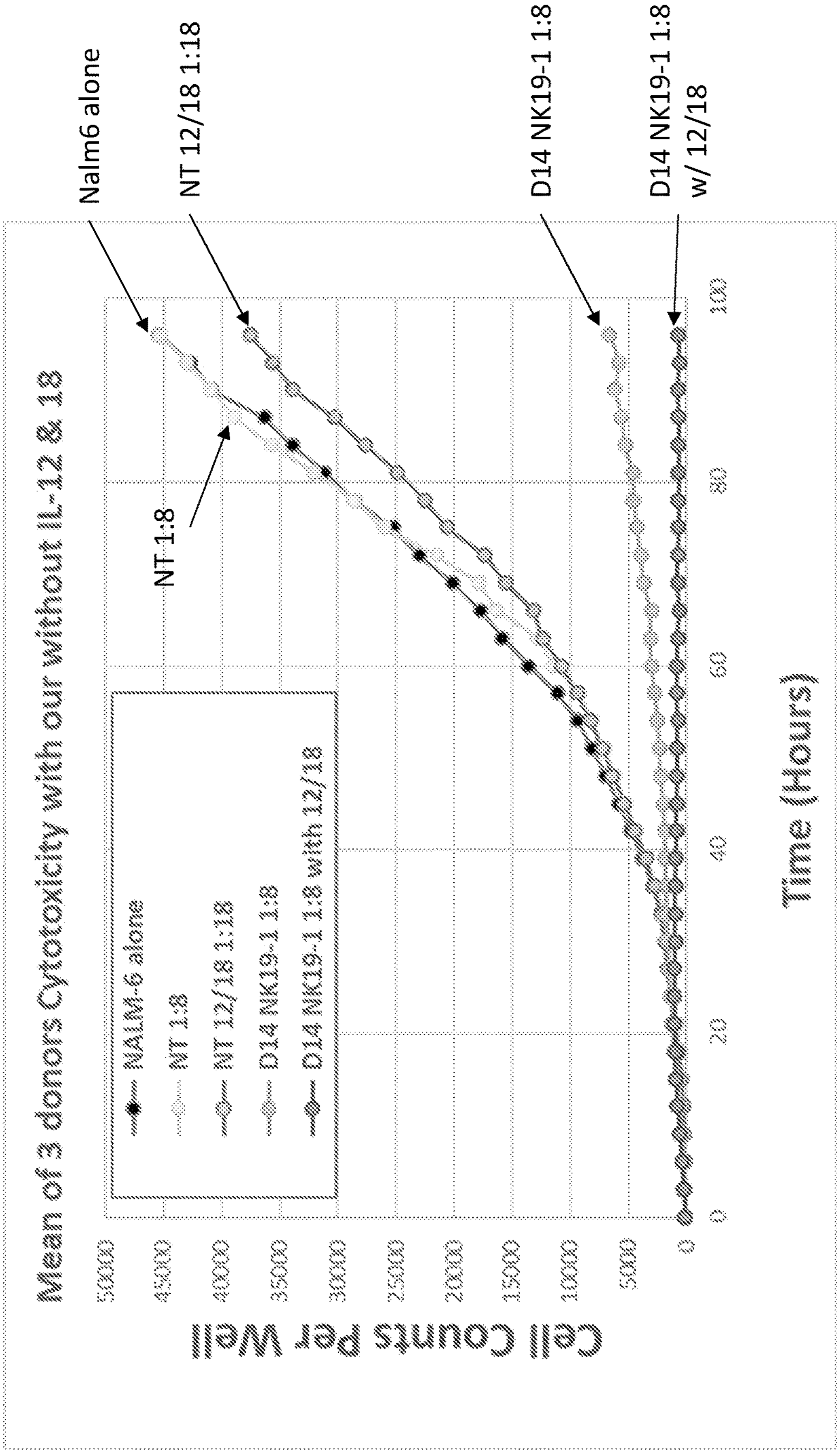
FIGS. 22A-22C show data related to the cytotoxicity of NK cells expressing an anti-CD19 CAR. NK cells were expanded using the indicated conditions and challenged with Nalm6 cells using the indicated E:T ratios in FIG. 22A (mean of 3 donors).
Figure 22B:
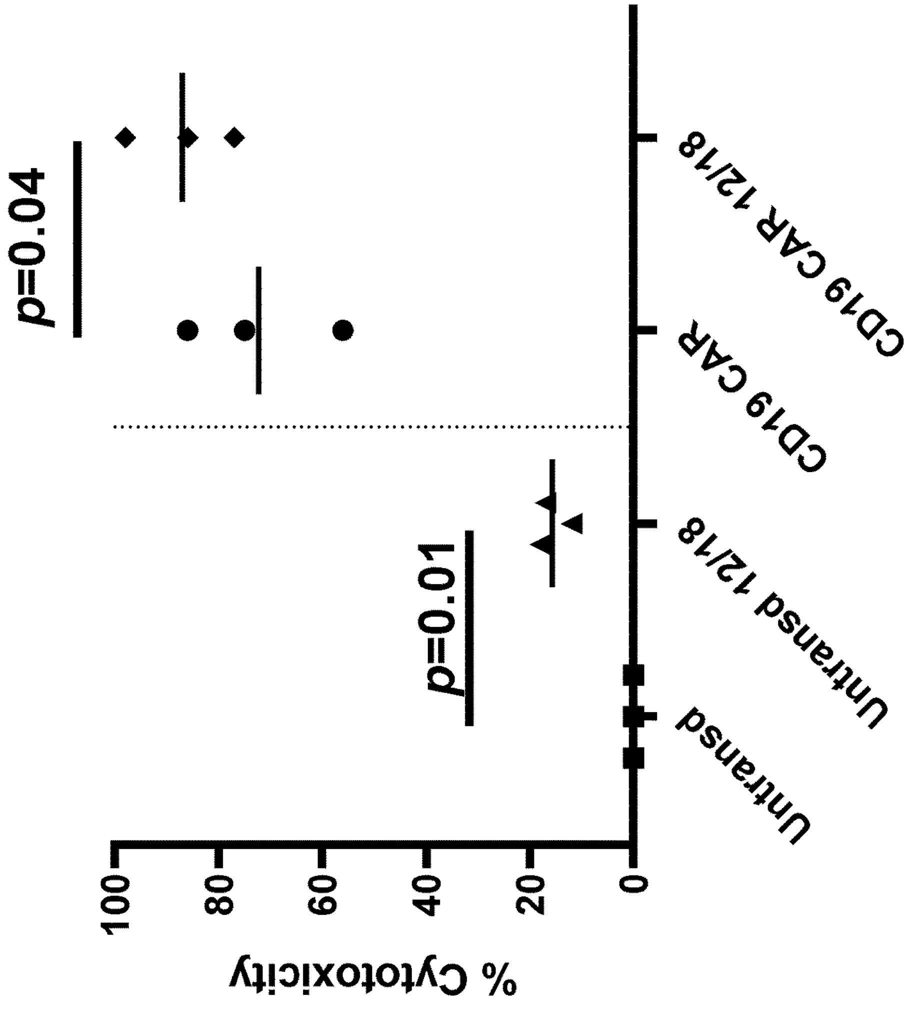
Figure 22C:
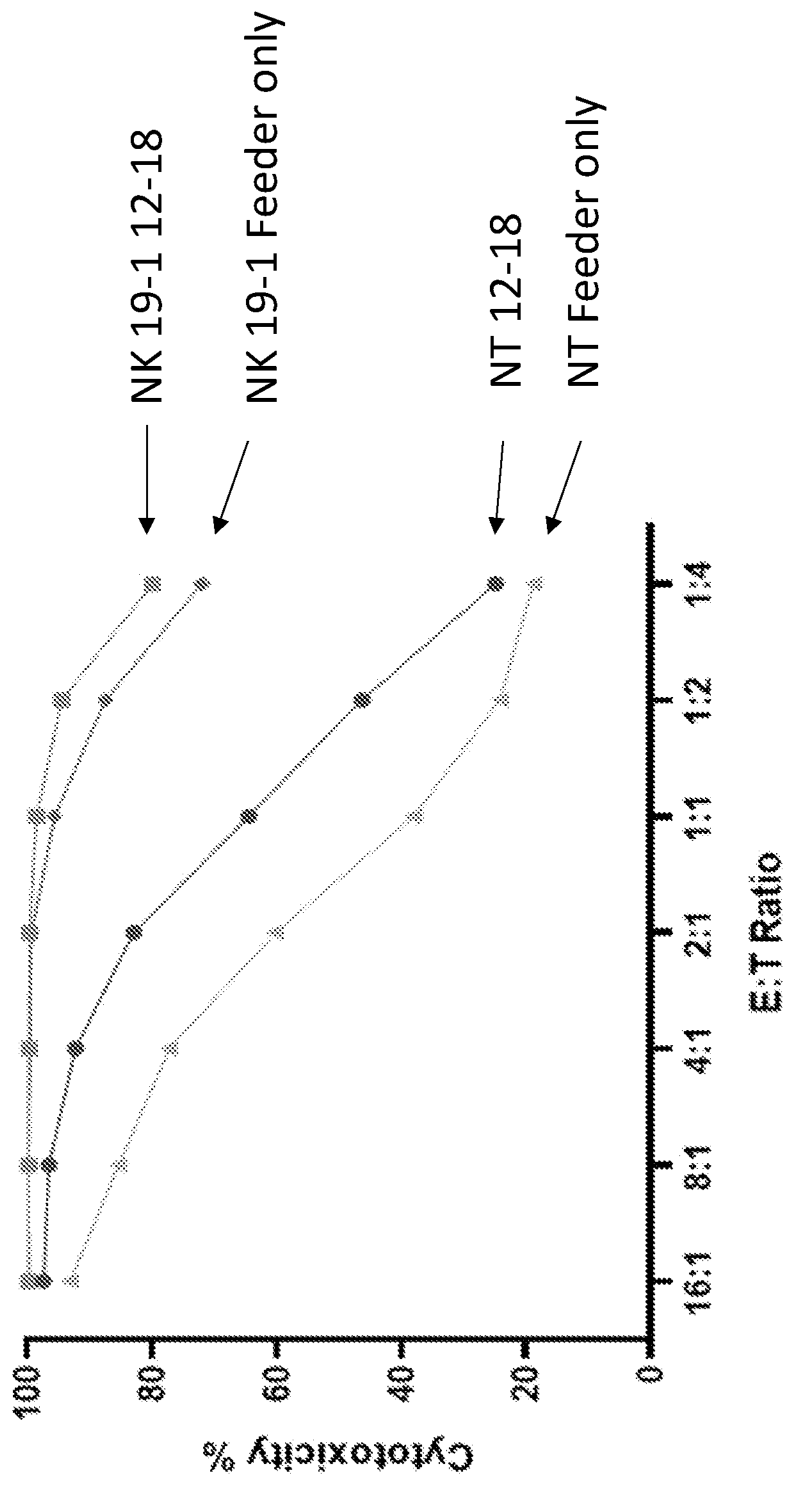

Further analysis of the effects of cryopreservation on NK cells was undertaken. A Nalm6-nuclear Red cell line was used as the target cell and were targeted by an NK cell line expressing an anti-CD19 CAR. By way of non-limiting example, this experiment employed a CAR encoded by SEQ ID NO: 1. Results of the assay are provided in FIGS. 22A-22B. FIG. 22A shows cell count curves (mean of three donors) over assay time. As shown, non-transduced NK cells and Nalm6 cells alone showing similar degrees of Nalm6 target cell increase. Non-transduced NK cells grown with soluble IL12/18 showed a slight cytotoxic effect (downward shift in the cell counts per well curve. Notably, cells that were cryopreserved at day 14 of culture showed a significant cytotoxic effect on the Nalm6 cells, limiting growth to the final hours of the experiment. Significantly, Day 14 cryopreserved cells grown in culture with soluble IL12/18 completely restricted Nalm6 cell growth. In several embodiments, cells expanded for longer periods of time (either fresh or cryopreserved) are also able to significantly reduce tumor growth. Summary data at 14 days is shown in FIG. 22B. With respect to untransduced NK cells, expansion of the NK cells with soluble IL12/18 added at Day 0 of culture significantly increased the cytotoxicity of the NK cells against target tumor cells. Similar data are shown for NK cell expressing a CAR. Even with the presence of a CAR leading to nearly 80% cytotoxicity against target cells, culturing the CAR-expressing NK cells with soluble IL12/18 significantly enhanced the cytotoxicity. FIG. 22C shows additional cytotoxicity data for NK cells cultured in the presence or absence of IL12/18 in the culture media during expansion, at various E:T ratios. As shown cells engineered to express a non-limiting embodiment of an anti-CD19 car exhibit enhanced cytotoxicity at nearly all E:T ratios. As the number of target cells increases, the cytotoxicity of NK cells expanded using IL12 and IL18, as disclosed herein, exhibit heightened cytotoxic effects as compared to cells expanded on feeder cells alone. Collectively, these data provide evidence that the use of IL12/18 in the culture media results in enhanced proliferation of NK cells as well as enhanced cytotoxicity. Additionally, these data provide important additional evidence that the activity of the cells is preserved, even after cells are cryopreserved. This data indicates that, according to some embodiments, an "out of the freezer" engineered NK cell product with robust anti-tumor effects has been generated.

Figure 23:
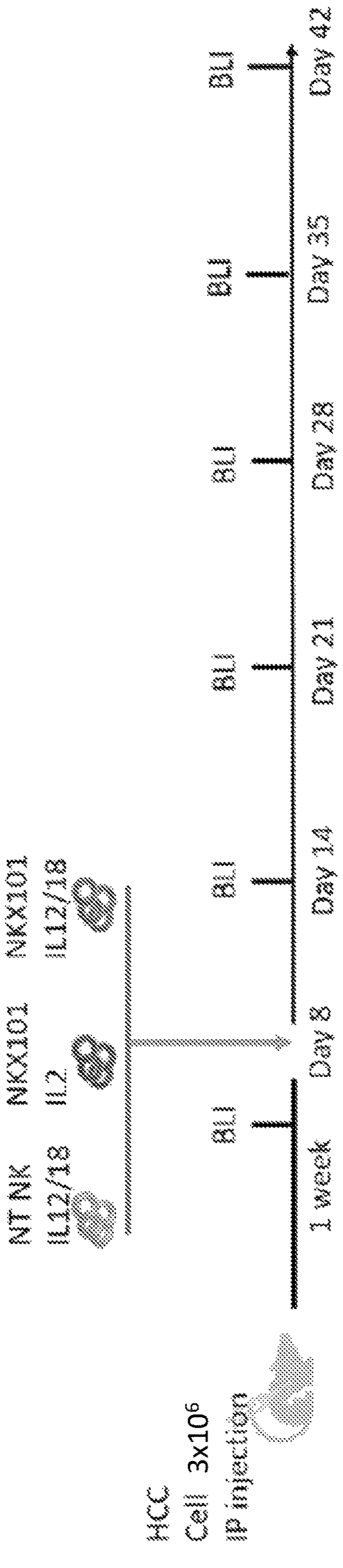
FIG. 23 shows a schematic of an experimental setup to assess the cytotoxicity of NK cells expressing a chimeric receptor targeting NKG2D ligands in a hepatocellular carcinoma xenograft model.
Figure 24:
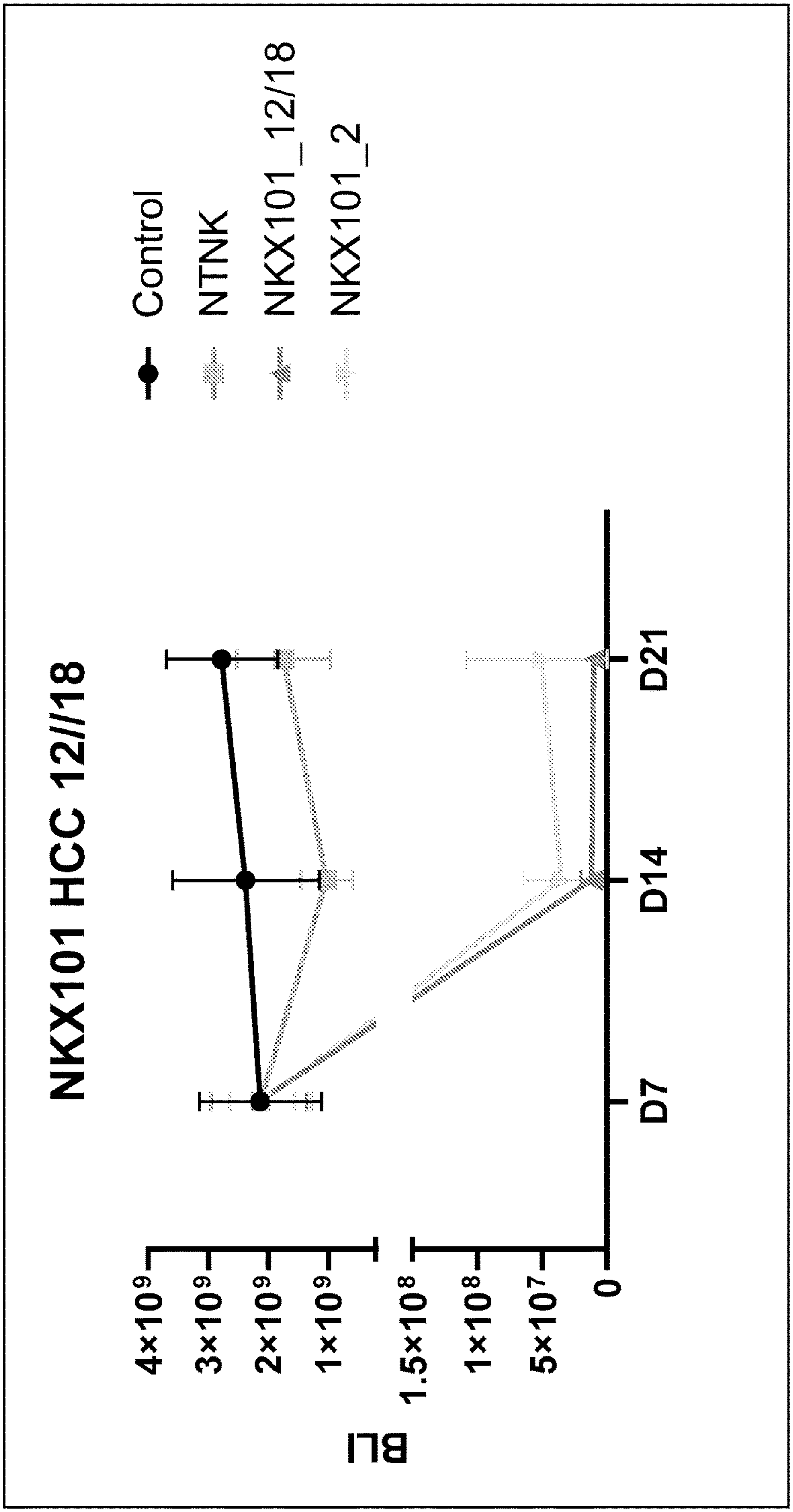
FIG. 24 shows a summary of tumor burden over time in mice under the indicated treatments.

FIG. 23 shows a schematic of an in vivo experiment wherein hepatocellular carcinoma cells are injected into donor mice and NK cells grown using various culture conditions are administered. Tumor burden is thereafter monitored using bioluminescence. Administered cells are either nontransduced NK cells grown in media supplemented with soluble IL12/IL18 at day 1, NK cells expressing NKX101 grown with IL2, or NK cells expressing NKX101 grown in media supplemented with soluble IL12/IL18 at day 1. All cells were grown on mbIL15-expressing feeder cells. FIG. 24 shows the results of tumor burden analysis over time. Control animals, as well as those receiving non-transduced NK cells shown moderate tumor growth over time. In contrast, those animals receiving NK cells expressing NKX101 and grown with IL12/18 or IL2 showed significantly more anti-tumor effects. Tumor burden decreased in both group, with only a slight increase from Day 14 to 21 in the IL2 group. These data further reinforce the use of stimulatory cytokines such as IL12, IL18, or IL21 in the expansion culture media in order to enhance the cytotoxicity of the cultured NK cells.

Figure 25:
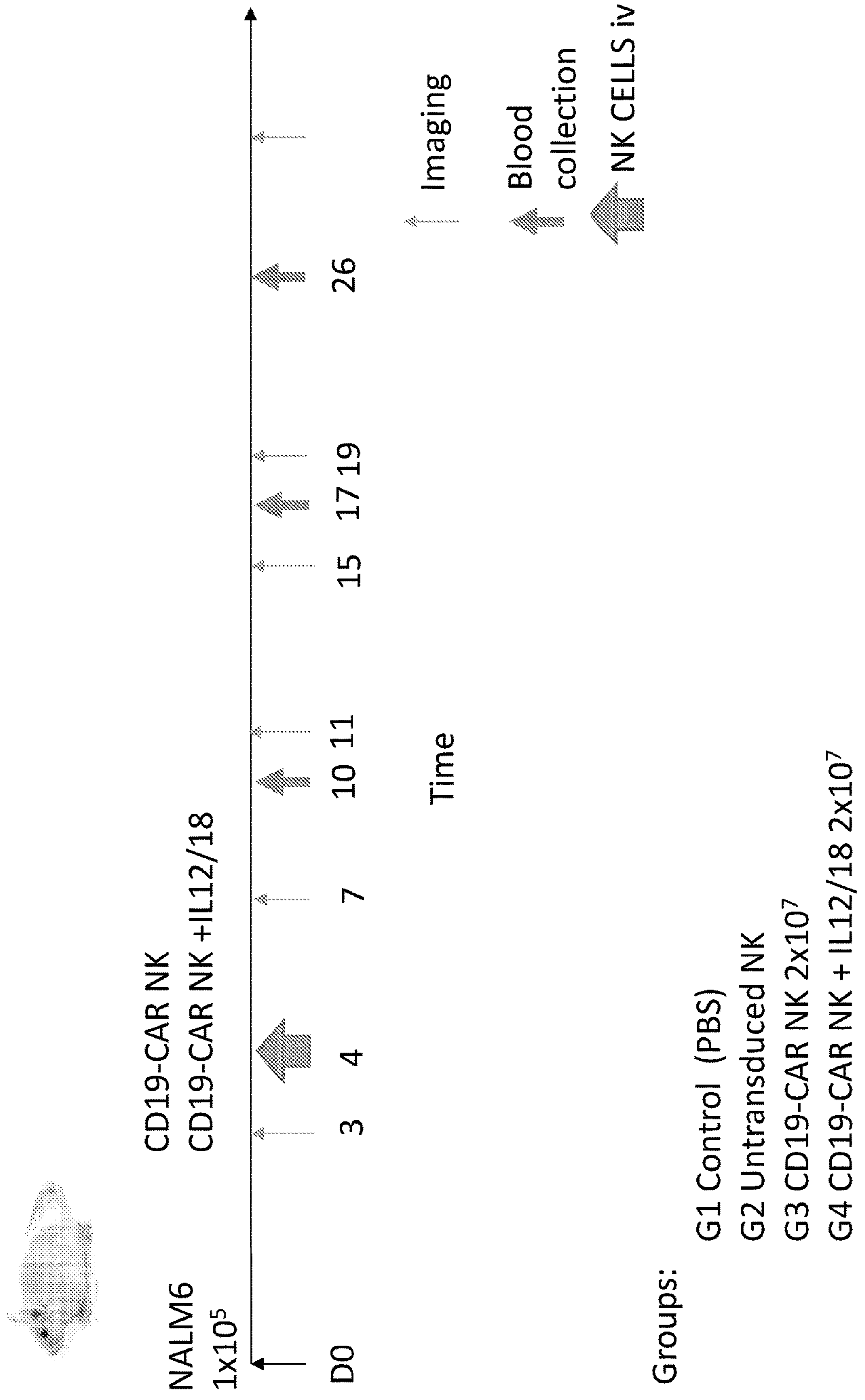
FIG. 25 shows a schematic experimental setup to assess the impact of expansion culture conditions on the cytotoxicity of NK cells in vivo.
Figure 26A:
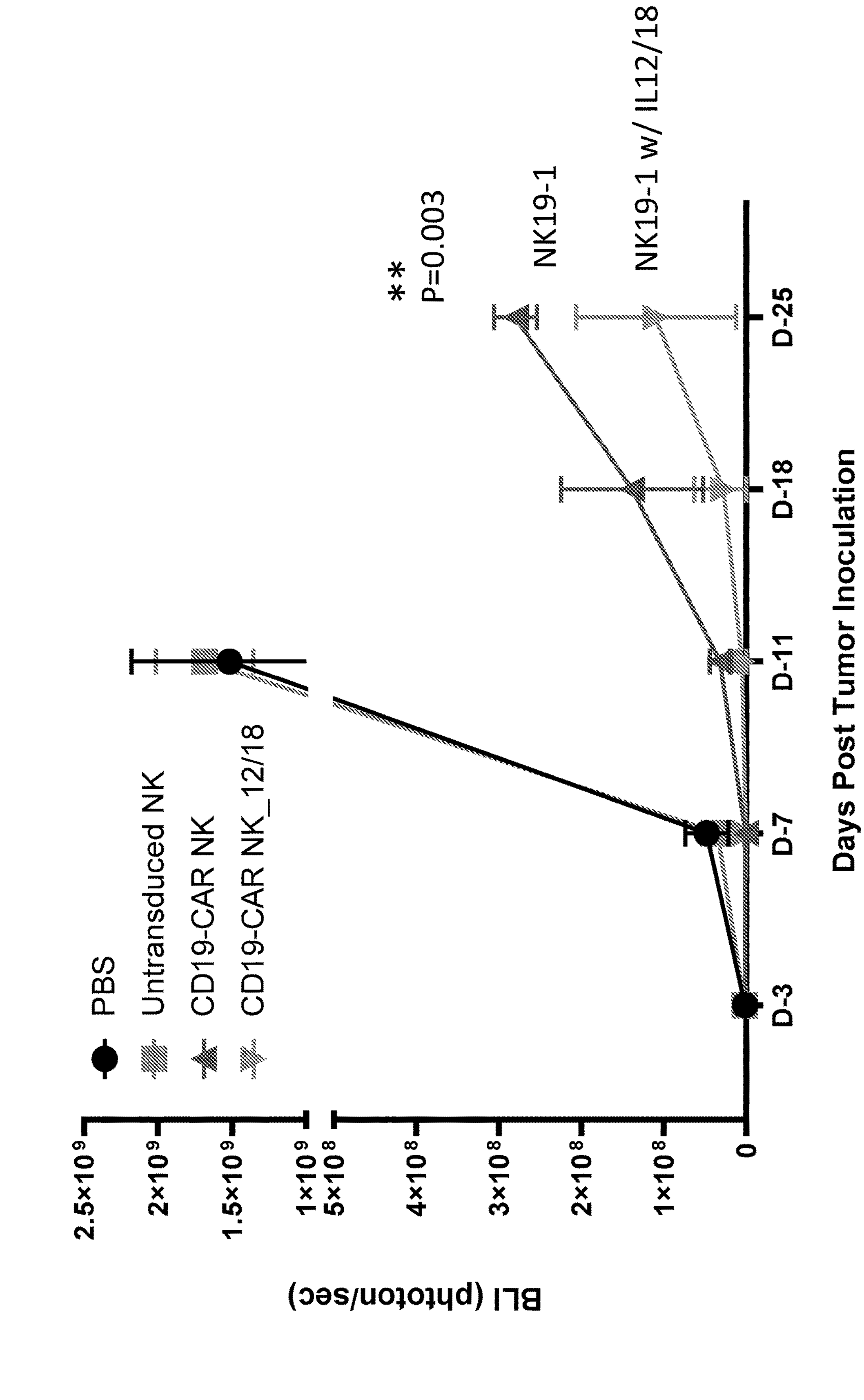
FIGS. 26A-26F show cytotoxicity, survival data, data related to NK cell persistence, and data related to CAR expression in fresh or cryopreserved NK cells.
Figure 26B:
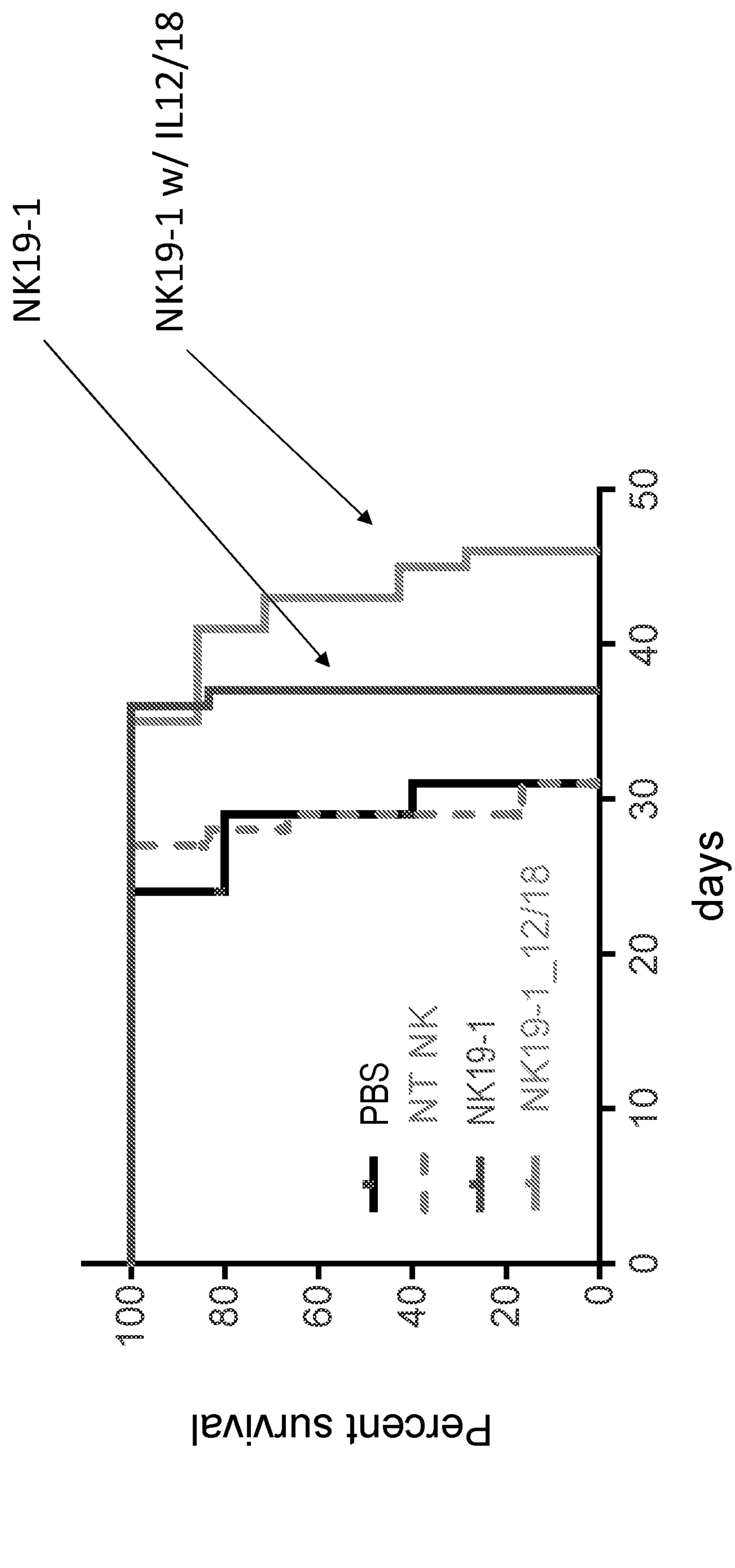
Figure 26C:
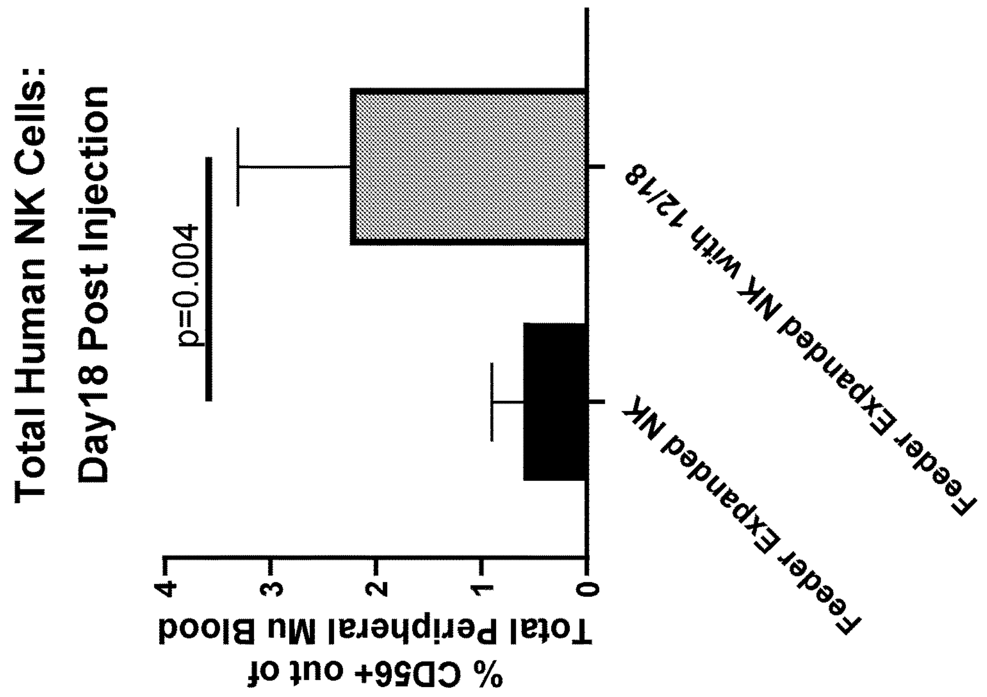
Figure 26D:
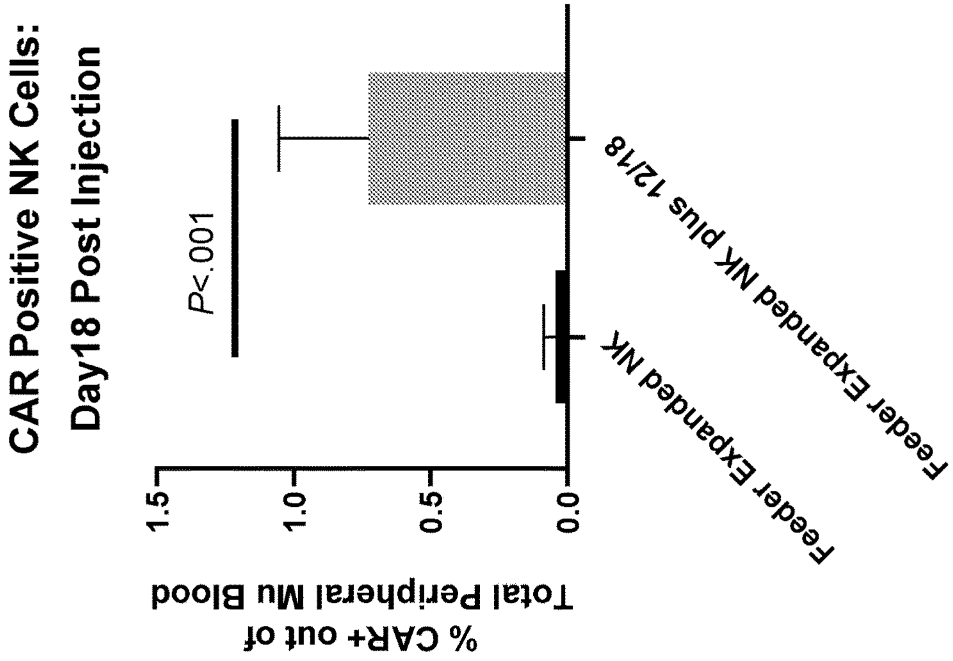

FIG. 25 shows a similar experimental setup, this time with xenograft of Nalm6 cells and treatment with NK cells expressing an anti-CD19 CAR. FIG. 26A shows the resulting bioluminescence data. As with the prior experiment, control animals and those receiving non-transduced NK cells showed a rapid increase in tumor burden, though it dropped off toward the later time points. Animals receiving NK cells expressing NK19-1 (the anti CD-19 CAR) showed an effective delay of tumor growth, limiting significant increases until the later time points. Cells expressing NK19-1 and grown with IL12/18 showed remarkable control of tumor growth, limiting increases until the late stages of the experiment and even then at markedly lower overall tumor burden as compared to other groups. Further data related to survival is shown in FIG. 26B. Mice receiving PBs (control) or NT NK cells showed a rapid drop off in survival around 30 days. NK19-1 receiving animals survived longer than those groups and NK19-1 IL12/18 animals were still 80% viable even when all other groups had no survivors. FIGS. 26C and 26D show data related to the persistence of NK cells in vivo when they are cultured in media supplemented with IL12/18. FIG. 26C shows a measure of the percentage of human CD56+ cells (a marker for NK cells) out of the total peripheral murine blood. As shown, the expansion of NK cells using soluble IL12/18 results in a significantly greater percentage of human NK cells within murine blood, even at 18 days post administration. This evidences the enhanced persistence imparted to NK cells through the use of stimulatory cytokines during expansion.

Figure 26E:
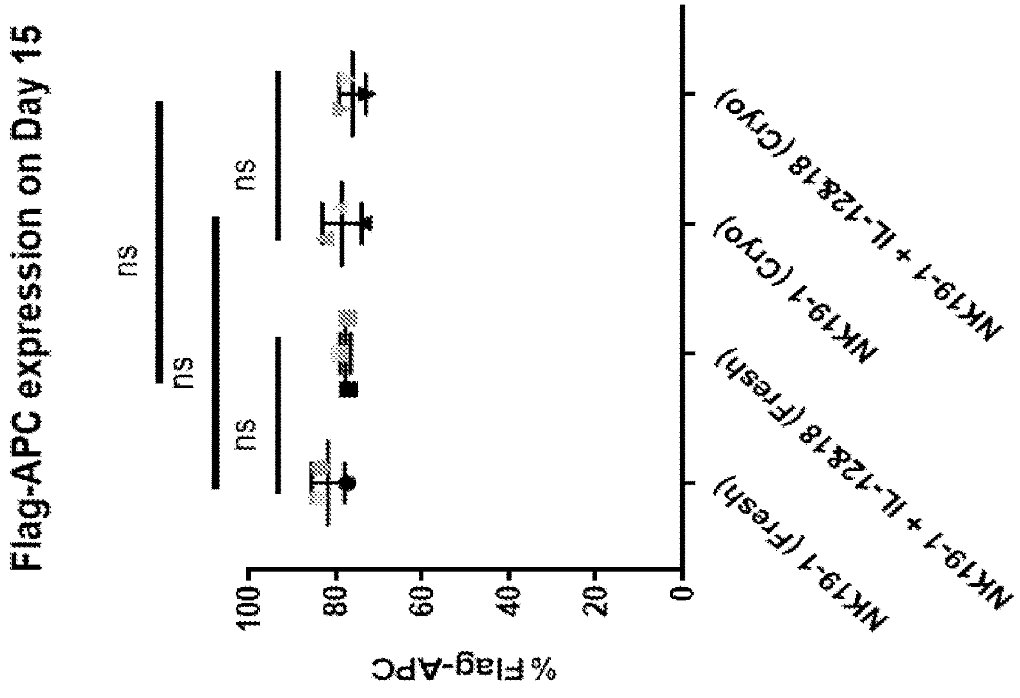
Figure 26F:
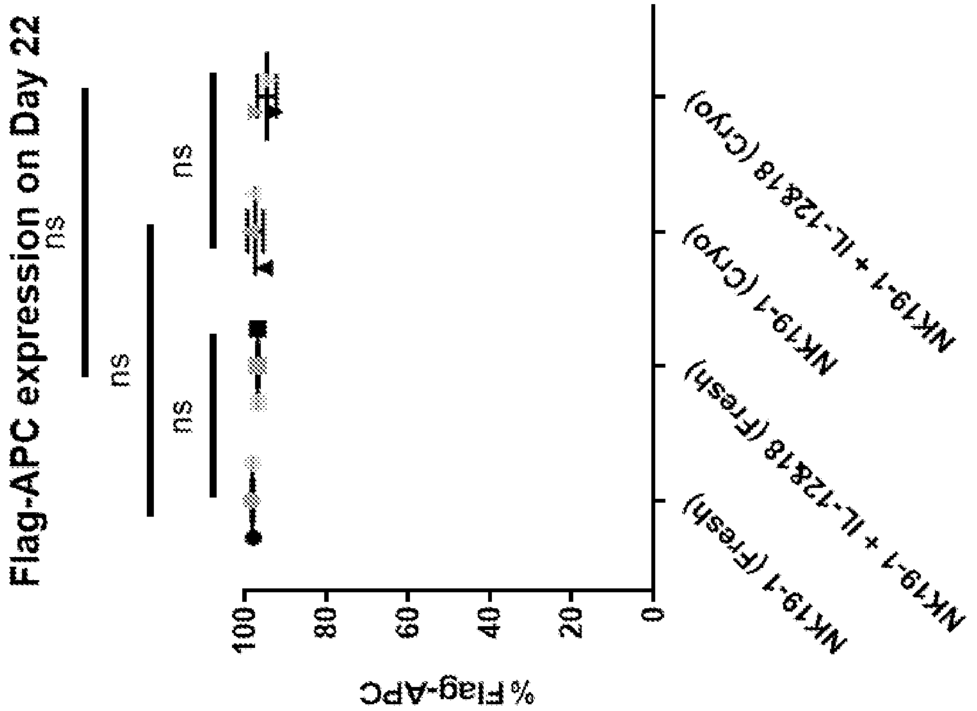

Likewise, it is not only NK cells generally that are persistent in vivo, but those expressing CARs enjoy enhanced persistence through the use of soluble IL12/18 (or other stimulatory molecules). FIG. 26D shows the percentage of anti-CD19 CAR positive NK cells (out of the total murine peripheral blood cell count) 18 days after injection in the xenograft recipient mice. As with the prior figure, these data show that engineered immune cells, such as NK cells expressing a chimeric antigen receptor, exhibit enhanced in vivo persistence when expanded using at least one stimulatory cytokine. An additional experiment was performed to evaluate the effects of cytokines used in expansion culture and cryopreservation (or lack thereof) on expression of CARs by NK cells. FIG. 26E shows that, at day 15 of culture, expression of a non-limiting embodiment of an anti-CD19 CAR is not changed when cytokines are used in expansion culture. That is, the enhanced effects demonstrated herein based on expansion culture using one or more additional stimulatory molecules is not counterbalanced by reduced CAR expression. Moreover, cryopreservation of NK cells does not adversely impact the expression of a CAR by the engineered NK cells. FIG. 26F confirms that CAR expression is not eroded after further time in culture. These data again support the enhanced cytotoxicity, persistence of, and stable CAR expression by NK cells grown under the influence of stimulatory cytokines, such as IL12 and IL18, among others. Likewise, cryopreservation of the engineered NK cells does not significantly adversely impact these beneficial characteristics.

Figure 27A:
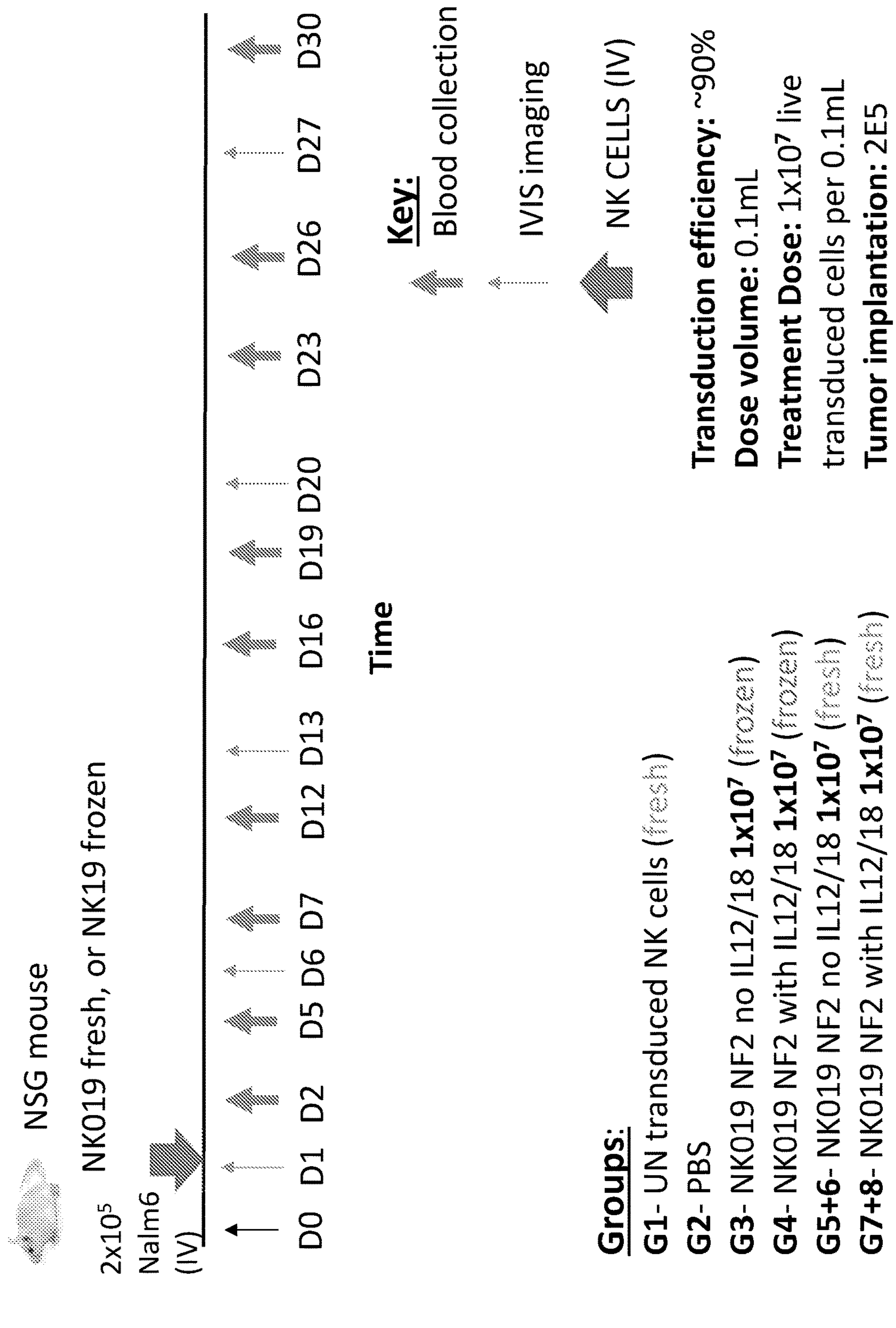
FIGS. 27A-27C relate to the in vivo efficacy of various CD19-directed CAR according to embodiments disclosed herein.

Example 4—Additional Experiments to Evaluate Effects of Cryopreservation and Expansion on Cytotoxicity, NK Cell Characteristics, and Survival of NK Cells Additional experiments were performed to determine whether the process of cryopreservation followed by thawing would adversely impact the engineered NK cells, such as by reducing their viability, persistence or cytotoxicity. FIG. 27A shows a schematic experimental protocol employed, as well as the experimental groups and other conditions used. As described above, for treatment groups with an "IL12/IL18" designation, the cells were expanded in the presence of soluble IL12 and/or IL18, in accordance with embodiments described herein. Treatment groups include fresh, untransduced NK cells (G1) and PBS (G2) as controls. Experimental groups included cryopreserved and thawed NK cells engineered to express a non-limiting embodiment of an anti-CD19 CAR and expanded without (G3) and with additional stimulatory cytokines (G4) as well as fresh NK cells engineered to express a non-limiting embodiment of an anti-CD19 CAR and expanded without (G5, G6) and with additional stimulatory cytokines (G7, G8). Blood collection and imaging were conducted at the indicated time points of FIG. 27A.

Figure 27B:
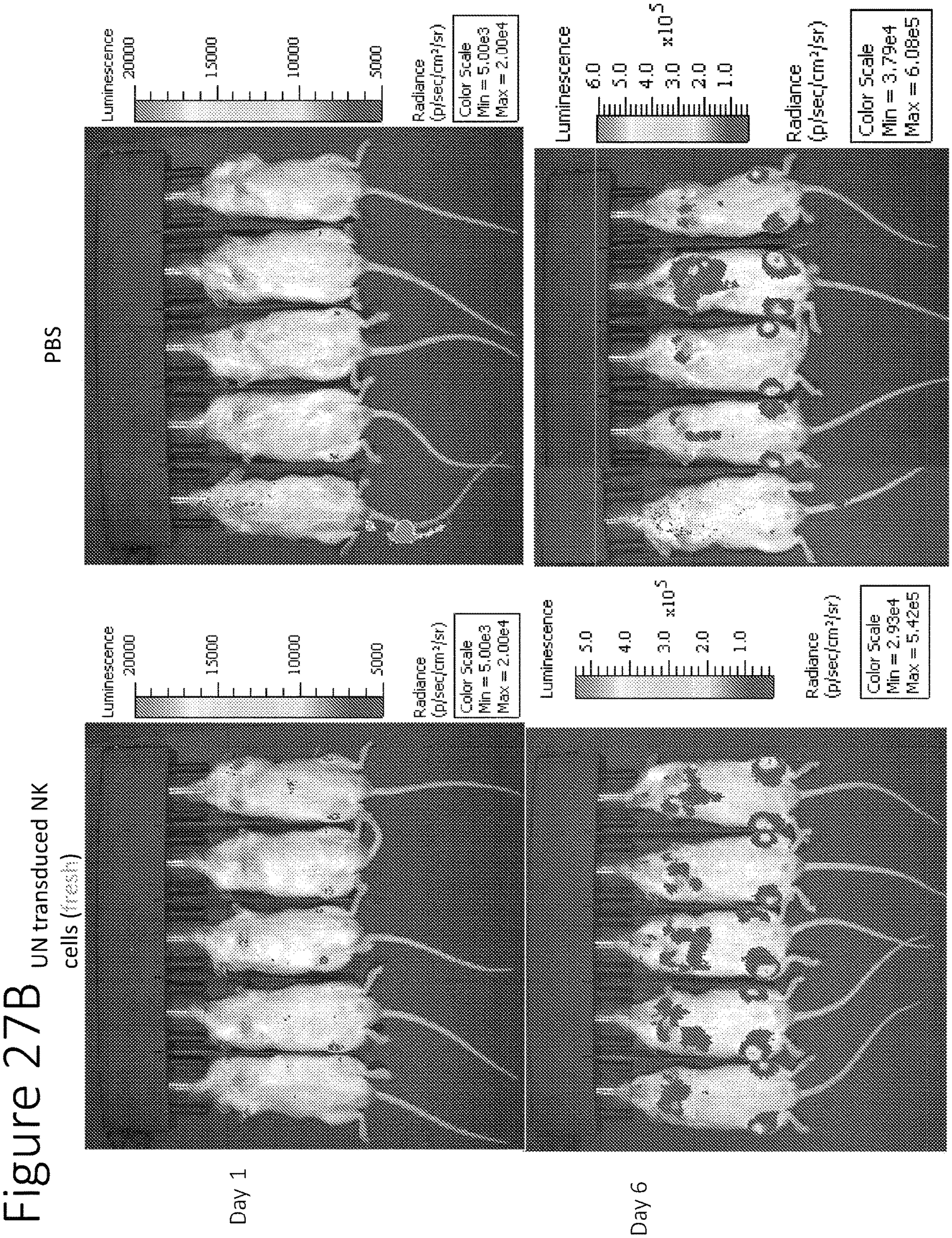
Figure 27B:
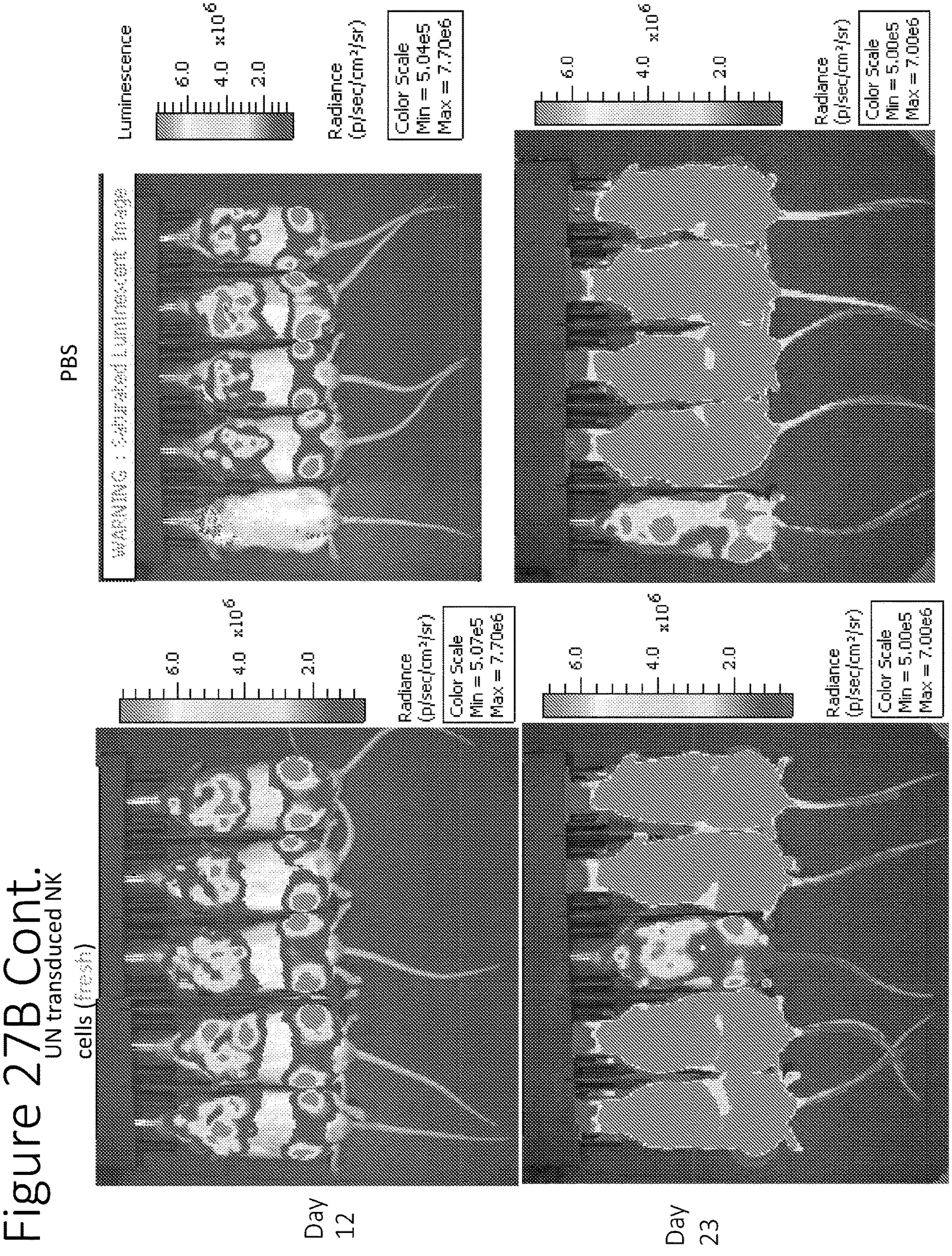
Figure 27B:
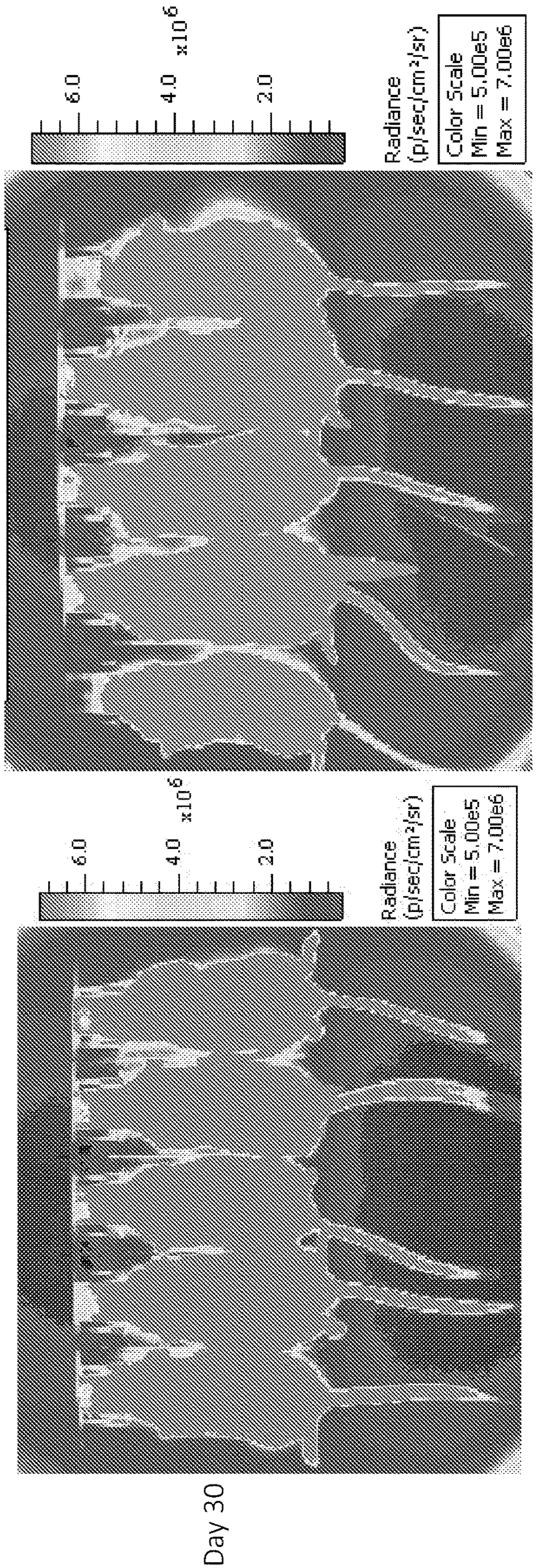
Figure 27B:
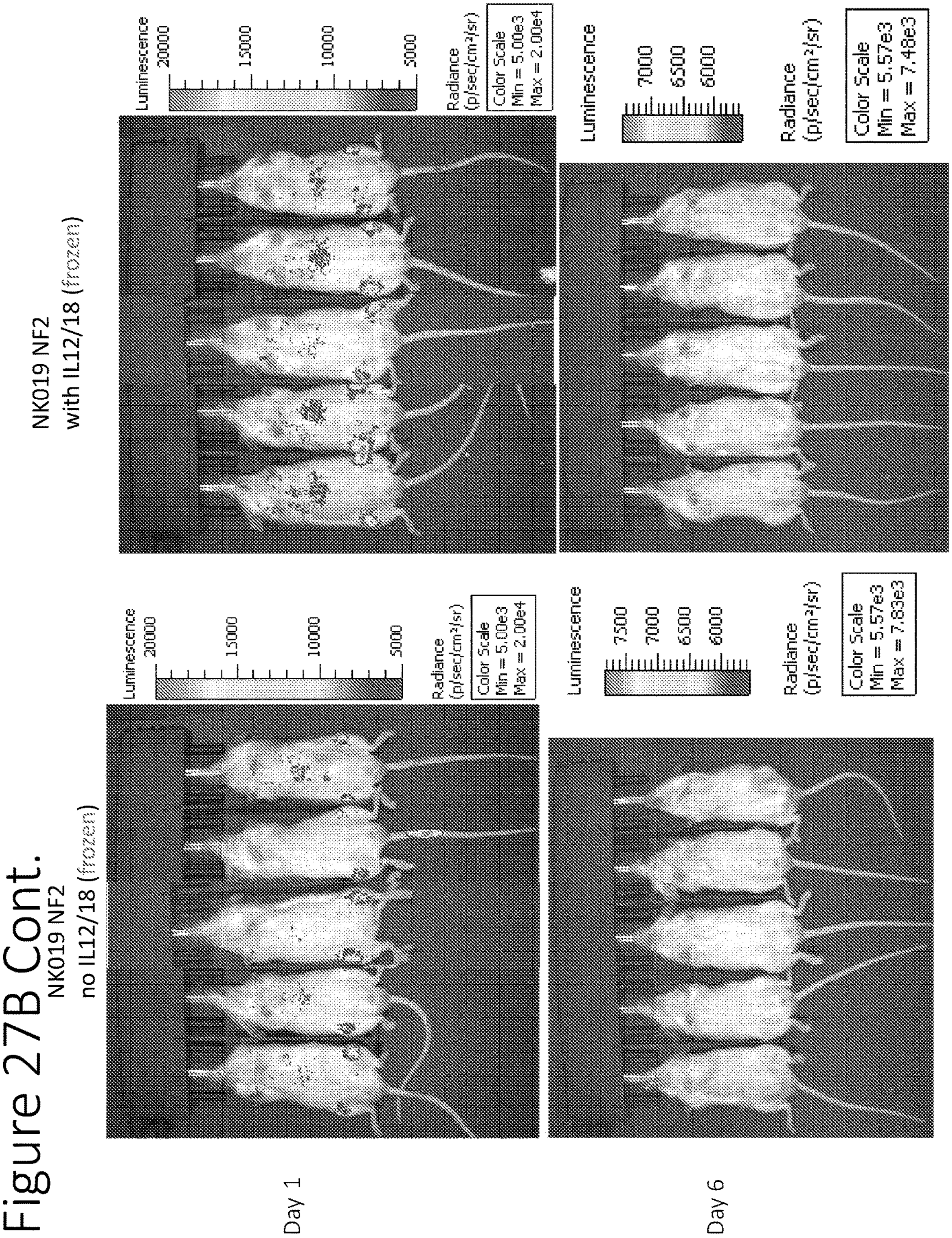
Figure 27B:
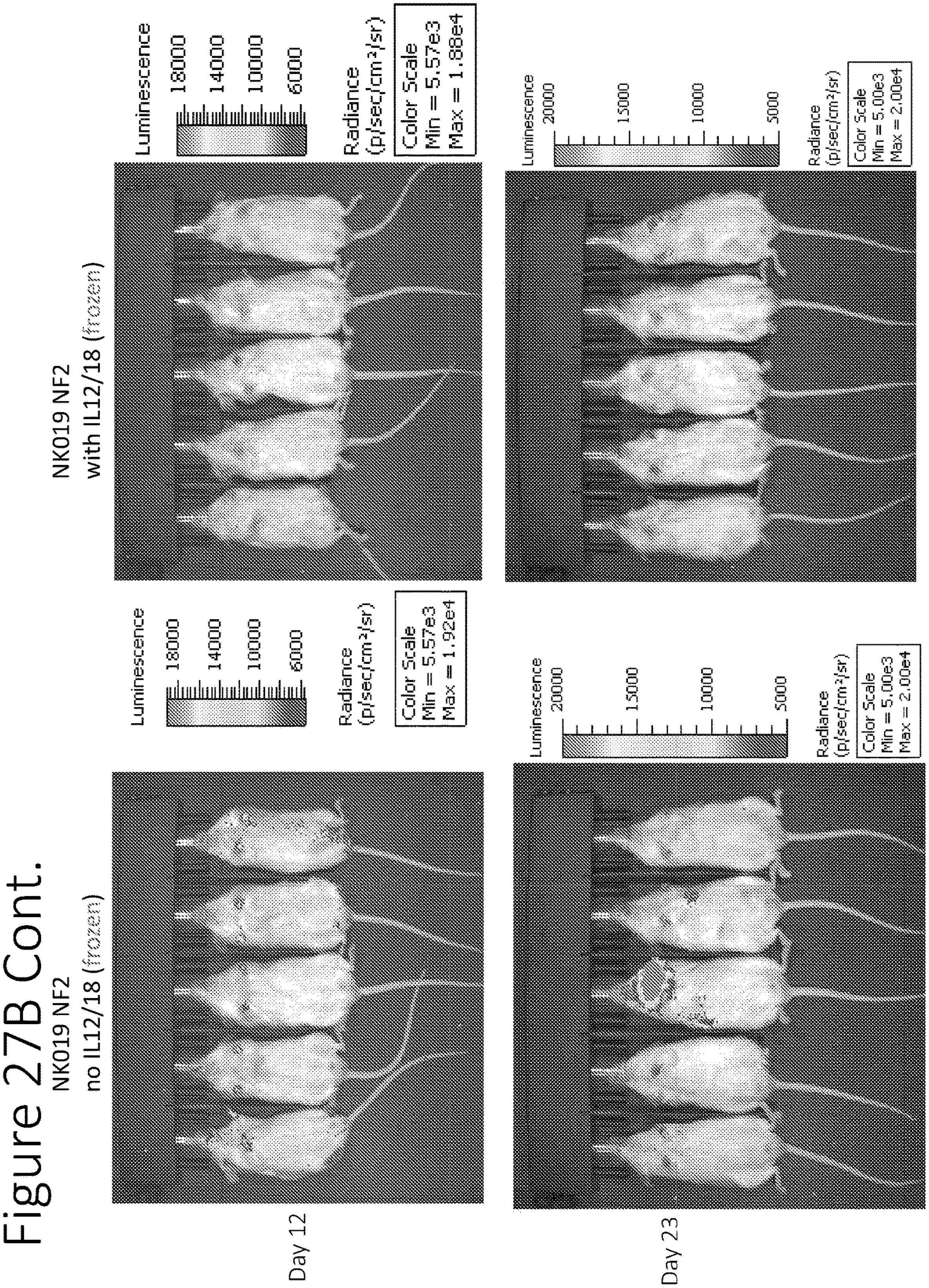
Figure 27B:
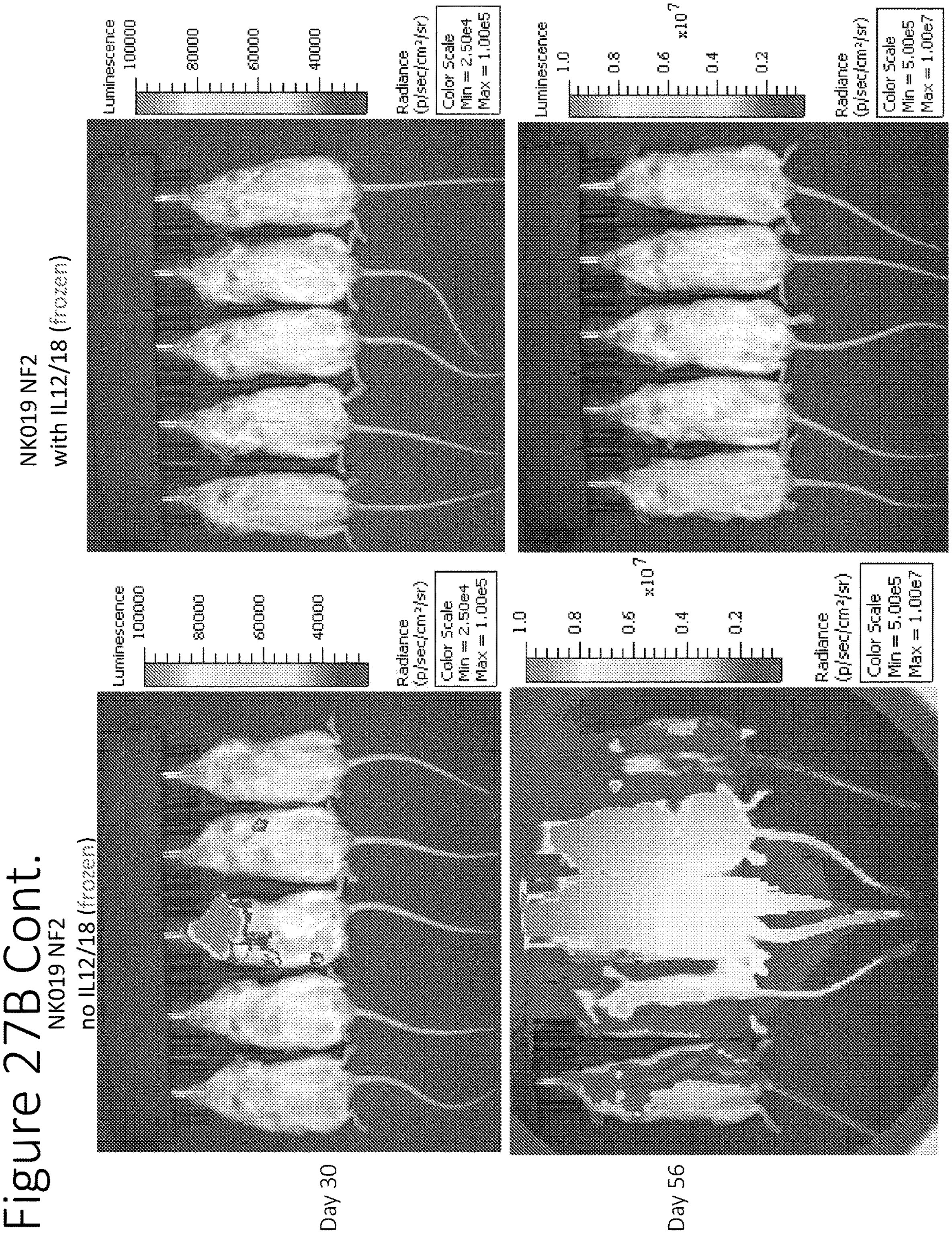
Figure 27B:
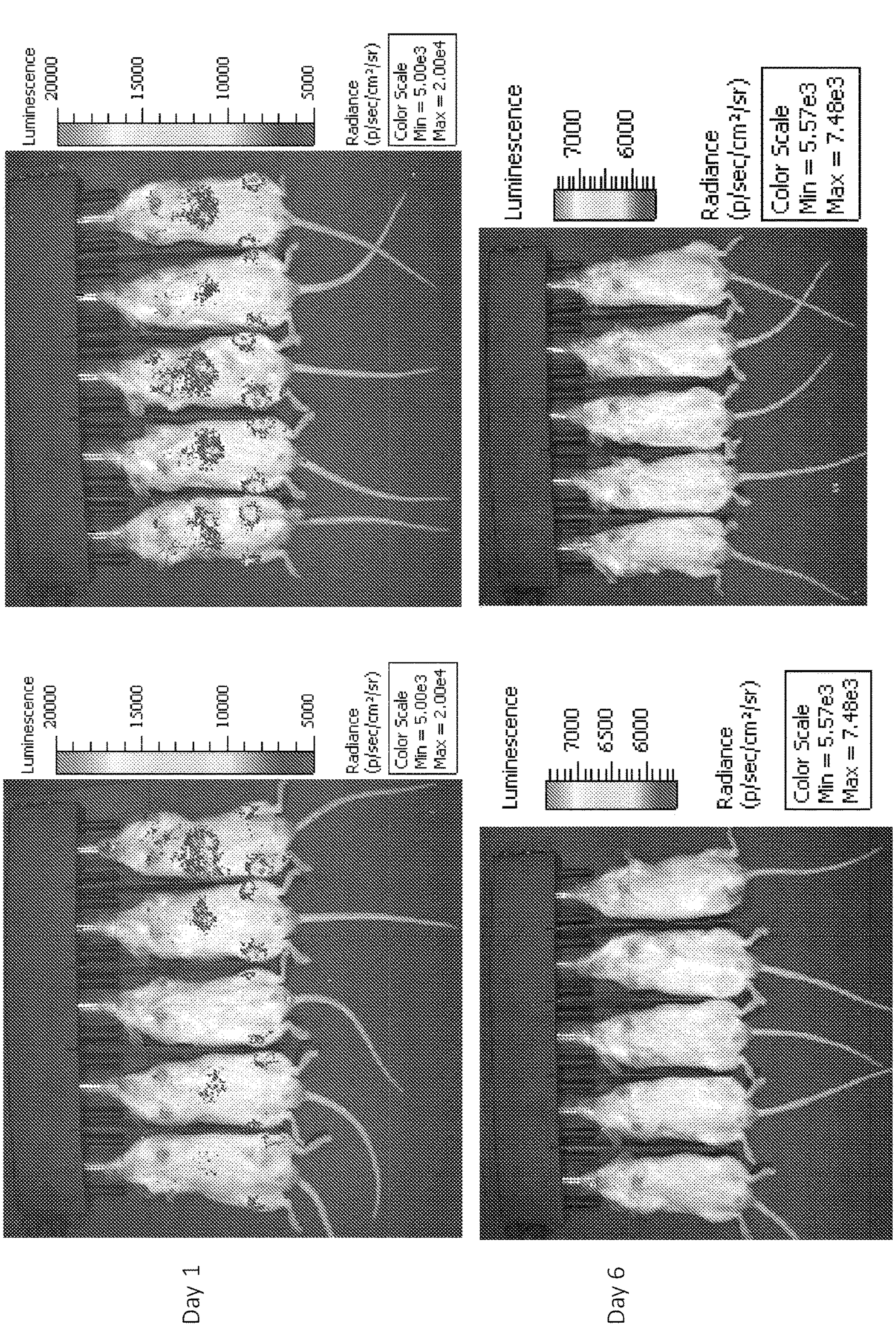
Figure 27B:
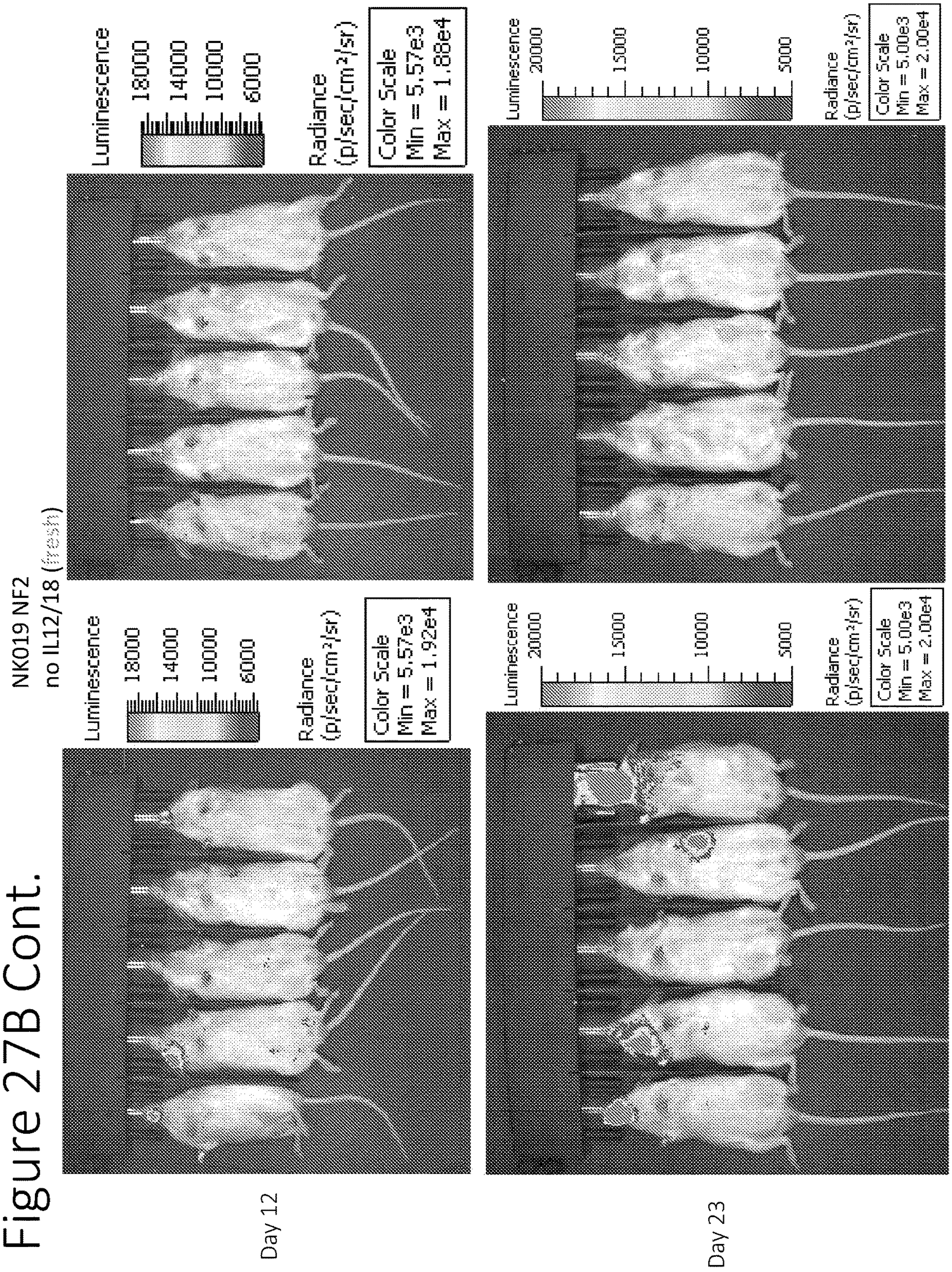
Figure 27B:
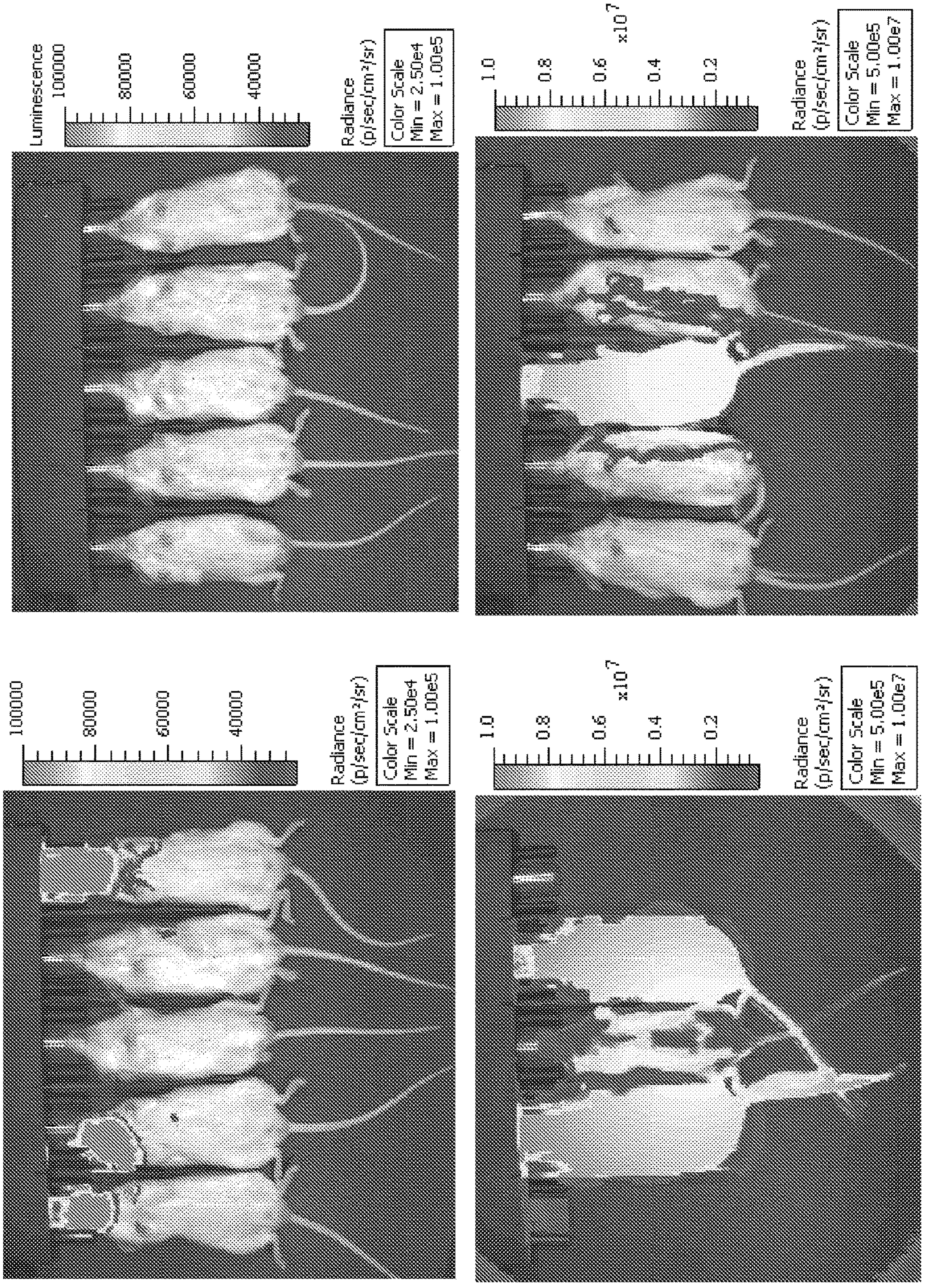
Figure 27B:
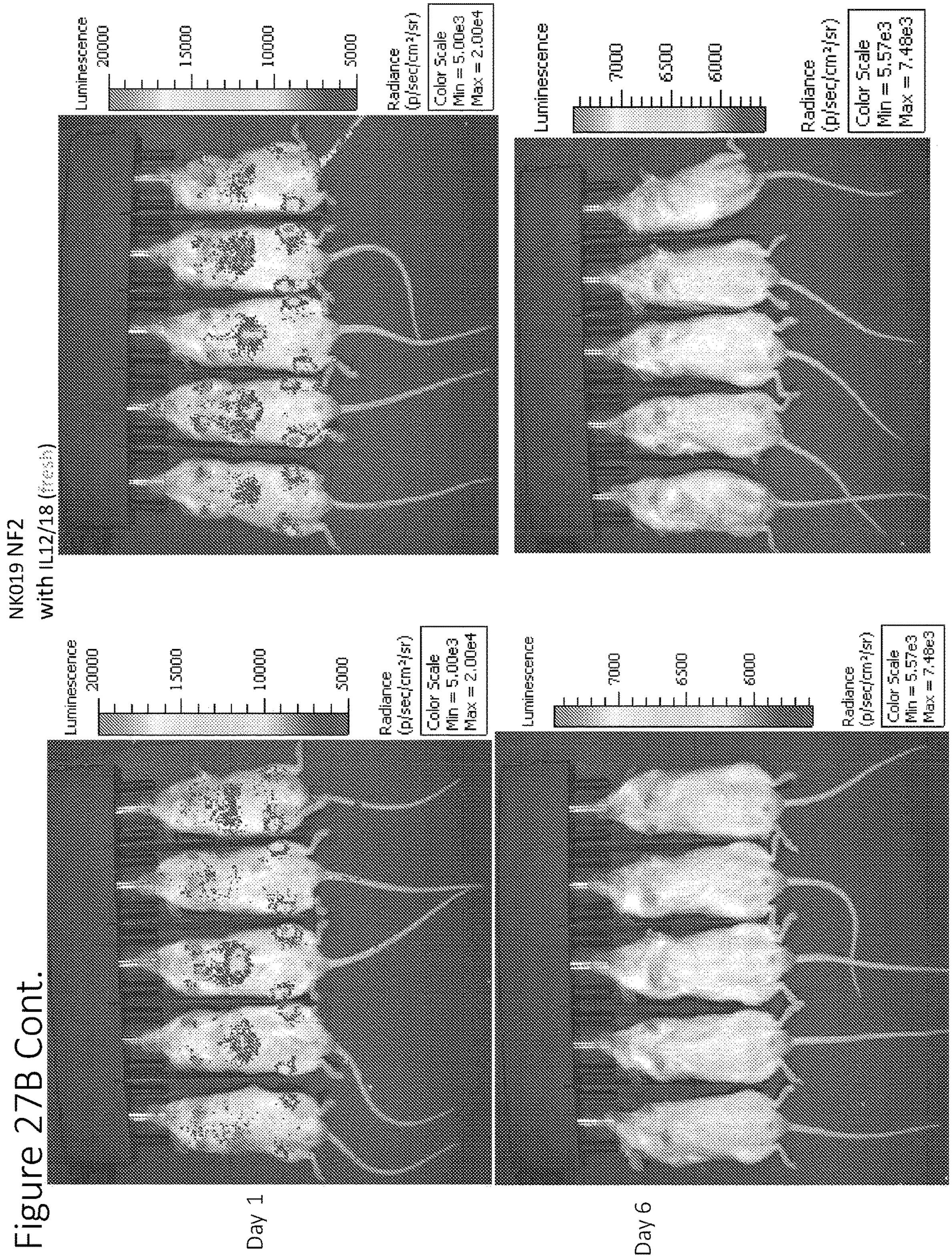
Figure 27B:
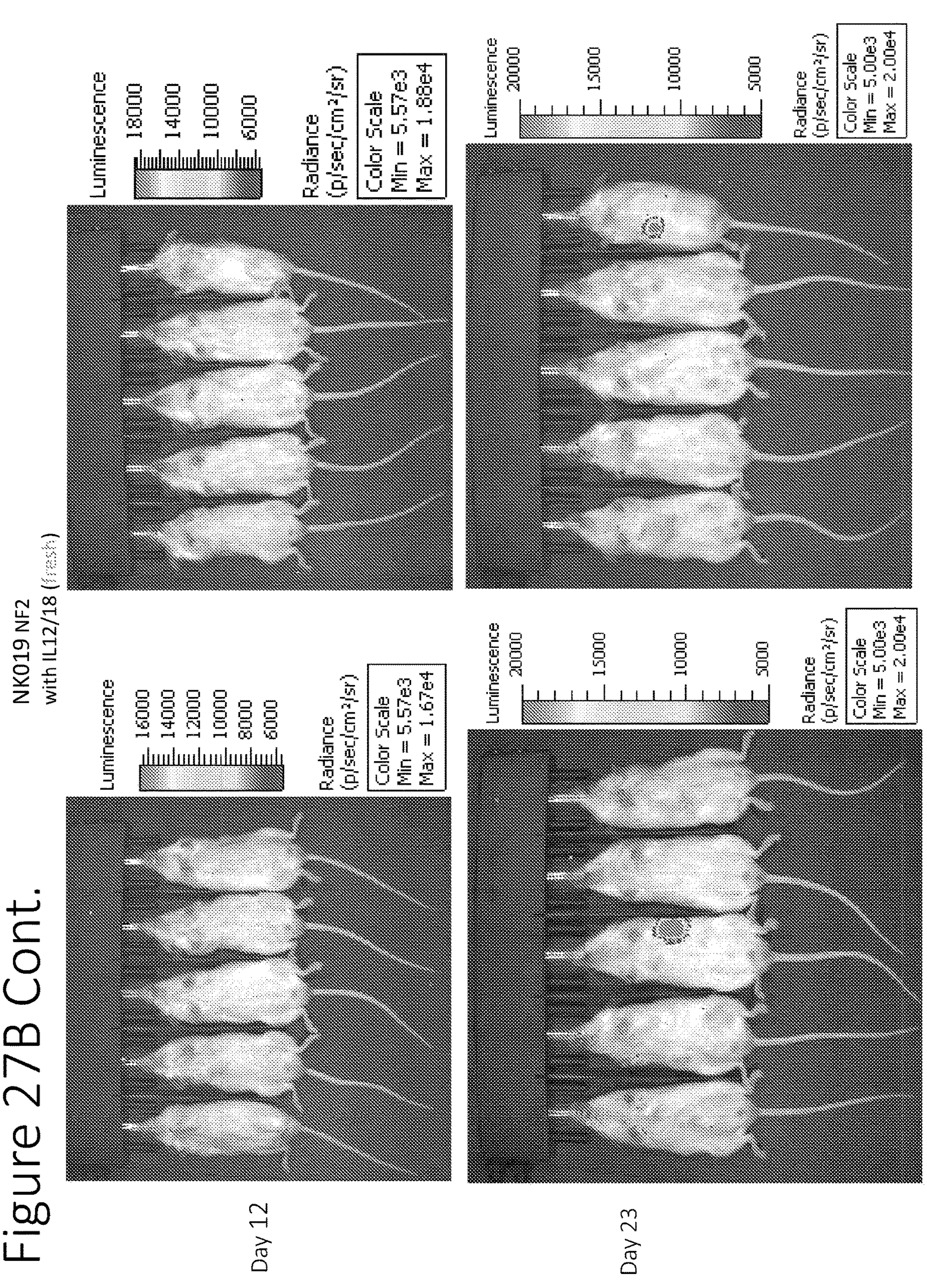
Figure 27B:
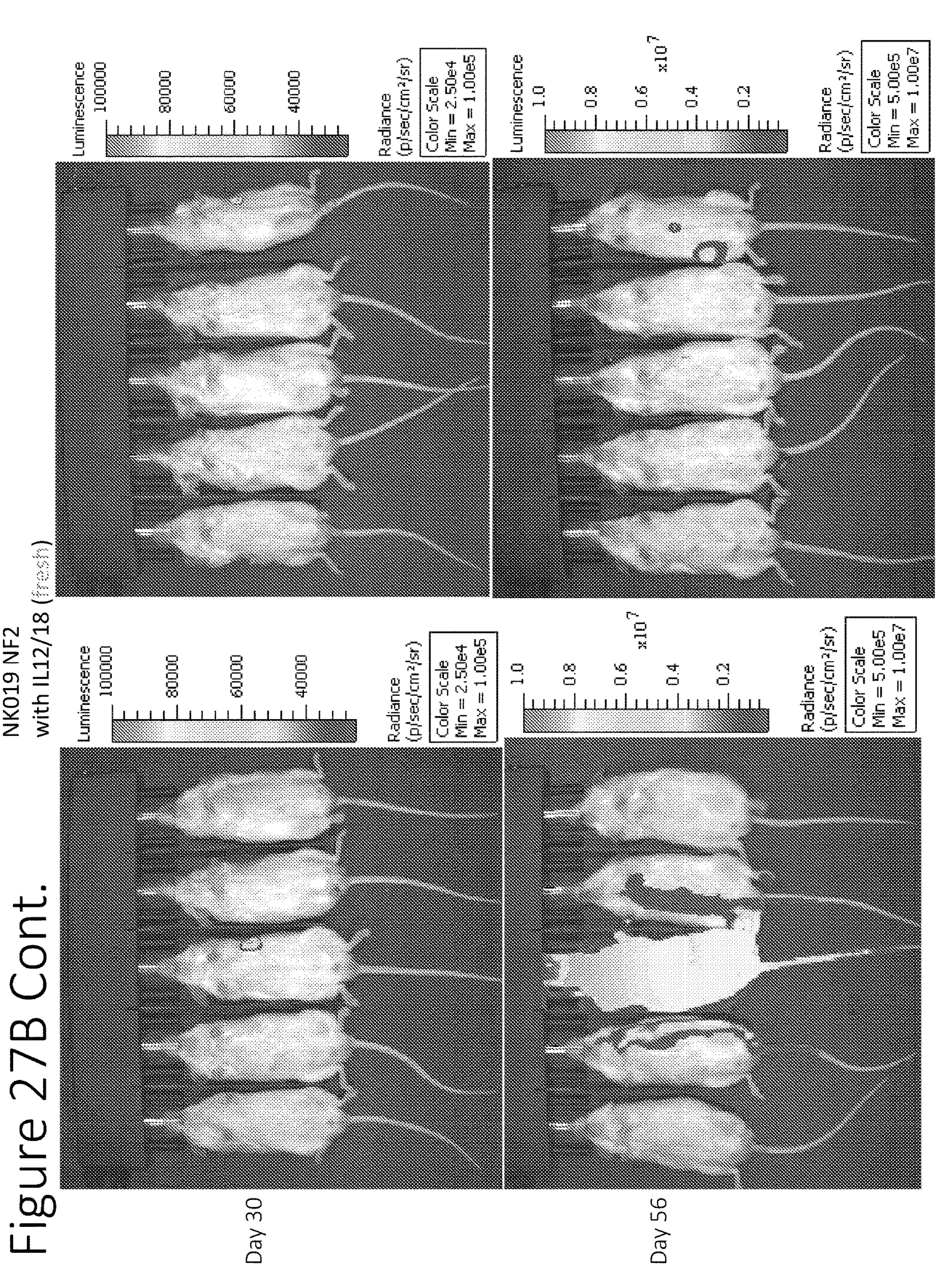
Figure 27C:
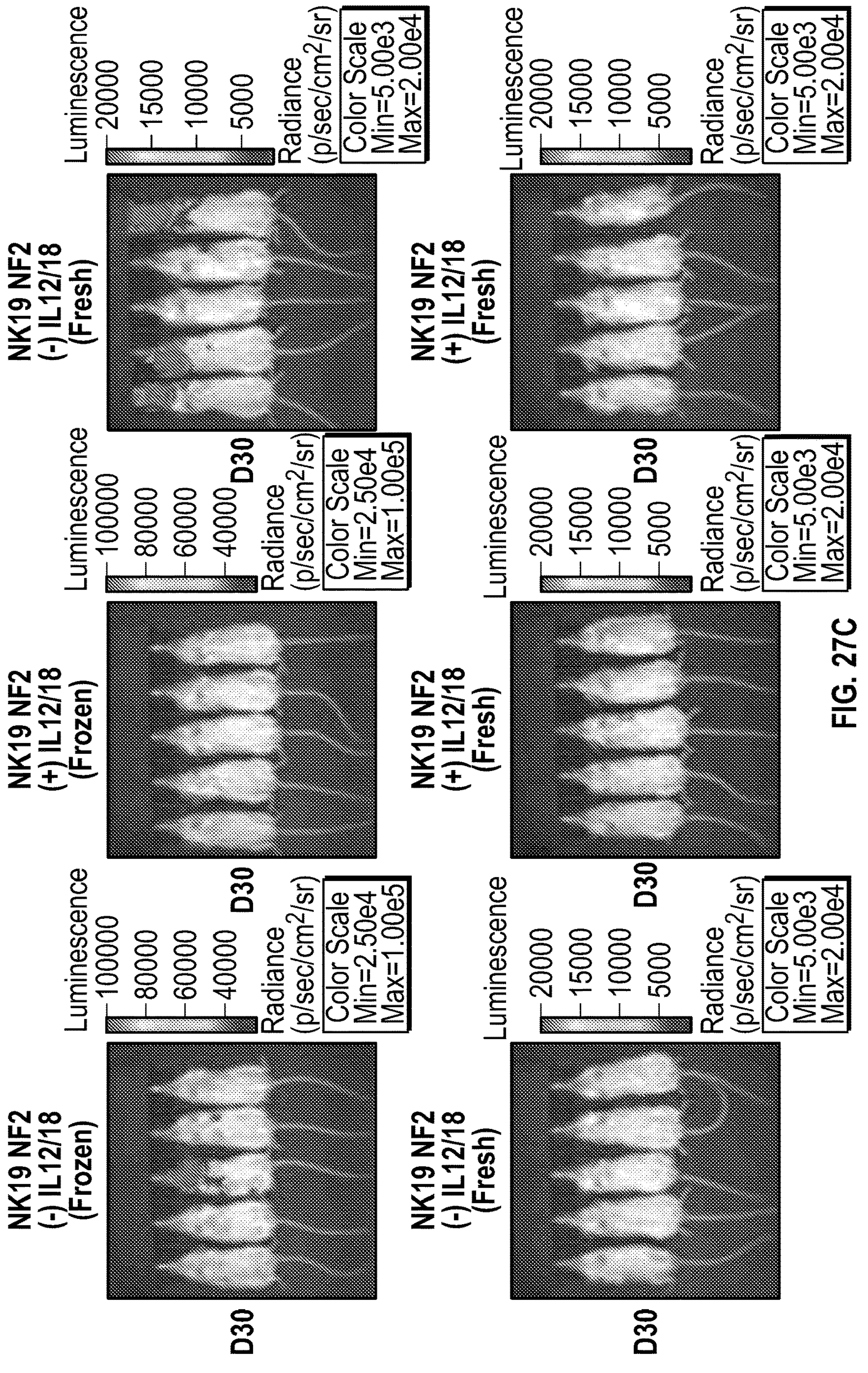
Figure 27C:
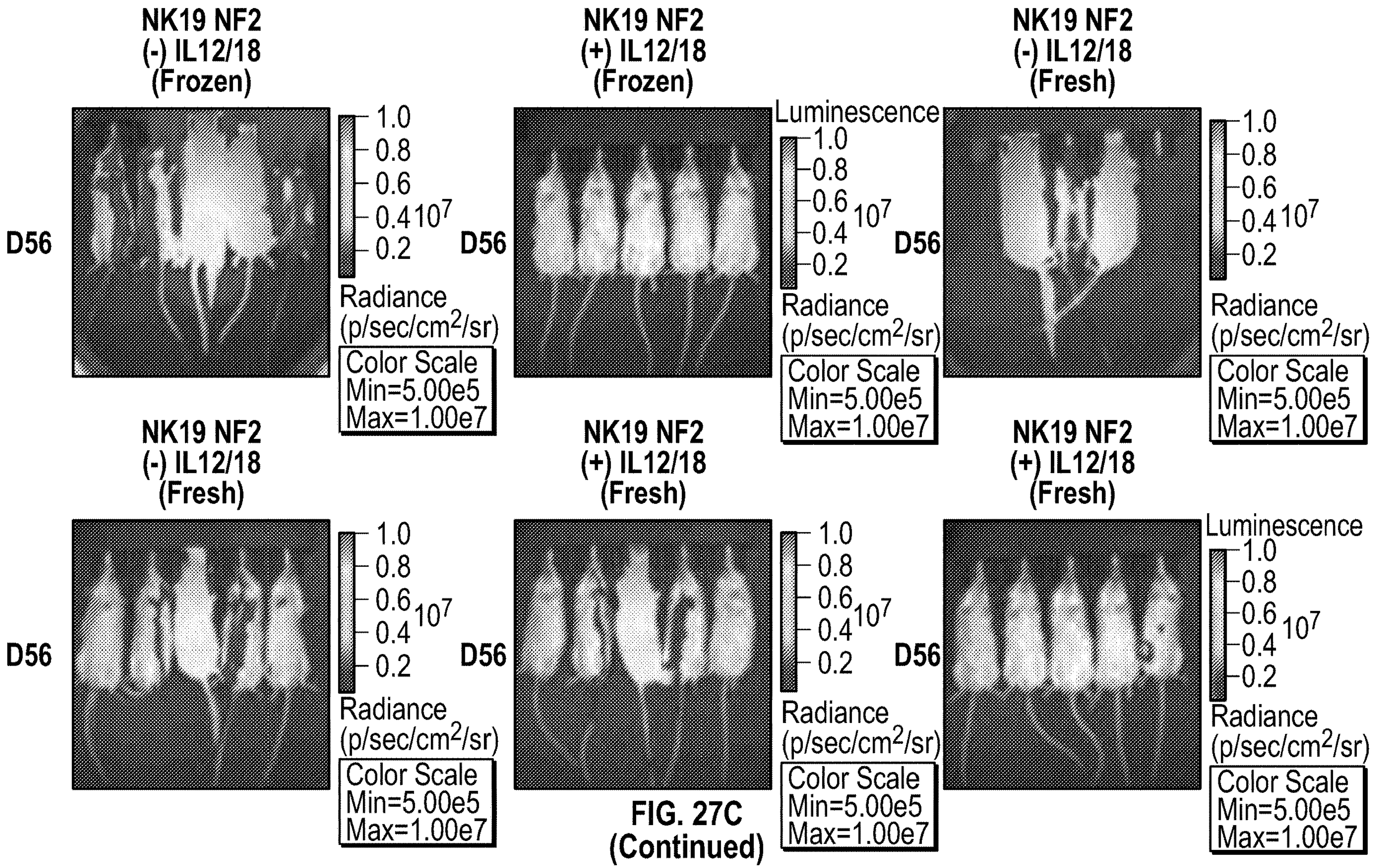
Figures 28A, 28B:
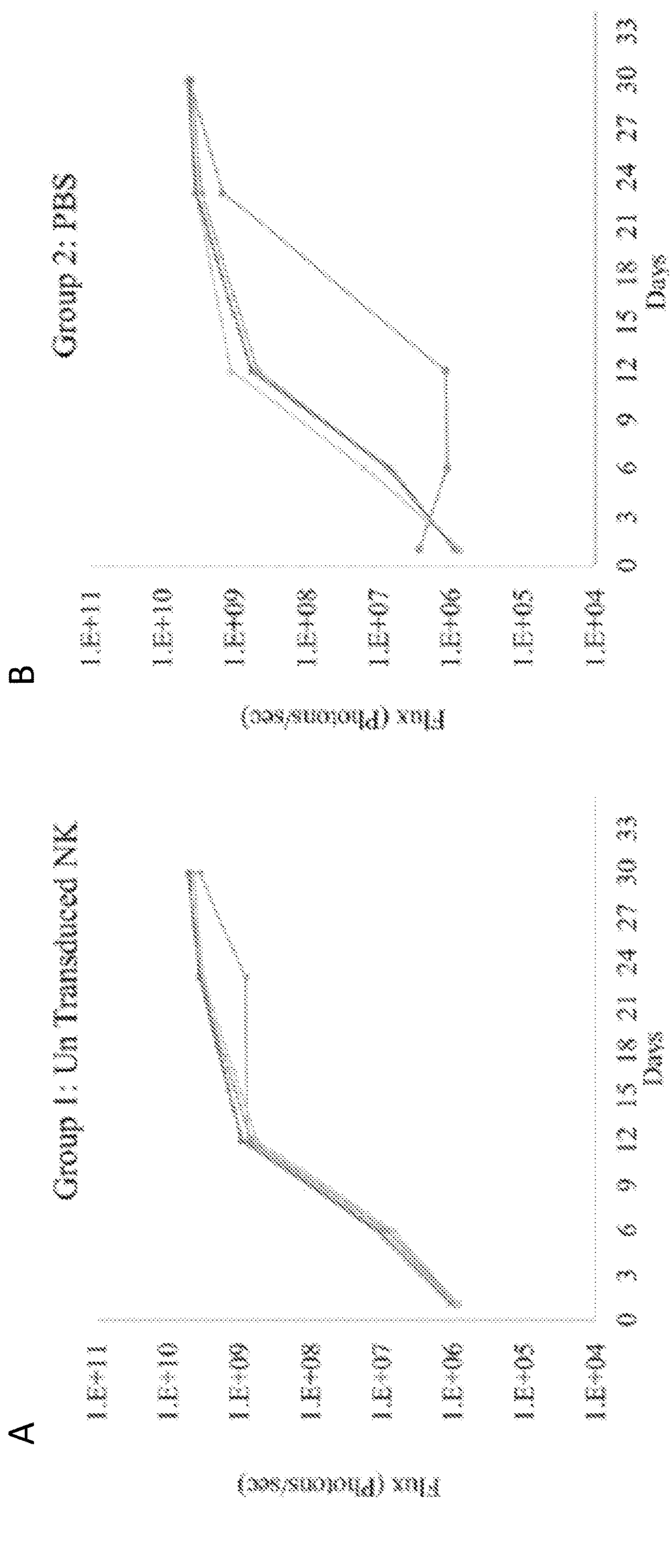
FIGS. 28A-28J show graphical depictions of the bioluminescence data from FIGS. 27B-27C.
Figures 28C, 28D:
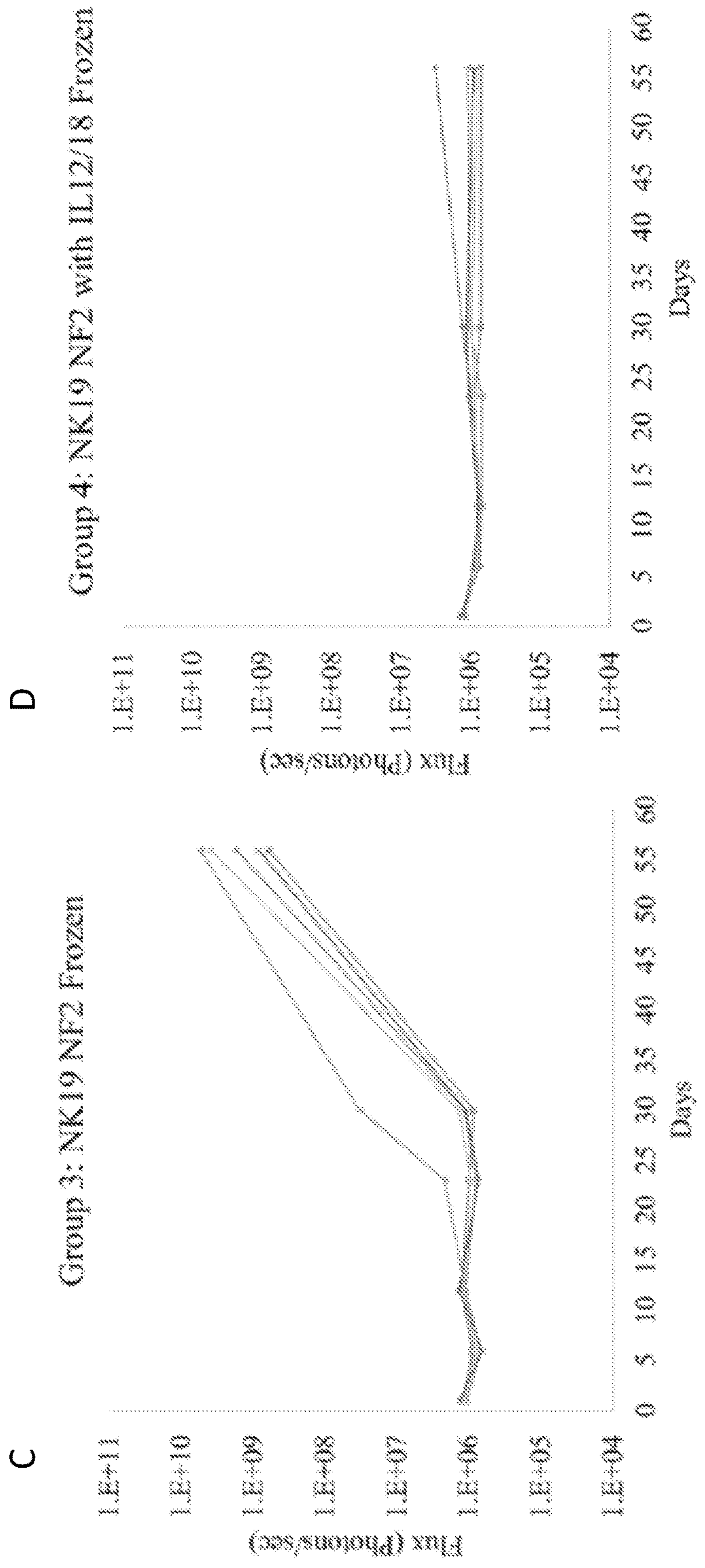
Figures 28E, 28F:
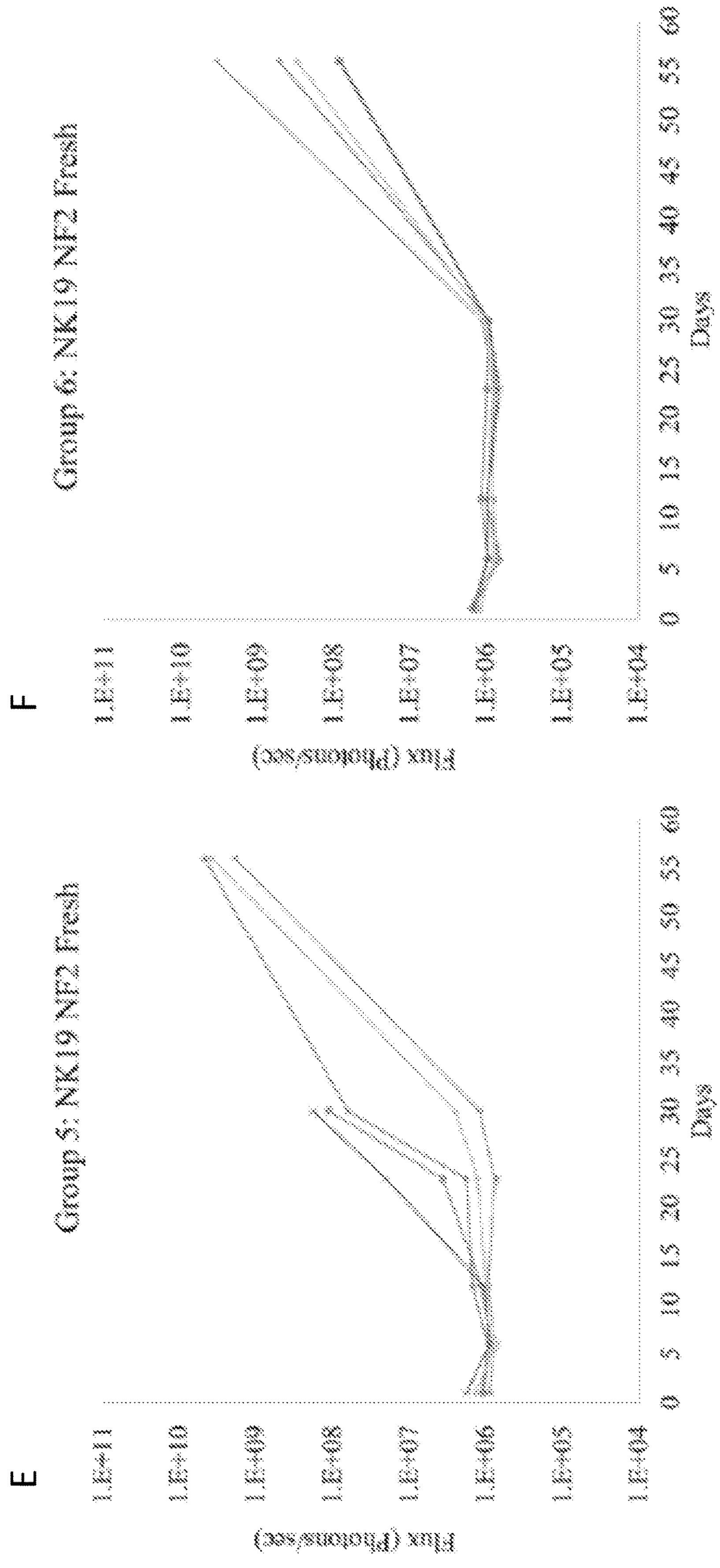
Figures 28G, 28H:
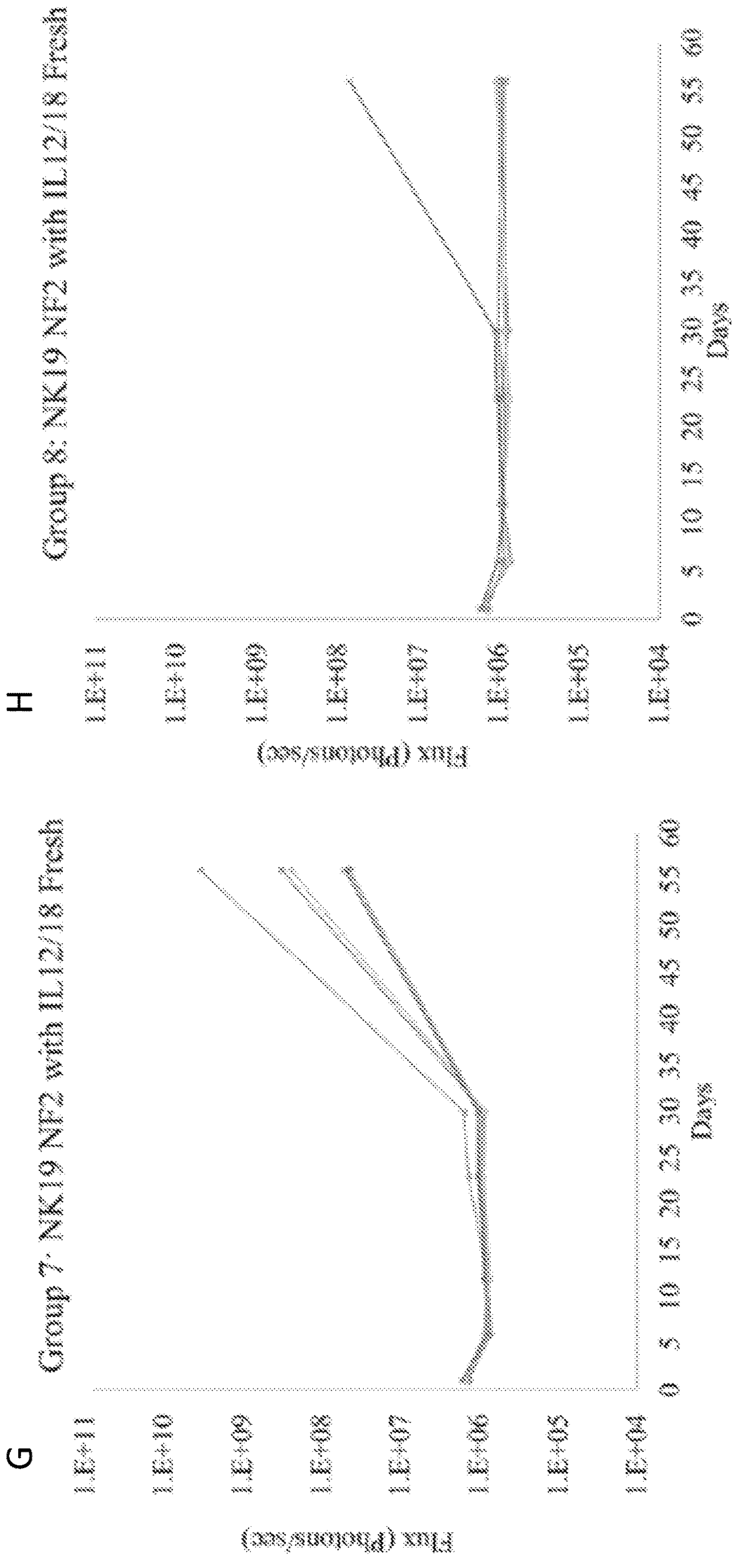
Figure 28I:
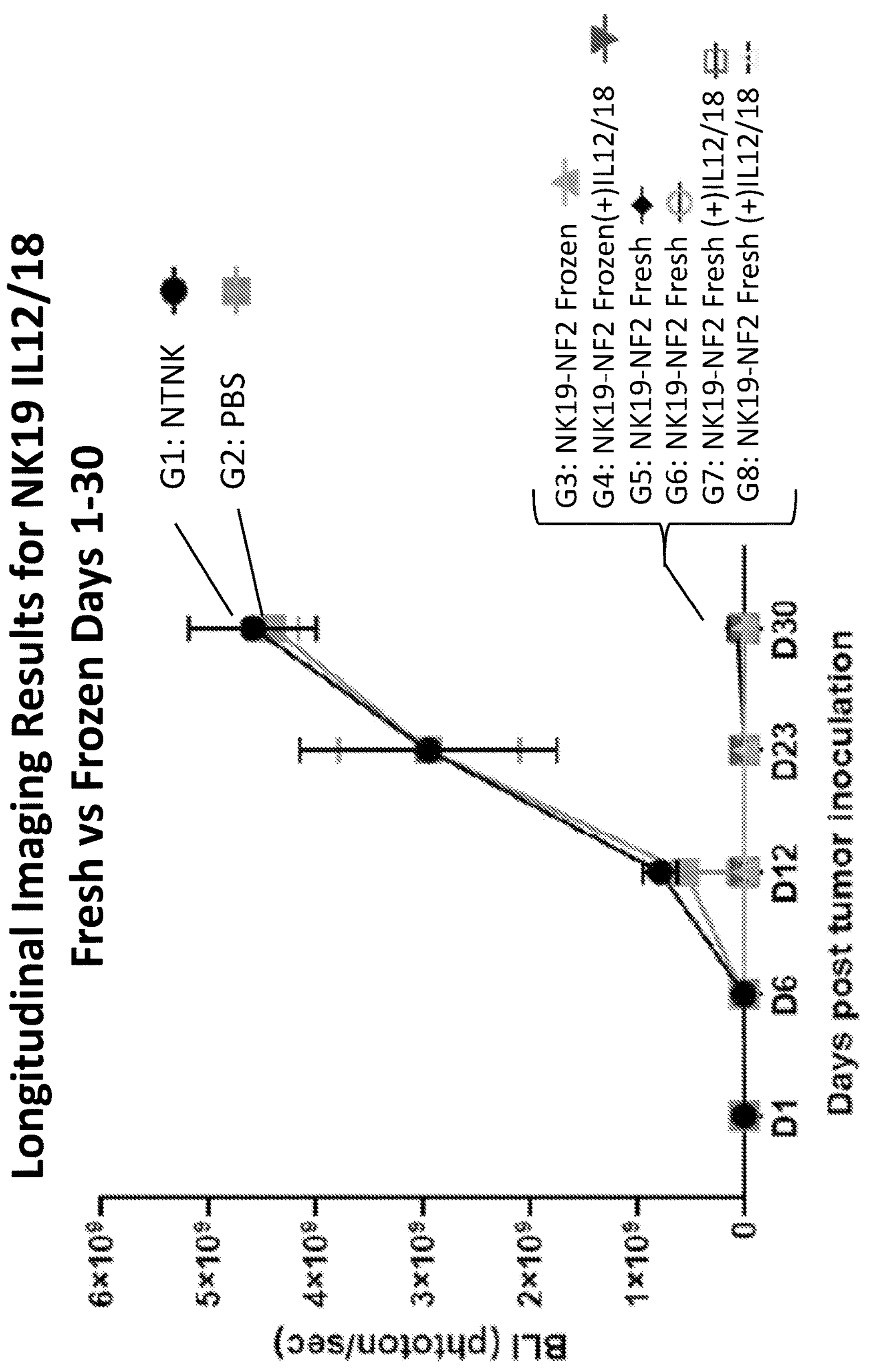
Figure 28J:
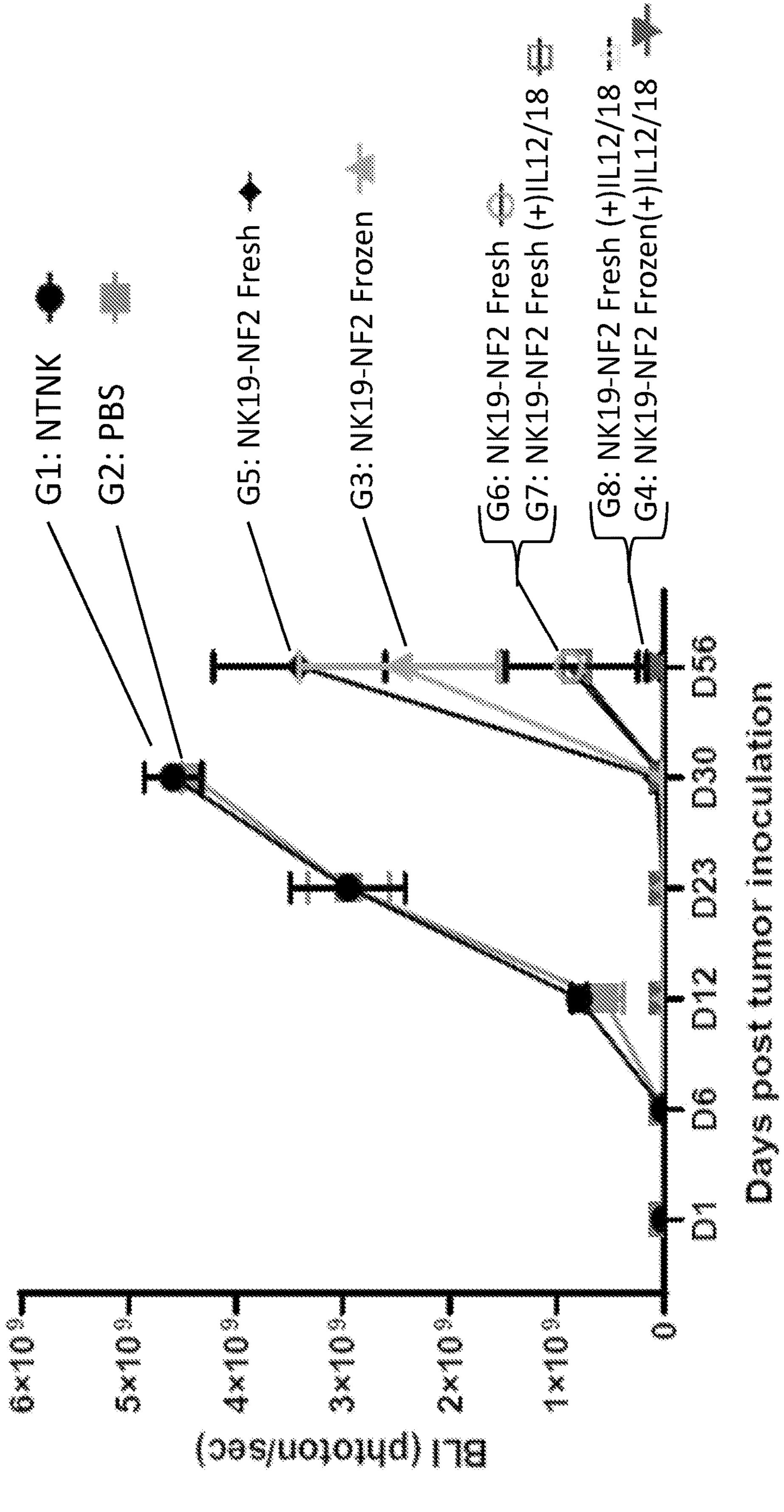

FIGS. 27B and 27C shows the in vivo bioluminescence imaging from the indicated experimental groups. FIG. 28A-28H show line graphs that reflect the bioluminescence intensity over time. These data are summarized in FIG. 28I, which shows the first 30 days post-treatment, and FIG. 28J which shows data through 56 days. While FIG. 28I shows a clear distinction between the NK cells expressing CD19 CARs and the two control groups, each of the experimental groups show limited to non-detectable increases in BLI measured over the first 30 days of the experiment (increased BLI is indicative of increased tumor growth), indicative of control of tumor growth. FIG. 28J shows data through 56 days, and there is a greater separation of the experimental groups expressing the various CAR constructs and processed under the indicated conditions at inhibiting tumor cell growth. Control groups (G1 and G2) showed significantly increased tumor growth, resulting in termination of the experiment at 30 days for those groups. The group receiving fresh NK cells expressing an anti-CD19 CAR and expanded without use of soluble interleukins (G5) showed a sharp increase in BLI between days 30 and 56. Another experimental replicate of this group (G6) showed a more marked ability to inhibit tumor growth. The group receiving frozen NK cells expressing an anti-CD19 CAR and expanded without use of soluble interleukins (G3) also showed an increase in BLI between days 30 and 56, but not to the same degree as was detected with fresh cells. The experimental groups receiving anti-CD19 CAR expressing NK cells, whether fresh or frozen, that were expanded using additional stimulating factors during expansion (as according to embodiments disclosed herein) exhibited the most robust prevention of tumor growth. Notably, Groups 4 and 8, which were both cryopreserved NK cells showed the most inhibition of tumor growth. In combination with the data collected when fresh engineered NK cells were administered, these data indicate, that, according to several embodiments, engineered NK cells expressing anti-CD19 CARs are effective not only when prepared and administered fresh, but also when prepared, frozen, then thawed and administered (e.g., as in an certain allogeneic embodiments).

Figure 29:
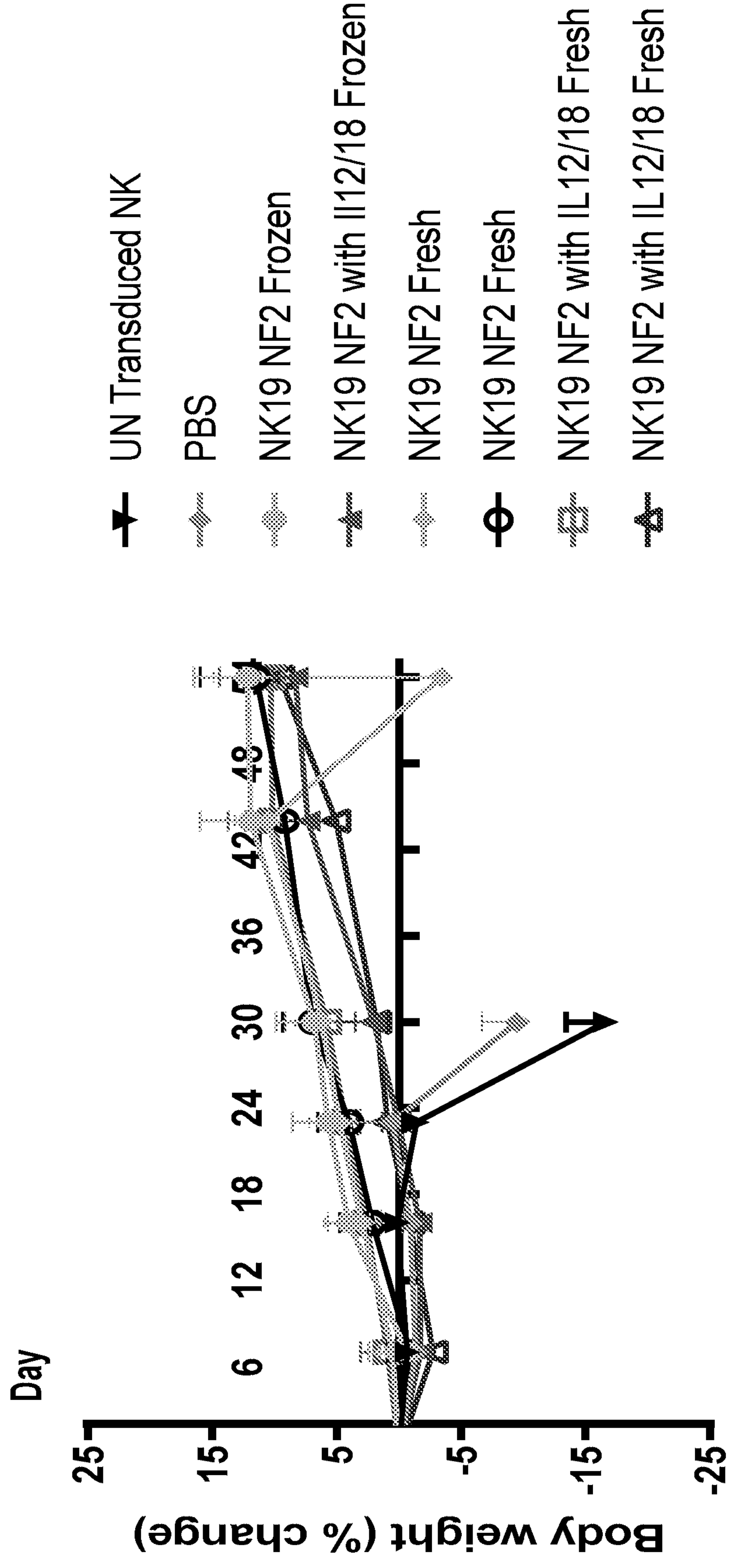
FIG. 29 shows data related to the body mass of mice over time when receiving the indicated therapy.

FIG. 29 shows a line graph of body mass of the mice treated with the indicated constructs over 56 days of the experiment. A reduction in body weight is correlated with increased tumor growth, e.g., progression of the tumor results in a decreased health of the mice, and corresponding loss of body weight (e.g., wasting). As shown, the control groups show substantial loss of body mass by 30 days, while all but one of the experimental groups are increasing in body mass for the majority of the experiment. As with the bioluminescence data discussed above, there is a notable trend that many of the fresh versus frozen preparations exhibit substantially similar effects on body weight. According to several embodiments, engineered NK cells expressing anti-CD19 CARs are effective not only when prepared and administered fresh. Additionally, according to several embodiments, engineered NK cells expressing anti-CD19 CARs are effective not only when prepared, frozen, then thawed and administered (e.g., as in an allogeneic context).

Figure 30A:
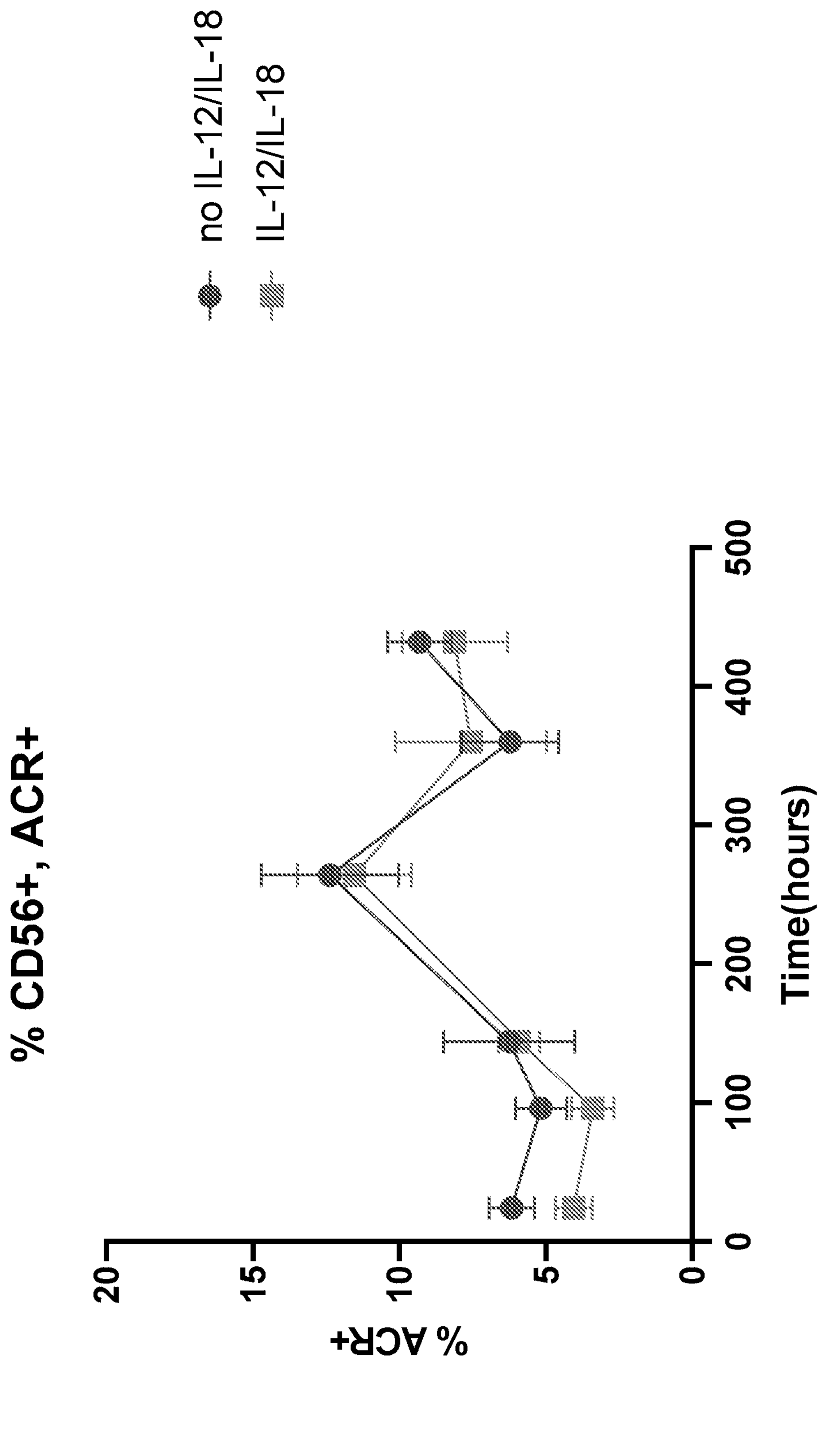
FIGS. 30A-30C show data related to data characterizing NK cells engineered to express CARs (as disclosed herein) and expanded in the presence or absence of one or more stimulatory cytokines.
Figure 30B:
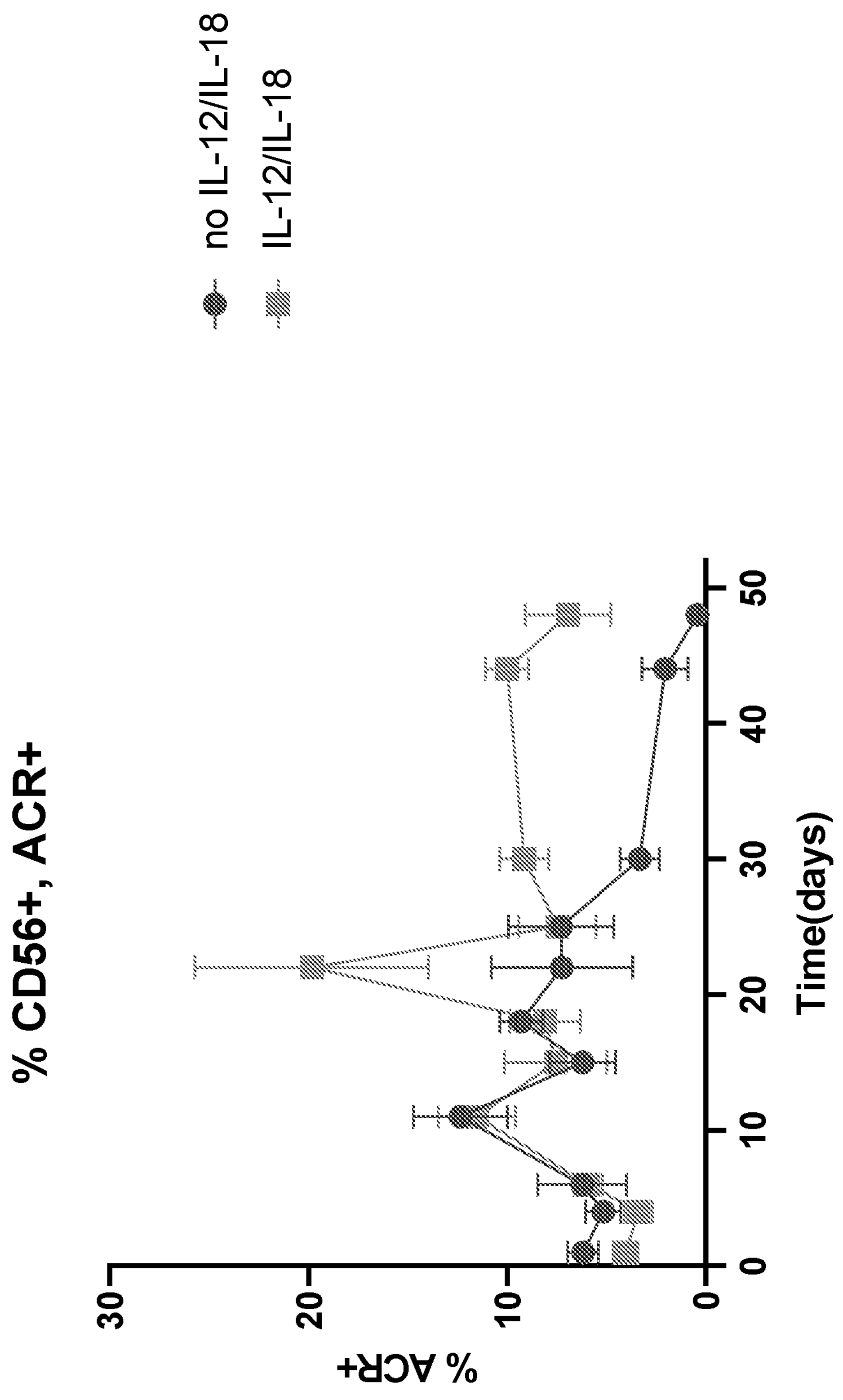
Figure 30C:
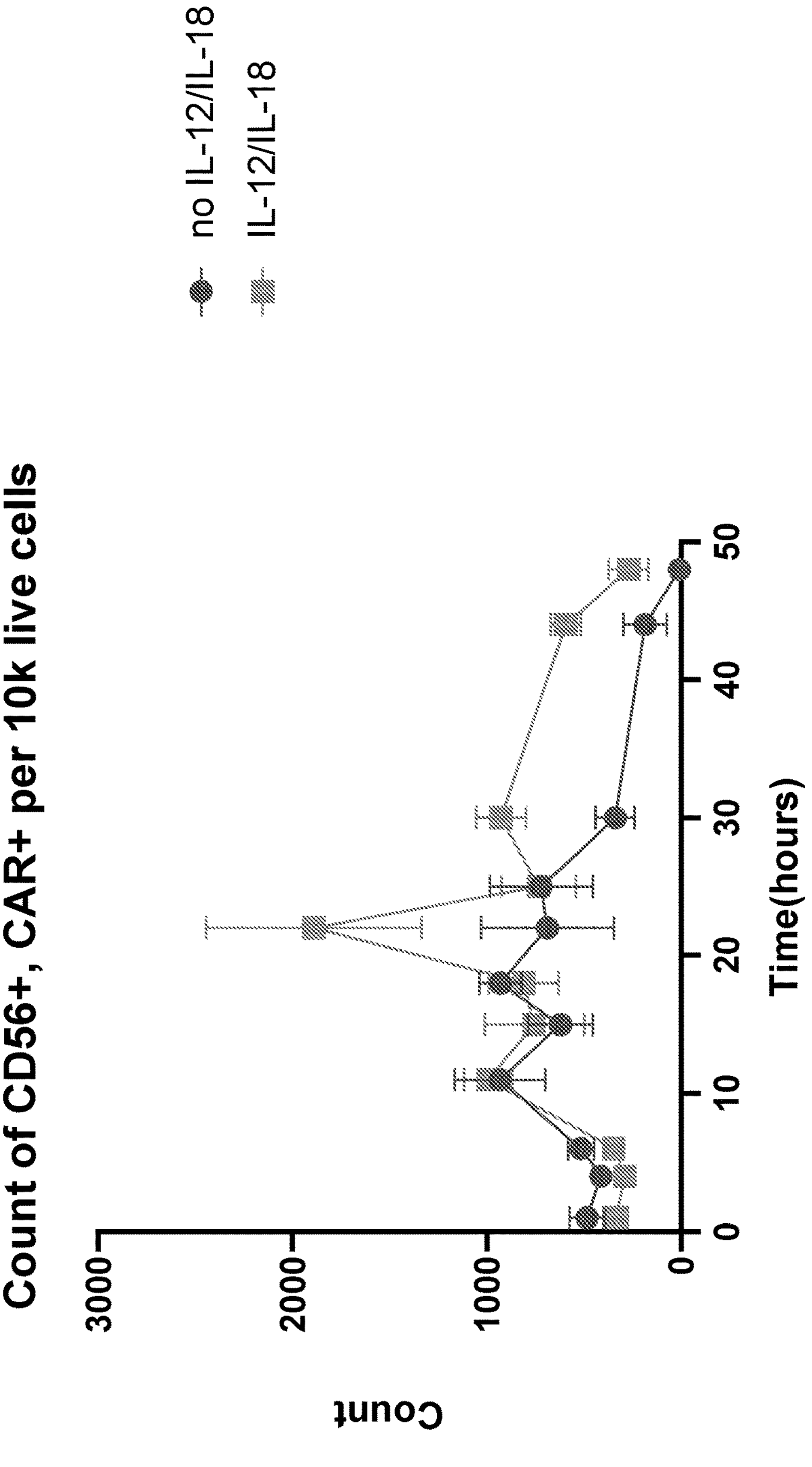

Additional data were collected to characterize the features of NK cells expanded with or without the use of one or more additional stimulatory factors. FIG. 30A shows data related to the longevity (e.g., persistence) of NK cells in culture. These data show the percentage of NK cells (based on CD56 positivity) that were engineered (based on Activating Chimeric Receptor (ACR) positivity). These data show that NK cells expanded with, or without additional stimulatory factors during expansion, such as IL12 and/or IL18, exhibit similar persistence profiles in vivo, with such engineered NK cells present at relatively consistent level in the blood (between about 5-10%) over about 7 days. Again measuring based on detection of expression of an engineered CAR and CD56-positivity, the percentage of NK cells present in the blood of animals was measured over ~50 days, the data for which is shown in FIG. 30B. In contrast to the similar profiles over the 7-day period, NK cells expanded without the use of one or more additional stimulatory factors began to decline in number after about 25-30 days. These cells continued a slow decline in number out to about 48 days, when cell numbers were close to zero. From the same time point of approximately 25-30 days, the engineered NK cells expanded with additional stimulatory factors (e.g., IL12 and/or IL18, according to several embodiments), continued to be present in the blood at about 10% through 45 days. Only in the last three days was there a slight decline (to about 5-7%). These data are a strong indicator that use of one or more additional stimulatory molecules, such as IL12, IL18, and/or IL21, impart engineered NK cells with an enhanced persistence in vivo, as compared to NK cells cultured/expanded without using such stimulatory molecules. FIG. 30C presents the persistence data in a different manner, based on a count of the number of engineered CAR-expressing NK cells per 10,000 live cells counted. These data mirror the general trend shown in FIG. 30B, that is, the cells expanded with the use of one or more stimulatory molecules (e.g., soluble IL12 and/or soluble IL18) remain in the blood at higher numbers over an extended period as compared to engineered NK cells expanded without such stimulatory molecules. In several embodiments, the methods disclosed herein are particularly advantageous in that they avoid cytokine addiction that is common among certain cytokine-based expansion methods. In some methods, use of high concentrations of soluble cytokines promote the growth of the cells, but the cells grow accustomed to those concentrations, and exhibit signs of withdrawal (e.g., apoptosis, reduced viability or other functional reductions) when exposed to an environment without those artificial conditions, such as upon administration to a patient. The lack of a need for ongoing high cytokine concentrations exhibited by engineered NK cells expanded according to the methods disclosed herein contributes, at least in part, to the longer life span (and active life span) of the cells in vivo.

Figures 31A, 31B:
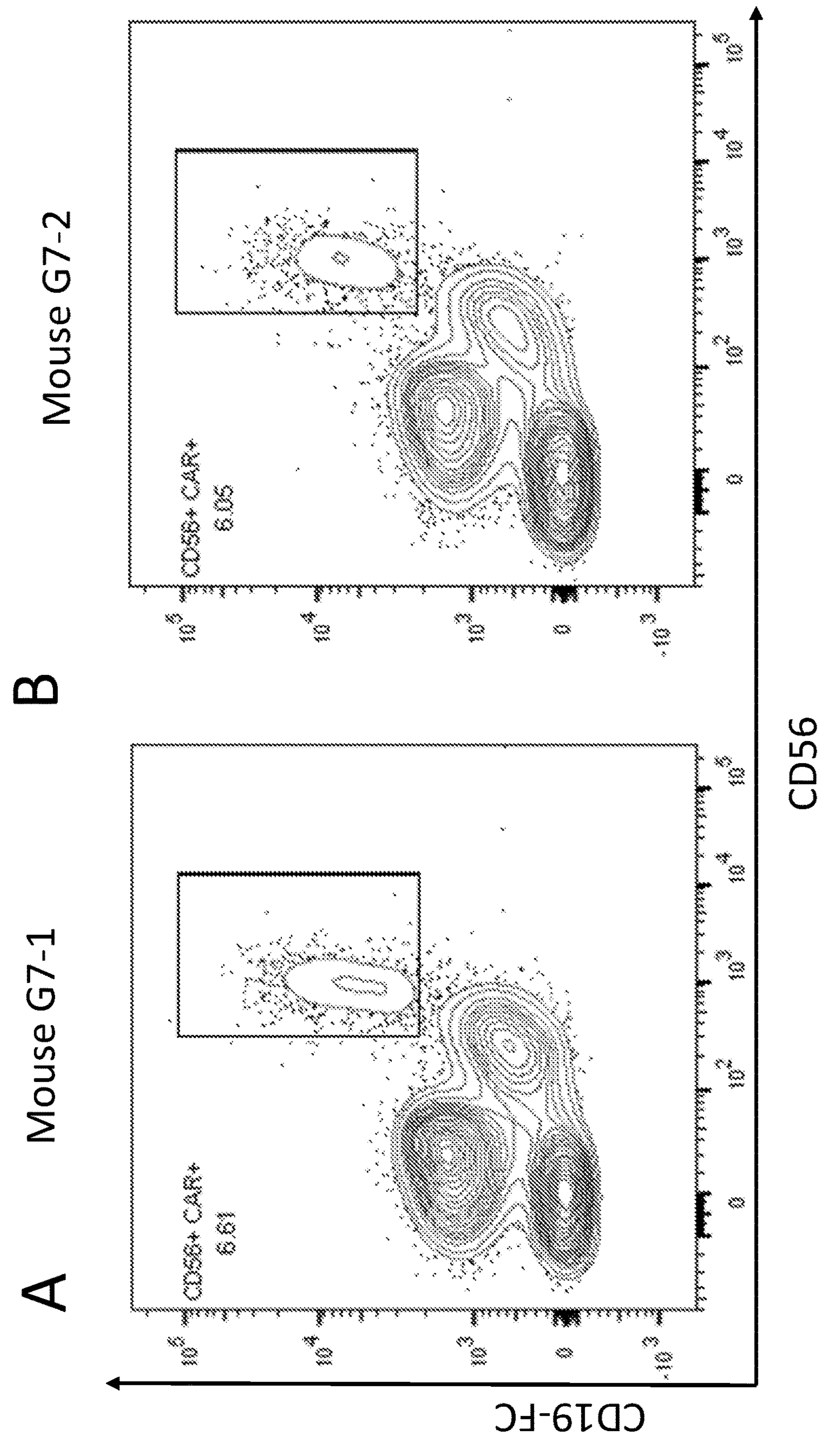
FIGS. 31A-31C show data from three different mice (31A, 31B, and 31C, respectively) related the expression of an anti-CD19 CAR and characterization of what cells express the CAR.
Figure 31C:
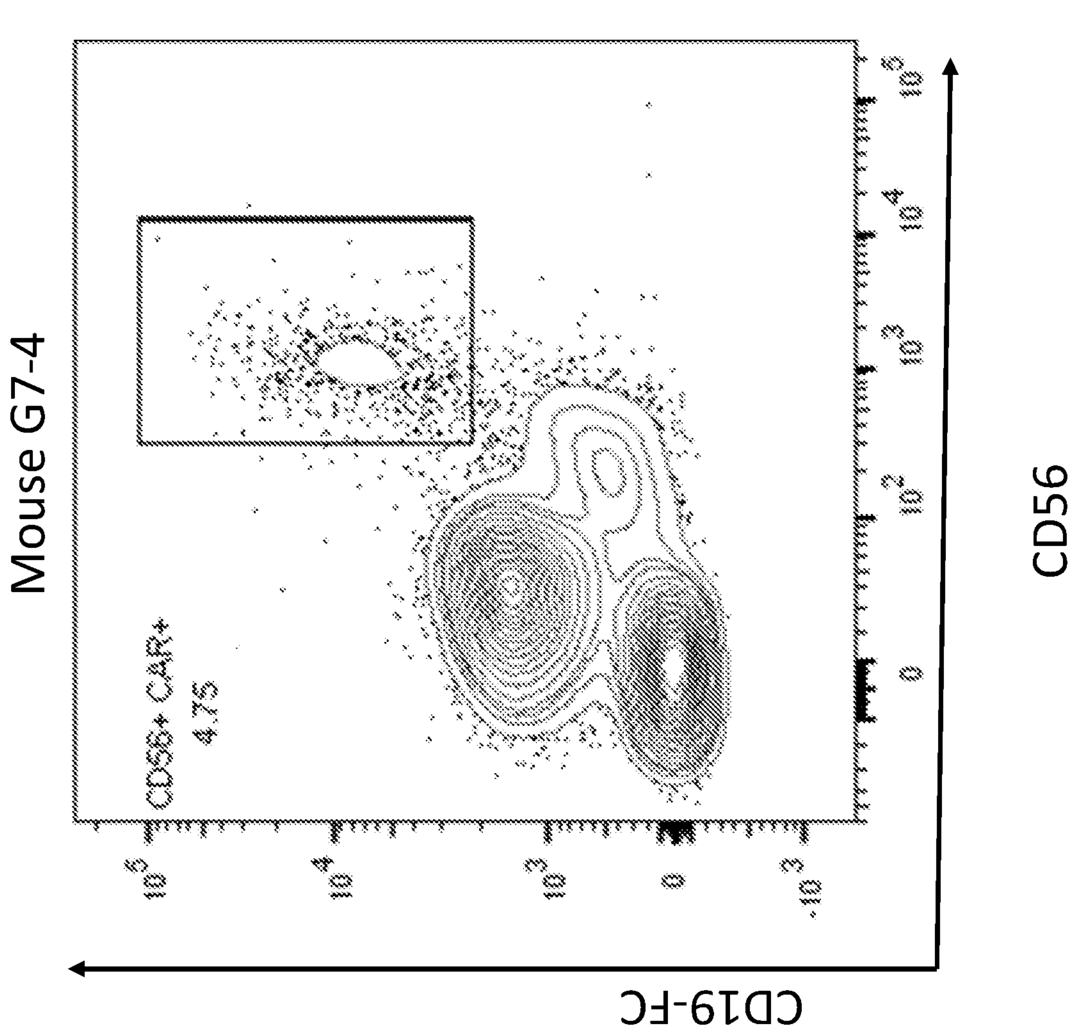
Figures 32A, 32B:
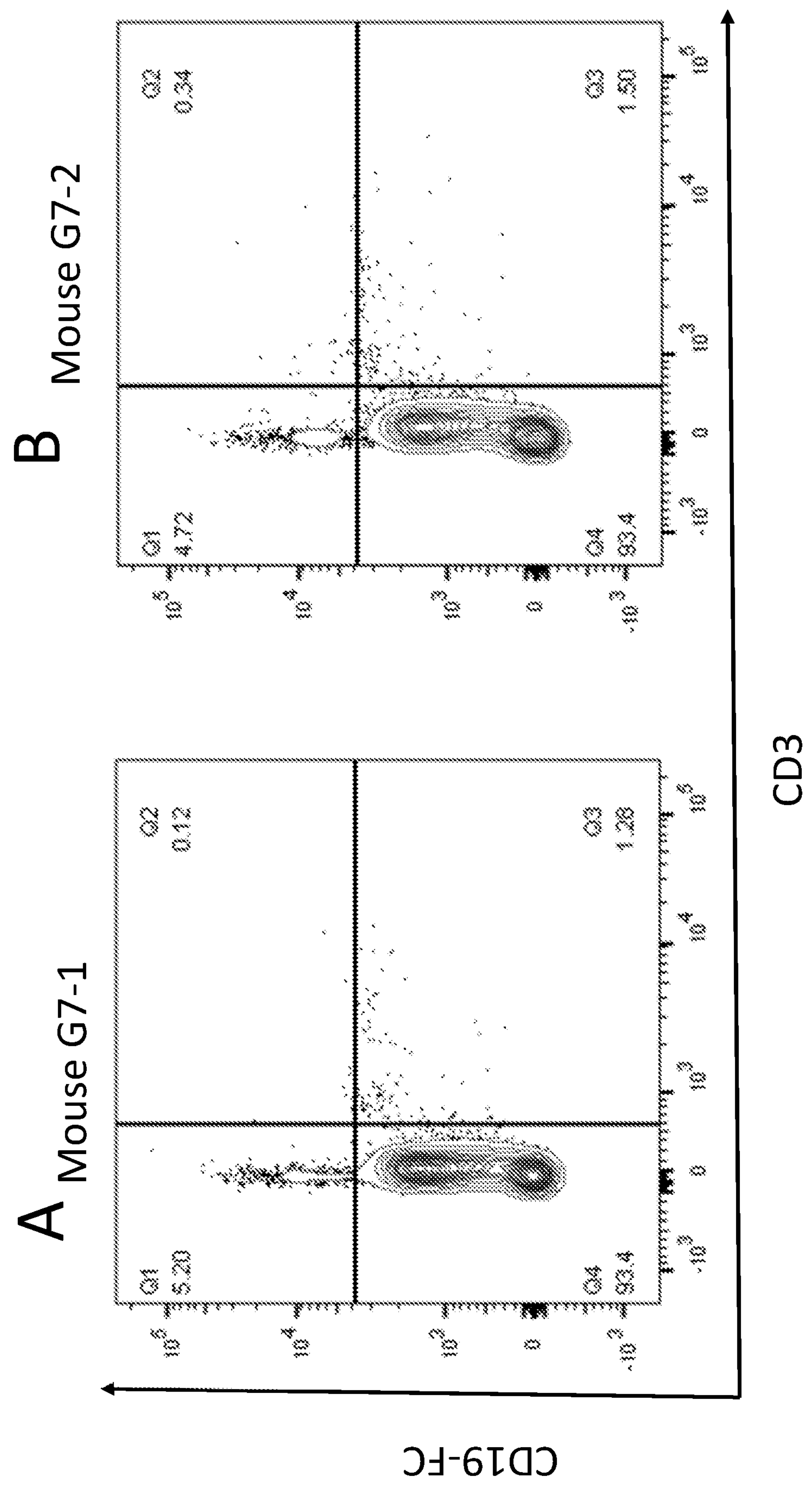
FIGS. 32A-32C show data from three different mice (32A, 32B, and 32C, respectively) related the expression of an anti-CD19 CAR and characterization of what cells express the CAR.
Figure 32C:
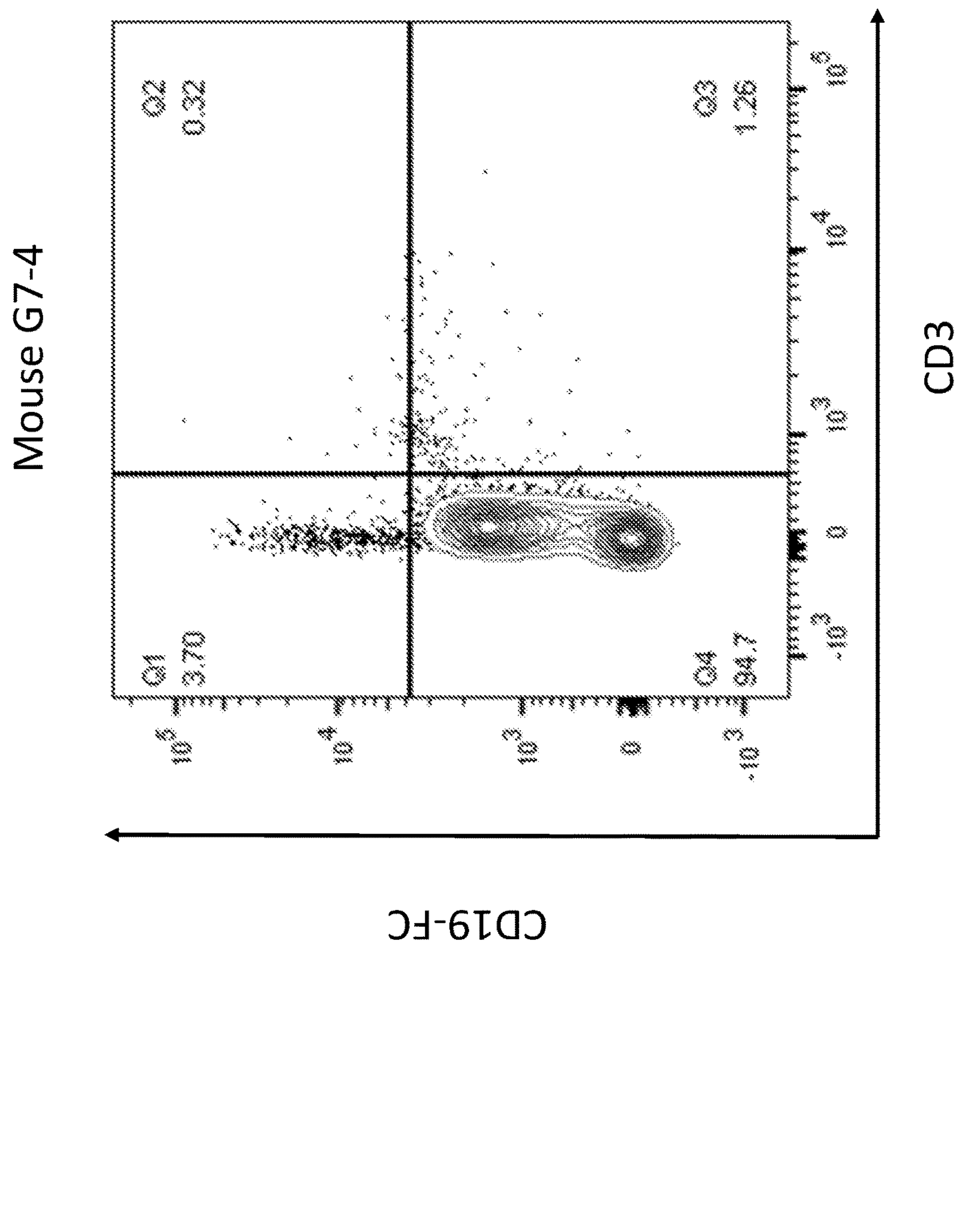

FIGS. 31A-31C shows additional data characterizing engineered NK cells produced according to embodiments disclosed herein. These data are collected from the blood of three mice (day 51 post-administration) administered fresh (not cryopreserved) engineered NK cells expressing an anti-CD19 CAR and expanded using, according to several embodiments disclosed herein, soluble IL12 and soluble IL18. The data depict the proportion of cells from a whole blood sample that are CD56-positive (indicative of NK cells) and CD19-Fc positive (indicative of cells expressing the engineered anti-CD19 CAR). As shown in each of FIGS. 31A, 31B, and 31C, the proportion of double-positive cells (boxed region in upper right) ranges from about 4.75% to about 6.7%. FIGS. 32A-32C show analysis of whole blood from the same mice as in FIG. 31, but identify cells that are CD19-Fc positive (indicative of cells expressing the engineered anti-CD19 CAR) and CD3-positive (indicative of T cells). These data demonstrate that the vast majority of cells expressing the anti-CD19 CAR are negative for CD3, which means that they are not T cells. According to several embodiments, certain NK cell production methods do involve steps to remove T cells from an initial donor whole blood sample, however, a nominal number of T cells may remain. In several embodiments, however, in accordance with the data shown in FIGS. 31A-32C, the majority of engineered cells expressing an anti-CD19 CAR exhibit features of NK cells (CD56-positive) and no features of T cell (CD3-negative).

Figure 33A:
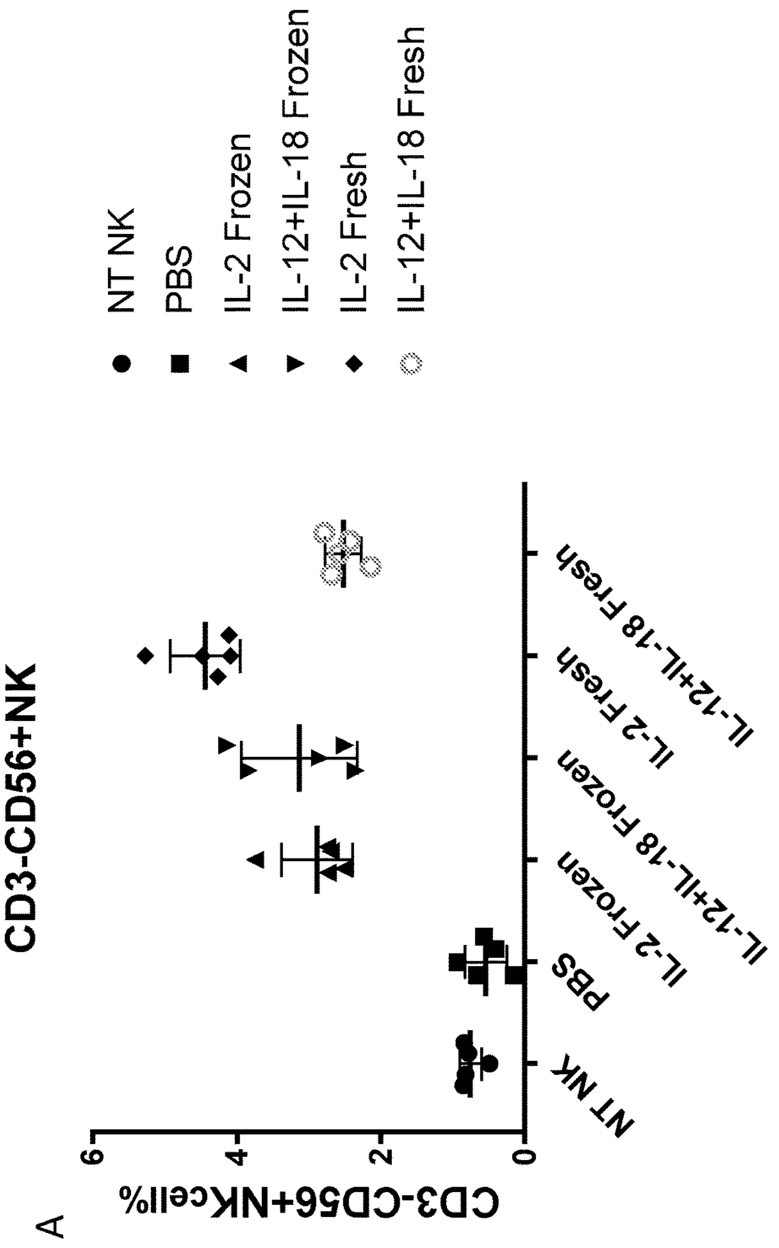
FIGS. 33A-33C show summary expression data from blood samples collected 4 days after in vivo administration (protocol of FIG. 27A).
Figure 33B:
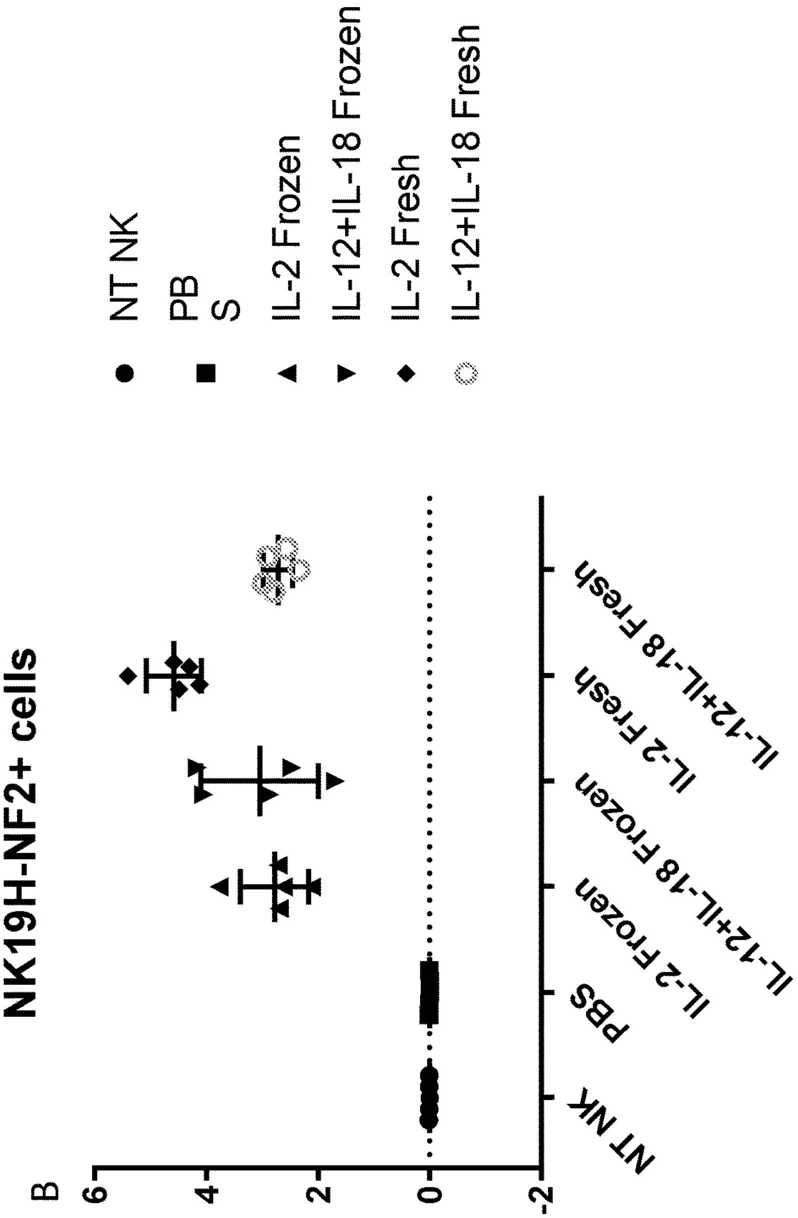
Figure 33C:
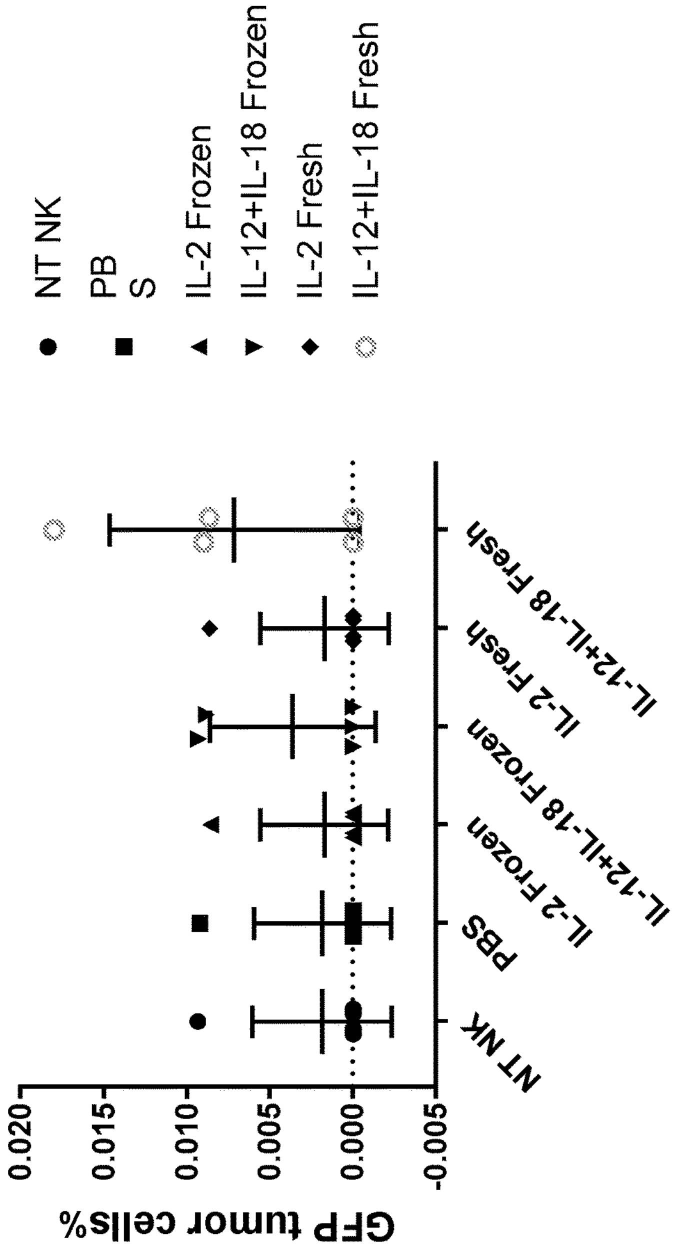
Figure 34A:
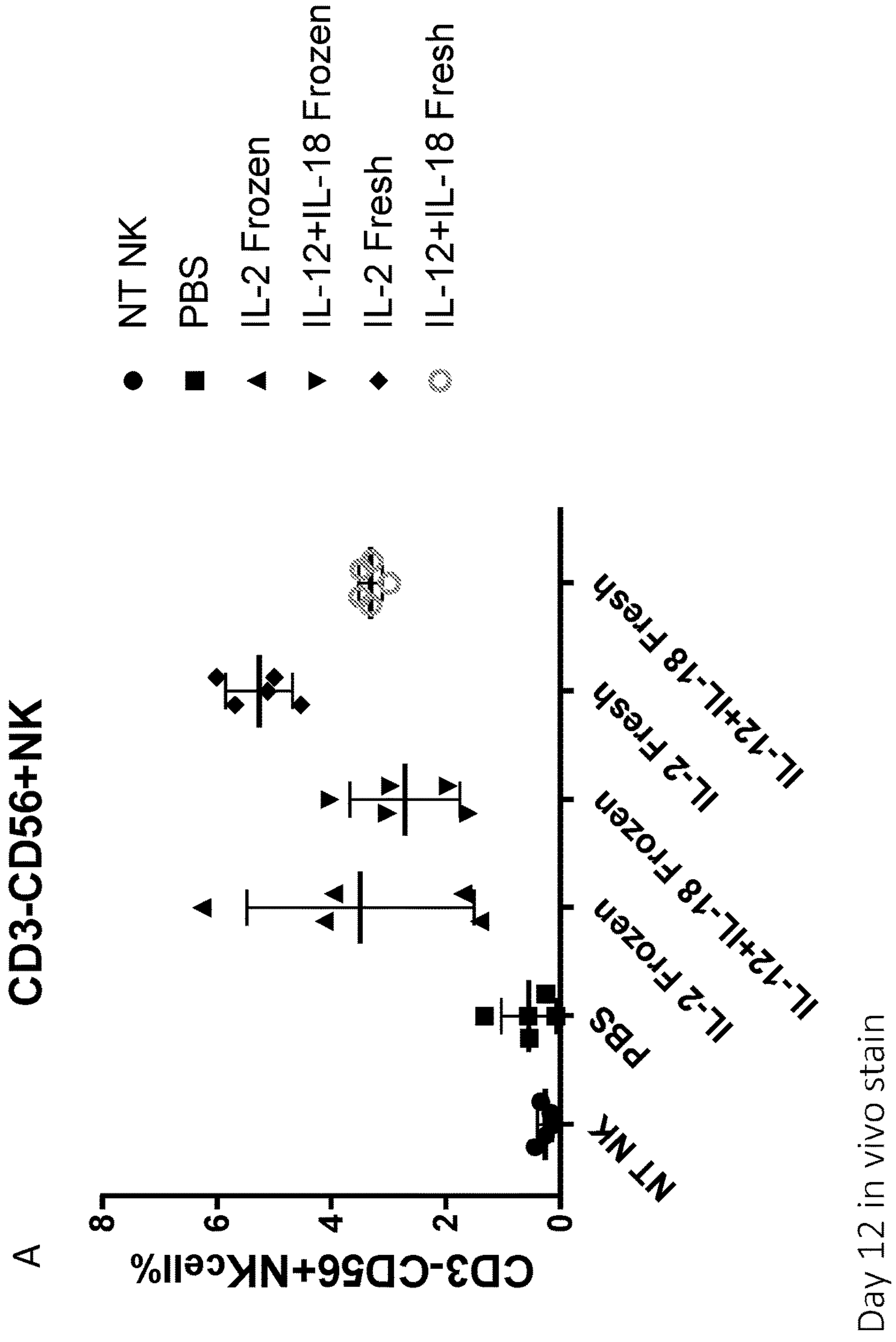
FIGS. 34A-34C show summary expression data from blood samples collected 12 days after in vivo administration (protocol of FIG. 27A).
Figure 34B:
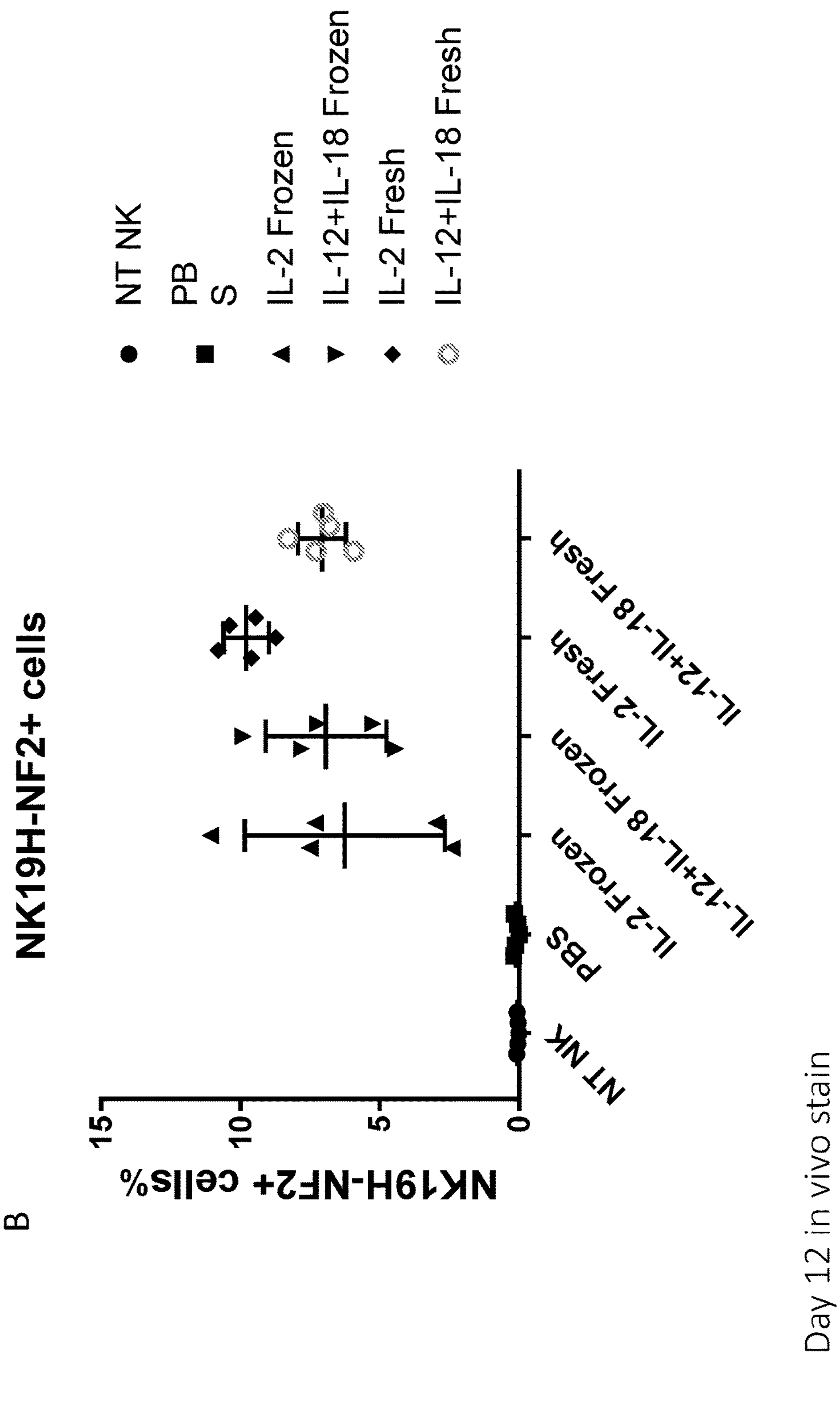
Figure 34C:
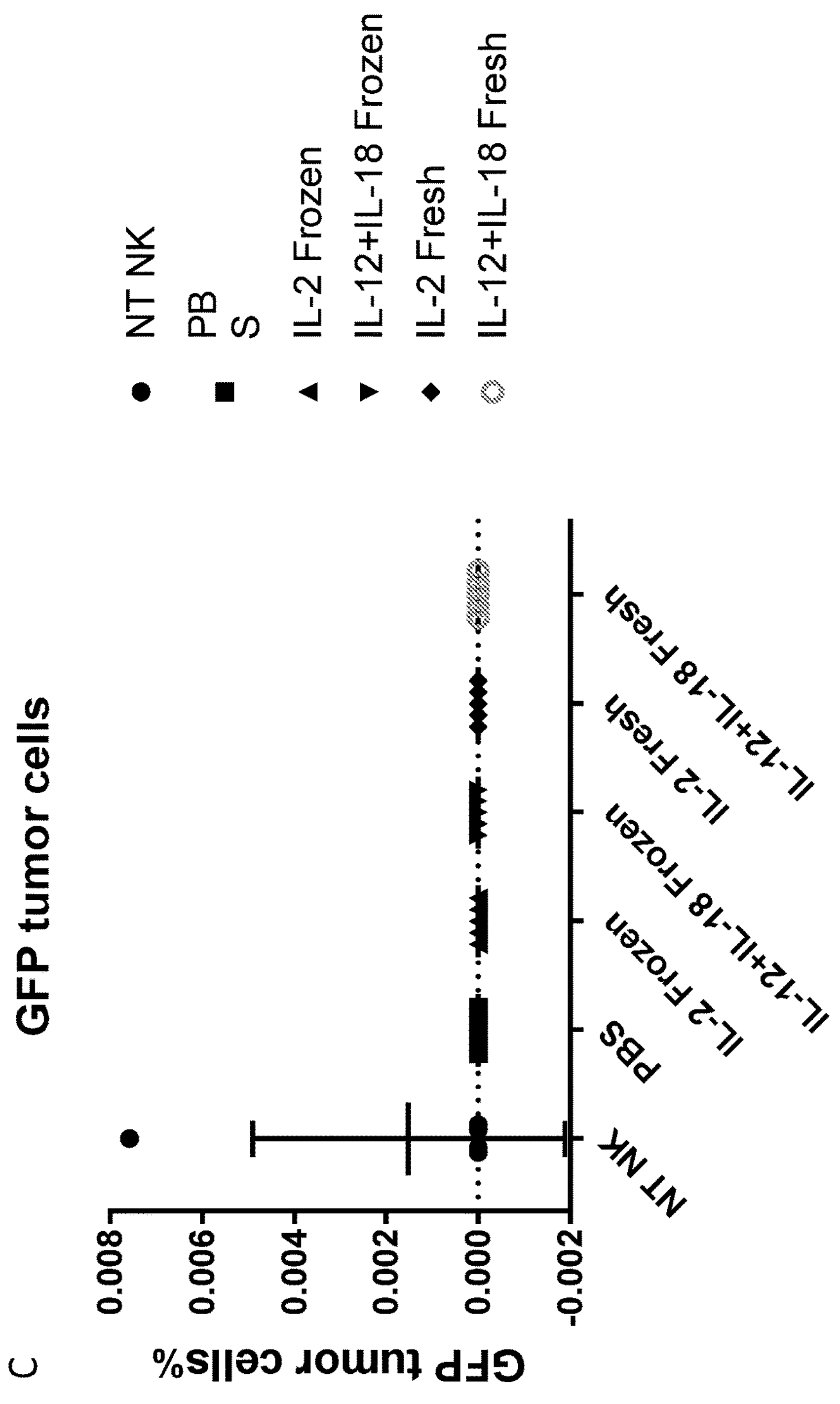

FIGS. 33, 34, and 35 relate to data further characterizing cells from the whole blood of animals at various time points post-tumor inoculation. FIG. 33 relates to data at day 4 post-administration, FIG. 34 relates to data at day 12 post-tumor inoculation, and FIG. 35 relates to data at day 18 post-tumor inoculation. These data relate to cells from the whole blood of animals treated as controls and receiving either non-transduced NK cells (NT NK) or PBS, or from one the other groups that received engineered NK cells expanded with IL2 in culture or IL12/18 in culture, with a fresh and frozen treatment group for each condition. FIG. 33A shows the percentage of NK cells (CD56-pos/CD3-neg) from whole blood of animals at Day 4. Each of the treatment groups were relatively similar in this regard, with about 3-5% of the cells in the whole blood being engineered NK cells. FIG. 33B shows data related to the percentage of cells that specifically express the non-limiting embodiment of an anti-CD19-CAR. Much like FIG. 33A, the percentage of anti-CD19-CAR-expressing cells in each of the treatment groups ranges from about 3-5%. FIG. 33C shows data related to the percentage of GFP-positive tumor cells present in the blood at day 4 post-administration. Consistent with the BLI imaging shown in prior figures, there is little detectable tumor cell presence in any treatment group. It may be that the low signal detected is reflective of the migration of the GFP+ tumor cells from the circulation into various tissues (making them potentially detectable by BLI imaging but not in a blood sample per se). FIG. 34A-34C shows corresponding data 12 days after tumor inoculation. As was the case with the earlier time-point, each of the treatment groups result in between about 3%-5% of the blood cells in a sample were NK cells (FIG. 34A). FIG. 34B shows the percentage of cells positive for the anti-CD19 CAR construct. While the expression levels were similar across the treatment groups at this time-point, each experimental groups was present at levels notable above the control groups. Also, at 12 days, the percent of anti-CD19 expressing CAR cells (e.g., NK cells) was slightly higher (approximately 7-9% of the blood cells), suggesting an increased persistence of the engineered cells in the circulation. FIG. 34C shows the number of tumor cells in whole blood. Interestingly, all groups show little GFP expression, despite the BLI imaging showing increased luminescence, particularly in controls. Again, these data may reflect the physiological "residency" that certain suspension tumor cells exhibit.

Figure 35A:
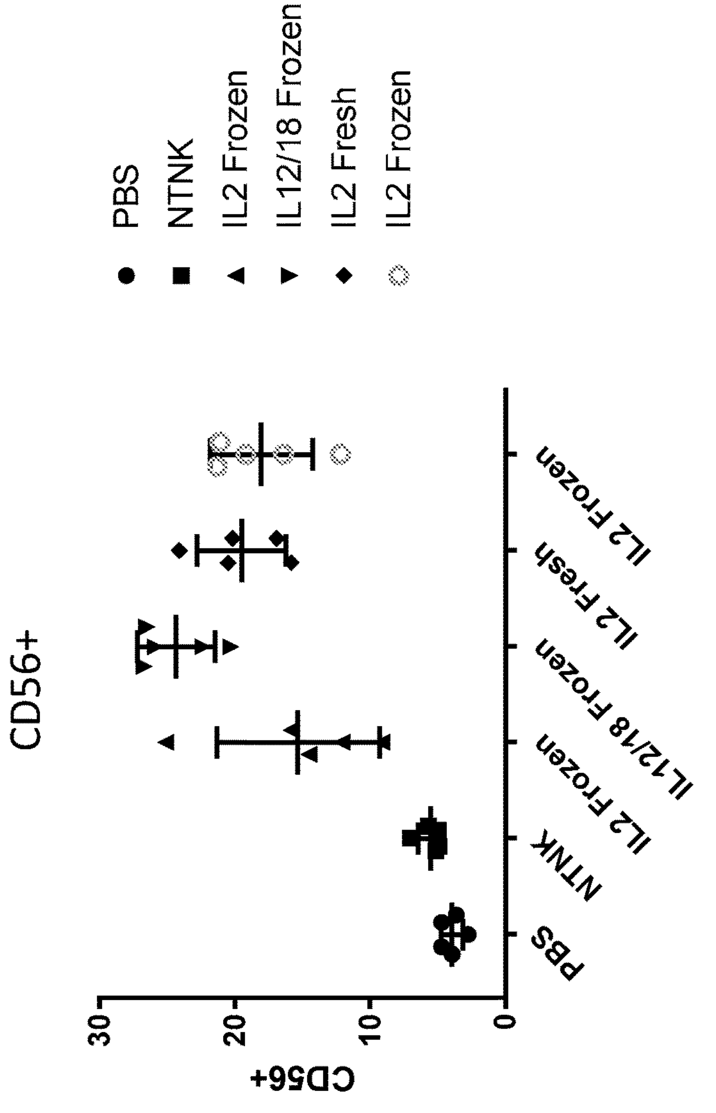
FIGS. 35A-35E show summary expression data from blood samples collected 18 days after in vivo administration (protocol of FIG. 27A).
Figure 35B:
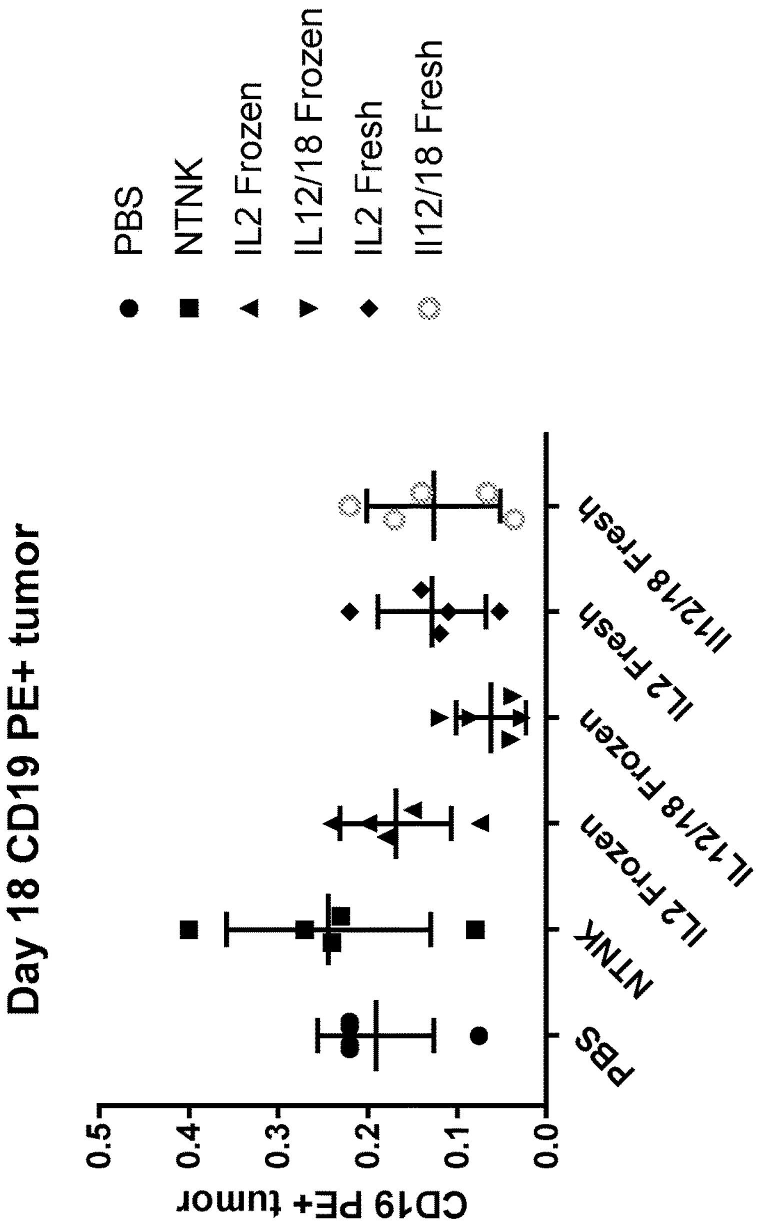
Figure 35C:
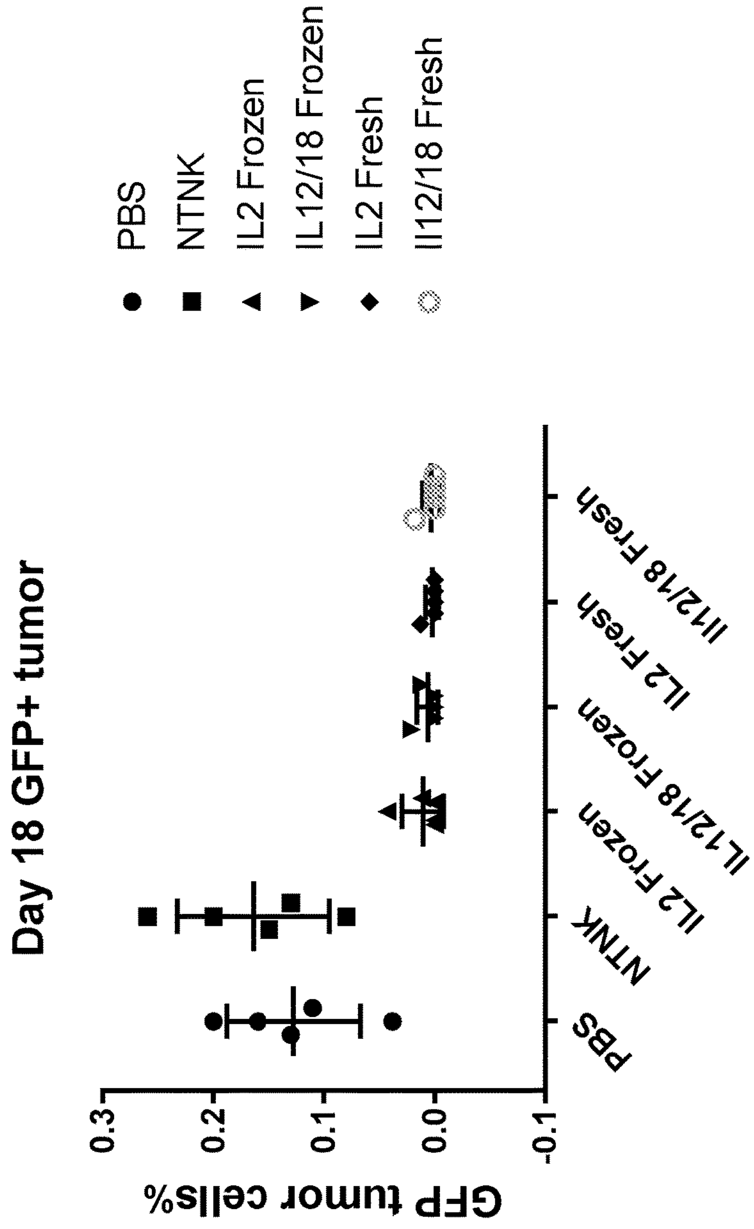
Figure 35D:
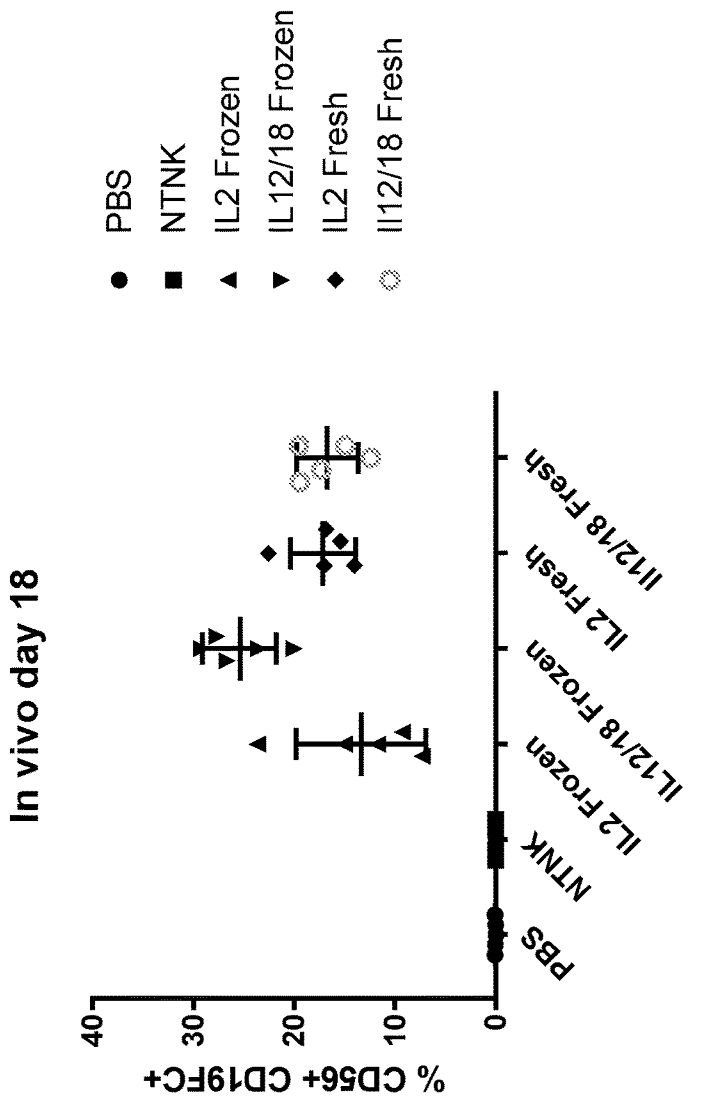
Figure 35E:
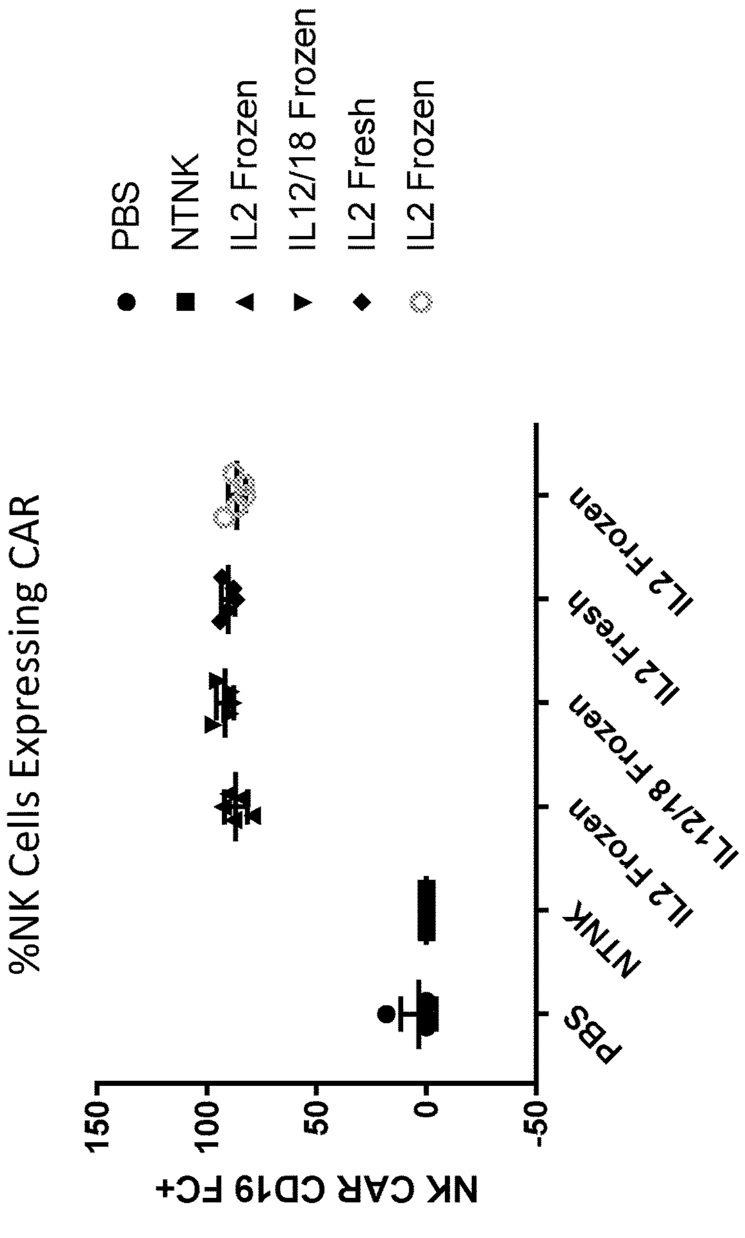

FIG. 35A shows the percentage of NK cells (based on CD56-positivity) at 18 days after tumor inoculation. The experimental groups all show markedly higher percentages as compared to control groups, with the groups ranging from about 15% to about 25% of the cells in the whole blood. This increased percentage is consistent with the time window of increased NK cells as shown in FIGS. 30B and 30C. While not statistically different in this particular experiment, these data show that NK cells expanded in IL12/IL18 media and cryopreserved were the most prolific of the experimental groups. According to several embodiments, the feeder cell plus cytokine based expansion, coupled with cryopreservation yields a more robust NK cell that can survive under more normal cytokine conditions (e.g., without cytokine addiction) and can persist for longer periods of time in a health state. FIGS. 35B and 35C show two measures of tumor burden at day 18. FIG. 35B shows the percentage of cells in the blood that are positive for CD19 (the target of the engineered CAR in this non-limiting embodiment) as measured using an anti-CD19 PE-coupled antibody. These data show the trend upwards in the tumor burden in control groups, and in contrast, the ability of the engineered NK cells of the treatment groups to limit tumor growth. FIG. 35C shows similar data, but through the detection of GFP signal (e.g., ~BLI). These data, while differing from those of 35B due to sensitivity of PE- versus GFP-based detection show a similar trend. The experimental NK cells show an enhanced ability to prevent the expansion of the tumor cells, as compared to controls. FIG. 35D relates to data regarding the number of NK cells that are expressing the engineered anti-CD19 (e.g., both CD56 and CD19 Fc positive). Similar to the data of FIG. 35A, these data show that an increased percentage of the NK cells in a blood sample are NK cells expressing the engineered anti-CD19 CAR, reflecting their enhanced persistence. FIG. 35E shows confirmatory data that nearly the entire population of NK cells of each experimental group that are positive for a CAR are NK cells that were engineered to express the anti-CD19 CAR disclosed herein.

Figure 36:
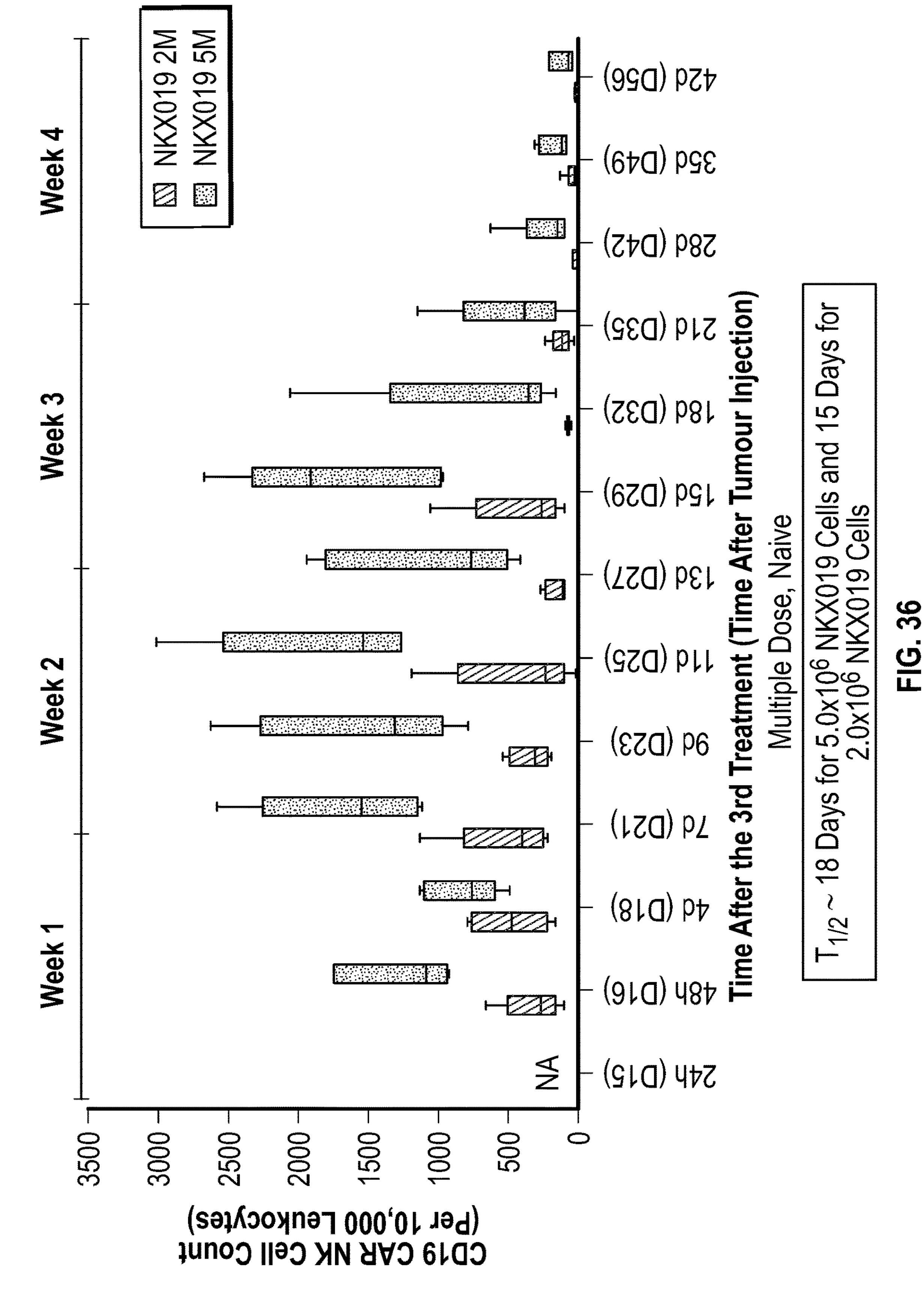
FIG. 36 shows data collected over 4 weeks relating to the half-life of NK cells expressing an anti-CD19 CAR, for each of two doses of NK cells, as measured by the count of NK cells per 10,000 leukocytes. The two doses were (i) 2 million NK cells expressing an anti-CD19 CAR and (ii) 5 million NK cells expressing an anti-CD19 CAR. These data were collected after a third dose of NK cells were administered.
Figure 37:
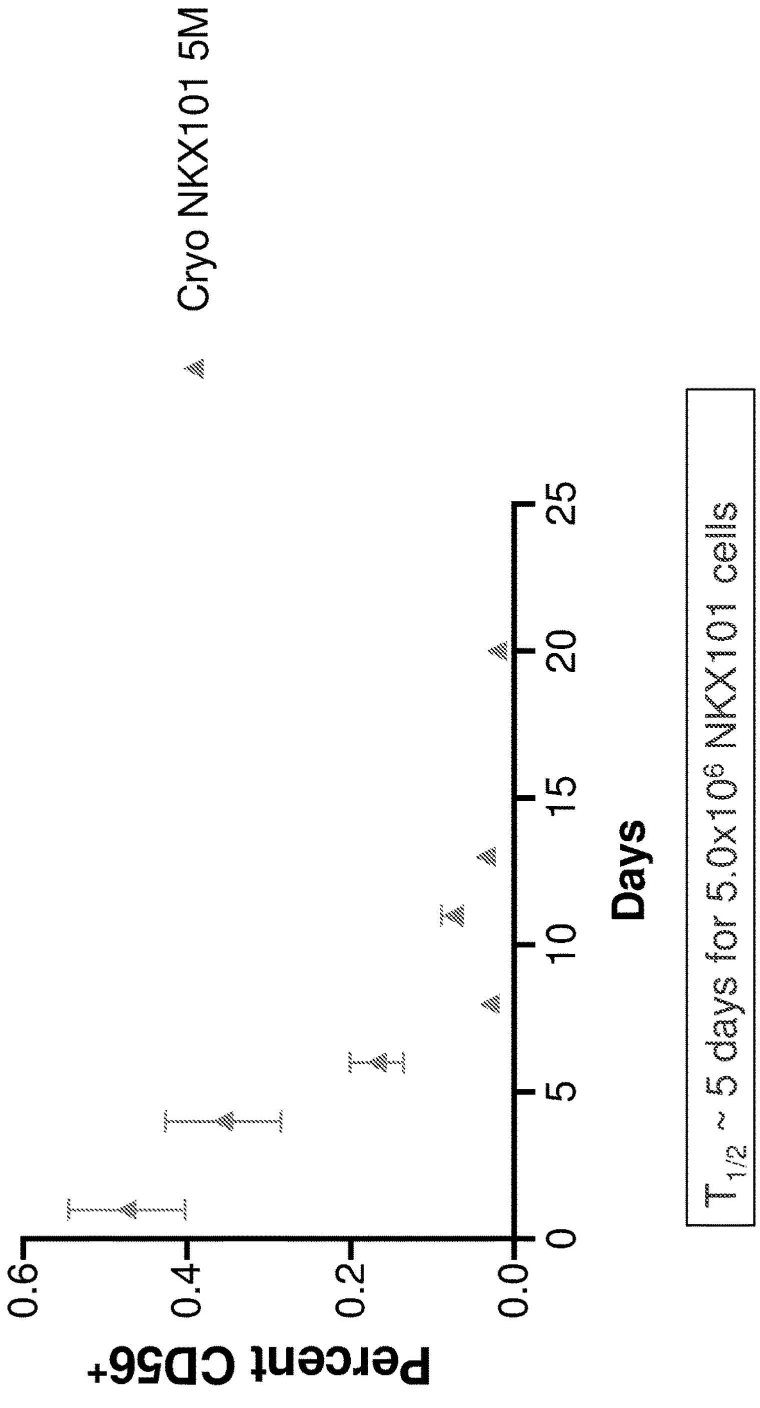
FIG. 37 shows data collected for the half-life of cryopreserved NK cells engineered to express a CAR targeting NKG2D ligands and expanded without the use of an additional stimulatory cytokine.

To further investigate the persistence of engineered NK cells expanded according to embodiments disclosed herein, two doses of engineered NK cells expanded using soluble cytokines as disclosed herein were administered to mice and cell numbers were tracked over four additional weeks (administration protocol per FIG. 27A). FIG. 36 shows a box plot of these data. In brief, the X axis of the box plot represents the time in two format, either: i) the time after the third administration or ii) total time since tumor inoculation (shows in parenthesis). The Y-axis represents the count of anti-CD19 CAR-expressing NK cells (per 10,000 leukocytes). The box plots for the 2 million NK cell dose are the lower trace of boxes (indicated by the dashed arrow), while the 5 million cell dose is the upper trace (indicated by the solid arrow). These data indicate that the half-life of engineered NK cells expanded in conditions where one or more stimulatory molecules (such as IL12 and/or IL18) are used (in conjunction with feeder cells, as described in several embodiments herein) is extended as compared to engineered NK cells expanded in feeder cell-only conditions. The half-life for a 2 million engineered NK cell dose is ~15 days. Based on variance in one or more of clearance and/or volume of distribution, the half-life of a 5 million engineered NK cell dose is ~18 days. These are in contrast to a dose of another engineered NK cell expanded without the use of the one or more additional stimulatory molecules, which is shown in FIG. 37, and indicates a half-life of ~5 days for a dose of 5 million cells. Thus, according to several embodiments disclosed herein, the expansion of engineered NK cells using one or more additional cytokines, in conjunction with a feeder cell system, allows for the increased expansion of the NK cells and imparts to those cells an enhanced persistence and/or cytotoxicity.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a population of expanded NK cells" includes "instructing the administration of a population of expanded NK cells." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "90%" includes "90%." In some embodiments, at sequence having at least 95% sequence identity with a reference sequence includes sequences having 96%, 97%, 98%, 99%, or 100% identical to the reference sequence. In addition, when a sequence is disclosed as "comprising" a nucleotide or amino acid sequence, such a reference shall also include, unless otherwise indicated, that the sequence "comprises", "consists of" or "consists essentially of" the recited sequence.

Articles such as "a", "an", "the" and the like, may mean one or more than one unless indicated to the contrary or otherwise evident from the context. The phrase "and/or" as used herein in the specification and in the claims, should be understood to mean "either or both" of the elements so conjoined. Multiple elements listed with "and/or" should be construed in the same fashion, i.e., "one or more" of the elements so conjoined. Other elements may optionally be present other than the elements specifically identified by the "and/or" clause. As used herein in the specification and in the claims, "or" should be understood to have the same meaning as "and/or" as defined above. For example, when used in a list of elements, "or" or "and/or" shall be interpreted as being inclusive, i.e., the inclusion of at least one, but optionally more than one, of list of elements, and, optionally, additional unlisted elements. Only terms clearly indicative to the contrary, such as "only one of" or "exactly one of" will refer to the inclusion of exactly one element of a number or list of elements. Thus claims that include "or" between one or more members of a group are considered satisfied if one, more than one, or all of the group members are present, employed in, or otherwise relevant to a given product or process unless indicated to the contrary. Embodiments are provided in which exactly one member of the group is present, employed in, or otherwise relevant to a given product or process. Embodiments are provided in which more than one, or all of the group members are present, employed in, or otherwise relevant to a given product or process. Any one or more claims may be amended to explicitly exclude any embodiment, aspect, feature, element, or characteristic, or any combination thereof. Any one or more claims may be amended to exclude any agent, composition, amount, dose, administration route, cell type, target, cellular marker, antigen, targeting moiety, or combination thereof.

In several embodiments, there are provided amino acid sequences that correspond to any of the nucleic acids disclosed herein, while accounting for degeneracy of the nucleic acid code. Furthermore, those sequences (whether nucleic acid or amino acid) that vary from those expressly disclosed herein, but have functional similarity or equivalency are also contemplated within the scope of the present disclosure. The foregoing includes mutants, truncations, substitutions, or other types of modifications.

Any titles or subheadings used herein are for organization purposes and should not be used to limit the scope of embodiments disclosed herein.

What is claimed is:

1. A method for expanding natural killer (NK) cells, comprising:

(a) culturing a population of NK cells with a feeder cell population in a culture media with cytokines consisting of soluble interleukin 2 (IL2) at a concentration of less than 50 IU/mL, soluble interleukin 12 (IL12) at a concentration of between about 0.01 ng/ml and about 8 ng/ml, and soluble interleukin 18 (IL18) at a concentration of between about 0.01 ng/ml and about 30 ng/mL, wherein the feeder cell population comprises K562 cells expressing 4-1BB ligand (4-1BBL) and membrane-bound interleukin-15 (mbIL15); and (b) contacting the NK cells after (a) with a vector encoding a chimeric antigen receptor (CAR).

2. The method of claim 1, wherein the culture media is further supplemented for a second time with IL2 at a concentration that is greater than that present in the culture media in (a).

3. The method of claim 2, wherein the concentration of the IL2 in the culture media after the further supplementation is less than 500 IU/mL.

4. The method of claim 1, wherein the K562 cells are irradiated prior to culture.

5. The method of claim 1, wherein the soluble interleukin 12 (IL12) and soluble interleukin 18 (IL18) in the culture media increases the IFN-γ production by NK cells.

* * * * *

SEQUENCE LISTING

<160> NUMBER OF SEQ ID NOS: 28

<210> SEQ ID NO 1
<211> LENGTH: 1797
<212> TYPE: DNA
<213> ORGANISM: Homo sapiens
<220> FEATURE:
<221> NAME/KEY: misc_feature
<223> OTHER INFORMATION: NK45-1 DNA

<400> SEQUENCE: 1

```
atggccttac cagtgaccgc cttgctcctg ccgctggcct tgctgctcca cgccgccagg     60

ccgttattca accaagaagt tcaaattccc ttgaccgaaa gttactgtgg cccatgtcct    120

aaaaactgga tatgttacaa aaataactgc taccaatttt ttgatgagag taaaaactgg    180

tatgagagcc aggcttcttg tatgtctcaa aatgccagcc ttctgaaagt atacagcaaa    240

gaggaccagg atttacttaa actggtgaag tcatatcatt ggatgggact agtacacatt    300

ccaacaaatg gatcttggca gtgggaagat ggctccattc tctcacccaa cctactaaca    360

ataattgaaa tgcagaaggg agactgtgca ctctatgcct cgagctttaa aggctatata    420

gaaaactgtt caactccaaa tacgtacatc tgcatgcaaa ggactgtgac cacgacgcca    480

gcgccgcgac caccaacacc ggcgcccacc atcgcgtcgc agcccctgtc cctgcgccca    540

gaggcgtgcc ggccagcggc ggggggcgca gtgcacacga gggggctgga cttcgcctgt    600

gatatctaca tctgggcgcc cttggccggg acttgtgggg tccttctcct gtcactggtt    660

atcacccttt actgccggag ggaccagagg ctgccccccg atgcccacaa gccccctggg    720

ggaggcagtt tccggacccc catccaagag gagcaggccg acgcccactc caccctggcc    780

aagatcagag tgaagttcag caggagcgca gacgcccccg cgtaccagca gggccagaac    840

cagctctata acgagctcaa tctaggacga agagaggagt acgatgtttt ggacaagaga    900

cgtggccggg accctgagat gggggggaaag ccgagaagga agaaccctca ggaaggcctg    960

tacaatgaac tgcagaaaga taagatggcg gaggcctaca gtgagattgg gatgaaaggc   1020

gagcgccgga ggggcaaggg gcacgatggc ctttaccagg gtctcagtac agccaccaag   1080

gacacctacg acgcccttca catgcaggcc ctgccccctc gcggctctgg cgagggaagg   1140

ggttccctgc ttacttgcgg cgacgtcgaa gagaatcccg gtccgatggc cctcccagta   1200

actgccctcc ttttgcccct cgcactcctt cttcatgccg ctcgccccaa ctgggtcaac   1260

gtgattagcg atttgaagaa aatcgaggac cttatacagt ctatgcatat tgacgctaca   1320

ctgtatactg agagtgatgt acacccgtcc tgtaaggtaa cggccatgaa atgctttctt   1380

ctggagctcc aggtcatcag cttggagtct ggggacgcaa gcatccacga tacggttgaa   1440

aacctcatca tccttgcgaa caactctctc tcatctaatg gaaacgttac agagagtggg   1500

tgtaaggagt gcgaagagtt ggaagaaaaa aacatcaaag aatttcttca atccttcgtt   1560

cacatagtgc aaatgttcat taacacgtcc actaccacac ccgccccgag gccacctacg   1620

ccggcaccga ctatcgccag tcaacccctc tctctgcgcc ccgaggcttg ccggcctgcg   1680

gctggtgggg cggtccacac ccggggcctg gattttgcgt gcgatatata catctgggca   1740

cctcttgccg gcacctgcgg agtgctgctt ctctcactcg ttattacgct gtactgc      1797
```

<210> SEQ ID NO 2
<211> LENGTH: 599
<212> TYPE: PRT
<213> ORGANISM: Homo sapiens
<220> FEATURE:

```
<221> NAME/KEY: MISC_FEATURE
<223> OTHER INFORMATION: NK45-5 AA

<400> SEQUENCE: 2

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
    210                 215                 220

Cys Arg Arg Asp Gln Arg Leu Pro Pro Asp Ala His Lys Pro Pro Gly
225                 230                 235                 240

Gly Gly Ser Phe Arg Thr Pro Ile Gln Glu Glu Gln Ala Asp Ala His
                245                 250                 255

Ser Thr Leu Ala Lys Ile Arg Val Lys Phe Ser Arg Ser Ala Asp Ala
            260                 265                 270

Pro Ala Tyr Gln Gln Gly Gln Asn Gln Leu Tyr Asn Glu Leu Asn Leu
        275                 280                 285

Gly Arg Arg Glu Glu Tyr Asp Val Leu Asp Lys Arg Arg Gly Arg Asp
    290                 295                 300

Pro Glu Met Gly Gly Lys Pro Arg Arg Lys Asn Pro Gln Glu Gly Leu
305                 310                 315                 320

Tyr Asn Glu Leu Gln Lys Asp Lys Met Ala Glu Ala Tyr Ser Glu Ile
                325                 330                 335

Gly Met Lys Gly Glu Arg Arg Arg Gly Lys Gly His Asp Gly Leu Tyr
            340                 345                 350

Gln Gly Leu Ser Thr Ala Thr Lys Asp Thr Tyr Asp Ala Leu His Met
        355                 360                 365

Gln Ala Leu Pro Pro Arg Gly Ser Gly Glu Gly Arg Gly Ser Leu Leu
    370                 375                 380

Thr Cys Gly Asp Val Glu Glu Asn Pro Gly Pro Met Ala Leu Pro Val
385                 390                 395                 400
```

-continued

Thr Ala Leu Leu Leu Pro Leu Ala Leu Leu Leu His Ala Ala Arg Pro
405 410 415

Asn Trp Val Asn Val Ile Ser Asp Leu Lys Lys Ile Glu Asp Leu Ile
420 425 430

Gln Ser Met His Ile Asp Ala Thr Leu Tyr Thr Glu Ser Asp Val His
435 440 445

Pro Ser Cys Lys Val Thr Ala Met Lys Cys Phe Leu Leu Glu Leu Gln
450 455 460

Val Ile Ser Leu Glu Ser Gly Asp Ala Ser Ile His Asp Thr Val Glu
465 470 475 480

Asn Leu Ile Ile Leu Ala Asn Asn Ser Leu Ser Ser Asn Gly Asn Val
485 490 495

Thr Glu Ser Gly Cys Lys Glu Cys Glu Glu Leu Glu Glu Lys Asn Ile
500 505 510

Lys Glu Phe Leu Gln Ser Phe Val His Ile Val Gln Met Phe Ile Asn
515 520 525

Thr Ser Thr Thr Thr Pro Ala Pro Arg Pro Pro Thr Pro Ala Pro Thr
530 535 540

Ile Ala Ser Gln Pro Leu Ser Leu Arg Pro Glu Ala Cys Arg Pro Ala
545 550 555 560

Ala Gly Gly Ala Val His Thr Arg Gly Leu Asp Phe Ala Cys Asp Ile
565 570 575

Tyr Ile Trp Ala Pro Leu Ala Gly Thr Cys Gly Val Leu Leu Leu Ser
580 585 590

Leu Val Ile Thr Leu Tyr Cys
595

<210> SEQ ID NO 3
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-No Flag-1

<400> SEQUENCE: 3
gaattcgccg ccaccatggc cttaccagtg accgccttgc tcctgccgct ggccttgctg 60
ctccacgccg ccaggccgga tattcagatg acccagagcc cgagcagcct gagcgcgagc 120
gtgggcgatc gcgtgaccat tacctgccgc gcgagccagg atattagcaa atatctgaac 180
tggtatcagc agaaaccggg cggcaccgtg aaactgctga tttatcatac cagccgcctg 240
catagcggcg tgccgagccg ctttagcggc agcggcagcg gcaccgattt taccctgacc 300
attagcagcc tgcagccgga agatattgcg acctattatt gccagcaggg caacaccctg 360
ccgtatacct ttggcggcgg caccaaactg gaaattaccg gtggcggtgg ctcgggcggt 420
ggtgggtcgg gtggcggcgg atctcaggtg cagctgcagg aaagcggccc gggcctggtg 480
aaaccgagcc agaccctgag cctgacctgc accgtgagcg gcgtgagcct gccggattat 540
ggcgtgagct ggattcgcca gccgccgggc aaaggcctgg aatggattgg cgtgatttgg 600
ggcagcgaaa ccacctatta taacagcgcg ctgaaaagcc gcctgaccat tagcaaagat 660
aacagcaaaa accaggtgag cctgaaactg agcagcgtga ccgcggcgga taccgcggtg 720
tattattgcg cgaaacatta ttattatggc ggcagctatg cgatggatta ttggggccag 780
ggcaccagcg tgaccgtgag cagcaccacg acgccagcgc cgcgaccacc aacaccggcg 840

```
cccaccatcg cgtcgcagcc cctgtccctg cgcccagagg cgtgccggcc agcggcgggg    900

ggcgcagtgc acacgagggg gctggacttc gcctgtgata tctacatctg ggcgcccttg    960

gccgggactt gtggggtcct tctcctgtca ctggttatca ccctttactg ccggagggac   1020

cagaggctgc cccccgatgc ccacaagccc cctgggggag gcagtttccg gacccccatc   1080

caagaggagc aggccgacgc ccactccacc ctggccaaga tcagagtgaa gttcagcagg   1140

agcgcagacg cccccgcgta ccagcagggc cagaaccagc tctataacga gctcaatcta   1200

ggacgaagag aggagtacga tgttttggac aagagacgtg gccgggaccc tgagatgggg   1260

ggaaagccga gaaggaagaa ccctcaggaa ggcctgtaca atgaactgca gaaagataag   1320

atggcggagg cctacagtga gattgggatg aaaggcgagc gccggagggg caaggggcac   1380

gatggccttt accagggtct cagtacagcc accaaggaca cctacgacgc ccttcacatg   1440

caggccctgc cccctcgcgg ctctggcgag ggaaggggtt ccctgcttac ttgcggcgac   1500

gtcgaagaga atcccggtcc gatggccctc ccagtaactg ccctcctttt gcccctcgca   1560

ctccttcttc atgccgctcg ccccaactgg gtcaacgtga ttagcgattt gaagaaaatc   1620

gaggacctta tacagtctat gcatattgac gctacactgt atactgagag tgatgtacac   1680

ccgtcctgta aggtaacggc catgaaatgc tttcttctgg agctccaggt catcagcttg   1740

gagtctgggg acgcaagcat ccacgatacg gttgaaaacc tcatcatcct tgcgaacaac   1800

tctctctcat ctaatggaaa cgttacagag agtgggtgta aggagtgcga agagttggaa   1860

gaaaaaaaca tcaaagaatt tcttcaatcc ttcgttcaca tagtgcaaat gttcattaac   1920

acgtccacta ccacacccgc cccgaggcca cctacgccgg caccgactat cgccagtcaa   1980

cccctctctc tgcgccccga ggcttgccgg cctgcggctg gtggggcggt ccacacccgg   2040

ggcctggatt ttgcgtgcga tatatacatc tgggcacctc ttgccggcac ctgcggagtg   2100

ctgcttctct cactcgttat tacgctgtac tgctaagcgg ccgcgtcgac               2150
```

<210> SEQ ID NO 4
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-No Flag-1

<400> SEQUENCE: 4

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Tyr Cys Gln Gln Gly
            100                 105                 110

Asn Thr Leu Pro Tyr Thr Phe Gly Gly Gly Thr Lys Leu Glu Ile Thr
        115                 120                 125
```

```
Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
```

```
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705


<210> SEQ ID NO 5
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-No Flag-2

<400> SEQUENCE: 5

gaattcgccg ccaccatggc cttaccagtg accgccttgc tcctgccgct ggccttgctg      60

ctccacgccg ccaggccgga tattcagatg acccagagcc cgagcagcct gagcgcgagc     120

gtgggcgatc gcgtgaccat tacctgccgc gcgagccagg atattagcaa atatctgaac     180

tggtatcagc agaaaccggg cggcaccgtg aaactgctga tttatcatac cagccgcctg     240

catagcggcg tgccgagccg ctttagcggc agcggcagcg gcaccgattt taccctgacc     300

attagcagcc tgcagccgga agatattgcg acctattttt gccagcaggg caacaccctg     360

ccgtatacct ttggcggcgg caccaaactg gaaattaccg gtggcggtgg ctcgggcggt     420

ggtgggtcgg gtggcggcgg atctcaggtg cagctgcagg aaagcggccc gggcctggtg     480

aaaccgagcc agaccctgag cctgacctgc accgtgagcg gcgtgagcct gccggattat     540

ggcgtgagct ggattcgcca gccgccgggc aaaggcctgg aatggattgg cgtgatttgg     600

ggcagcgaaa ccacctatta taacagcgcg ctgaaaagcc gcctgaccat tagcaaagat     660

aacagcaaaa accaggtgag cctgaaactg agcagcgtga ccgcggcgga taccgcggtg     720

tattattgcg cgaaacatta ttattatggc ggcagctatg cgatggatta ttggggccag     780

ggcaccagcg tgaccgtgag cagcaccacg acgccagcgc cgcgaccacc aacaccggcg     840

cccaccatcg cgtcgcagcc cctgtccctg cgcccagagg cgtgccggcc agcggcgggg     900

ggcgcagtgc acacgagggg gctggacttc gcctgtgata tctacatctg ggcgcccttg     960

gccgggactt gtggggtcct tctcctgtca ctggttatca ccctttactg ccggagggac    1020

cagaggctgc cccccgatgc ccacaagccc cctgggggag gcagtttccg gacccccatc    1080
```

```
caagaggagc aggccgacgc ccactccacc ctggccaaga tcagagtgaa gttcagcagg   1140

agcgcagacg cccccgcgta ccagcagggc cagaaccagc tctataacga gctcaatcta   1200

ggacgaagag aggagtacga tgttttggac aagagacgtg gccgggaccc tgagatgggg   1260

ggaaagccga gaaggaagaa ccctcaggaa ggcctgtaca atgaactgca gaaagataag   1320

atggcggagg cctacagtga gattgggatg aaaggcgagc gccggagggg caaggggcac   1380

gatggccttt accagggtct cagtacagcc accaaggaca cctacgacgc ccttcacatg   1440

caggccctgc cccctcgcgg ctctggcgag ggaaggggtt ccctgcttac ttgcggcgac   1500

gtcgaagaga atcccggtcc gatggccctc ccagtaactg ccctcctttt gcccctcgca   1560

ctccttcttc atgccgctcg ccccaactgg gtcaacgtga ttagcgattt gaagaaaatc   1620

gaggacctta tacagtctat gcatattgac gctacactgt atactgagag tgatgtacac   1680

ccgtcctgta aggtaacggc catgaaatgc tttcttctgg agctccaggt catcagcttg   1740

gagtctgggg acgcaagcat ccacgatacg gttgaaaacc tcatcatcct tgcgaacaac   1800

tctctctcat ctaatggaaa cgttacagag agtgggtgta aggagtgcga agagttggaa   1860

gaaaaaaaca tcaaagaatt tcttcaatcc ttcgttcaca tagtgcaaat gttcattaac   1920

acgtccacta ccacacccgc cccgaggcca cctacgccgg caccgactat cgccagtcaa   1980

cccctctctc tgcgccccga ggcttgccgg cctgcggctg gtggggcggt ccacacccgg   2040

ggcctggatt ttgcgtgcga tatatacatc tgggcacctc ttgccggcac ctgcggagtg   2100

ctgcttctct cactcgttat tacgctgtac tgctaagcgg ccgcgtcgac              2150
```

<210> SEQ ID NO 6
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-No Flag-2

<400> SEQUENCE: 6

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Leu Thr Cys Thr Val Ser Gly Val Ser Leu Pro Asp Tyr Gly
                165                 170                 175
```

```
Val Ser Trp Ile Arg Gln Pro Pro Gly Lys Gly Leu Glu Trp Ile Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590
```

```
Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705
```

<210> SEQ ID NO 7
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-No Flag-3

<400> SEQUENCE: 7

```
gaattcgccg ccaccatggc cttaccagtg accgccttgc tcctgccgct ggccttgctg     60

ctccacgccg ccaggccgga tattcagatg acccagagcc cgagcagcct gagcgcgagc    120

gtgggcgatc gcgtgaccat tacctgccgc gcgagccagg atattagcaa atatctgaac    180

tggtatcagc agaaaccgga tggcaccgtg aaactgctga tttatcatac cagccgcctg    240

catagcggcg tgccgagccg ctttagcggc agcggcagcg gcaccgatta taccctgacc    300

attagcagcc tgcagccgga agatattgcg acctattttt gccagcaggg caacaccctg    360

ccgtatacct ttggcggcgg caccaaactg gaaattaccg gtggcggtgg ctcgggcggt    420

ggtgggtcgg gtggcggcgg atctcaggtg cagctgcagg aaagcggccc gggcctggtg    480

aaaccgagcc agaccctgag cctgacctgc accgtgagcg gcgtgagcct gccggattat    540

ggcgtgagct ggattcgcca gccgccgggc aaaggcctgg aatggattgg cgtgatttgg    600

ggcagcgaaa ccacctatta taacagcgcg ctgaaaagcc gcctgaccat tagcaaagat    660

aacagcaaaa accaggtgag cctgaaactg agcagcgtga ccgcggcgga taccgcggtg    720

tattattgcg cgaaacatta ttattatggc ggcagctatg cgatggatta ttggggccag    780

ggcaccagcg tgaccgtgag cagcaccacg acgccagcgc cgcgaccacc aacaccggcg    840

cccaccatcg cgtcgcagcc cctgtccctg cgcccagagg cgtgccggcc agcggcgggg    900

ggcgcagtgc acacgagggg gctggacttc gcctgtgata tctacatctg ggcgcccttg    960

gccgggactt gtggggtcct tctcctgtca ctggttatca ccctttactg ccggagggac   1020

cagaggctgc cccccgatgc ccacaagccc cctgggggag gcagtttccg gacccccatc   1080

caagaggagc aggccgacgc ccactccacc ctggccaaga tcagagtgaa gttcagcagg   1140

agcgcagacg cccccgcgta ccagcagggc cagaaccagc tctataacga gctcaatcta   1200

ggacgaagag aggagtacga tgttttggac aagagacgtg gccgggaccc tgagatgggg   1260

ggaaagccga gaaggaagaa ccctcaggaa ggcctgtaca atgaactgca gaaagataag   1320
```

```
atggcggagg cctacagtga gattgggatg aaaggcgagc gccggagggg caaggggcac   1380

gatggccttt accagggtct cagtacagcc accaaggaca cctacgacgc ccttcacatg   1440

caggccctgc cccctcgcgg ctctggcgag ggaaggggtt ccctgcttac ttgcggcgac   1500

gtcgaagaga atcccggtcc gatggccctc ccagtaactg ccctcctttt gcccctcgca   1560

ctccttcttc atgccgctcg ccccaactgg gtcaacgtga ttagcgattt gaagaaaatc   1620

gaggacctta tacagtctat gcatattgac gctacactgt atactgagag tgatgtacac   1680

ccgtcctgta aggtaacggc catgaaatgc tttcttctgg agctccaggt catcagcttg   1740

gagtctgggg acgcaagcat ccacgatacg gttgaaaacc tcatcatcct tgcgaacaac   1800

tctctctcat ctaatggaaa cgttacagag agtgggtgta aggagtgcga agagttggaa   1860

gaaaaaaaca tcaaagaatt tcttcaatcc ttcgttcaca tagtgcaaat gttcattaac   1920

acgtccacta ccacacccgc cccgaggcca cctacgccgg caccgactat cgccagtcaa   1980

cccctctctc tgcgccccga ggcttgccgg cctgcggctg gtggggcggt ccacacccgg   2040

ggcctggatt ttgcgtgcga tatatacatc tgggcacctc ttgccggcac ctgcggagtg   2100

ctgcttctct cactcgttat tacgctgtac tgctaagcgg ccgcgtcgac               2150
```

<210> SEQ ID NO 8
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-No Flag-3

<400> SEQUENCE: 8

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Asn Gln Val Ser Leu Lys
```

```
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640
```

```
Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705


<210> SEQ ID NO 9
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-No Flag-4

<400> SEQUENCE: 9

gaattcgccg ccaccatggc cttaccagtg accgccttgc tcctgccgct ggccttgctg     60

ctccacgccg ccaggccgga tattcagatg acccagagcc cgagcagcct gagcgcgagc    120

gtgggcgatc gcgtgaccat tacctgccgc gcgagccagg atattagcaa atatctgaac    180

tggtatcagc agaaaccggg cggcaccgtg aaactgctga tttatcatac cagccgcctg    240

catagcggcg tgccgagccg ctttagcggc agcggcagcg gcaccgattt taccctgacc    300

attagcagcc tgcagccgga agatattgcg acctattatt gccagcaggg caacaccctg    360

ccgtatacct ttggcggcgg caccaaactg gaaattaccg gtggcggtgg ctcgggcggt    420

ggtgggtcgg gtggcggcgg atctcaggtg cagctgcagg aaagcggccc gggcctggtg    480

aaaccgagcc agaccctgag cctgacctgc accgtgagcg gcgtgagcct gccggattat    540

ggcgtgagct ggattcgcca gccgccgggc aaaggcctgg aatggctggg cgtgatttgg    600

ggcagcgaaa ccacctatta taacagcgcg ctgaaaagcc gcctgaccat tagcaaagat    660

aacagcaaaa gccaggtgag cctgaaactg agcagcgtga ccgcggcgga taccgcggtg    720

tattattgcg cgaaacatta ttattatggc ggcagctatg cgatggatta ttggggccag    780

ggcaccagcg tgaccgtgag cagcaccacg acgccagcgc cgcgaccacc aacaccggcg    840

cccaccatcg cgtcgcagcc cctgtccctg cgcccagagg cgtgccggcc agcggcgggg    900

ggcgcagtgc acacgagggg gctggacttc gcctgtgata tctacatctg ggcgcccttg    960

gccgggactt gtggggtcct tctcctgtca ctggttatca ccctttactg ccggagggac   1020

cagaggctgc cccccgatgc ccacaagccc cctgggggag gcagtttccg gacccccatc   1080

caagaggagc aggccgacgc ccactccacc ctggccaaga tcagagtgaa gttcagcagg   1140

agcgcagacg cccccgcgta ccagcagggc cagaaccagc tctataacga gctcaatcta   1200

ggacgaagag aggagtacga tgttttggac aagagacgtg gccgggaccc tgagatgggg   1260

ggaaagccga gaaggaagaa ccctcaggaa ggcctgtaca atgaactgca gaaagataag   1320

atggcggagg cctacagtga gattgggatg aaaggcgagc gccggagggg caaggggcac   1380

gatggccttt accagggtct cagtacagcc accaaggaca cctacgacgc ccttcacatg   1440

caggccctgc cccctcgcgg ctctggcgag ggaaggggtt ccctgcttac ttgcggcgac   1500

gtcgaagaga atcccggtcc gatggccctc ccagtaactg ccctcctttt gcccctcgca   1560
```

```
ctccttcttc atgccgctcg ccccaactgg gtcaacgtga ttagcgattt gaagaaaatc   1620

gaggacctta tacagtctat gcatattgac gctacactgt atactgagag tgatgtacac   1680

ccgtcctgta aggtaacggc catgaaatgc tttcttctgg agctccaggt catcagcttg   1740

gagtctgggg acgcaagcat ccacgatacg gttgaaaacc tcatcatcct tgcgaacaac   1800

tctctctcat ctaatggaaa cgttacagag agtgggtgta aggagtgcga agagttggaa   1860

gaaaaaaaca tcaaagaatt tcttcaatcc ttcgttcaca tagtgcaaat gttcattaac   1920

acgtccacta ccacacccgc cccgaggcca cctacgccgg caccgactat cgccagtcaa   1980

cccctctctc tgcgccccga ggcttgccgg cctgcggctg gtggggcggt ccacacccgg   2040

ggcctggatt ttgcgtgcga tatatacatc tgggcacctc ttgccggcac ctgcggagtg   2100

ctgcttctct cactcgttat tacgctgtac tgctaagcgg ccgcgtcgac              2150
```

<210> SEQ ID NO 10
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-No Flag-4

<400> SEQUENCE: 10

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Tyr Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255
```

-continued

```
Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
```

675 680 685

Leu Ala Gly Thr Cys Gly Val Leu Leu Leu Ser Leu Val Ile Thr Leu
690 695 700

Tyr Cys
705

<210> SEQ ID NO 11
<211> LENGTH: 2153
<212> TYPE: DNA
<213> ORGANISM: Homo sapiens
<220> FEATURE:
<221> NAME/KEY: misc_feature
<223> OTHER INFORMATION: DNA NK19H-No Flag-5

<400> SEQUENCE: 11
gaattcgccg ccaccatggc cttaccagtg accgccttgc tcctgccgct ggccttgctg 60
ctccacgccg ccaggccgga tattcagatg acccagagcc cgagcagcct gagcgcgagc 120
gtgggcgatc gcgtgaccat tacctgccgc gcgagccagg atattagcaa atatctgaac 180
tggtatcagc agaaaccggg cggcaccgtg aaactgctga tttatcatac cagccgcctg 240
catagcggcg tgccgagccg ctttagcggc agcggcagcg gcaccgattt taccctgacc 300
attagcagcc tgcagccgga agatattgcg acctattttt gccagcaggg caacaccctg 360
ccgtatacct ttggcggcgg caccaaactg gaaattaccg gtggcggtgg ctcgggcggt 420
ggtgggtcgg gtggcggcgg atctcaggtg cagctgcagg agtcaggacc tggcctggtg 480
aaaccctcac agactctgtc cctgacatgc actgtctcag ggtctcatt acccgactat 540 ggtgtaagct ggattcgcca gcctccaggt aagggtctgg agtggctggg agtaatatgg 600
ggtagtgaaa ccacatacta taattcagct ctcaaatcca gactgaccat ctccaaggac 660
aactccaaga gccaagtttc cttaaaatta agtagtgtta ctgctgctga cacagccgtc 720
tactactgtg ccaaacatta ttactacggt ggtagctatg ctatggacta ctggggccaa 780
ggaacctcag tcaccgtctc ctcaaccacg acgccagcgc cgcgaccacc aacaccggcg 840
cccaccatcg cgtcgcagcc cctgtccctg cgcccagagg cgtgccggcc agcggcgggg 900
ggcgcagtgc acacgagggg gctggacttc gcctgtgata tctacatctg ggcgcccttg 960
gccgggactt gtggggtcct tctcctgtca ctggttatca ccctttactg ccggagggac 1020
cagaggctgc cccccgatgc ccacaagccc cctgggggag gcagtttccg gacccccatc 1080
caagaggagc aggccgacgc ccactccacc ctggccaaga tcagagtgaa gttcagcaga 1140
tctagcgcag acgcccccgc gtaccagcag ggccagaacc agctctataa cgagctcaat 1200
ctaggacgaa gagaggagta cgatgttttg gacaagagac gtggccggga ccctgagatg 1260
gggggaaagc cgagaaggaa gaaccctcag gaaggcctgt acaatgaact gcagaaagat 1320
aagatggcgg aggcctacag tgagattggg atgaaaggcg agcgccggag gggcaagggg 1380
cacgatggcc tttaccaggg tctcagtaca gccaccaagg acacctacga cgcccttcac 1440
atgcaggccc tgccccctcg cggctctggc gagggaaggg gttccctgct tacttgcggc 1500
gacgtcgaag agaatcccgg tccgatggcc ctcccagtaa ctgccctcct tttgcccctc 1560
gcactccttc ttcatgccgc tcgccccaac tgggtcaacg tgattagcga tttgaagaaa 1620
atcgaggacc ttatacagtc tatgcatatt gacgctacac tgtatactga gagtgatgta 1680
cacccgtcct gtaaggtaac ggccatgaaa tgctttcttc tggagctcca ggtcatcagc 1740
ttggagtctg gggacgcaag catccacgat acggttgaaa acctcatcat ccttgcgaac 1800

```
aactctctct catctaatgg aaacgttaca gagagtgggt gtaaggagtg cgaagagttg   1860

gaagaaaaaa acatcaaaga atttcttcaa tccttcgttc acatagtgca aatgttcatt   1920

aacacgtcca ctaccacacc cgccccgagg ccacctacgc cggcaccgac tatcgccagt   1980

caacccctct ctctgcgccc cgaggcttgc cggcctgcgg ctggtggggc ggtccacacc   2040

cggggcctgg attttgcgtg cgatatatac atctgggcac ctcttgccgg cacctgcgga   2100

gtgctgcttc tctcactcgt tattacgctg tactgctaag cggccgcgtc gac           2153


<210> SEQ ID NO 12
<211> LENGTH: 707
<212> TYPE: PRT
<213> ORGANISM: Homo sapiens
<220> FEATURE:
<221> NAME/KEY: MISC_FEATURE
<223> OTHER INFORMATION: AA NK19H-No Flag-5

<400> SEQUENCE: 12

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300
```

```
Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg Gly Ser Gly Glu Gly Arg Gly Ser Leu Leu Thr Cys Gly Asp
                485                 490                 495

Val Glu Glu Asn Pro Gly Pro Met Ala Leu Pro Val Thr Ala Leu Leu
            500                 505                 510

Leu Pro Leu Ala Leu Leu Leu His Ala Ala Arg Pro Asn Trp Val Asn
        515                 520                 525

Val Ile Ser Asp Leu Lys Lys Ile Glu Asp Leu Ile Gln Ser Met His
    530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
                565                 570                 575

Glu Ser Gly Asp Ala Ser Ile His Asp Thr Val Glu Asn Leu Ile Ile
            580                 585                 590

Leu Ala Asn Asn Ser Leu Ser Ser Asn Gly Asn Val Thr Glu Ser Gly
        595                 600                 605

Cys Lys Glu Cys Glu Glu Leu Glu Glu Lys Asn Ile Lys Glu Phe Leu
    610                 615                 620

Gln Ser Phe Val His Ile Val Gln Met Phe Ile Asn Thr Ser Thr Thr
625                 630                 635                 640

Thr Pro Ala Pro Arg Pro Pro Thr Pro Ala Pro Thr Ile Ala Ser Gln
                645                 650                 655

Pro Leu Ser Leu Arg Pro Glu Ala Cys Arg Pro Ala Ala Gly Gly Ala
            660                 665                 670

Val His Thr Arg Gly Leu Asp Phe Ala Cys Asp Ile Tyr Ile Trp Ala
        675                 680                 685

Pro Leu Ala Gly Thr Cys Gly Val Leu Leu Leu Ser Leu Val Ile Thr
    690                 695                 700

Leu Tyr Cys
705
```

<210> SEQ ID NO 13
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-No Flag-6

<400> SEQUENCE: 13
gaattcgccg ccaccatggc cttaccagtg accgccttgc tcctgccgct ggccttgctg 60
ctccacgccg ccaggccgga catccagatg acacagagcc cgtcctccct gtctgcctct 120
gtgggagaca gagtcaccat cacctgcagg gcaagtcagg acattagtaa atatttaaat 180
tggtatcagc agaaaccaga cggaactgtt aaactcctga tctaccatac atcaagatta 240
cactcaggag tcccatcaag gttcagtggc agtgggtctg gaacagatta caccctcacc 300
attagcagcc tgcaaccgga agatattgcc acttacttct gccaacaggg taatacgctt 360
ccgtacacgt tcggaggggg gaccaagctg gagatcacag gtggcggtgg ctcgggcggt 420
ggtgggtcgg gtggcggcgg atctcaggtg cagctgcagg agtcaggacc tggcctggtg 480
aaaccctcac agactctgtc cctgacatgc actgtctcag ggtctcatt acccgactat 540 ggtgtaagct ggattcgcca gcctccaggt aagggtctgg agtggctggg agtaatatgg 600
ggtagtgaaa ccacatacta taattcagct ctcaaatcca gactgaccat ctccaaggac 660
aactccaaga gccaagtttc cttaaaatta agtagtgtta ctgctgctga cacagccgtc 720
tactactgtg ccaaacatta ttactacggt ggtagctatg ctatggacta ctggggccaa 780
ggaacctcag tcaccgtctc ctcaaccacg acgccagcgc cgcgaccacc aacaccggcg 840
cccaccatcg cgtcgcagcc cctgtccctg cgcccagagg cgtgccggcc agcggcgggg 900
ggcgcagtgc acacgagggg gctggacttc gcctgtgata tctacatctg ggcgcccttg 960
gccgggactt gtggggtcct tctcctgtca ctggttatca ccctttactg ccggagggac 1020
cagaggctgc cccccgatgc ccacaagccc cctgggggag gcagtttccg gacccccatc 1080
caagaggagc aggccgacgc ccactccacc ctggccaaga tcagagtgaa gttcagcagg 1140
agcgcagacg cccccgcgta ccagcagggc cagaaccagc tctataacga gctcaatcta 1200
ggacgaagag aggagtacga tgttttggac aagagacgtg gccgggaccc tgagatgggg 1260
ggaaagccga gaaggaagaa ccctcaggaa ggcctgtaca atgaactgca gaaagataag 1320
atggcggagg cctacagtga gattgggatg aaaggcgagc gccggagggg caaggggcac 1380
gatggccttt accagggtct cagtacagcc accaaggaca cctacgacgc ccttcacatg 1440
caggccctgc cccctcgcgg ctctggcgag ggaaggggtt ccctgcttac ttgcggcgac 1500
gtcgaagaga atcccggtcc gatggccctc ccagtaactg ccctcctttt gcccctcgca 1560
ctccttcttc atgccgctcg ccccaactgg gtcaacgtga ttagcgattt gaagaaaatc 1620
gaggacctta tacagtctat gcatattgac gctacactgt atactgagag tgatgtacac 1680
ccgtcctgta aggtaacggc catgaaatgc tttcttctgg agctccaggt catcagcttg 1740
gagtctgggg acgcaagcat ccacgatacg gttgaaaacc tcatcatcct tgcgaacaac 1800
tctctctcat ctaatggaaa cgttacagag agtgggtgta aggagtgcga agagttggaa 1860
gaaaaaaaca tcaaagaatt tcttcaatcc ttcgttcaca tagtgcaaat gttcattaac 1920
acgtccacta ccacacccgc cccgaggcca cctacgccgg caccgactat cgccagtcaa 1980
cccctctctc tgcgccccga ggcttgccgg cctgcggctg gtggggcggt ccacacccgg 2040
ggcctggatt ttgcgtgcga tatatacatc tgggcacctc ttgccggcac ctgcggagtg 2100
ctgcttctct cactcgttat tacgctgtac tgctaagcgg ccgcgtcgac 2150

<210> SEQ ID NO 14
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-No Flag-6

<400> SEQUENCE: 14

Met Ala Leu Pro Val Thr Ala Leu Leu Leu Pro Leu Ala Leu Leu Leu
1 5 10 15

His Ala Ala Arg Pro Asp Ile Gln Met Thr Gln Ser Pro Ser Ser Leu
20 25 30

Ser Ala Ser Val Gly Asp Arg Val Thr Ile Thr Cys Arg Ala Ser Gln
35 40 45

Asp Ile Ser Lys Tyr Leu Asn Trp Tyr Gln Gln Lys Pro Asp Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Tyr Thr Leu Thr Ile
85 90 95

Ser Ser Leu Gln Pro Glu Asp Ile Ala Thr Tyr Phe Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Gly Ser Gln
130 135 140

Val Gln Leu Gln Glu Ser Gly Pro Gly Leu Val Lys Pro Ser Gln Thr
145 150 155 160

Leu Ser Leu Thr Cys Thr Val Ser Gly Val Ser Leu Pro Asp Tyr Gly
165 170 175

Val Ser Trp Ile Arg Gln Pro Pro Gly Lys Gly Leu Glu Trp Leu Gly
180 185 190

Val Ile Trp Gly Ser Glu Thr Thr Tyr Tyr Asn Ser Ala Leu Lys Ser
195 200 205

Arg Leu Thr Ile Ser Lys Asp Asn Ser Lys Ser Gln Val Ser Leu Lys
210 215 220

Leu Ser Ser Val Thr Ala Ala Asp Thr Ala Val Tyr Tyr Cys Ala Lys
225 230 235 240

His Tyr Tyr Tyr Gly Gly Ser Tyr Ala Met Asp Tyr Trp Gly Gln Gly
245 250 255

Thr Ser Val Thr Val Ser Ser Thr Thr Thr Pro Ala Pro Arg Pro Pro
260 265 270

Thr Pro Ala Pro Thr Ile Ala Ser Gln Pro Leu Ser Leu Arg Pro Glu
275 280 285

Ala Cys Arg Pro Ala Ala Gly Gly Ala Val His Thr Arg Gly Leu Asp
290 295 300

Phe Ala Cys Asp Ile Tyr Ile Trp Ala Pro Leu Ala Gly Thr Cys Gly
305 310 315 320

Val Leu Leu Leu Ser Leu Val Ile Thr Leu Tyr Cys Arg Arg Asp Gln
325 330 335

Arg Leu Pro Pro Asp Ala His Lys Pro Pro Gly Gly Gly Ser Phe Arg

```
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705


<210> SEQ ID NO 15
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-No Flag-7
```

<400> SEQUENCE: 15
gaattcgccg ccaccatggc cttaccagtg accgccttgc tcctgccgct ggccttgctg 60
ctccacgccg ccaggccgga catccagatg acacagagcc cgtcctccct gtctgcctct 120
gtgggagaca gagtcaccat cacctgcagg gcaagtcagg acattagtaa atatttaaat 180
tggtatcagc agaaaccagg tggaactgtt aaactcctga tctaccatac atcaagatta 240
cactcaggag tcccatcaag gttcagtggc agtgggtctg gaacagattt caccctcacc 300
attagcagcc tgcaaccgga agatattgcc acttactact gccaacaggg taatacgctt 360
ccgtacacgt tcggaggggg gaccaagctg gagatcacag gtggcggtgg ctcgggcggt 420
ggtgggtcgg gtggcggcgg atctcaggtg cagctgcagg agtcaggacc tggcctggtg 480
aaaccctcac agactctgtc cgtgacatgc actgtctcag ggtctcatt acccgactat 540
ggtgtaagct ggattcgcca gcctccaggt aagggtctgg agtggctggg agtaatatgg 600
ggtagtgaaa ccacatacta taattcagct ctcaaatcca gactgaccat ctccaaggac 660
aactccaaga gccaagtttc cttaaaatta agtagtgtta ctgctgctga cacagccgtc 720
tactactgtg ccaaacatta ttactacggt ggtagctatg ctatggacta ctggggccaa 780
ggaacctcag tcaccgtctc ctcaaccacg acgccagcgc cgcgaccacc aacaccggcg 840
cccaccatcg cgtcgcagcc cctgtccctg cgcccagagg cgtgccggcc agcggcgggg 900
ggcgcagtgc acacgagggg gctggacttc gcctgtgata tctacatctg ggcgcccttg 960
gccgggactt gtggggtcct tctcctgtca ctggttatca ccctttactg ccggagggac 1020
cagaggctgc cccccgatgc ccacaagccc cctgggggag gcagtttccg gacccccatc 1080
caagaggagc aggccgacgc ccactccacc ctggccaaga tcagagtgaa gttcagcagg 1140
agcgcagacg cccccgcgta ccagcagggc cagaaccagc tctataacga gctcaatcta 1200
ggacgaagag aggagtacga tgttttggac aagagacgtg gccgggaccc tgagatgggg 1260
ggaaagccga gaaggaagaa ccctcaggaa ggcctgtaca atgaactgca gaaagataag 1320
atggcggagg cctacagtga gattgggatg aaaggcgagc gccggagggg caaggggcac 1380
gatggccttt accagggtct cagtacagcc accaaggaca cctacgacgc ccttcacatg 1440
caggccctgc cccctcgcgg ctctggcgag ggaaggggtt ccctgcttac ttgcggcgac 1500
gtcgaagaga atcccggtcc gatggccctc ccagtaactg ccctcctttt gcccctcgca 1560
ctccttcttc atgccgctcg ccccaactgg gtcaacgtga ttagcgattt gaagaaaatc 1620
gaggacctta tacagtctat gcatattgac gctacactgt atactgagag tgatgtacac 1680
ccgtcctgta aggtaacggc catgaaatgc tttcttctgg agctccaggt catcagcttg 1740
gagtctgggg acgcaagcat ccacgatacg gttgaaaacc tcatcatcct tgcgaacaac 1800
tctctctcat ctaatggaaa cgttacagag agtgggtgta aggagtgcga agagttggaa 1860
gaaaaaaaca tcaaagaatt tcttcaatcc ttcgttcaca tagtgcaaat gttcattaac 1920
acgtccacta ccacacccgc cccgaggcca cctacgccgg caccgactat cgccagtcaa 1980
cccctctctc tgcgccccga ggcttgccgg cctgcggctg gtggggcggt ccacacccgg 2040
ggcctggatt ttgcgtgcga tatatacatc tgggcacctc ttgccggcac ctgcggagtg 2100
ctgcttctct cactcgttat tacgctgtac tgctaagcgg ccgcgtcgac 2150

<210> SEQ ID NO 16
<211> LENGTH: 706
<212> TYPE: PRT

<213> ORGANISM: Homo sapiens
<220> FEATURE:
<221> NAME/KEY: MISC_FEATURE
<223> OTHER INFORMATION: AA NK19H-No Flag-7

<400> SEQUENCE: 16

Met Ala Leu Pro Val Thr Ala Leu Leu Leu Pro Leu Ala Leu Leu Leu
1 5 10 15

His Ala Ala Arg Pro Asp Ile Gln Met Thr Gln Ser Pro Ser Ser Leu
20 25 30

Ser Ala Ser Val Gly Asp Arg Val Thr Ile Thr Cys Arg Ala Ser Gln
35 40 45

Asp Ile Ser Lys Tyr Leu Asn Trp Tyr Gln Gln Lys Pro Gly Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Phe Thr Leu Thr Ile
85 90 95

Ser Ser Leu Gln Pro Glu Asp Ile Ala Thr Tyr Tyr Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Gly Ser Gln
130 135 140

Val Gln Leu Gln Glu Ser Gly Pro Gly Leu Val Lys Pro Ser Gln Thr
145 150 155 160

Leu Ser Val Thr Cys Thr Val Ser Gly Val Ser Leu Pro Asp Tyr Gly
165 170 175

Val Ser Trp Ile Arg Gln Pro Pro Gly Lys Gly Leu Glu Trp Leu Gly
180 185 190

Val Ile Trp Gly Ser Glu Thr Thr Tyr Tyr Asn Ser Ala Leu Lys Ser
195 200 205

Arg Leu Thr Ile Ser Lys Asp Asn Ser Lys Ser Gln Val Ser Leu Lys
210 215 220

Leu Ser Ser Val Thr Ala Ala Asp Thr Ala Val Tyr Tyr Cys Ala Lys
225 230 235 240

His Tyr Tyr Tyr Gly Gly Ser Tyr Ala Met Asp Tyr Trp Gly Gln Gly
245 250 255

Thr Ser Val Thr Val Ser Ser Thr Thr Thr Pro Ala Pro Arg Pro Pro
260 265 270

Thr Pro Ala Pro Thr Ile Ala Ser Gln Pro Leu Ser Leu Arg Pro Glu
275 280 285

Ala Cys Arg Pro Ala Ala Gly Gly Ala Val His Thr Arg Gly Leu Asp
290 295 300

Phe Ala Cys Asp Ile Tyr Ile Trp Ala Pro Leu Ala Gly Thr Cys Gly
305 310 315 320

Val Leu Leu Leu Ser Leu Val Ile Thr Leu Tyr Cys Arg Arg Asp Gln
325 330 335

Arg Leu Pro Pro Asp Ala His Lys Pro Pro Gly Gly Gly Ser Phe Arg
340 345 350

Thr Pro Ile Gln Glu Glu Gln Ala Asp Ala His Ser Thr Leu Ala Lys
355 360 365

Ile Arg Val Lys Phe Ser Arg Ser Ala Asp Ala Pro Ala Tyr Gln Gln
370 375 380

```
Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705
```

<210> SEQ ID NO 17
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-No Flag-8

<400> SEQUENCE: 17

```
gaattcgccg ccaccatggc cttaccagtg accgccttgc tcctgccgct ggccttgctg      60

ctccacgccg ccaggccgga catccagatg acacagagcc cgtcctccct gtctgcctct     120

gtgggagaca gagtcaccat cacctgcagg gcaagtcagg acattagtaa atatttaaat     180
```

```
tggtatcagc agaaaccagg tggaactgtt aaactcctga tctaccatac atcaagatta    240
cactcaggag tcccatcaag gttcagtggc agtgggtctg gaacagattt caccctcacc    300
attagcagcc tgcaaccgga agatattgcc acttacttct gccaacaggg taatacgctt    360
ccgtacacgt tcggaggggg gaccaagctg gagatcacag gtggcggtgg ctcgggcggt    420
ggtgggtcgg gtggcggcgg atctcaggtg cagctgcagg agtcaggacc tggcctggtg    480
aaaccctcac agactctgtc cgtgacatgc actgtctcag ggtctcatt acccgactat     540
ggtgtaagct ggattcgcca gcctccaggt aagggtctgg agtggctggg agtaatatgg    600
ggtagtgaaa ccacatacta taattcagct ctcaaatcca gactgaccat ctccaaggac    660
aactccaaga gccaagtttc cttaaaatta agtagtgtta ctgctgctga cacagccgtc    720
tactactgtg ccaaacatta ttactacggt ggtagctatg ctatggacta ctggggccaa    780
ggaacctcag tcaccgtctc ctcaaccacg acgccagcgc cgcgaccacc aacaccggcg    840
cccaccatcg cgtcgcagcc cctgtccctg cgcccagagg cgtgccggcc agcggcgggg    900
ggcgcagtgc acacgagggg gctggacttc gcctgtgata tctacatctg ggcgcccttg    960
gccgggactt gtggggtcct tctcctgtca ctggttatca ccctttactg ccggagggac   1020
cagaggctgc cccccgatgc ccacaagccc cctgggggag gcagtttccg gacccccatc   1080
caagaggagc aggccgacgc ccactccacc ctggccaaga tcagagtgaa gttcagcagg   1140
agcgcagacg cccccgcgta ccagcagggc cagaaccagc tctataacga gctcaatcta   1200
ggacgaagag aggagtacga tgttttggac aagagacgtg gccgggaccc tgagatgggg   1260
ggaaagccga gaaggaagaa ccctcaggaa ggcctgtaca atgaactgca gaaagataag   1320
atggcggagg cctacagtga gattgggatg aaaggcgagc gccggagggg caaggggcac   1380
gatggccttt accagggtct cagtacagcc accaaggaca cctacgacgc ccttcacatg   1440
caggccctgc cccctcgcgg ctctggcgag ggaaggggtt ccctgcttac ttgcggcgac   1500
gtcgaagaga atcccggtcc gatggccctc ccagtaactg ccctcctttt gcccctcgca   1560
ctccttcttc atgccgctcg ccccaactgg gtcaacgtga ttagcgattt gaagaaaatc   1620
gaggacctta tacagtctat gcatattgac gctacactgt atactgagag tgatgtacac   1680
ccgtcctgta aggtaacggc catgaaatgc tttcttctgg agctccaggt catcagcttg   1740
gagtctgggg acgcaagcat ccacgatacg gttgaaaacc tcatcatcct tgcgaacaac   1800
tctctctcat ctaatggaaa cgttacagag agtgggtgta aggagtgcga agagttggaa   1860
gaaaaaaaca tcaaagaatt tcttcaatcc ttcgttcaca tagtgcaaat gttcattaac   1920
acgtccacta ccacacccgc cccgaggcca cctacgccgg caccgactat cgccagtcaa   1980
cccctctctc tgcgccccga ggcttgccgg cctgcggctg gtggggcggt ccacacccgg   2040
ggcctggatt ttgcgtgcga tatatacatc tgggcacctc ttgccggcac ctgcggagtg   2100
ctgcttctct cactcgttat tacgctgtac tgctaagcgg ccgcgtcgac               2150
```

<210> SEQ ID NO 18
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-No Flag-8

<400> SEQUENCE: 18

Met Ala Leu Pro Val Thr Ala Leu Leu Leu Pro Leu Ala Leu Leu Leu

-continued

```
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430
```

```
Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705
```

<210> SEQ ID NO 19
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-No Flag-9

<400> SEQUENCE: 19

```
gaattcgccg ccaccatggc cttaccagtg accgccttgc tcctgccgct ggccttgctg      60

ctccacgccg ccaggccgga catccagatg acacagagcc cgtcctccct gtctgcctct     120

gtgggagaca gagtcaccat cacctgcagg gcaagtcagg acattagtaa atatttaaat     180

tggtatcagc agaaaccaga cggaactgtt aaactcctga tctaccatac atcaagatta     240

cactcaggag tcccatcaag gttcagtggc agtgggtctg gaacagatta caccctcacc     300

attagcagcc tgcaaccgga agatattgcc acttacttct gccaacaggg taatacgctt     360

ccgtacacgt tcggaggggg gaccaagctg gagatcacag gtggcggtgg ctcgggcggt     420
```

```
ggtgggtcgg gtggcggcgg atctcaggtg cagctgcagg agtcaggacc tggcctggtg    480

aaaccctcac agactctgtc cgtgacatgc actgtctcag ggtctcatt acccgactat    540

ggtgtaagct ggattcgcca gcctccaggt aagggtctgg agtggctggg agtaatatgg    600

ggtagtgaaa ccacatacta taattcagct ctcaaatcca gactgaccat ctccaaggac    660

aactccaaga gccaagtttc cttaaaatta agtagtgtta ctgctgctga cacagccgtc    720

tactactgtg ccaaacatta ttactacggt ggtagctatg ctatggacta ctggggccaa    780

ggaacctcag tcaccgtctc ctcaaccacg acgccagcgc cgcgaccacc aacaccggcg    840

cccaccatcg cgtcgcagcc cctgtccctg cgcccagagg cgtgccggcc agcggcgggg    900

ggcgcagtgc acacgagggg gctggacttc gcctgtgata tctacatctg ggcgcccttg    960

gccgggactt gtggggtcct tctcctgtca ctggttatca ccctttactg ccggagggac   1020

cagaggctgc cccccgatgc ccacaagccc cctgggggag gcagtttccg gacccccatc   1080

caagaggagc aggccgacgc ccactccacc ctggccaaga tcagagtgaa gttcagcagg   1140

agcgcagacg cccccgcgta ccagcagggc cagaaccagc tctataacga gctcaatcta   1200

ggacgaagag aggagtacga tgttttggac aagagacgtg gccgggaccc tgagatgggg   1260

ggaaagccga gaaggaagaa ccctcaggaa ggcctgtaca atgaactgca gaaagataag   1320

atggcggagg cctacagtga gattgggatg aaaggcgagc gccggagggg caaggggcac   1380

gatggccttt accagggtct cagtacagcc accaaggaca cctacgacgc ccttcacatg   1440

caggccctgc cccctcgcgg ctctggcgag ggaaggggtt ccctgcttac ttgcggcgac   1500

gtcgaagaga atcccggtcc gatggccctc ccagtaactg ccctcctttt gcccctcgca   1560

ctccttcttc atgccgctcg ccccaactgg gtcaacgtga ttagcgattt gaagaaaatc   1620

gaggacctta tacagtctat gcatattgac gctacactgt atactgagag tgatgtacac   1680

ccgtcctgta aggtaacggc catgaaatgc tttcttctgg agctccaggt catcagcttg   1740

gagtctgggg acgcaagcat ccacgatacg gttgaaaacc tcatcatcct tgcgaacaac   1800

tctctctcat ctaatggaaa cgttacagag agtgggtgta aggagtgcga agagttggaa   1860

gaaaaaaaca tcaaagaatt tcttcaatcc ttcgttcaca tagtgcaaat gttcattaac   1920

acgtccacta ccacacccgc cccgaggcca cctacgccgg caccgactat cgccagtcaa   1980

cccctctctc tgcgccccga ggcttgccgg cctgcggctg gtggggcggt ccacacccgg   2040

ggcctggatt ttgcgtgcga tatatacatc tgggcacctc ttgccggcac ctgcggagtg   2100

ctgcttctct cactcgttat tacgctgtac tgctaagcgg ccgcgtcgac               2150

<210> SEQ ID NO 20
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-No Flag-9

<400> SEQUENCE: 20

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45
```

```
Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
```

465 470 475 480

Arg Gly Ser Gly Glu Gly Arg Gly Ser Leu Leu Thr Cys Gly Asp Val
485 490 495

Glu Glu Asn Pro Gly Pro Met Ala Leu Pro Val Thr Ala Leu Leu Leu
500 505 510

Pro Leu Ala Leu Leu Leu His Ala Ala Arg Pro Asn Trp Val Asn Val
515 520 525

Ile Ser Asp Leu Lys Lys Ile Glu Asp Leu Ile Gln Ser Met His Ile
530 535 540

Asp Ala Thr Leu Tyr Thr Glu Ser Asp Val His Pro Ser Cys Lys Val
545 550 555 560

Thr Ala Met Lys Cys Phe Leu Leu Glu Leu Gln Val Ile Ser Leu Glu
565 570 575

Ser Gly Asp Ala Ser Ile His Asp Thr Val Glu Asn Leu Ile Ile Leu
580 585 590

Ala Asn Asn Ser Leu Ser Ser Asn Gly Asn Val Thr Glu Ser Gly Cys
595 600 605

Lys Glu Cys Glu Glu Leu Glu Glu Lys Asn Ile Lys Glu Phe Leu Gln
610 615 620

Ser Phe Val His Ile Val Gln Met Phe Ile Asn Thr Ser Thr Thr Thr
625 630 635 640

Pro Ala Pro Arg Pro Pro Thr Pro Ala Pro Thr Ile Ala Ser Gln Pro
645 650 655

Leu Ser Leu Arg Pro Glu Ala Cys Arg Pro Ala Ala Gly Gly Ala Val
660 665 670

His Thr Arg Gly Leu Asp Phe Ala Cys Asp Ile Tyr Ile Trp Ala Pro
675 680 685

Leu Ala Gly Thr Cys Gly Val Leu Leu Leu Ser Leu Val Ile Thr Leu
690 695 700

Tyr Cys
705

<210> SEQ ID NO 21
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-No Flag-10

<400> SEQUENCE: 21
gaattcgccg ccaccatggc cttaccagtg accgccttgc tcctgccgct ggccttgctg 60
ctccacgccg ccaggccgga tattcagatg acccagagcc cgagcagcct gagcgcgagc 120
gtgggcgatc gcgtgaccat tacctgccgc gcgagccagg atattagcaa atatctgaac 180
tggtatcagc agaaaccggg cggcaccgtg aaactgctga tttatcatac cagccgcctg 240
catagcggcg tgccgagccg ctttagcggc agcggcagcg gcaccgattt taccctgacc 300
attagcagcc tgcagccgga agatattgcg acctattatt gccagcaggg caacaccctg 360
ccgtatacct ttggcggcgg caccaaactg gaaattaccg gtggcggtgg ctcgggcggt 420
ggtgggtcgg gtggcggcgg atctcaggtg cagctgcagg aaagcggccc gggcctggtg 480
aaaccgagcc agaccctgag cgtgacctgc accgtgagcg gcgtgagcct gccggattat 540
ggcgtgagct ggattcgcca gccgccgcgc aaaggcctgg aatggctggg cgtgatttgg 600
ggcagcgaaa ccacctatta taacagcgcg ctgaaaagcc gcctgaccat tagcaaagat 660

```
aacagcaaaa gccaggtgag cctgaaaatg agcagcgtga ccgcggcgga taccgcgatt    720
tattattgcg cgaaacatta ttattatggc ggcagctatg cgatggatta ttggggccag    780
ggcaccagcg tgaccgtgag cagcaccacg acgccagcgc cgcgaccacc aacaccggcg    840
cccaccatcg cgtcgcagcc cctgtccctg cgcccagagg cgtgccggcc agcggcgggg    900
ggcgcagtgc acacgagggg gctggacttc gcctgtgata tctacatctg ggcgcccttg    960
gccgggactt gtggggtcct tctcctgtca ctggttatca ccctttactg ccggagggac   1020
cagaggctgc cccccgatgc ccacaagccc cctgggggag gcagtttccg gacccccatc   1080
caagaggagc aggccgacgc ccactccacc ctggccaaga tcagagtgaa gttcagcagg   1140
agcgcagacg cccccgcgta ccagcagggc cagaaccagc tctataacga gctcaatcta   1200
ggacgaagag aggagtacga tgttttggac aagagacgtg gccgggaccc tgagatgggg   1260
ggaaagccga gaaggaagaa ccctcaggaa ggcctgtaca atgaactgca gaaagataag   1320
atggcggagg cctacagtga gattgggatg aaaggcgagc gccggagggg caaggggcac   1380
gatggccttt accagggtct cagtacagcc accaaggaca cctacgacgc ccttcacatg   1440
caggccctgc cccctcgcgg ctctggcgag ggaaggggtt ccctgcttac ttgcggcgac   1500
gtcgaagaga atcccggtcc gatggccctc ccagtaactg ccctcctttt gcccctcgca   1560
ctccttcttc atgccgctcg ccccaactgg gtcaacgtga ttagcgattt gaagaaaatc   1620
gaggacctta tacagtctat gcatattgac gctacactgt atactgagag tgatgtacac   1680
ccgtcctgta aggtaacggc catgaaatgc tttcttctgg agctccaggt catcagcttg   1740
gagtctgggg acgcaagcat ccacgatacg gttgaaaacc tcatcatcct tgcgaacaac   1800
tctctctcat ctaatggaaa cgttacagag agtgggtgta aggagtgcga agagttggaa   1860
gaaaaaaaca tcaaagaatt tcttcaatcc ttcgttcaca tagtgcaaat gttcattaac   1920
acgtccacta ccacacccgc cccgaggcca cctacgccgg caccgactat cgccagtcaa   1980
cccctctctc tgcgccccga ggcttgccgg cctgcggctg gtggggcggt ccacacccgg   2040
ggcctggatt ttgcgtgcga tatatacatc tgggcacctc ttgccggcac ctgcggagtg   2100
ctgcttctct cactcgttat tacgctgtac tgctaagcgg ccgcgtcgac              2150
```

<210> SEQ ID NO 22
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-No Flag-10

<400> SEQUENCE: 22

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95
```

-continued

```
Ser Ser Leu Gln Pro Glu Asp Ile Ala Thr Tyr Tyr Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Met Ser Ser Val Thr Ala Ala Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510
```

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705

<210> SEQ ID NO 23
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-No Flag-11

<400> SEQUENCE: 23
gaattcgccg ccaccatggc cttaccagtg accgccttgc tcctgccgct ggccttgctg 60
ctccacgccg ccaggccgga tattcagatg acccagagcc cgagcagcct gagcgcgagc 120
gtgggcgatc gcgtgaccat tacctgccgc gcgagccagg atattagcaa atatctgaac 180
tggtatcagc agaaaccggg cggcaccgtg aaactgctga tttatcatac cagccgcctg 240
catagcggcg tgccgagccg ctttagcggc agcggcagcg gcaccgattt taccctgacc 300
attagcagcc tgcagccgga agatattgcg acctattttt gccagcaggg caacaccctg 360
ccgtatacct ttggcggcgg caccaaactg gaaattaccg gtggcggtgg ctcgggcggt 420
ggtgggtcgg gtggcggcgg atctcaggtg cagctgcagg aaagcggccc gggcctggtg 480
aaaccgagcc agaccctgag cgtgacctgc accgtgagcg gcgtgagcct gccggattat 540
ggcgtgagct ggattcgcca gccgccgcgc aaaggcctgg aatggctggg cgtgatttgg 600
ggcagcgaaa ccacctatta taacagcgcg ctgaaaagcc gcctgaccat tagcaaagat 660
aacagcaaaa gccaggtgag cctgaaaatg agcagcgtga ccgcggcgga taccgcgatt 720
tattattgcg cgaaacatta ttattatggc ggcagctatg cgatggatta ttggggccag 780
ggcaccagcg tgaccgtgag cagcaccacg acgccagcgc cgcgaccacc aacaccggcg 840
cccaccatcg cgtcgcagcc cctgtccctg cgcccagagg cgtgccggcc agcggcgggg 900

```
ggcgcagtgc acacgagggg gctggacttc gcctgtgata tctacatctg ggcgcccttg    960

gccgggactt gtggggtcct tctcctgtca ctggttatca ccctttactg ccggagggac   1020

cagaggctgc cccccgatgc ccacaagccc cctgggggag gcagtttccg gacccccatc   1080

caagaggagc aggccgacgc ccactccacc ctggccaaga tcagagtgaa gttcagcagg   1140

agcgcagacg cccccgcgta ccagcagggc cagaaccagc tctataacga gctcaatcta   1200

ggacgaagag aggagtacga tgttttggac aagagacgtg gccgggaccc tgagatgggg   1260

ggaaagccga gaaggaagaa ccctcaggaa ggcctgtaca atgaactgca gaaagataag   1320

atggcggagg cctacagtga gattgggatg aaaggcgagc gccggagggg caaggggcac   1380

gatggccttt accagggtct cagtacagcc accaaggaca cctacgacgc ccttcacatg   1440

caggccctgc cccctcgcgg ctctggcgag ggaaggggtt ccctgcttac ttgcggcgac   1500

gtcgaagaga atcccggtcc gatggccctc ccagtaactg ccctcctttt gcccctcgca   1560

ctccttcttc atgccgctcg ccccaactgg gtcaacgtga ttagcgattt gaagaaaatc   1620

gaggacctta tacagtctat gcatattgac gctacactgt atactgagag tgatgtacac   1680

ccgtcctgta aggtaacggc catgaaatgc tttcttctgg agctccaggt catcagcttg   1740

gagtctgggg acgcaagcat ccacgatacg gttgaaaacc tcatcatcct tgcgaacaac   1800

tctctctcat ctaatggaaa cgttacagag agtgggtgta aggagtgcga agagttggaa   1860

gaaaaaaaca tcaaagaatt tcttcaatcc ttcgttcaca tagtgcaaat gttcattaac   1920

acgtccacta ccacacccgc cccgaggcca cctacgccgg caccgactat cgccagtcaa   1980

cccctctctc tgcgccccga ggcttgccgg cctgcggctg gtggggcggt ccacacccgg   2040

ggcctggatt ttgcgtgcga tatatacatc tgggcacctc ttgccggcac ctgcggagtg   2100

ctgcttctct cactcgttat tacgctgtac tgctaagcgg ccgcgtcgac               2150
```

<210> SEQ ID NO 24
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-No Flag-11

<400> SEQUENCE: 24

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
```

-continued

```
    130                 135                 140

Val Gln Leu Gln Glu Ser Gly Pro Gly Leu Val Lys Pro Ser Gln Thr
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Met Ser Ser Val Thr Ala Ala Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560
```

```
Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705
```

```
<210> SEQ ID NO 25
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-No Flag-12

<400> SEQUENCE: 25

gaattcgccg ccaccatggc cttaccagtg accgccttgc tcctgccgct ggccttgctg     60

ctccacgccg ccaggccgga tattcagatg acccagagcc cgagcagcct gagcgcgagc    120

gtgggcgatc gcgtgaccat tacctgccgc gcgagccagg atattagcaa atatctgaac    180

tggtatcagc agaaaccgga tggcaccgtg aaactgctga tttatcatac cagccgcctg    240

catagcggcg tgccgagccg ctttagcggc agcggcagcg gcaccgatta taccctgacc    300

attagcagcc tgcagccgga agatattgcg acctattttt gccagcaggg caacaccctg    360

ccgtatacct ttggcggcgg caccaaactg gaaattaccg gtggcggtgg ctcgggcggt    420

ggtgggtcgg gtggcggcgg atctcaggtg cagctgcagg aaagcggccc gggcctggtg    480

aaaccgagcc agaccctgag cgtgacctgc accgtgagcg gcgtgagcct gccggattat    540

ggcgtgagct ggattcgcca gccgccgcgc aaaggcctgg aatggctggg cgtgatttgg    600

ggcagcgaaa ccacctatta taacagcgcg ctgaaaagcc gcctgaccat tagcaaagat    660

aacagcaaaa gccaggtgag cctgaaaatg agcagcgtga ccgcggcgga taccgcgatt    720

tattattgcg cgaaacatta ttattatggc ggcagctatg cgatggatta ttggggccag    780

ggcaccagcg tgaccgtgag cagcaccacg acgccagcgc cgcgaccacc aacaccggcg    840

cccaccatcg cgtcgcagcc cctgtccctg cgcccagagg cgtgccggcc agcggcgggg    900

ggcgcagtgc acacgagggg gctggacttc gcctgtgata tctacatctg ggcgcccttg    960

gccgggactt gtggggtcct tctcctgtca ctggttatca ccctttactg ccggagggac   1020

cagaggctgc cccccgatgc ccacaagccc cctgggggag gcagtttccg gacccccatc   1080

caagaggagc aggccgacgc ccactccacc ctggccaaga tcagagtgaa gttcagcagg   1140
```

```
agcgcagacg cccccgcgta ccagcagggc cagaaccagc tctataacga gctcaatcta   1200

ggacgaagag aggagtacga tgttttggac aagagacgtg gccgggaccc tgagatgggg   1260

ggaaagccga gaaggaagaa ccctcaggaa ggcctgtaca atgaactgca gaaagataag   1320

atggcggagg cctacagtga gattgggatg aaaggcgagc gccggagggg caaggggcac   1380

gatggccttt accagggtct cagtacagcc accaaggaca cctacgacgc ccttcacatg   1440

caggccctgc cccctcgcgg ctctggcgag ggaaggggtt ccctgcttac ttgcggcgac   1500

gtcgaagaga atcccggtcc gatggccctc ccagtaactg ccctcctttt gccccctcgca   1560

ctccttcttc atgccgctcg ccccaactgg gtcaacgtga ttagcgattt gaagaaaatc   1620

gaggacctta tacagtctat gcatattgac gctacactgt atactgagag tgatgtacac   1680

ccgtcctgta aggtaacggc catgaaatgc tttcttctgg agctccaggt catcagcttg   1740

gagtctgggg acgcaagcat ccacgatacg gttgaaaacc tcatcatcct tgcgaacaac   1800

tctctctcat ctaatggaaa cgttacagag agtgggtgta aggagtgcga agagttggaa   1860

gaaaaaaaca tcaaagaatt tcttcaatcc ttcgttcaca tagtgcaaat gttcattaac   1920

acgtccacta ccacacccgc cccgaggcca cctacgccgg caccgactat cgccagtcaa   1980

cccctctctc tgcgccccga ggcttgccgg cctgcggctg gtggggcggt ccacacccgg   2040

ggcctggatt ttgcgtgcga tatatacatc tgggcacctc ttgccggcac ctgcggagtg   2100

ctgcttctct cactcgttat tacgctgtac tgctaagcgg ccgcgtcgac              2150
```

<210> SEQ ID NO 26
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-No Flag-12

<400> SEQUENCE: 26

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Val Thr Cys Thr Val Ser Gly Val Ser Leu Pro Asp Tyr Gly
                165                 170                 175
```

-continued

```
Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Met Ser Ser Val Thr Ala Ala Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
```

```
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705


<210> SEQ ID NO 27
<211> LENGTH: 2210
<212> TYPE: DNA
<213> ORGANISM: Homo sapiens
<220> FEATURE:
<221> NAME/KEY: misc_feature
<223> OTHER INFORMATION: DNA NK19-1

<400> SEQUENCE: 27

ggatccgaat tcgccgccac catggcctta ccagtgaccg ccttgctcct gccgctggcc      60

ttgctgctcc acgccgccag gccggactac aaagacgatg acgataaagg cggtggtggc     120

tctggtggtg gcggcagcga catccagatg acacagacta catcctccct gtctgcctct     180

ctgggagaca gagtcaccat cagttgcagg gcaagtcagg acattagtaa atatttaaat     240

tggtatcagc agaaaccaga tggaactgtt aaactcctga tctaccatac atcaagatta     300

cactcaggag tcccatcaag gttcagtggc agtgggtctg gaacagatta ttctctcacc     360

attagcaacc tggagcaaga agatattgcc acttactttt gccaacaggg taatacgctt     420

ccgtacacgt tcggaggggg gaccaagctg gagatcacag gtggcggtgg ctcgggcggt     480

ggtgggtcgg gtggcggcgg atctgaggtg aaactgcagg agtcaggacc tggcctggtg     540

gcgccctcac agagcctgtc cgtcacatgc actgtctcag gggtctcatt acccgactat     600

ggtgtaagct ggattcgcca gcctccacga aagggtctgg agtggctggg agtaatatgg     660

ggtagtgaaa ccacatacta taattcagct ctcaaatcca gactgaccat catcaaggac     720

aactccaaga gccaagtttt cttaaaaatg aacagtctgc aaactgatga cacagccatt     780

tactactgtg ccaaacatta ttactacggt ggtagctatg ctatggacta ctggggccaa     840

ggaacctcag tcaccgtctc ctcaaccacg acgccagcgc cgcgaccacc aacaccggcg     900

cccaccatcg cgtcgcagcc cctgtccctg cgcccagagg cgtgccggcc agcggcgggg     960

ggcgcagtgc acacgagggg gctggacttc gcctgtgata tctacatctg ggcgcccttg    1020

gccgggactt gtggggtcct tctcctgtca ctggttatca ccctttactg ccggagggac    1080

cagaggctgc cccccgatgc ccacaagccc cctgggggag gcagtttccg gacccccatc    1140

caagaggagc aggccgacgc ccactccacc ctggccaaga tcagagtgaa gttcagcagg    1200

agcgcagacg cccccgcgta ccagcagggc cagaaccagc tctataacga gctcaatcta    1260

ggacgaagag aggagtacga tgttttggac aagagacgtg gccgggaccc tgagatgggg    1320

ggaaagccga gaaggaagaa ccctcaggaa ggcctgtaca atgaactgca gaaagataag    1380
```

```
atggcggagg cctacagtga gattgggatg aaaggcgagc gccggagggg caaggggcac   1440

gatggccttt accagggtct cagtacagcc accaaggaca cctacgacgc ccttcacatg   1500

caggccctgc cccctcgcgg ctctggcgag ggaaggggtt ccctgcttac ttgcggcgac   1560

gtcgaagaga atcccggtcc gatggccctc ccagtaactg ccctcctttt gcccctcgca   1620

ctccttcttc atgccgctcg ccccaactgg gtcaacgtga ttagcgattt gaagaaaatc   1680

gaggacctta tacagtctat gcatattgac gctacactgt atactgagag tgatgtacac   1740

ccgtcctgta aggtaacggc catgaaatgc tttcttctgg agctccaggt catcagcttg   1800

gagtctgggg acgcaagcat ccacgatacg gttgaaaacc tcatcatcct tgcgaacaac   1860

tctctctcat ctaatggaaa cgttacagag agtgggtgta aggagtgcga agagttggaa   1920

gaaaaaaaca tcaaagaatt tcttcaatcc ttcgttcaca tagtgcaaat gttcattaac   1980

acgtccacta ccacacccgc cccgaggcca cctacgccgg caccgactat cgccagtcaa   2040

cccctctctc tgcgccccga ggcttgccgg cctgcggctg gtggggcggt ccacacccgg   2100

ggcctggatt ttgcgtgcga tatatacatc tgggcacctc ttgccggcac ctgcggagtg   2160

ctgcttctct cactcgttat tacgctgtac tgctaagcgg ccgcgtcgac               2210
```

```
<210> SEQ ID NO 28
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19-1

<400> SEQUENCE: 28

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205
```

```
Leu Gly Val Ile Trp Gly Ser Glu Thr Thr Tyr Tyr Asn Ser Ala Leu
    210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
```

-continued

| | | | | | | | | | | | | | | | |
|---|---|---|---|---|---|---|---|---|---|---|---|---|---|---|---|
| 625 | | | | | 630 | | | | | 635 | | | | | 640 |
| Leu | Gln | Ser | Phe | Val | His | Ile | Val | Gln | Met | Phe | Ile | Asn | Thr | Ser | Thr |
| | | | | 645 | | | | | 650 | | | | | 655 | |
| Thr | Thr | Pro | Ala | Pro | Arg | Pro | Pro | Thr | Pro | Ala | Pro | Thr | Ile | Ala | Ser |
| | | | 660 | | | | | 665 | | | | | 670 | | |
| Gln | Pro | Leu | Ser | Leu | Arg | Pro | Glu | Ala | Cys | Arg | Pro | Ala | Ala | Gly | Gly |
| | | 675 | | | | | 680 | | | | | 685 | | | |
| Ala | Val | His | Thr | Arg | Gly | Leu | Asp | Phe | Ala | Cys | Asp | Ile | Tyr | Ile | Trp |
| | 690 | | | | | 695 | | | | | 700 | | | | |
| Ala | Pro | Leu | Ala | Gly | Thr | Cys | Gly | Val | Leu | Leu | Leu | Ser | Leu | Val | Ile |
| 705 | | | | | 710 | | | | | 715 | | | | | 720 |
| Thr | Leu | Tyr | Cys | | | | | | | | | | | | |